United States Patent [19]
Takase et al.

[11] Patent Number: 6,048,885
[45] Date of Patent: *Apr. 11, 2000

[54] OXIME DERIVATIVE AND BACTERICIDE CONTAINING THE SAME AS ACTIVE INGREDIENT

[75] Inventors: Akira Takase, Otsu; Hiroyuki Kai, Yamatokoriyama; Kuniyoshi Nishida, Shiga; Tsuneo Iwakawa, Kusatsu; Kazuo Ueda, Mie; Michio Masuko, Shiga, all of Japan

[73] Assignee: Shionogi & Co., Ltd., Osaka, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/693,224

[22] PCT Filed: Mar. 30, 1995

[86] PCT No.: PCT/JP95/00604

§ 371 Date: Aug. 21, 1996

§ 102(e) Date: Aug. 21, 1996

[87] PCT Pub. No.: WO95/26956

PCT Pub. Date: Oct. 12, 1995

[30] Foreign Application Priority Data

Apr. 1, 1994 [JP] Japan ..................... 6-087819

[51] Int. Cl.⁷ ............... C07D 231/12; C07D 233/10; C07D 233/61; C07D 307/52
[52] U.S. Cl. ............... 514/378; 514/380; 514/274; 548/240; 548/243; 548/247; 544/316
[58] Field of Search .................. 548/247, 243, 548/240; 514/378, 380

[56] References Cited

U.S. PATENT DOCUMENTS

| | | | |
|---|---|---|---|
| 5,206,956 | 5/1993 | Clough et al. | 514/269 |
| 5,238,956 | 8/1993 | Clough et al. | 514/506 |

FOREIGN PATENT DOCUMENTS

| | | |
|---|---|---|
| 7679 | 2/1980 | European Pat. Off. . |
| 2449205 | 4/1975 | Germany . |
| 4404373 | 8/1995 | Germany . |
| 1-308260 | 12/1989 | Japan . |
| 3-68559 | 3/1991 | Japan . |
| WO 94/22844 | 10/1994 | WIPO . |

*Primary Examiner*—Mukund J. Shah
*Assistant Examiner*—Bruck Kifle
*Attorney, Agent, or Firm*—Foley & Lardner

[57] ABSTRACT

A compound represented by general formula (I) or a salt thereof, a process for producing the same, an intermediate for the production thereof, and a bactericide (fungicide) containing the same as the active ingredient wherein $R^1$ represent optionally substituted aryl, optionally substituted heterocycle, mono- or di-substituted methyleneamino, optionally substituted (substituted imino)methyl, optionally substituted alkyl, optionally substituted alkenyl, optionally substituted alkynyl, substituted carbonyl or substituted sulfonyl; $R^2$ represents alkyl, alkenyl, alkynyl or cycloalkyl; $R^3$ represents optionally substituted heterocycle; $R^4$ represents hydrogen, alkyl, alkoxy, halogen, nitro, cyano or haloalkyl; M represents oxygen, S(O)i (i being 0, 1 or 2), $NR^{16}$ ($R^{16}$ being hydrogen, alkyl or acyl) or a single bond; n represents 0 or 1, provided n represent 1 when R3 represents imidazol-1-yl or 1H-1, 2, 4-triazol-1-yl; and the symbol ~ represents the E form, Z form or a mixture thereof:

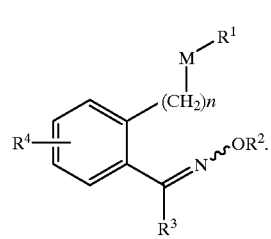

I

13 Claims, No Drawings

OXIME DERIVATIVE AND BACTERICIDE CONTAINING THE SAME AS ACTIVE INGREDIENT

TECHNICAL FIELD

The present invention relates to an oxime derivative, particularly a heterocyclic compound substituted with α-(O-substituted oxyimino)-2-substituted benzyl, a process for producing it, intermediates therefor, and a bactericide (fungicide) containing it as an active ingredient.

BACKGROUND ART

Compounds containing α-(O-substituted oxyimino)-benzyl known so far include benzohydroxymoylazole derivatives having insecticidal activity (JP-A 1-308260, JP-A 5-1046, W092/09581, JP-A 5-331011, JP-A 5-331012, JP-A 6-41086), oxime derivatives having insecticidal activity (JP-A 3-68559), 1-azolyl-substituted oxime ethers having fungicidal activity (JP-A 60-87269), etc.

The present invention is to provide a compound having more potent fungicidal activity, higher utility, etc., than the known compounds as well as low toxicity.

DISCLOSURE OF INVENTION

The present inventors have intensively studied to achieve the above object. As a result, it has been found that a heterocyclic compound substituted with (α-(O-substituted oxyimino)-2-substituted benzyl has potent fungicidal activity. After further studies, the present invention has been completed.

The present invention provides:

1. A compound of the formula (I):

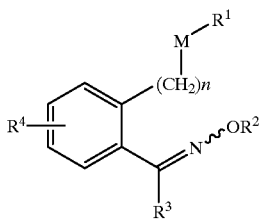

wherein $R^1$ is optionally substituted aryl, an optionally substituted heterocyclic group, mono or disubstituted methyleneamino, optionally substituted (substituted imino) methyl, optionally substituted alkyl, optionally substituted alkenyl, optionally substituted alkynyl, substituted carbonyl or substituted sulfonyl; $R^2$ is alkyl, alkenyl, alkynyl or cycloalkyl; $R^3$ is an optionally substituted heterocyclic group; $R^4$ is hydrogen, alkyl, alkoxy, halogen, nitro, cyano or halogenated alkyl; M is an oxygen atom, S(O)i (in which i is 0, 1 or 2), $NR^{16}$ (in which $R^{16}$ is hydrogen, alkyl or acyl) or a single bond; n is 0 or 1, provided that, when $R^3$ is imidazol-1-yl or 1H-1,2,4-triazol-1-yl, n is 1; and ~ indicates an E- or Z-isomer or a mixture thereof; or a salt thereof;

2. A compound according to the above item 1, wherein the optionally substituted heterocyclic group represented by $R^1$ is pyridyl, pyrimidinyl, benzoxazolyl, benzothiazolyl, benzimidazolyl, isoxazolyl, isothiazolyl, thiadiazolyl, pyridazinyl, pyrrolyl, pyrazolyl, furyl, thienyl, imidazolyl, oxazolyl, thiazolyl, oxadiazolyl, triazolyl, quinolyl, indolyl, benzisothiazolyl, benzisoxazolyl or pyrazinyl, each of which is unsubstituted or substituted, or a salt thereof;

3. A compound according to the above item 1, wherein $R^1$ is phenyl or a heterocyclic group, each of which is unsubstituted or substituted with 1 or 2 substituents selected from the group consisting of halogen, lower alkyl, halogenated lower alkyl, lower alkoxy, lower alkylthio, phenyl, phenoxy and nitro, or a salt thereof;

4. A compound according to the above item 1, wherein $R^1$ is phenyl; phenyl substituted with halogen and/or lower alkyl; or pyridyl substituted with halogen and/or halogenated lower alkyl; or a salt thereof:

5. A compound according to the above item 1, wherein $R^1$ is phenyl, 2-chlorophenyl, 3-chlorophenyl, 4-chlorophenyl, 2-methylphenyl, 3-methylphenyl, 4-methylphenyl, 2-ethylphenyl, 2,5-dimethylphenyl, 2,6-dimethylphenyl, 4-chloro-2-methylphenyl, 2-chloropyridin-3-yl, 3,5-dichloropyridin-2-yl, 5-trifluoromethylpyridin-2-yl, 5-trifluoromethyl-3-chloropyridin-2-yl or 3-trifluoromethyl-5-chloropyridin-2-yl, or a salt thereof;

6. A compound according to the above item 1, wherein $R^1$ is a group of the formula (a):

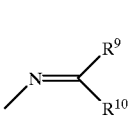

wherein $R^9$ and $R^{10}$ are the same or different and are hydrogen, optionally substituted alkyl, acyl, alkylthio, alkylsulfinyl alkylsulfonyl, optionally substituted amino, cycloalkyl, optionally substituted aryl or an optionally substituted heterocyclic group, or $R^9$ and $R^{10}$ are linked together to form a monocyclic or polycyclic ring which may contain a heteroatom, or a salt thereof;

7. A compound according to the above item 1, wherein $R^9$ and $R^{10}$ are the same or different and are hydrogen, alkyl, haloalkyl, alkoxyalkyl, alkylcarbonyl, optionally substituted phenyl, optionally substituted naphthyl or an optionally substituted heterocyclic group, or $R^9$ and $R^{10}$ are linked together to form a cyclopentane or cyclohexane ring which may form a condensed ring with another ring, or a salt thereof;

8. A compound according to the above item 1, wherein $R^9$ is phenyl which is unsubstituted or substituted with 1 to 3 substituents selected from the group consisting of halogen, optionally substituted alkyl, optionally substituted hydroxyl, alkylthio, optionally substituted amino, nitro, phenyl and cyano, or a salt thereof;

9. A compound according to the above item 1, wherein $R^9$ is phenyl which is unsubstituted or substituted with 1 to 3 substituents selected from the group consisting of chlorine, methyl, trifluoromethyl and methoxy, or a salt thereof;

10. A compound according to the above item 1, wherein $R^9$ is morpholino, pyridyl, pyridazinyl, pyrazolyl, pyrimidinyl, furyl, thienyl, oxazolyl, isoxazolyl, benzothiazolyl, quinolyl, quinazolinyl or pyrazinyl, each of which is unsubstituted or substituted, or a salt thereof;

11. A compound according to the above item 1, wherein $R^{10}$ is hydrogen or alkyl, or a salt thereof;

12. A compound according to the above item 1, wherein $R^{10}$ is hydrogen, methyl or ethyl, or a salt thereof;

13. A compound according to the above item 1, wherein $R^2$ is alkyl or alkenyl, or a salt thereof;

14. A compound according to the above item 1, wherein $R^2$ is methyl, ethyl or allyl, or a salt thereof;

15. A compound according to the above item 1, wherein $R^3$ is isoxazolyl, oxazolyl, thiazolyl, isothiazolyl, thiadiazolyl, pyrrolyl, pyrazolyl, furyl, thienyl, imidazolyl, triazolyl, tetrazolyl, oxadiazolyl, thiazolinyl, isoxazolinyl, imidazolinyl, oxazolinyl or thiazolidinyl, each of which is unsubstituted or substituted, or a salt thereof;

16. A compound according to the above item 1, wherein R³ is imidazolyl; imidazolyl substituted with lower alkyl; imidazolinyl; triazolyl; imidazolinyl substituted with lower alkyl; isoxazolyl; isoxazolyl substituted with lower alkyl; oxadiazolyl; oxadiazolyl substituted with lower alkyl; isoxazolinyl; isoxazolinyl substituted with lower alkyl; oxazolinyl; pyrazolyl; pyrazolyl substituted with lower alkyl; thiazolinyl; furyl; tetrazolyl substituted with lower alkyl; oxazolyl; isothiazolyl substituted with lower alkyl; thiazolidinyl; or thiazolidinyl substituted with lower alkyl; or a salt thereof;

17. A compound according to the above item 1, wherein R³ is imidazol-1-yl, imidazol-2-yl, 1-methylimidazol-2-yl, 2-methylimidazol-1-yl, 4-methylimidazol-1-yl, 5-methylimidazol-1-yl, 2-imidazolin-2-yl, 1H-1,2,4-triazol-1-yl, 1-methyl-2-imidazolin-2-yl, isoxazol-3-yl, 3-methylisoxazol-5-yl, 5-methylisoxazol-3-yl, 5-methyl-1,2,4-oxadiazol-3-yl, 3-ethyl- 1,2,4-oxadiazol-5-yl, 2-isoxazolin-3-yl, 2-oxazolin-2-yl, 3-methyl-2-isoxazolin-5-yl, pyrazol-1-yl, 1-methylpyrazol-5-yl, 2-thiazolin-2-yl, 2-furyl, 3-methylisothiazol-5-yl, 1,2,4-oxadiazol-3-yl, 1,2,4-oxadiazol-5-yl, 1,3,4-oxadiazol-2-yl, 5-methyl-1,3,4-oxadiazol-2-yl, 2-methyltetrazol-5-yl, oxazol-5-yl, isoxazol-5-yl, thiazolidin-2-yl or 3-methylthiazolidin-2-yl, or a salt thereof;

18. A compound according to the above item 1, wherein R⁴ is hydrogen, or a salt thereof;

19. A compound according to the above item 1, wherein M is an oxygen atom, or a salt thereof;

20. A fungicidal composition comprising a compound according to any one of the above items 1 to 19 or a salt thereof as an active ingredient;

21. A process for producing a compound of the formula (I):

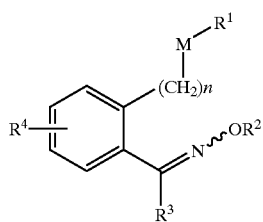

wherein each symbol is as defined in the above item 1, which comprises reacting the compound of the formula (V):

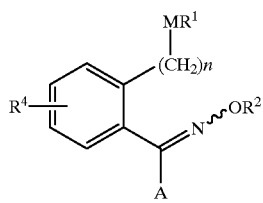

wherein A is halogen and the other symbols are as defined in the above item 1, with a compound of the formula (X):

R³—H (X)

wherein R³ is an optionally substituted heterocyclic group;

22. A process according to the above item 21, wherein R³ is pyrrolyl, imidazolyl, pyrazolyl or triazolyl, each of which is unsubstituted or substituted;

23. A compound of the formula (V):

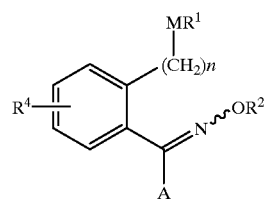

wherein A is halogen and the other symbols are as defined in the above item 1, or a salt thereof;

24. A compound according to the above item 23, wherein M is an oxygen atom, or a salt thereof;

25. A compound of the formula (XIV):

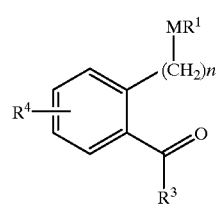

wherein each symbol is as defined in the above item 1, provided that, when M is an oxygen atom and R³ is isoxazol-4-yl, n is 1, or a salt thereof;

26. A compound according to the above item 25, wherein M is an oxygen atom, or a salt thereof; and 27. A compound of the formula (XLVIII):

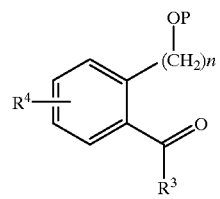

wherein P is a protective group of a hydroxyl group, and the other symbols are as defined in the above item 1, or a salt thereof.

The term "lower" used herein means having 1 to 8 carbon atoms, preferably 1 to 6 carbon atoms, more preferably 1 to 4 carbon atoms, unless otherwise indicated.

The aryl of the optionally substituted aryl represented by R¹ includes aryl having 6 to 14 carbon atoms such as phenyl, naphthyl, etc.

The optionally substituted heterocyclic group represented by R¹ includes unsubstituted or substituted heterocyclic groups. Examples of the heterocyclic group include 5- to 7-membered heterocyclic groups containing 1 to 4 heteroatoms selected from nitrogen, sulfur and oxygen in the ring, such as pyridyl (e.g., pyridin-2-yl, pyridin-3-yl), pyrimidinyl (e.g., pyrimidin-2-yl, pyrimidin-4-yl), benzoxazolyl (e.g., benzoxazol-2-yl), benzothiazolyl (e.g., benzothiazol-2-yl), benzimidazolyl, isoxazolyl (e.g., isoxazol-3-yl, isoxazol-5-yl), isothiazolyl, thiadiazolyl [e.g., 1,3,4-thiadiazolyl (e.g., 1,3,4-thiadiazol-2-yl), 1,2,4-thiadiazolyl, etc.], pyridazinyl, pyrrolyl, pyrazolyl, furyl, thienyl, imidazolyl, oxazolyl, thiazolyl, oxadiazolyl (e.g., 1,3,4-oxadiazolyl, 1,2,4-oxadiazolyl, etc.), triazolyl (e.g., 1,2,3-triazolyl, 1,2,4- triazolyl, etc.), quinolyl (e.g., quinolin-2-yl), indolyl, benzisothiazolyl, benzisoxazolyl, pyrazinyl (e.g., pyrazin-2-yl), etc. The heterocyclic group may form a condensed cyclic group with a carbocycle or another heterocycle. The heterocycle has a bond to M at any possible position in the ring.

The substituent of the substituted aryl and substituted heterocyclic group represented by $R^1$ includes, for example, lower alkyl (e.g., methyl, ethyl, propyl, butyl, etc.), lower alkenyl (e.g., vinyl, allyl, crotyl, etc.), lower alkynyl (e.g., ethynyl, propargyl, butynyl, etc.), cycloalkyl (e.g., cyclopropyl, cyclopentyl, cyclohexyl, etc.), cycloalkenyl (e.g., cyclopentenyl, cyclohexenyl, etc.), lower alkanoyl (e.g., acetyl, propionyl, isobutyryl, etc.), lower trialkylsilyl (e.g., trimethylsilyl, triethylsilyl, tripropylsilyl, tributylsilyl, etc.), halogenated lower alkyl (e.g., trifluoromethyl, trichloromethyl, chloromethyl, 2-bromoethyl, 1,2-dichloropropyl, etc.), di(lower)alkylamino (e.g., dimethylamino, diethylamino, etc.), phenyl, phenyl(lower) alkyl (e.g., benzyl, phenethyl, etc.), phenyl(lower)alkenyl (e.g., styryl, cinnamyl, etc.), furyl(lower)alkyl (e.g., 3-furylmethyl, 2-furylethyl, etc.), furyl(lower)alkenyl (e.g., 3-furylvinyl, 2-furylallyl, etc.), halogen (e.g., fluorine, chlorine, bromine, iodine), nitro, cyano, lower alkylthio (e.g., methylthio, ethylthio, propylthio, etc.), $—OR^{11}$ [wherein $R^{11}$ is hydrogen, lower alkyl group (e.g., methyl, ethyl, propyl, etc.), lower alkenyl (e.g., vinyl, allyl, crotyl, etc.), lower alkynyl (e.g., ethynyl, 2-propynyl, 3-butynyl, etc.), lower alkanoyl (e.g., acetyl, propionyl, butyryl, etc.), phenyl, lower alkoxyphenyl (e.g., 3-methoxyphenyl, 4-ethoxyphenyl, etc.), nitrophenyl (e.g., 3-nitrophenyl, 4-nitrophenyl, etc.), phenyl(lower)alkyl (e.g., benzyl, phenethyl, phenylpropyl, etc.), cyanophenyl(lower)alkyl (e.g., 3-cyanophenylmethyl, 4-cyanophenylethyl, etc.), benzoyl, tetrahydropyranyl, pyridyl, trifluoromethylpyridyl, pyrimidinyl, benzothiazolyl, quinolyl, benzoyl(lower)alkyl (e.g., benzoylmethyl, benzoylethyl, etc.), benzensulfonyl, or lower alkylbenzenesulfonyl (e.g., toluenesulfonyl, etc.)], $—CH_2—Z—R^{12}$ [wherein Z is $—O—$, $—S—$ or $—NR^{13}—$ (in which $R^{13}$ is hydrogen or lower alkyl), $R^{12}$ is phenyl, halophenyl (e.g., 2-chlorophenyl, 4-fluorophenyl, etc.), lower alkoxyphenyl (e.g., 2-methoxyphenyl, 4-ethoxyphenyl, etc.), pyridyl, or pyrimidinyl], etc. In particular, halogen, lower alkyl, halogenated lower alkyl, lower alkoxy, lower alkylthio, phenyl, phenoxy and nitro are preferred. More preferred are halogen and lower alkyl. The substituent may be at any possible position in the ring. The number of the substituent(s) is 1 to 5, preferably 1 to 4, more preferably 1 to 3. The substituents may be the same or different.

$R^1$ is preferably phenyl or a heterocyclic group each of which is unsubstituted or substituted with 1 or 2 substituents selected from the group consisting of halogen, lower alkyl, halogenated lower alkyl, lower alkoxy, lower alkylthio, phenyl, phenoxy and nitro. Preferred examples of $R^1$ include phenyl, phenyl substituted with halogen (preferably chlorine) and/or lower alkyl (preferably methyl) (e.g., 2-chlorophenyl, 3-chlorophenyl, 4-chlorophenyl, 2-methylphenyl, 3-methylphenyl, 4-methylphenyl, 2-ethylphenyl, 2,5-dimethylphenyl, 2,6-dimethylphenyl, 4-chloro-2-methylphenyl, etc.), pyridyl substituted with halogen (preferably chlorine) and/or halogenated lower alkyl (preferably trifluoromethyl) (e.g., 2-chloropyridin-3-yl, 3,5-dichloropyridin-2-yl, 5-trifluoromethylpyridin-2-yl, 5-trifluoromethyl-3-chloropyridin-2-yl, 3-trifluoromethyl-5-chloropyridin-2-yl, etc.), etc.

Mono or disubstituted methyleneamino is also preferred for $R^1$. The mono or disubstituted methyleneamino is represented, for example, by the above formula (a). The alkyl of the optionally substituted alkyl represented by $R^9$ or $R^{10}$ in the formula (a) includes, for example, alkyl having 1 to 8 carbon atoms, preferably 1 to 4 carbon atoms, such as methyl, ethyl, propyl, isopropyl, butyl, isobutyl, t-butyl, pentyl, hexyl, etc. In particular, methyl or ethyl is preferred. Examples of the substituted alkyl include haloalkyl containing as the substituent at least one halogen (e.g., fluorine, chlorine, bromine, iodine, preferably fluorine) (e.g., difluoromethyl, trifluoromethyl, chloromethyl, 2-bromoethyl, 2,3-dichloropropyl, etc.); alkoxyalkyl containing as the substituent alkoxy having 1 to 8 carbon atoms, preferably 1 to 4 carbon atoms (e.g., methoxy, ethoxy, propoxy, butoxy, etc.)(e.g., methoxymethyl, ethoxymethyl, methoxyethyl, etc.); etc. In particular, trifluoromethyl is preferred for the haloalkyl, and methoxymethyl is preferred for the alkoxyalkyl.

The acyl represented by $R^9$ or $R^{10}$ includes, for example, alkylcarbonyl, arylcarbonyl, etc. Examples of the alkylcarbonyl includes $C_{1-6}$ alkylcarbonyl, preferably $C_{1-4}$ alkylcarbonyl, such as acetyl, trifluoroacetyl, propionyl, butyryl, etc. Examples of the arylcarbonyl include $C_{6-14}$ arylcarbonyl such as benzoyl, naphthoyl, etc.

The alkyl of the alkylthio, alkylsulfinyl and alkylsulfonyl represented by $R^9$ or $R^{10}$ includes the above alkyl of the optionally substituted alkyl represented by $R^9$ or $R^{10}$.

The optionally substituted amino represented by $R^9$ $R^{10}$ includes, for example, amino, amino mono or disubstituted with alkyl having 1 to 8 carbon atoms, preferably 1 to 4 carbon atoms (e.g., monomethylamino, dimethylamino, monoethylamino, etc.), amino monosubstituted with formyl, amino monosubstituted with alkylcarbonyl having 2 to 8 carbon atoms, preferably 2 to 4 carbon atoms (e.g., methylcarbonylamino, etc.), etc.

The cylcloalkyl represented by $R^9$ or $R^{10}$ includes cycoaklyl having 3 to 7 carbon atoms, preferably 5 to 6 carbon atoms, such as cyclopropyl, cyclobutyl, cyclopentyl, cyclohexyl, cycloheptyl, etc.

The optionally substituted aryl represented by $R^9$ or $R^{10}$ includes, for example, $C_{6-14}$ aryl such as phenyl, naphthyl (e.g., 1-naphthyl, etc.), fluorenyl, etc. In particular, phenyl is preferred. The aryl may be substituted at any possible position in the group. The number of the substituent(s) is 1 to 3. Examples the substituent include halogen, optionally substituted alkyl, optionally substituted hydroxyl, alkylthio, optionally substituted amino, nitro, phenyl, cyano, etc.

Examples of the halogen as the substituent of the optionally substituted aryl represented by $R^9$ or $R^{10}$ include fluorine, chlorine, bromine, and iodine.

Examples of the optionally substituted alkyl as the substituent of the optionally substituted aryl represented by $R^9$ or $R^{10}$ include the optionally substituted alkyl represented by $R^1$ described hereinafter. Of them, alkyl or haloalkyl, in particular methyl or trifluoromethyl, is preferred.

Examples of the optionally substituted hydroxyl as the substituent of the optionally substituted aryl represented by $R^9$ or $R^{10}$ include hydroxyl, alkoxy, alkenyloxy, alkynyloxy, haloalkoxy, aryloxy, etc. The alkoxy includes, for example, alkoxy having 1 to 8 carbon atoms, preferably 1 to 4 carbon atoms, such as methoxy, ethoxy, propoxy, butoxy, etc. In particular, methoxy is preferred. The alkenyloxy includes, for example, alkenyloxy having 2 to 8 carbon atoms, preferably 2 to 4 carbon atoms, such as vinyloxy, allyloxy, crotyloxy, etc. In particular, allyloxy is preferred. The alkynyloxy includes, for example, alkynyloxy having 2 to 8 carbon atoms, preferably 2 to 4 carbon atoms, such as ethynyloxy, propargyloxy, butynyloxy, etc. In particular, propargyloxy is preferred. The haloalkoxy includes alkoxy described above which is substituted with at least one halogen (e.g., fluorine, chlorine, bromine iodine) such as difluoromethoxy, trifluoromethoxy, chloromethoxy, etc. In particular, difluoromethoxy is preferred. The aryloxy includes, aryloxy having 6 to 12 carbon atoms, preferably 6 to 8 carbon atoms, such as phenoxy, naphthoxy, etc.

Examples of the alkylthio as the substituent of the optionally substituted aryl represented by $R^9$ or $R^{10}$ include alkylthio having 1 to 8 carbon atoms, preferably 1 to 4 carbon atoms, more preferably 1 to 2 carbon atoms, such as methylthio, ethylthio, propylthio, butylthio, etc. In particular, methylthio is preferred.

Examples of the optionally substituted amino as the substituent of the optionally substituted aryl represented by $R^9$ or $R^{10}$ include amino, amino mono or disubstituted with alkyl having 1 to 8 carbon atoms, preferably 1 to 4 carbon atoms (e.g., monomethylamino, dimethylamino, monoethylamino, etc.), etc.

The optionally substituted heterocyclic group represented by $R^9$ or $R^{10}$ includes, for example, heterocyclic groups containing 1 to 4, preferably 1 to 2 heteroatoms (e.g., oxygen, nitrogen, sulfur, etc.) in the ring. At any possible position in the ring, the heterocyclic group contains the bond to the methylene carbon atom in the formula (a). Examples of the heterocyclic group include morpholinyl, pyridyl, pyridazinyl, pyrazolyl, pyrimidinyl, furyl, thienyl, oxazolyl, isoxazolyl, benzothiazolyl, quinolyl, quinazolinyl, pyrazinyl, etc. In particular, morpholinyl (e.g., morpholino, etc.), furyl (e.g., 2-furyl, etc.), thienyl (e.g., 2-thienyl, etc.), pyridyl (e.g., 2-pyridyl, etc.), pyrazinyl (e.g., 2-pyrazinyl, etc.), or pyrimidinyl (e.g., 2-pyrimidinyl, etc.) is preferred. The heterocyclic group is unsubstituted or substituted. Examples of the substituent include the above substituents of the optionally substituted aryl represented by $R^9$ or $R^{10}$.

The monocyclic or polycyclic ring which may contain a heteroatom and is formed by $R^9$ and $R^{10}$ is a 4 to 8 membered ring which is formed by $R^9$ and $R^{10}$ together with the carbon atom to which $R^9$ and $R^{10}$ are attached and which may contain at least one heteroatom (e.g., oxygen, nitrogen, sulfur, etc.). The ring may form a condensed ring with another ring. Examples of the monocyclic or polycyclic ring include cyclopentane, cyclohexane, indan, 1,2,3,4-tetrahydronaphthalene, 5,6,7,8-tetrahydroquinoline, 4,5,6,7-tetrahydrobenzo[b]furan, etc. At any possible position in the ring, the monocyclic or polycyclic ring contains the bivalent bond to the methyleneamino nitrogen atom.

$R^9$ is preferably phenyl unsubstituted or substituted with 1 to 3 substituents selected from the group consisting of halogen (preferably chlorine), optionally substituted alkyl [e.g., alkyl (preferably in particular methyl), haloalkyl (preferably trifluoromethyl), alkoxyalkyl, etc.], optionally substituted hydroxyl [e.g., hydroxyl, alkoxy (preferably methoxy), alkenyloxy, alkynyloxy, haloalkoxy, aryloxy, etc.], alkylthio, optionally substituted amino, nitro, phenyl and cyano; or morpholino, pyridyl, pyridazinyl, pyrazolyl, pyrimidinyl, furyl, thienyl, oxazolyl, isoxazolyl, benzothiazolyl, quinolyl, quinazolinyl or pyrazinyl, each of which is unsubstituted or substituted.

$R^{10}$ is preferably hydrogen or alkyl (preferably methyl or ethyl).

The optionally substituted (substituted imino)methyl represented by $R^1$ is represented, for example, by the formula (b):

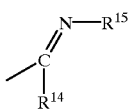

wherein $R^{14}$ and $R^{15}$ have the same meanings as the above $R^{10}$ and $R^9$, respectively.

The optionally substituted alkyl represented by $R^1$ includes, for example, alkyl having 1 to 8 carbon atoms, preferably 1 to 4 carbon atoms, such as methyl, ethyl, propyl, isopropyl, butyl, isobutyl, t-butyl, pentyl, hexyl, etc. In particular, methyl and ethyl are preferred. The substituted alkyl includes, for example, haloalkyl containing as the substituent at least one halogen atom (e.g., fluorine, chlorine, bromine, iodine, preferably fluorine)(e.g., difluoromethyl, trifluoromethyl, chloromethyl, 2-bromoethyl, 2,3-dichloropropyl, etc.); alkoxyalkyl groups containing as the substituent alkoxy having 1 to 8 carbon atoms, preferably 1 to 4 carbon atoms (e.g., methoxy, ethoxy, propoxy, butoxy, etc.)(e.g., methoxymethyl ethoxymethyl, methoxyethyl, etc.), etc. In particular, trifluoromethyl is preferred for the haloalkyl, and methoxymethyl is preferred for the alkoxyalkyl.

The optionally substituted alkenyl represented by $R^1$ includes, for example, alkenyl having 2 to 8 carbon atoms, preferably 3 to 6 carbon atoms, such as allyl, propenyl, isopropenyl, butenyl, isobutenyl, pentenyl, hexenyl, hexadienyl, etc. In particular, allyl is preferred. When the alkenyl is substituted, the substituent is, for example, halogen (e.g., fluorine, chlorine, bromine, iodine, preferably fluorine), alkoxy having 1 to 8, preferably 1 to 4 carbon atoms (e.g., methoxy, ethoxy, propoxy, butoxy, etc.), etc.

The alkynyl represented by $R^1$ includes, for example, alkynyl having 2 to 6 carbon atoms, preferably 2 to 4 carbon atoms, such as propargyl, ethynyl, butynyl, etc. When the alkynyl is substituted, the substituent is, for example, halogen (e.g., fluorine, chlorine, bromine, iodine, preferably fluorine), alkoxy having 1 to 8 carbon atoms, preferably 1 to 4 carbon atoms (e.g., methoxy, ethoxy, propoxy, butoxy, etc.), etc.

The substituted carbonyl represented by $R^1$ includes, for example, (optionally substituted alkyl)carbonyl, (optionally substituted aryl)carbonyl, (optionally substituted heterocyclic group)carbonyl, etc.

The substituted sulfonyl represented by $R^1$ includes, for example, (optionally substituted alkyl)sulfonyl, (optionally substituted aryl)sulfonyl, (optionally substituted heterocyclic group)sulfonyl, etc.

The optionally substituted alkyl, optionally substituted aryl and optionally substituted heterocyclic group in the substituted carbonyl or substituted sulfonyl include those represented by $R^1$ described above.

The alkyl represented by $R^2$ includes, for example, alkyl having 1 to 6 carbon atoms, preferably 1 to 4 carbon atoms, such as methyl, ethyl propyl, isopropyl, butyl, isobutyl, t-butyl, etc. In particular, methyl or ethyl is preferred.

The alkenyl represented by $R^2$ includes, for example, alkenyl having 2 to 8 carbon atoms, preferably 3 to 6 carbon atoms, such as allyl, butenyl, isobutenyl, pentenyl, hexenyl, hexadienyl, etc. In particular, allyl is preferred.

The alkynyl represented by $R^2$ includes, for example, alkynyl having 2 to 6 carbon atoms, preferably 2 to 4 carbon atoms, such as propargyl, ethynyl, butynyl, etc.

The cycloalkyl represented by $R^2$ includes, for example, cycloalkyl having 3 to 8 carbon atoms, preferably 3 to 6 carbon atoms, such as cyclopropyl, cyclopentyl cyclohexyl, etc.

$R^2$ is preferably alkyl or alkenyl. In particular, methyl, ethyl and allyl are preferred.

The optionally substituted heterocyclic group represented by $R^3$ includes unsubstituted or substituted heterocyclic groups. The heterocyclic group is a 5 to 7 membered heterocyclic group containing in the ring 1 to 4 heteroatoms selected from nitrogen, sulfur and oxygen. Examples of the heterocyclic group include isoxazolyl (e.g., isoxazol-3-yl, isoxazol-5-yl), oxazolyl (e.g., oxazol-2-yl, oxazol-5-yl), thiazolyl (e.g., thiazol-2-yl), isothiazolyl (e.g., isothiazol-5-yl), thiadiazolyl [e.g., 1,3,4-thiadiazolyl (e.g., 1,3,4-thiadiaz-2-yl), 1,2,4-thiadiazolyl, etc.], pyrrolyl, pyrazolyl (e.g., pyrazol-1-yl, pyrazol-5-yl), furyl (e.g., 2-furyl), thienyl (e.g., 2-thienyl), imidazolyl (e.g., imidazol-1-yl, imidazol-2-yl), triazolyl [e.g., 1,2,4-triazolyl (e.g., 1H-1,2,4-triazol-1-yl, 4H-1,2,4-triazol-4-yl, 1,2,4-triazol-5-yl), etc.], tetrazolyl (e.g., 1H-tetrazol-5-yl, 2H-tetrazol-5-yl), oxadiazolyl [e.g., 1,3,4-oxadiazolyl (e.g., 1,3,4-oxadiazol-2-yl), 1,2,4-oxadiazolyl (e.g., 1,2,4-oxadiazol-3-yl, 1,2,4-oxadiazol-5-yl), etc.], thiazolinyl (e.g., 2-thiazolin-2-yl), isoxazolinyl (e.g., 2-isoxazolin-3-yl), imidazolinyl (e.g., 2-imidazolin-2-yl), oxazolinyl (e.g., 2-oxazolin-2-yl), thiazolidinyl, etc. The heterocyclic group may form a condensed ring with a carbocycle or another heterocycle. At any possible position, the heterocyclic group contains a bond to the oxime carbon atom in the formula (I).

Examples of the substituent of the substituted heterocyclic group represented by $R^3$ include the above substituents of the substituted heterocyclic group represented by $R^1$. In particular, halogenated lower alkyl or lower alkyl is preferred.

$R^3$ is preferably imidazolyl (e.g., imidazol-1-yl, imidazol-2-yl, etc.), imidazolinyl (e.g., 2-imidazolin-2-yl, etc.), triazolyl (e.g., 1H-1,2,4-triazol-1-yl, etc.), isoxazolyl (e.g., isoxazol-3-yl, isoxazol-5-yl, etc.), oxazolyl (e.g., oxazol-2-yl, etc.), tetrazolyl (e.g., 1H-tetrazol-5-yl, etc.), oxadiazolyl (e.g., 1,2,4-oxadiazol-3-yl, 1,3,4-oxadiazol-2-yl, etc.), isoxazolinyl (e.g., 2-isoxazolin-3-yl, 2-isoxazolin-5-yl, etc.), oxazolinyl (e.g., 2-oxazolin-2-yl, etc.), pyrazolyl (e.g., pyrazol-1-yl, pyrazol-5-yl, etc.), thiazolinyl (e.g., 2-thiazolin-2-yl, etc.), furyl (2-furyl, etc.), isothiazolyl (e.g., isothiazol-5-yl, etc.), thiazolidinyl (e.g., thiazolidin-2-yl, etc.), etc., each of which is unsubstituted or substituted.

$R^3$ is more preferably imidazolyl (e.g., imidazol-1-yl, imidazol-2-yl, etc.); imidazolyl substituted with lower alkyl (preferably methyl) (e.g., 1-methylimidazol-2-yl, 2-methylimidazol-1-yl, 4-methylimidazol-1-yl, 5-methylimidazol-1-yl, etc.); imidazolinyl (e.g., 2-imidazolin-2-yl, etc.); triazolyl (e.g., 1H-1,2,4-triazol-1-yl, etc.); imidazolinyl substituted with lower alkyl (preferably methyl) (e.g., 1-methyl-2-imidazolin-2-yl, etc.); isoxazolyl (e.g., isoxazol-3-yl, isoxazol-5-yl, etc.); isoxazolyl substituted with lower alkyl (preferably methyl) (e.g., 3-methylisoxazol-5-yl, 5-methylisoxazol-3-yl, etc.); oxadiazolyl (e.g., 1,2,4-oxadiazol-3-yl, 1,3,4-oxadiazol-2-yl, etc.); oxadiazolyl substituted with lower alkyl (preferably methyl or ethyl) (e.g., 5-methyl-1,2,4-oxadiazol-3-yl, 5-methyl-1,3,4-oxadiazol-2-yl, 3-ethyl-1,2,4-oxadiazol-5-yl, etc.); isoxazolinyl (e.g., 2-isoxazolin-3-yl, etc.); isoxazolinyl substituted with lower alkyl (preferably methyl) (e.g., 3-methyl-2-isoxazolin-5-yl, etc.); oxazolinyl (e.g., 2-oxazolin-2-yl, etc.); pyrazolyl (e.g., pyrazol-1-yl, etc.); pyrazolyl substituted with lower alkyl (preferably methyl) (e.g., 1-methylpyrazol-5-yl, etc.); thiazolinyl (e.g., 2-thiazolin-2-yl, etc.); furyl (e.g., 2-furyl, etc.); tetrazolyl substituted with lower alkyl (preferably methyl) (e.g., 2-methyltetrazol-5-yl, etc.); isothiazolyl substituted with lower alkyl (preferably methyl) (e.g., 3-methylisothiazol-5-yl, etc.); thiazolidinyl (e.g., thiazolidin-2-yl, etc.); thiazolidinyl substituted with lower alkyl (e.g., 3-methylthizolidin-2-yl, etc.), etc.

The alkyl represented by $R^4$ includes the above alkyl represented by $R^2$.

The alkoxy represented by $R^4$ includes, for example, alkoxy having 1 to 6 carbon atoms, preferably 1 to 4 carbon atoms, such as methoxy, ethoxy, propoxy, isopropoxy, butoxy, isobutoxy, s-butoxy, t-butoxy, etc.

The halogen represented by $R^4$ includes, for example, fluorine, chlorine, bromine, and iodine.

The halogenated alkyl represented by $R^4$ includes the above alkyl represented by $R^2$ which is substituted with at least one halogen (e.g., fluorine, chlorine, bromine, iodine), such as trifluoromethyl, etc.

$R^4$ is preferably hydrogen.

The alkyl and acyl represented by $R^{16}$ include the above alkyl and acyl represented by $R^9$ or $R^{10}$, respectively.

M is preferably an oxygen atom, sulfur atom or $NR^{16}$, more preferably an oxygen atom.

When $R^3$ is imidazol-1-yl or 1,2,4-triazol-1-yl, n is 1.

The compound of the present invention has two kinds of isomers: E and Z isomers. The present invention includes these isomers and mixtures of the isomers in any mixing ratios. This is herein indicated by the wave line (~) in the formulas.

In addition, the compound of the present invention includes its hydrochloric acid salt, sulfuric acid salt, nitric acid salt, oxalic acid salt and p-toluenesulfonic acid salt.

Specific examples of the compound of the formula (I) of the present invention include compounds described in Examples hereinafter. Particularly preferred are the compounds of the formula (I) wherein $R^1$ is phenyl, $R^2$ is methyl, $R^3$ is imidazol-1-yl, $R^4$ is hydrogen, and n is 1 (Compound No. 1: Compound Nos. correspond to those in Examples hereinafter);

$R^1$ is 4-chlorophenyl, $R^2$ is methyl, $R^3$ is imidazol-1-yl, $R^4$ is hydrogen, and n is 1 (Compound No. 7);

$R^1$ is 2-methylphenyl, $R^2$ is methyl, $R^3$ is imidazol-1-yl, $R^4$ is hydrogen, and n is 1 (Compound No. 13);

$R^1$ is 4-methylphenyl, $R^2$ is methyl, $R^3$ is imidazol-1-yl, $R^4$ is hydrogen, and n is 1 (Compound No. 15);

$R^1$ is 2-ethylphenyl, $R^2$ is methyl, $R^3$ is imidazol-1-yl, $R^4$ is hydrogen, and n is 1 (Compound No. 16);

$R^1$ is 2,5-dimethylphenyl, $R^2$ is methyl, $R^3$ is imidazol-1-yl, $R^4$ is hydrogen, and n is 1 (Compound No. 39);

$R^1$ is phenyl, $R^2$ is ethyl, $R^3$ is imidazol-1-yl, $R^4$ is hydrogen, and n is 1 (Compound No. 61);

$R^1$ is phenyl, $R^2$ is allyl, $R^3$ is imidazol-1-yl, $R^4$ is hydrogen, and n is 1 (Compound No. 81);

$R^1$ is 2,5-dimethylphenyl, $R^2$ is methyl, $R^3$ is 1-methylimidazol-2-yl, $R^4$ is hydrogen, and n is 1 (Compound No. 136);

$R^1$ is 4-chloro-2-methylphenyl, $R^2$ is methyl, $R^3$ is 1-methylimidazol-2-yl, $R^4$ is hydrogen, and n is 1 (Compound No. 141);

$R^1$ is 2,5-dimethylphenyl, $R^2$ is methyl, $R^3$ is isoxazol-3-yl, $R^4$ is hydrogen, and n is 1 (Compound No. 336);

$R^1$ is 5-trifluoromethylpyridin-2-yl, $R^2$ is methyl, $R^3$ is isoxazol-3-yl, $R^4$ is hydrogen, and n is 1 (Compound No. 387);

$R^1$ is 5-trifluoromethyl-3-chloropyridin-2-yl, $R^2$ is methyl, $R^3$ is isoxazol-3-yl, $R^4$ is hydrogen, and n is 1 (Compound No. 390);

$R^1$ is 2,5-dimethylphenyl, $R^2$ is methyl, $R^3$ is 5-methylisoxazol-3-yl, $R^4$ is hydrogen, and n is 1 (Compound No. 436);

$R^1$ is 2,5-dimethylphenyl, $R^2$ is methyl, $R^3$ is 3-methylisoxazol-5-yl, $R^4$ is hydrogen, and n is 1 (Compound No. 636);

$R^1$ is 5-trifluoromethyl-3-chloropyridin-2-yl, $R^2$ is methyl, $R^3$ is 3-methylisoxazol-5-yl, $R^4$ is hydrogen, and n is 1 (Compound No. 690);

$R^1$ is 2-methylphenyl, $R^2$ is methyl, $R^3$ is 1,3,4-oxadiazol-2-yl, $R^4$ is hydrogen, and n is 1 (Compound No. 712);

$R^1$ is 2,5-dimethylphenyl, $R^2$ is methyl, $R^3$ is 1,3,4-oxadiazol-2-yl, $R^4$ is hydrogen, and n is 1 (Compound No. 736);

$R^1$ is 4-chloro-2-methylphenyl, $R^2$ is methyl, $R^3$ is 1,3,4-oxadiazol-2-yl, $R^4$ is hydrogen, and n is 1 (Compound No. 741);

$R^1$ is 4-chlorophenyl, $R^2$ is methyl, $R^3$ is 1,2,4-oxadiazol-3-yl, $R^4$ is hydrogen, and n is 1 (Compound No. 807);

$R^1$ is 2-methylphenyl, $R^2$ is methyl, $R^3$ is 1,2,4-oxadiazol-3-yl, $R^4$ is hydrogen, and n is 1 (Compound No. 812);

$R^1$ is 2,5-dimethylphenyl, $R^2$ is methyl, $R^3$ is 1,2,4-oxadiazol-3-yl, $R^4$ is hydrogen, and n is 1 (Compound No. 836);

$R^1$ is 2-methylphenyl, $R^2$ is methyl, $R^3$ is 5-methyl-1,2,4-oxadiazol-3-yl, $R^4$ is hydrogen, and n is 1 (Compound No. 912);

$R^1$ is 2,5-dimethylphenyl, $R^2$ is methyl, $R^3$ is 5-methyl-1,2,4-oxadiazol-3-yl, $R^4$ is hydrogen, and n is 1 (Compound No. 936);

$R^1$ is 2,5-dimethylphenyl, $R^2$ is methyl, $R^3$ is 1-methyl-2-imidazolin-2-yl, $R^4$ is hydrogen, and n is 1 (Compound No. 1136);

$R^1$ is 4-chlorophenyl, $R^2$ is methyl, $R^3$ is 1,2,4-oxadiazol-5-yl, $R^4$ is hydrogen, and n is 1 (Compound No. 1584);

$R^1$ is 2,5-dimethylphenyl, $R^2$ is methyl, $R^3$ is 2-methyl-2H-tetrazol-5-yl, $R^4$ is hydrogen, and n is 1 (Compound No. 2036);

$R^1$ is 3,5-dichloropyridin-2-yl, $R^2$ is methyl, $R^3$ is isoxazol-3-yl, $R^4$ is hydrogen, and n is 1 (Compound No. 2276);

$R^1$ is 5-chloro-3-trifluoromethylpyridin-2-yl, $R^2$ is methyl, $R^3$ is isoxazol-3-yl, $R^4$ is hydrogen, and n is 1 (Compound No. 2306);

$R^1$ is a group represented by the formula (a), $R^9$ is 4-chlorophenyl, $R^{10}$ is methyl, $R^2$ is methyl, $R^3$ is isoxazol-3-yl, $R^4$ is hydrogen, and n is 1 (Compound No. 2387);

$R^1$ is a group of by the formula (a), $R^9$ is 3-trifluoromethylphenyl, $R^{10}$ is methyl, $R^2$ is methyl, $R^3$ is isoxazol-3-yl, $R^4$ is hydrogen, and n is 1 (Compound No. 2399);

$R^1$ is a group of the formula (a), $R^9$ is 3,4-dichlorophenyl, $R^{10}$ is methyl, $R^2$ is methyl, $R^3$ is isoxazol-3-yl, $R^4$ is hydrogen, and n is 1 (Compound No. 2408);

$R^1$ is a group represented by the formula (a), $R^9$ is 4-chlorophenyl, $R^{10}$ is methyl, $R^2$ is methyl, $R^3$ is 3-methylisoxazol-5-yl, $R^4$ is hydrogen, and n is 1 (Compound No. 2507);

$R^1$ is a group of the formula (a), $R^9$ is 3-trifluoromethylphenyl, $R^{10}$ is methyl, $R^2$ is methyl, $R^3$ is thiazolidin-2-yl, $R^4$ is hydrogen, and n is 1 (Compound No. 2799); or $R^1$ is a group of the formula (a), $R^9$ is 3-trifluoromethylphenyl, $R^{10}$ is methyl, $R^2$ is methyl, $R^3$ is 3-methylthiazolidin-2-yl, $R^4$ is hydrogen, and n is 1 (Compound No. 2839).

The compound (I) (i.e., the compound of the formula (I); hereinafter the compounds of other formulas are sometimes abbreviated likewise) can be prepared, for example, according to the following synthetic routes.

Route 1

(Scheme 1)

wherein A is halogen (e.g., chlorine, bromine, iodine, etc.), and the other symbols are as defined above.

The compound of the formula (IV) can be prepared by reacting the compound (IIa) with the compound (III) or a salt thereof (e.g., hydrochloric acid salt, sulfuric acid salt) in the presence of a base in the absence of a solvent or in an appropriate solvent (alone or as a mixture).

In this reaction, the amount of the compound (III) to be used is 1 equivalent or more, preferably 1 to 2 equivalents, based on the compound (IIa).

Examples of the base to be used include metal hydroxides (e.g., sodium hydroxide, potassium hydroxide, etc.), metal carbonates (e.g., sodium carbonate, potassium carbonate, etc.), metal alkoxides (e.g., sodium methoxide, sodium ethoxide, potassium tert-butoxide, etc.), amines (e.g., pyridine, triethylamine, etc.), etc. The amount of the base to be used is 1 equivalent or more, preferably 1 to 3 equivalents.

Examples of the solvent to be used include aromatic hydrocarbons (e.g., toluene, benzene, xylene, etc.), saturated hydrocarbons (e.g., cyclohexane, hexane, etc.), halogenated hydrocarbons (e.g., dichloromethane, 1,2-dichloroethane, etc.), ethers (e.g., tetrahydrofuran (THF), dioxane, etc.), water, mixtures thereof, etc.

The reaction temperature is −30° C. to 150° C., preferably −10° C. to 100° C. The reaction time varies with the kind of compound, and is 0.5 to 48 hours.

The compound (IV) thus obtained can be used in the next step as the crude product or after purifying it by a conventional method (e.g., chromatography, recrystallization, etc.).

The acid halide (IIa) used as the starting material in this reaction can be prepared according to JP-A 5-331124, for example, by halogenating the corresponding carboxylic acid with a thionyl halide (e.g., thionyl chloride, etc.), phosphoryl halide (e.g., phosphoryl chloride, etc.), phosgene, etc.

Route 1 (continued)

(Scheme 2)

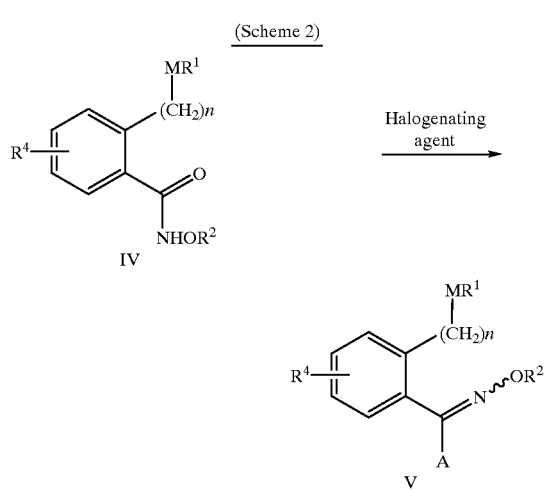

wherein each symbol is as defined above.

The compound of the formula (V) can be prepared by reacting the above compound (IV) with a halogenating agent in the absence of a solvent or in an appropriate solvent (alone or as a mixture).

Examples of the halogenating agent to be used include thionyl halides (e.g., thionyl chloride, thionyl bromide, etc.), phosphoryl halides (e.g., phosphoryl chloride, phosphoryl bromide, etc.), phosphorus halides (e.g., phosphorus pentachloride, phosphorus trichloride, phosphorus pentabromide, phosphorus tribromide, etc.), phosgene, oxalyl halides (e.g., oxalyl chloride, etc.), triphenylphosphine/carbon tetrachloride, triphenylphosphine/carbon tetrabromide, etc. The amount of the halogenating agent to be used is 1 equivalent or more, preferably 1 to 4 equivalents.

Examples of the solvent to be used include aromatic hydrocarbons (e.g., toluene, benzene, xylene, etc.), saturated hydrocarbons (e.g., cyclohexane, hexane, etc.), halogenated hydrocarbons (e.g., dichloromethane, 1,2-dichloroethane, etc.), nitriles (e.g., acetonitrile, etc.), mixed solvents thereof, etc.

The reaction temperature is −30° C. to 150° C., preferably −10° C. to 120° C. The reaction time varies with the kind of compound, and is 0.1 to 48 hours.

The compound (V) thus obtained can be used in the next step as the crude product or after purifying it by a conventional method (e.g., chromatography, recrystallization, etc.).

Route 1 (continued)

(Scheme 3)

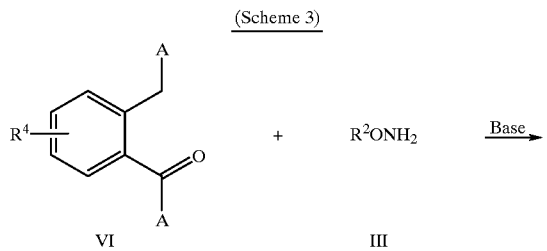

wherein each symbol is as defined above.

The compound of the formula (VII) can be prepared by reacting the compound (VI) with the compound (III) or a salt thereof (e.g., hydrochloric acid salt, sulfuric acid salt) in the presence of a base in the absence of a solvent or in an appropriate solvent (alone or as a mixture).

The amount of the compound (III) to be used in this reaction is 1 equivalent or more, preferably 1 to 2 equivalents, based on the compound (VI).

Examples of the base to be used include metal hydroxides (e.g., sodium hydroxide, potassium hydroxide, etc.), metal carbonates (e.g., sodium carbonate, potassium carbonate, etc.), metal alkoxides (e.g., sodium methoxide, sodium ethoxide, potassium tert-butoxide, etc.), amines (e.g., pyridine, triethylamine, etc.), etc. The amount of the base to be used is 1 equivalent or more, preferably 1 to 3 equivalents.

Examples of the solvent to be used include aromatic hydrocarbons (e.g., toluene, benzene, xylene, etc.), saturated hydrocarbons (e.g., cyclohexane, hexane, etc.), halogenated hydrocarbons (e.g., dichloromethane, 1,2-dichloroethane, etc.), ethers (e.g., THF, dioxane, etc.), water, mixed solvents thereof, etc.

The reaction temperature is −30° C. to 150° C., preferably −10° C. to 100° C. The reaction time varies with the kind of compound, and is 0.5 to 48 hours.

The compound (VII) thus obtained can be used in the next step as the reaction mixture or the crude product or after purifying it by a conventional method (e.g., chromatography, recrystallization, etc.).

The compound (VI) used as the starting material in this reaction can be prepared according to Takahashi et al. Tetrahedron Letters 22 (28), 2651–2654 (1981), for example, by halogenating the corresponding phthalide with triphenylphosphine dichloride, etc.

Route 1 (continued)

(Scheme 4)

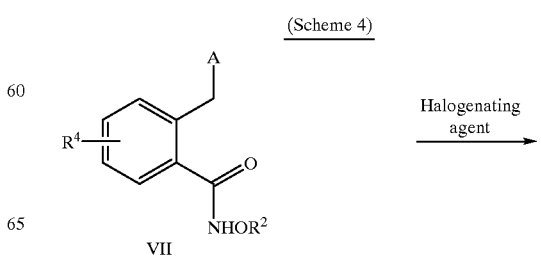

-continued

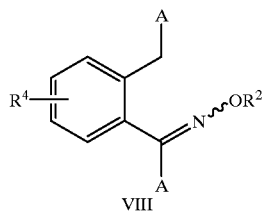

VIII wherein each symbol is as defined above.

The compound of the formula (VIII) can be prepared by reacting the compound (VII) with a halogenating agent in the absence of a solvent or in an appropriate solvent (alone or as a mixture).

Examples of the halogenating agent to be used include thionyl halides (e.g., thionyl chloride, thionyl bromide, etc.), phosphoryl halides (e.g., phosphoryl chloride, phosphoryl bromide, etc.), phosphorus halides (e.g., phosphorus pentachloride, phosphorus trichloride, etc.), phosgene, and oxalyl halides (e.g., oxalyl chloride, etc.). The amount of the halogenating agent to be used is 1 equivalent or more, preferably 1 to 2 equivalents.

Examples of the solvent to be used include aromatic hydrocarbons (e.g., toluene, benzene, xylene, etc.), saturated hydrocarbons (e.g., cyclohexane, hexane, etc.), halogenated hydrocarbons (e.g., dichloromethane, 1,2-dichloroethane, etc.), mixed solvents thereof, etc.

The reaction temperature is −30° C. to 150° C., preferably −10° C. to 120° C. The reaction time varies with the kind of compound, and is 0.1 to 48 hours.

The compound (VIII) thus obtained can be used in the next step as the crude product or after purifying it by a conventional method (e.g., chromatography, recrystallization, etc.).

Route 1 (continued)

(Scheme 5)

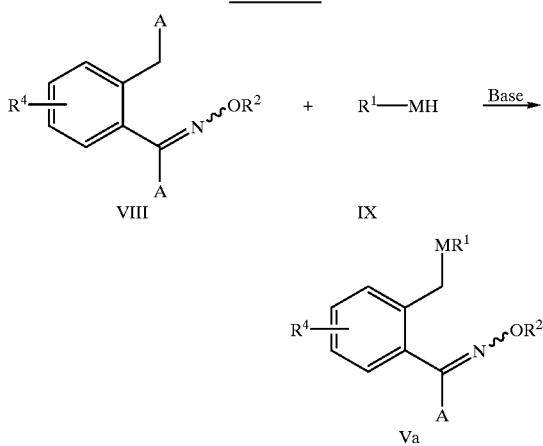

wherein each symbol is as defined above.

The compound of the formula (Va) can be prepared by reacting the compound (VIII) with the compound (IX) in the presence of a base in the absence of a solvent or in an appropriate solvent (alone or as a mixture).

The amount of the compound (IX) to be used in this reaction is 1 equivalent or more, preferably 1 to 2 equivalents, based on the compound (VIII).

Examples of the base to be used include metal hydroxides (e.g., sodium hydroxide, potassium hydroxide, etc.), metal carbonates (e.g., sodium carbonate, potassium carbonate, etc.), metal alkoxides (e.g., sodium methoxide, sodium ethoxide, potassium tert-butoxide, etc.), etc. The amount of the base to be used is 1 equivalent or more, preferably 1 to 3 equivalents.

Examples of the solvent to be used include N,N-dimethylformamide (DMF), dimethyl sulfoxide (DMSO), aromatic hydrocarbons (e.g., toluene, benzene, xylene, etc.), saturated hydrocarbons (e.g., cyclohexane, hexane, etc.), halogenated hydrocarbons (e.g., dichloromethane, 1,2-dichloroethane, etc.), ethers (e.g., THF, dioxane, etc.), ketones (e.g., acetone, methyl ethyl ketone, etc.), nitriles (e.g., acetonitrile, etc.), water, mixed solvents thereof, etc.

The reaction temperature is −30° C. to 150° C., preferably −10° C. to 100° C. The reaction time varies with the kind of compound, and is 0.5 to 120 hours.

The compound (Va) thus obtained can be used in the next step as the reaction mixture or the crude product, or after purifying it by a conventional method (e.g., chromatography, recrystallization, etc.).

Route 1 (continued)

(Scheme 6)

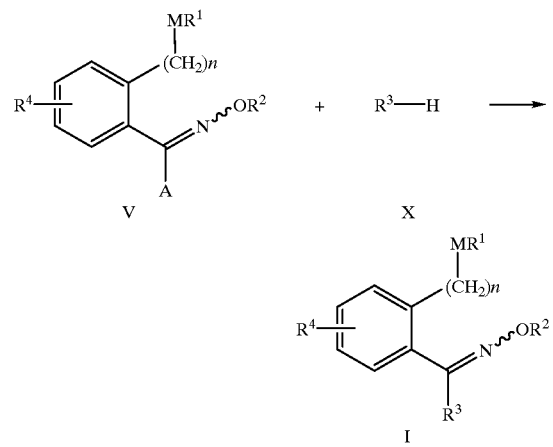

wherein each symbol is as defined above, and, in this reaction, $R^3$ is preferably pyrrolyl (e.g., pyrrol-1-yl, etc.), imidazolyl (e.g., imidazol-1-yl, etc.), pyrazolyl (e.g., pyrazol-1-yl, etc.) or triazolyl (e.g., 1H-1,2,4-triazol-1-yl, etc.).

The compound of the formula (I) of the present invention can be prepared by reacting the compound (V) with the compound (X) in the presence or absence of a base in the absence of a solvent or in an appropriate solvent (alone or as a mixture).

The amount of the compound (X) to be used in this reaction is 1 equivalent or more, preferably 1 to 5 equivalents, based on the compound (V).

Examples of the base to be used include metal hydroxides (e.g., sodium hydroxide, potassium hydroxide, etc.), metal hydrides (e.g., sodium hydride, etc.), metal carbonates (e.g., sodium carbonate, potassium carbonate, etc.), metal alkoxides (e.g., sodium methoxide, sodium ethoxide, potassium tert-butoxide, etc.), amines (e.g., pyridine, triethylamine, etc.), etc. The amount of the base to be used is 1 equivalent or more, preferably 1 to 5 equivalents.

Examples of the solvent to be used include N,N-dimethylformamide (DMF), dimethyl sulfoxide (DMSO), aromatic hydrocarbons (e.g., toluene, benzene, xylene, etc.), saturated hydrocarbons (e.g., cyclohexane, hexane, etc.), halogenated hydrocarbons (e.g., dichloromethane, 1,2- dichloroethane, etc.), ethers (e.g., THF, dioxane, etc.), ketones (e.g., acetone, methyl ethyl ketone, etc.), nitrites (e.g., acetonitrile, etc.), water, mixed solvents thereof, etc.

The reaction temperature is −30° C. to 170° C., preferably −10° C. to 140° C. The reaction time varies with the kind of compound, and is 0.5 to 80 hours.

If necessary, the desired compound (I) thus obtained can be purified by a conventional method (e.g., chromatography, recrystallization, etc.).

Route 2

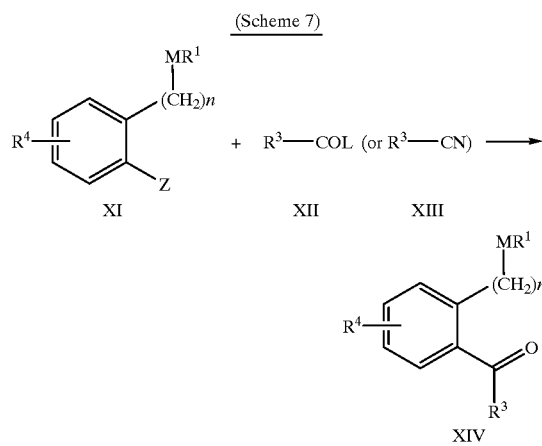

wherein Z is lithium or magnesium halide (e.g., —MgBr, —MgI, etc.), L is halogen (e.g., chlorine, bromine, iodine, etc.), alkoxy (e.g., lower alkoxy such as methoxy, ethoxy, propoxy, etc.), imidazol-1-yl or N-methyl-N-methoxyamino, $R^3$ is an optionally substituted heterocyclic group, and the other symbols are as defined above.

The compound of the formula (XIV) can be prepared by reacting the compound (XI) with the compound (XII) or (XIII) in an appropriate solvent (alone or as a mixture).

The amount of the compound (XII) or (XIII) to be used in this reaction is 1 equivalent or more, preferably 1 to 3 equivalents, based on the compound (XI).

Examples of the solvent to be used include aromatic hydrocarbons (e.g., toluene, benzene, xylene, etc.), saturated hydrocarbons (e.g., cyclohexane, hexane, etc.), ethers (e.g., THF, diethyl ether, dioxane, etc.), triethylamine, mixed solvents thereof, etc.

The reaction temperature is −100° C. to 100° C., preferably −80° C. to 40° C. The reaction time varies with the kind of compound, and is 0.5 to 80 hours.

The compound (XIV) thus obtained can be used in the next step as the crude product, or after purifying it by a conventional method (e.g., chromatography, recrystallization, etc.).

The compound (XI) used as the starting material in this reaction can be prepared according to JP-A 3-246268 or JP-A 5-97768, for example, by reacting a compound corresponding to the compound (XI) wherein the moiety z is halogen with butyl lithium or magnesium.

Route 2 (continued)

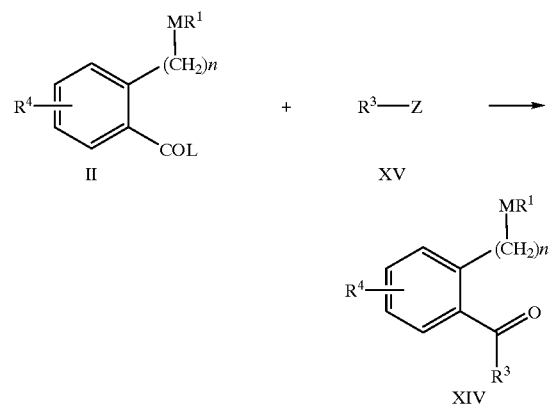

wherein each symbol is as defined above.

The compound of the formula (XIV) can be prepared by reacting the compound (II) with the compound (XV) in an appropriate solvent (alone or as a mixture).

The amount of the compound (XV) to be used in this reaction is 1 equivalent or more, preferably 1 to 2 equivalents, based on the compound (II).

Examples of the solvent to be used include aromatic hydrocarbons (e.g., toluene, benzene, xylene, etc.), saturated hydrocarbons (e.g., cyclohexane, hexane, etc.), ethers (e.g., THF, diethyl ether, dioxane, etc.), triethylamine, mixed solvents thereof, etc.

The reaction temperature is −100° C. to 100° C., preferably −80° C. to 40° C. The reaction time varies with the kind of compound, and is 0.5 to 80 hours.

The compound (XIV) thus obtained can be used in the next step as the crude product, or after purifying it by a conventional method (e.g., chromatography, recrystallization, etc.).

The compound (XV) can be prepared by reference to A. R. Katritzky, Handbook of Heterocyclic Chemistry, 360–361 (1985), for example, by lithiating the corresponding heterocyclic compound with butyl lithium, etc., or by reacting the corresponding halogenated heterocyclic compound with magnesium.

Route 2 (continued)

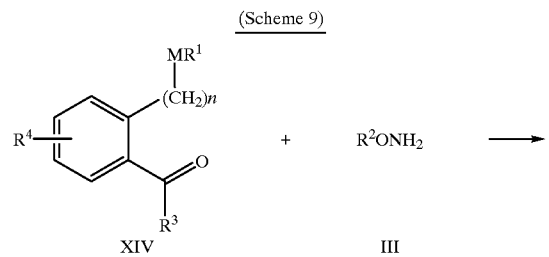

-continued

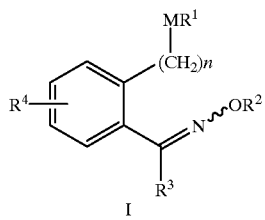

wherein each symbol is as defined above.

The compound of the formula (I) of the present invention can be prepared by reacting the compound (XIV) with the compound (III) or a salt thereof (e.g., hydrochloric acid salt, sulfuric acid salt) in an appropriate solvent (alone or as a mixture).

The amount of the compound (III) to be used in this reaction is 1 equivalent or more, preferably 1 to 4 equivalents, based on the compound (XIV).

Examples of the solvent to be used include aromatic hydrocarbons (e.g., toluene, benzene, xylene, etc.), saturated hydrocarbons (e.g., cyclohexane, hexane, etc.), alcohols (e.g., methanol, ethanol, propanol, etc.), water, mixed solvents thereof, etc.

The reaction temperature is 0° C. to 160° C., preferably 60° C. to 130° C. The reaction time varies with the kind of compound, and is 0.5 to 90 hours.

If necessary, the desired compound (I) thus obtained can be purified by a conventional method (e.g., chromatography, recrystallization, etc.).

Route 2 (continued)

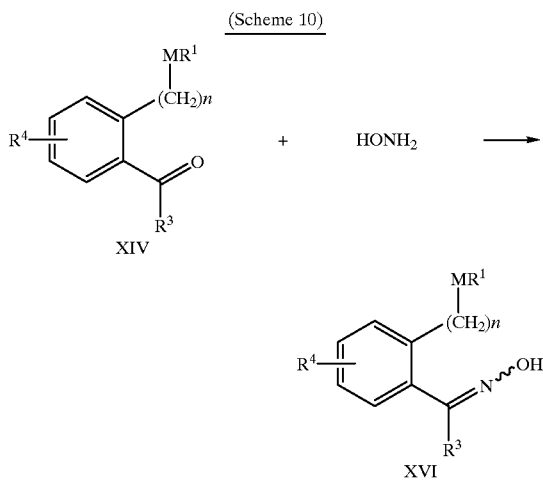

wherein each symbol is as defined above.

The compound of the formula (XVI) can be prepared by reacting the compound (XIV) with hydroxylamine or a salt thereof (e.g., hydrochloric acid salt, sulfuric acid salt) in an appropriate solvent (alone or as a mixture).

The amount of the hydroxylamine or a salt thereof to be used in this reaction is 1 equivalent or more, preferably 1 to 4 equivalents, based on the compound (XIV).

Examples of the solvent to be used include aromatic hydrocarbons (e.g., toluene, benzene, xylene, etc.), saturated hydrocarbons (e.g., cyclohexane, hexane, etc.), alcohols (e.g., methanol, ethanol, propanol, etc.), water, mixed solvents thereof, etc.

The reaction temperature is 0° C. to 160° C., preferably 60° C. to 130° C. The reaction time varies with the kind of compound, and is 0.5 to 90 hours.

The compound (XVI) thus obtained can be used in the next step as the reaction mixture or the crude product, or after purifying it by a conventional method (e.g., chromatography, recrystallization, etc.).

Route 2 (continued)

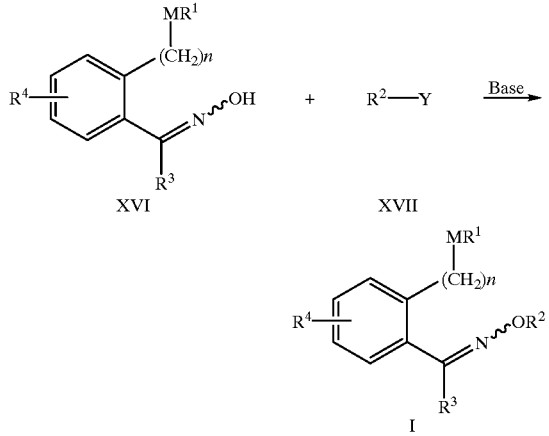

wherein Y is halogen (e.g., chlorine, bromine, iodine, etc.), alkylsulfonyloxy (e.g., lower alkylsulfonyloxy such as methylsulfonyloxy, ethylsulfonyloxy, etc.) or alkoxysulfonyloxy (e.g., lower alkoxysulfonyloxy such as methoxysulfonyloxy, ethoxysulfonyloxy, etc.), and the other symbols are as defined above.

The compound of the formula (I) of the present invention can be prepared by reacting the compound (XVI) with the compound (XVII) in the presence of a base in an appropriate solvent (alone or as a mixture).

The amount of the compound (XVII) to be used in this reaction is 1 equivalent, preferably 1 to 2 equivalents, based on the compound (XVI).

Examples of the base to be used include metal hydroxides (e.g., sodium hydroxide, potassium hydroxide, etc.), metal carbonates (e.g., sodium carbonate, potassium carbonate, etc.), metal alkoxides (e.g., sodium methoxide, sodium ethoxide, potassium tert-butoxide, etc.), etc. The amount of the base to be used is 1 equivalent or more, preferably 1 to 2 equivalents.

Examples of the solvent to be used include N,N-dimethylformamide (DMF), dimethyl sulfoxide (DMSO), aromatic hydrocarbons (e.g., toluene, benzene, xylene, etc.), saturated hydrocarbons (e.g., cyclohexane, hexane, etc.), halogenated hydrocarbons (e.g., dichloromethane, 1,2-dichloroethane, etc.), ethers (e.g., THF, dioxane, etc.), ketones (e.g., acetone, methyl ethyl ketone, etc.), nitriles (e.g., acetonitrile, etc.), water, mixed solvents thereof, etc.

The reaction temperature is −30° C. to 150° C., preferably −10° C. to 100° C. The reaction time varies with the kind of compound, and is 0.5 to 90 hours.

If necessary, the desired compound (I) thus obtained can be purified by a conventional method (e.g., chromatography, recrystallization, etc.).

Route 3

(Scheme 12)

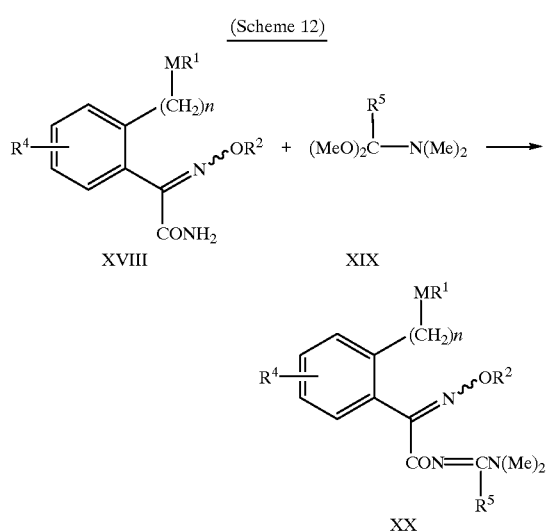

wherein $R^5$ is hydrogen or alkyl (e.g., lower alkyl such as methyl, ethyl, propyl, etc.), and the other symbols are as defined above.

The compound of the formula (XX) can be prepared by reacting the compound (XVIII) with the compound (XIX) in the absence of a solvent or in an appropriate solvent (alone or as a mixture), for example, by reference to Y. Lin et al., J. Org. Chem., 44, 4160 (1979).

The amount of the compound (XIX) to be used in this reaction is 1 equivalent or more, preferably 1 to 5 equivalents, based on the compound (XVIII).

Examples of the solvent to be used include aromatic hydrocarbons (e.g., toluene, benzene, xylene, etc.), saturated hydrocarbons (e.g., cyclohexane, hexane, etc.), ethers (e.g., THF, diethyl ether, dioxane, etc.), mixed solvents thereof, etc.

The reaction temperature is 0° C. to 180° C., preferably 20° C. to 120° C. The reaction time varies with the kind of compound, and is 0.5 to 80 hours.

The compound (XX) thus obtained can be used in the next step as the reaction mixture or the crude product, or after purifying it by a conventional method (e.g., chromatography, recrystallization, etc.).

The compound (XVIII) used as the starting material in this reaction can be prepared, for example, according to JP-A 3-246268 or JP-A 5-97768, for example, by reacting the corresponding carboxylic acid ester with ammonia or by subjecting the corresponding α-ketoamide to oximation.

Route 3 (continued)

(Scheme 13)

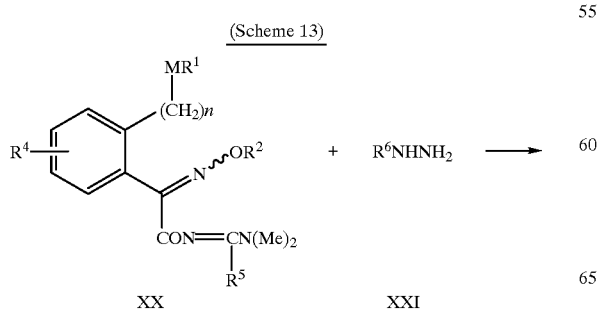

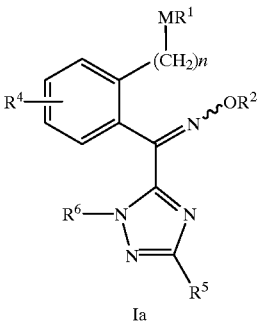

wherein $R^6$ is hydrogen or alkyl (e.g., lower alkyl such as methyl, ethyl, propyl, etc.), and the other symbols are as defined above.

The compound of the formula (Ia) of the present invention can be prepared by reacting the compound (XX) with the compound (XXI) in the presence of an acid in the absence of a solvent or in an appropriate solvent (alone or as a mixture) by reference to Y. Lin et al., J. Org. Chem., 44, 4160 (1979).

The amount of the compound (XXI) to be used in this reaction is 1 equivalent or more, preferably 1 to 2 equivalents, based on the compound (XX).

Examples of the acid to be used include aliphatic carboxylic acids (e.g., acetic acid, etc.). The amount of the acid to be used is 1 equivalent or more, preferably 5 to 50 equivalents, based on the compound (XX).

Examples of the solvent to be used include aromatic hydrocarbons (e.g., toluene, benzene, xylene, etc.), saturated hydrocarbons (e.g., cyclohexane, hexane, etc.), ethers (e.g., THF, dioxane, etc.), mixed solvents thereof, etc.

The reaction temperature is 0° C. to 180° C., preferably 20° C. to 120° C. The reaction time varies with the kind of compound, and is 0.5 to 80 hours.

If necessary, the desired compound (Ia) thus obtained can be purified by a conventional method (e.g., chromatography, recrystallization, etc.).

Route 4

(Scheme 14)

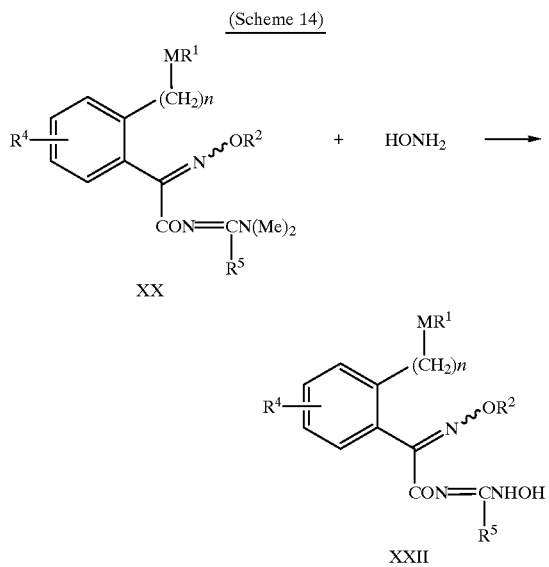

wherein each symbol is as defined above.

The compound of the formula (XXII) can be prepared by reacting the compound (XX) with hydroxylamine in the presence of an acid in the absence of a solvent or in an appropriate solvent (alone or as a mixture) by reference to Y. Lin et al., J. Org. Chem., 44, 4160 (1979).

The amount of the hydroxylamine to be used in this reaction is 1 equivalent or more, preferably 1 to 3 equivalents, based on the compound (XX).

Examples of the acid to be used include aliphatic carboxylic acids (e.g., acetic acid, etc.). The amount of the acid to be used is 1 equivalent or more, preferably 5 to 50 equivalents, based on the compound (XX).

Examples of the solvent to be used include aromatic hydrocarbons (e.g., toluene, benzene, xylene, etc.), saturated hydrocarbons (e.g., cyclohexane, hexane, etc.), ethers (e.g., THF, dioxane, etc.), water, mixed solvents thereof, etc.

The reaction temperature is −10° C. to 120° C., preferably 0° C. to 80° C. The reaction time varies with the kind of compound, and is 0.1 to 40 hours.

The compound (XXII) thus obtained can be used in the next step as the reaction mixture or the crude product, or after purifying it by a conventional method (e.g., chromatography, recrystallization, etc.).

Route 4 (continued)

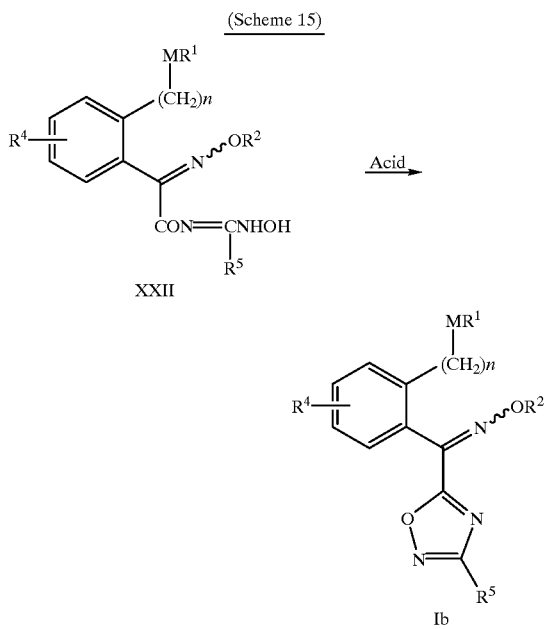

wherein each symbol is as defined above.

The compound of the formula (Ib) of the present invention can be prepared by subjecting the compound (XXII) to ring closure reaction in the presence of an acid in the absence of a solvent or in an appropriate solvent (alone or as a mixture) by reference to Y. Lin et al., J. Org. Chem., 44, 4160 (1979).

Examples of the acid to be used include aliphatic carboxylic acids (e.g., acetic acid, etc.). The amount of the acid to be used is 1 equivalent or more, preferably 5 to 50 equivalents, based on the compound (XXII).

Examples of the solvent to be used include aromatic hydrocarbons (e.g., toluene, benzene, xylene, etc.), saturated hydrocarbons (e.g., cyclohexane, hexane, etc.), ethers (e.g., THF, dioxane, etc.), mixed solvents thereof, etc.

The reaction temperature is 20° C. to 180° C., preferably 50° C. to 140° C. The reaction time varies with the kind of compound, and is 0.5 to 80 hours.

If necessary, the desired compound (Ib) thus obtained can be purified by a conventional method (e.g., chromatography, recrystallization, etc.).

Route 5

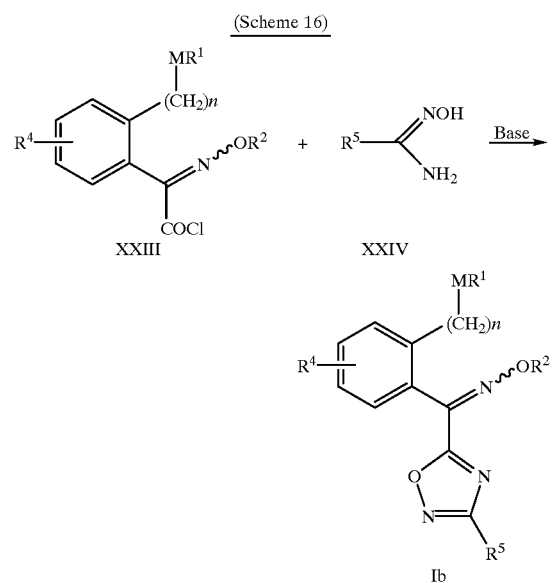

wherein each symbol is as defined above.

The compound of the formula (Ib) of the present invention can be prepared by reacting the compound (XXIII) with the compound (XXIV) in the presence of a base in the absence of a solvent or in an appropriate solvent (alone or as a mixture) by reference to S. Chiou et al., J. Heterocyclic Chem., 26, 125 (1989).

The amount of the compound (XXIV) to be used in this reaction is 1 equivalent or more, preferably 1 to 3 equivalents, based on the compound (XXIII).

Examples of the base to be used include amines (e.g., pyridine, triethylamine, etc.). The amount of the base to be used is 1 equivalent or more, preferably 3 to 20 equivalents, based on the compound (XXIII).

Examples of the solvent to be used include aromatic hydrocarbons (e.g., toluene, benzene, xylene, etc.), saturated hydrocarbons (e.g., cyclohexane, hexane, etc.), ethers (e.g., THF, dioxane, etc.), mixed solvents thereof, etc.

The reaction temperature is 20° C. to 180° C., preferably 50° C. to 140° C. The reaction time varies with the kind of compound, and is 0.5 to 80 hours.

If necessary, the desired compound (Ib) thus obtained can be purified by a conventional method (e.g., chromatography, recrystallization, etc.).

The compound (XXIII) used as the starting material in this reaction can be prepared, for example, according to Japanese Patent Application No. 5-56143, for example, by subjecting the corresponding α-methoxyimino(substituted) benzyl cyanide to hydrolysis with a base (e.g., sodium hydroxide, potassium hydroxide, etc.) to give a carboxylic acid, and then halogenating the carboxylic acid with a thionyl halide (e.g., thionyl chloride, etc.), phosphoryl halide (e.g., phosphoryl chloride, etc.), etc.

Route 6

(Scheme 17)

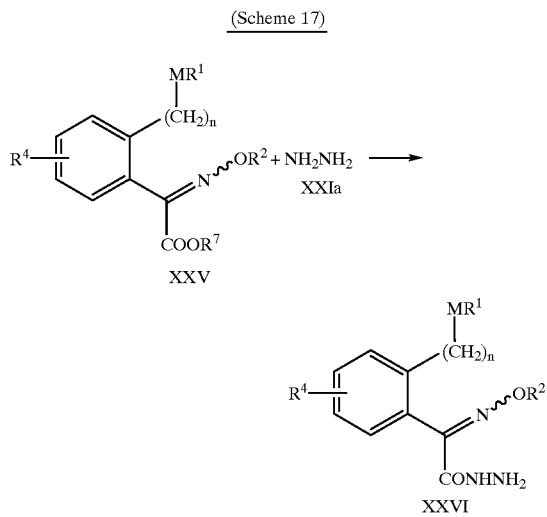

wherein R[7] is alkyl (e.g., lower alkyl such as methyl, ethyl, propyl, etc.), and the other symbols are as defined above.

The compound of the formula (XXVI) can be prepared by reacting the compound (XXV) with a monohydrate of the compound (XXIa) or a salt thereof (e.g., hydrochloric acid salt, sulfuric acid salt) in an appropriate solvent (alone or as a mixture).

The amount of the compound (XXIa) to be used in this reaction is 1 equivalent or more, preferably 1 to 5 equivalents, based on the compound (XXV).

Examples of the solvent to be used include aromatic hydrocarbons (e.g., toluene, benzene, xylene, etc.), saturated hydrocarbons (e.g., cyclohexane, hexane, etc.), alcohols (e.g., methanol, ethanol, propanol, etc.), ethers (e.g., THF, dioxane, etc.), water, mixed solvents thereof, etc.

The reaction temperature is 0° C. to 160° C., preferably 10° C. to 130° C. The reaction time varies with the kind of compound, and is 0.5 to 90 hours.

The compound (XXVI) thus obtained can be used in the next step as the reaction mixture or the crude product, or after purifying it by a conventional method (e.g., chromatography, recrystallization, etc.).

The compound (XXV) used as the starting material in this reaction can be prepared, for example, according to JP-A 4-295454, for example, by subjecting the corresponding α-ketocarboxylic acid ester or a ketal at the α-position of the ester to oximation.

Route 6 (continued)

(Scheme 18)

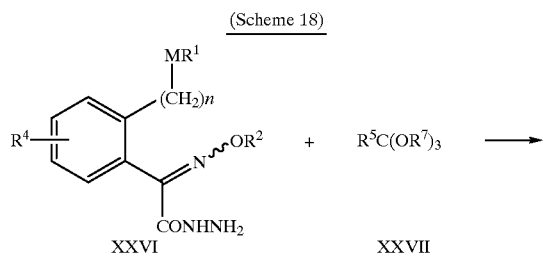

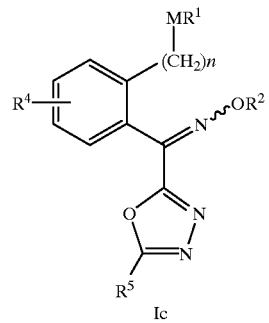

wherein each symbol is as defined above.

The compound of the formula (Ic) of the present invention can be prepared by reacting the compound (XXVI) with the compound (XXVII) in the absence of a solvent or in an appropriate solvent (alone or as a mixture) by reference to C. Ainaworth, J. Am. Chem. Soc., 77, 1148 (1955).

The amount of the compound (XXVII) to be used in this reaction is 1 equivalent or more, preferably 1 to 20 equivalents, based on the compound (XXVI).

Examples of the solvent to be used include aromatic hydrocarbons (e.g., toluene, benzene, xylene, etc.), saturated hydrocarbons (e.g., cyclohexane, hexane, etc.), ethers (e.g., THF, dioxane, etc.), mixed solvents thereof, etc.

The reaction temperature is 20° C. to 200° C., preferably 50° C. to 170° C. The reaction time varies with the kind of compound, and is 0.5 to 90 hours.

If necessary, the desired compound (Ic) thus obtained can be purified by a conventional method (e.g., chromatography, recrystallization, etc.).

Route 7

(Scheme 19)

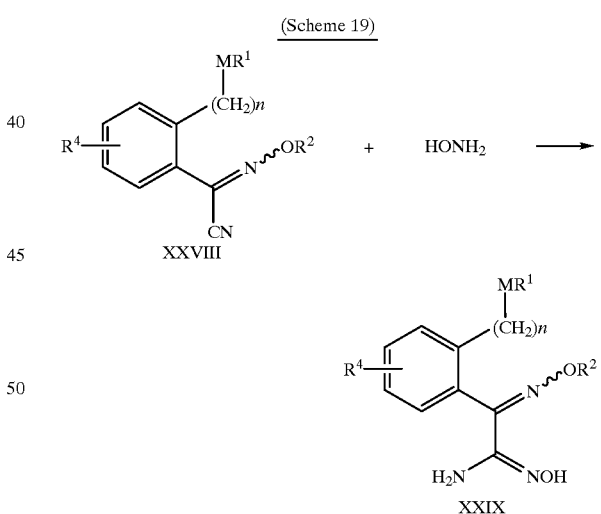

wherein each symbol is as defined above.

The compound of the formula (XXIX) can be prepared by reacting the compound (XXVIII) with hydroxylamine or a salt thereof (e.g., hydrochloric acid salt, sulfuric acid salt) in the presence or absence of a base in an appropriate solvent (alone or as a mixture).

The amount of the hydroxylamine or a salt thereof to be used in this reaction is 1 equivalent or more, preferably 1 to 3 equivalents, based on the compound (XXVIII).

Examples of the base to be used include metal hydroxides (e.g., sodium hydroxide, potassium hydroxide, etc.), metal alkoxides (e.g., sodium methoxide, sodium ethoxide, etc.), amines (e.g., pyridine, triethylamine, etc.), etc. The amount of the base to be used is 1 equivalent or more, preferably 1 to 2 equivalents.

Examples of the solvent to be used include aromatic hydrocarbons (e.g., toluene, benzene, xylene, etc.), saturated hydrocarbons (e.g., cyclohexane, hexane, etc.), alcohols (e.g., methanol, ethanol, propanol, etc.), water, mixed solvents thereof, etc.

The reaction temperature is 0° C. to 160° C., preferably 20° C. to 110° C. The reaction time varies with the kind of compound, and is 0.5 to 90 hours.

The compound (XXIX) thus obtained can be used in the next step as the crude product, or after purifying it by a conventional method (e.g., chromatography, recrystallization, etc.).

The compound (XXVIII) used as the starting material in this reaction can be prepared, for example, according to Route 13, 14 or 15, or Japanese Patent Application No. 4-324120, for example, by introducing the cyano moiety to the corresponding (substituted)benzyl halide using an alkaline metal cyanide (e.g., sodium cyanide, etc.), and then subjecting the resulting compound to oximation.

Route 7 (continued)

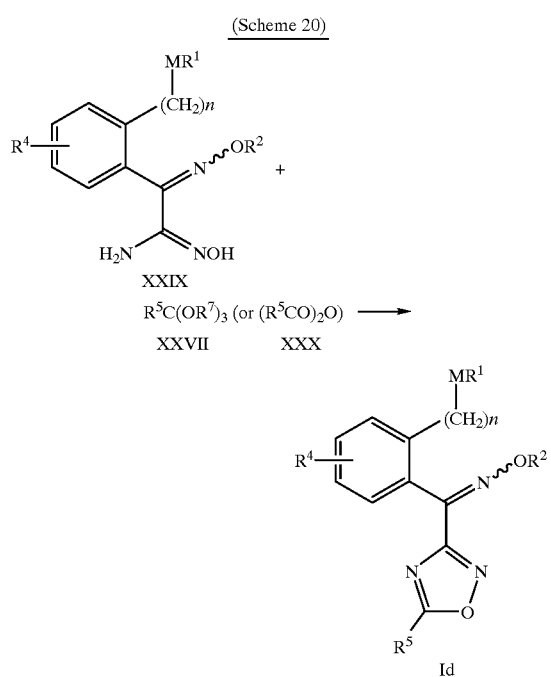

wherein each symbol is as defined above except that $R^5$ of the compound (XXX) is other than hydrogen and preferably lower alkyl such as methyl, ethyl, propyl, etc.

The compound of the formula (Id) of the present invention can be prepared by reacting the compound (XXIX) with the compound (XXVII) or (XXX) in the absence of a solvent or in an appropriate solvent (alone or as a mixture) by reference to U.S. Pat. No. 3,910,942.

The amount of the compound (XXVII) or (XXX) to be used in this reaction is 1 equivalent or more, preferably 1 to 20 equivalents, based on the compound (XXIX).

Examples of the solvent to be used include aromatic hydrocarbons (e.g., toluene, benzene, xylene, etc.), saturated hydrocarbons (e.g., cyclohexane, hexane, etc.), ethers (e.g., THF, dioxane, etc.), mixed solvents thereof, etc.

The reaction temperature is 40° C. to 200° C., preferably 60° C. to 180° C. The reaction time varies with the kind of compound, and is 0.5 to 120 hours.

If necessary, the desired compound (Id) thus obtained can be purified by a conventional method (e.g., chromatography, recrystallization, etc.).

The compounds of the formulas (Ie), (If) and (Ig) of the present invention can be prepared according to the following Route 8.

Route 8

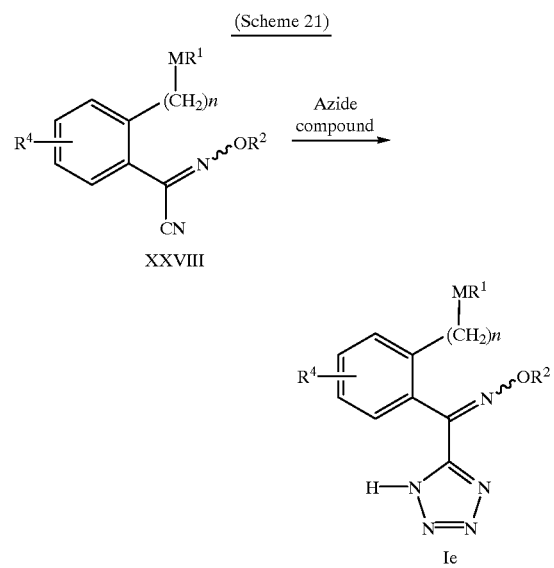

wherein each symbol is as defined above.

The compound of the formula (Ie) of the present invention can be prepared by reacting the compound (XXVIII) with an azide compound in the presence of ammonium chloride in an appropriate solvent (alone or as a mixture) by reference to K. Kubo, J. Med. Chem., 36, 2182 (1993).

Examples of the azide compound to be used include alkaline metal azides (e.g., sodium azide, potassium azide, etc.), etc. The amount of the azide compound to be used is 1 equivalent or more, preferably 1 to 15 equivalents, based on the compound (XXVIII). The amount of the ammonium chloride to be used is 1 equivalent or more, preferably 1 to 15 equivalents, based on the compound (XXVIII).

Examples of the solvent to be used include N,N-dimethylformamide (DMF), dimethyl sulfoxide (DMSO), aromatic hydrocarbons (e.g., toluene, benzene, xylene, etc.), ethers (e.g., dioxane, etc.), mixed solvents thereof, etc.

The reaction temperature is 40° C. to 200° C., preferably 60° C. to 180° C. The reaction time varies with the kind of compound, and is 0.5 to 120 hours.

The desired compound (Ie) thus obtained can be used in the next step as the reaction mixture or the crude product, or after purifying it by a conventional method (e.g., chromatography, recrystallization, etc.).

Route 8 (continued)

(Scheme 22)

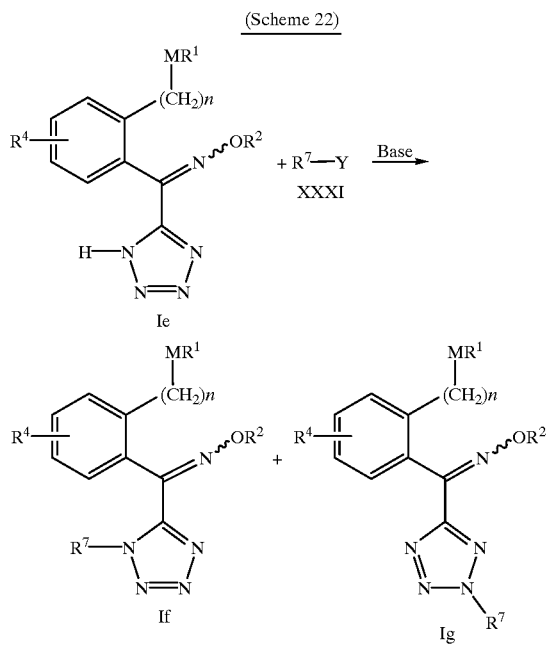

Route 9

(Scheme 23)

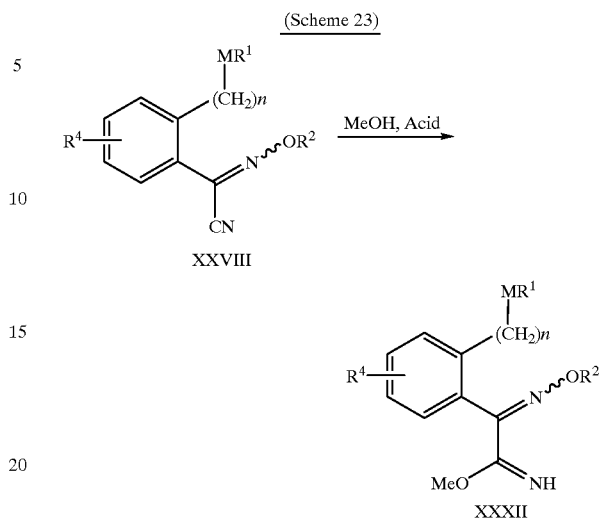

wherein each symbol is as defined above.

The compound of the formula (If) or (Ig) of the present invention can be prepared by reacting the compound (Ie) with the compound (XXXI) in the presence of a base in an appropriate solvent (alone or as a mixture).

The amount of the compound (XXXI) be used in this reaction is 1 equivalent or more, preferably 1 to 2 equivalents, based on the compound (Ie).

Examples of the base to be used include metal hydroxides (e.g., sodium hydroxide, potassium hydroxide, etc.), metal carbonates (e.g., sodium carbonate, potassium carbonate, etc.), metal alkoxides (e.g., sodium methoxide, sodium ethoxide, potassium tert-butoxide, etc.), etc. The amount of the base to be used is 1 equivalent or more, preferably 1 to 3 equivalents.

Examples of the solvent to be used include N,N-dimethylformamide (DMF), dimethyl sulfoxide (DMSO), aromatic hydrocarbons (e.g., toluene, benzene, xylene, etc.), saturated hydrocarbons (e.g., cyclohexane, hexane, etc.), halogenated hydrocarbons (e.g., dichloromethane, 1,2-dichloroethane, etc.), ethers (e.g., THF, dioxane, etc.), ketones (e.g., acetone, methyl ethyl ketone, etc.), nitriles (e.g., acetonitrile, etc.), water, mixed solvents thereof, etc.

The reaction temperature is −30° C. to 150° C., preferably −10° C. to 100° C. The reaction time varies with the kind of compound, and is 0.5 to 90 hours.

If necessary, the desired compound (If) and (Ig) thus obtained can be purified by a conventional method (e.g., chromatography, recrystallization, etc.).

The compounds of the formulas (Ih) and (Ii) of the present invention can be prepared according to the following Route 9.

wherein each symbol is as defined above.

The compound of the formula (XXXII) can be prepared by reacting the compound (XXVIII) with methanol in the presence of an acid by reference to, for example, JP-A 5-271223.

The amount of the methanol to be used in this reaction is 1 equivalent or more, preferably 1 to 1.2 equivalents, based on the compound (XXVIII).

Examples of the acid to be used include hydrochloric acid, hydrobromic acid, etc. The amount of the acid to be used is 1 equivalent or more, preferably 1 to 2 equivalents, based on the compound (XXVIII).

Examples of the solvent to be used include aromatic hydrocarbons (e.g., toluene, benzene, xylene, etc.), saturated hydrocarbons (e.g., cyclohexane, hexane, etc.), halogenated hydrocarbons (e.g., dichloromethane, 1,2-dichloroethane, etc.), ethers (e.g., THF, dioxane, ethyl ether, etc.), mixed solvents thereof, etc.

The reaction temperature is −30° C. to 150° C., preferably 0° C. to 120° C. The reaction time varies with the kind of compound, and is 0.5 to 120 hours.

The compound (XXXII) thus obtained can be used in the next step as the reaction mixture or the crude product, or after purifying it by a conventional method (e.g., chromatography, recrystallization, etc.).

Route 9 (continued)

(Scheme 24)

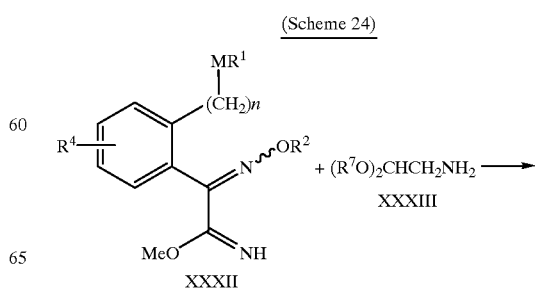

-continued

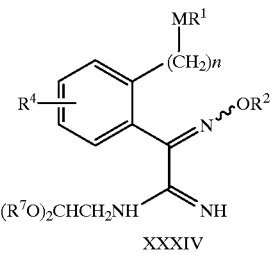

XXXIV wherein each symbol is as defined above.

The compound of the formula (XXXIV) can be prepared by reacting the compound (XXXII) or a salt thereof (e.g., hydrochloric acid, hydrobromic acid, etc.) with the compound (XXXIII) by reference to, for example, JP-A 5-271223.

The amount of the compound (XXXIII) to be used in this reaction is 1 equivalent or more, preferably 1 to 1.2 equivalents, based on the compound (XXXII).

Examples of the solvent to be used include alcohols (e.g., methanol, ethanol, propanol, etc.), ethers (e.g., THF, dioxane, etc.), mixed solvents thereof, etc.

The reaction temperature is $-30°$ C. to $150°$ C., preferably $0°$ C. to $120°$ C. The reaction time varies with the kind of compound, and is 0.5 to 120 hours.

The compound (XXXIV) thus obtained can be used in the next step as the reaction mixture or the crude product, or after purifying it by a conventional method (e.g., chromatography, recrystallization, etc.).

Route 9 (continued)

(Scheme 25)

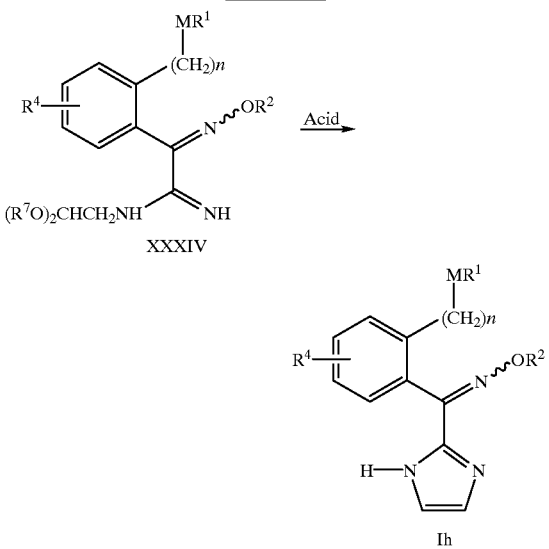

wherein each symbol is as defined above.

The compound of the formula (Ih) of the present invention can be prepared by subjecting the compound (XXXIV) or a salt thereof (e.g., hydrochloric acid, hydrobromic acid, etc.) to ring closure reaction in the presence of an acid in the absence of a solvent or in an appropriate solvent (alone or as a mixture) by reference to, for example, JP-A 5-271223.

Examples of the acid to be used include hydrochloric acids, hydrobromic acid, etc. The amount of the acid to be used is 1 equivalent or more, preferably 1 to 2 equivalents, based on the compound (XXXIV).

Examples of the solvent to be used include alcohols (e.g., methanol, ethanol, propanol, etc.), ethers (e.g., THF, dioxane, etc.), mixed solvents thereof, etc.

The reaction temperature is $10°$ C. to $150°$ C., preferably $30°$ C. to $120°$ C. The reaction time varies with the kind of compound, and is 0.5 to 120 hours.

If necessary, the desired compound (Ih) thus obtained can be purified by a conventional method (e.g., chromatography, recrystallization, etc.).

Route 9 (continued)

(Scheme 26)

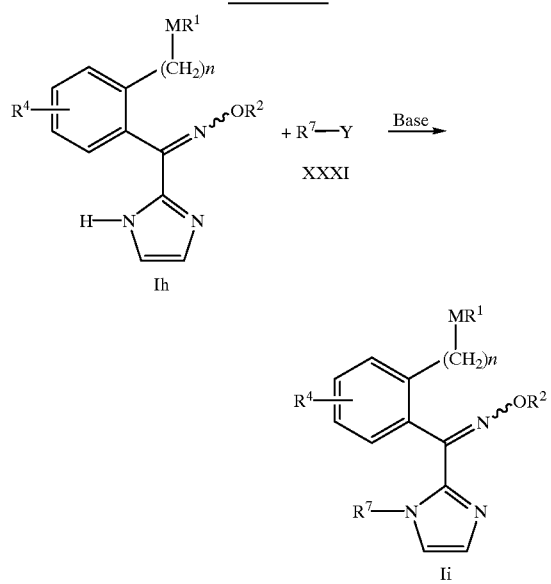

wherein each symbol is as defined above.

The compound of the formula (Ii) of the present invention can be prepared by reacting the compound (Ih) with the compound (XXXI) in the presence of a base in an appropriate solvent (alone or as a mixture).

The amount of the compound (XXXI) to be used in this reaction is 1 equivalent or more, preferably 1 to 2 equivalents, based on the compound (Ih).

Examples of the base to be used include metal hydroxides (e.g., sodium hydroxide, potassium hydroxide, etc.), metal carbonates (e.g., sodium carbonate, potassium carbonate, etc.), metal alkoxides (e.g., sodium methoxide, sodium ethoxide, potassium tert-butoxide, etc.), etc. The amount of the base to be used is 1 equivalent or more, preferably 1 to 2 equivalents.

Examples of the solvent to be used is N,N-dimethylformamide (DMF), dimethyl sulfoxide (DMSO), aromatic hydrocarbons (e.g., toluene, benzene, xylene, etc.), saturated hydrocarbons (e.g., cyclohexane, hexane, etc.), halogenated hydrocarbons (e.g., dichloromethane, 1,2-dichloroethane, etc.), ethers (e.g., THF, dioxane, etc.), ketones (e.g., acetone, methyl ethyl ketone, etc.), nitrites (e.g., acetonitrile, etc.), water, mixed solvents thereof, etc.

The reaction temperature is $-30°$ C. to $150°$ C., preferably $-10°$ C. to $100°$ C. The reaction time varies with the kind of compound, and is 0.5 to 90 hours.

If necessary, the desired compound (Ii) thus obtained can be purified by a conventional method (e.g., chromatography, recrystallization, etc.).

The compound of the formula (Ij) of the present invention can be prepared according to the following Route 10.

Route 10

(Scheme 27)

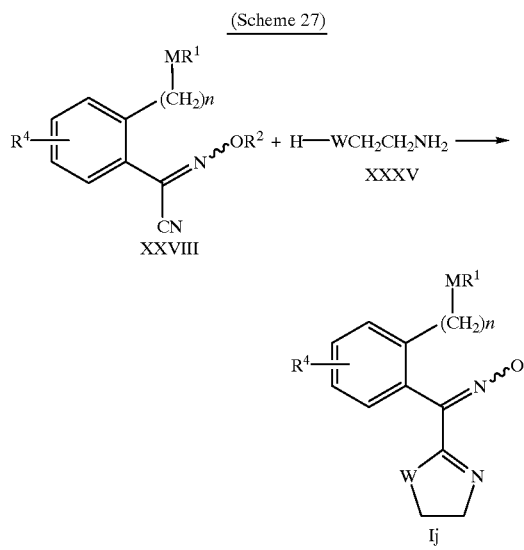

wherein W is oxygen, sulfur or N—R⁵, and R⁵ and the other symbols are as defined above.

The compound of the formula (Ij) of the present invention can be prepared by reacting the compound (XXVIII) with the compound (XXXV) or a salt thereof (e.g., hydrochloric acid salt, hydrobromic acid salt, etc.) in the presence or absence of a base in the presence or absence of a metal salt in the absence of a solvent or in an appropriate solvent (alone or as a mixture) by reference to Doris P. Schumacher et al., J. Org. Chem., 55, 5291 (1990).

The amount of the compound (XXXV) to be used in this reaction is 1 equivalent or more, preferably 1 to 5 equivalents, based on the compound (XXVIII).

Examples of the base to be used include amines (e.g., triethylamine, etc.). The amount of the base to be used is 1 equivalent or more, preferably 1 to 6 equivalents, based on the compound (XXVIII).

Examples of the metal salt to be used include potassium carbonate, zinc acetate, etc. The amount of the metal salt to be used is 0.01 to 0.5 equivalent, preferably 0.02 to 0.2 equivalent, based on the compound (XXVIII).

Examples of the solvent to be used include N,N-dimethylformamide (DMF), dimethyl sulfoxide (DMSO), aromatic hydrocarbons (e.g., toluene, benzene, xylene, etc.), saturated hydrocarbons (e.g., cyclohexane, hexane, etc.), halogenated hydrocarbons (e.g., dichloromethane, 1,2-dichloroethane, etc.), ethers (e.g., THF, dioxane, etc.), alcohols (e.g., butanol, 2-methoxyethanol, ethylene glycol, glycerol, etc.), mixed solvents thereof, etc.

The reaction temperature is 20° C. to 200° C., preferably 50° C. to 160° C. The reaction time varies with the kind of compound, and is 0.5 to 90 hours.

If necessary, the desired compound (Ij) thus obtained can be purified by a conventional method (e.g., chromatography, recrystallization, etc.).

The compound of the formula (Ik) of the present invention can be prepared according to the following Route 11.

Route 11

(Scheme 28)

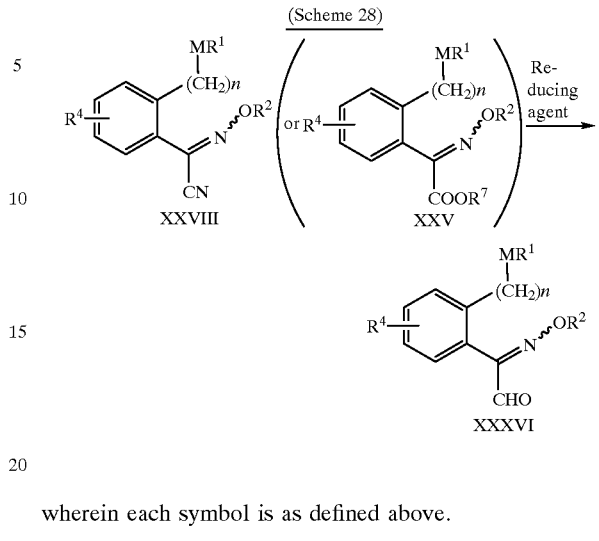

wherein each symbol is as defined above.

The compound of the formula (XXXVI) can be prepared by reacting the compound (XXVIII) or the compound (XXV) with a reducing agent in an appropriate solvent (alone or as a mixture) by reference to, for example, L.-F Tietze and Th. Eicher, "Reaktionen und Synthesen im organisch-chemischen Praktikum", pp. 84–97 (1981).

Examples of the reducing agent to be used include alkylaluminum hydrides (e.g., diisobutylaluminum hydride, etc.). The amount of the reducing agent to be used is 1 equivalent or more, preferably 1 to 2 equivalents.

Examples of the solvent to be used include aromatic hydrocarbons (e.g., toluene, benzene, xylene, etc.), saturated hydrocarbons (e.g., cyclohexane, hexane, etc.), halogenated hydrocarbons (e.g., dichloromethane, 1,2-dichloroethane, etc.), ethers (e.g., THF, dioxane, ethyl ether, etc.), mixed solvents thereof, etc.

The reaction temperature is −100° C. to 80° C., preferably −70° C. to 30° C. The reaction time varies with the kind of compound, and is 0.5 to 120 hours.

The compound (XXXVI) thus obtained can be used in the next step as the crude product, or after purifying it by a conventional method (e.g., chromatography, recrystallization, etc.).

Route 11 (continued)

(Scheme 29)

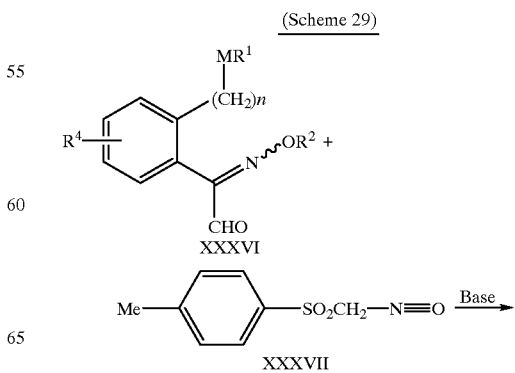

-continued

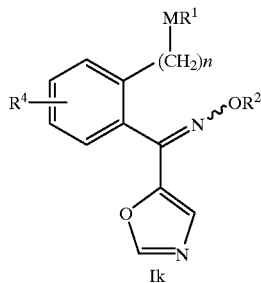

Ik wherein each symbol is as defined above.

The compound of the formula (Ik) of the present invention can be prepared by reacting the compound (XXXVI) with the compound (XXXVII) in the presence of a base in an appropriate solvent (alone or as a mixture) according to, for example, JP-A 58-131984.

The amount of the compound (XXXVII) to be used in this reaction is 1 equivalent or more, preferably 1 to 2 equivalents, based on the compound (XXXVI).

Examples of the base to be used include metal hydroxides (e.g., sodium hydroxide, potassium hydroxide, etc.), metal carbonates (e.g., sodium carbonate, potassium carbonate, etc.), metal alkoxides (e.g., sodium methoxide, sodium ethoxide, potassium tert-butoxide, etc.), etc. The amount of the base to be used is 1 equivalent or more, preferably 1 to 2 equivalents.

Examples of the solvent to be used include aromatic hydrocarbons (e.g., toluene, benzene, xylene, etc.), saturated hydrocarbons (e.g., cyclohexane, hexane, etc.), alcohols (e.g., methanol, ethanol, propanol, etc.), mixed solvents thereof, etc.

The reaction temperature is 30° C. to 150° C., preferably 50° C. to 100° C. The reaction time varies with the kind of compound, and is 0.5 to 90 hours.

If necessary, the desired compound (Ik) thus obtained can be purified by a conventional method (e.g., chromatography, recrystallization, etc.).

The compound of the formula (In) of the present invention can be prepared according to the following Route 12.

Route 12

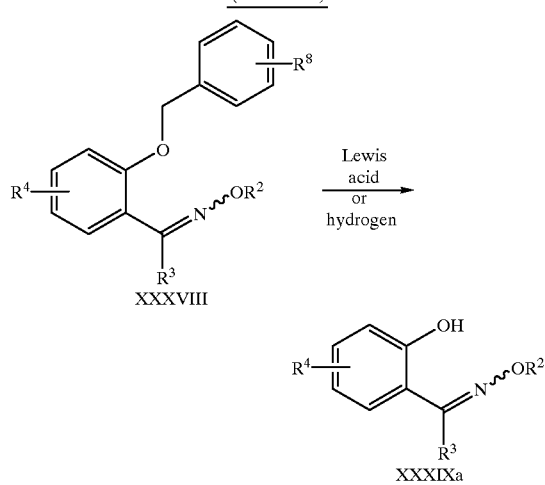

wherein $R^8$ is hydrogen, alkyl (e.g., lower alkyl such as methyl, ethyl, propyl, etc.) or halogen (e.g., fluorine, chlorine, bromine, iodine), and the other symbols are as defined above.

The compound of the formula (XXXIXa) can be prepared by reacting the compound (XXXVIII) with a Lewis acid in an appropriate solvent (alone or a mixture).

The compound (XXXVIII) is synthesized by a modified method of Routes 1 to 11.

Examples of the Lewis acid to be used include aluminium chloride, aluminium bromide, boron trifluoride, boron trichloride, ferric chloride, etc.

The amount of the Lewis acid to be used is 1 equivalent or more, preferably 1 to 3 equivalents, based on the compound (XXXVIII).

Examples of the solvent to be used include anisole, nitromethane, nitroethane, mixed solvents thereof, etc.

The reaction temperature is −30° C. to 120° C., preferably −10° C. to 80° C. The reaction time varies with the kind of compound, and is 0.5 to 90 hours.

Alternatively, the compound (XXXIXa) can be prepared by reacting the compound (XXXVIII) with hydrogen in the presence of a catalyst in an appropriate solvent (alone or as a mixture).

The amount of the hydrogen to be used is 1 equivalent or more, preferably 1 to 2 equivalents, based on the compound (XXXVIII).

Examples of the catalyst to be used include palladium-carbon, etc. The amount of the catalyst to be used is 0.01 equivalent or more, preferably 0.01 to 0.2 equivalent, based on the compound (XXXVIII).

Examples of the solvent to be used include ethyl acetate, alcohols (e.g., methanol, ethanol, propanol, etc.), water, mixed solvents thereof, etc.

The reaction temperature is −30° C. to 120° C., preferably −10° C. to 80° C. The reaction time varies with the kind of compound, and is 0.5 to 90 hours.

The compound (XXXIXa) thus obtained can be used in the next step as the crude product, or after purifying it by a conventional method (e.g., chromatography, recrystallization, etc.).

Route 12 (continued)

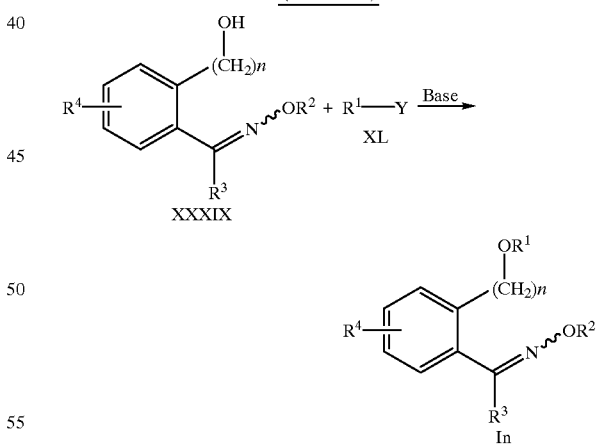

wherein each symbol is as defined above.

The compound of the formula (In) of the present invention can be prepared by reacting the compound (XXXIX) with the compound (XL) in the presence of a base in an appropriate solvent (alone or as a mixture).

The amount of the compound (XL) to be used in this reaction is 1 equivalent or more, preferably 1 to 2 equivalents, based on the compound (XXXIX).

Examples of the base to be used include metal hydroxides (e.g., sodium hydroxide, potassium hydroxide, etc.), metal carbonates (e.g., sodium carbonate, potassium carbonate, etc.), metal alkoxides (e.g., sodium methoxide, sodium ethoxide, potassium tert-butoxide, etc.), etc. The amount of the base to be used is 1 equivalent or more, preferably 1 to 2 equivalents.

Examples of the solvent to be used is N,N-dimethylformamide (DMF), dimethyl sulfoxide (DMSO), aromatic hydrocarbons (e.g., toluene, benzene, xylene, etc.), saturated hydrocarbons (e.g., cyclohexane, hexane, etc.), halogenated hydrocarbons (e.g., dichloromethane, 1,2-dichloroethane, etc.), ethers (e.g., THF, dioxane, etc.), ketones (e.g., acetone, methyl ethyl ketone, etc.), nitrites (e.g., acetonitrile, etc.), water, mixed solvents thereof, etc.

The reaction temperature is 0° C. to 190° C., preferably 10° C. to 160° C. The reaction time varies with the kind of compound, and is 0.5 to 90 hours.

If necessary, the desired compound (In) thus obtained can be purified by a conventional method (e.g., chromatography, recrystallization, etc.).

The compound (XXVIII) which can be used as the starting material in the above Schemes 19, 21, 23, 27 and 28 can be prepared according to the following Route 13, 14 or 15.

Route 13

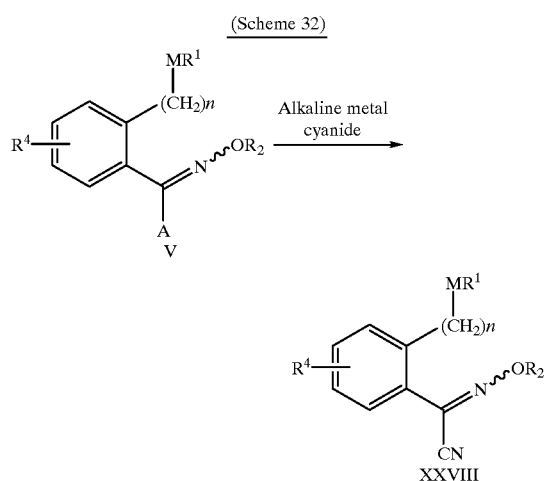

wherein each symbol is as defined above.

The compound of the formula (XXVIII) can be prepared by reacting the compound (V) with an alkaline metal cyanide (e.g., sodium cyanide, potassium cyanide, etc.) in an appropriate solvent (alone or as a mixture).

The amount of the alkaline metal cyanide to be used in this reaction is 1 equivalent or more, preferably 1 to 3 equivalents, based on the compound (V).

Examples of the solvent to be used is N,N-dimethylformamide (DMF), dimethyl sulfoxide (DMSO), aromatic hydrocarbons (e.g., toluene, benzene, xylene, etc.), saturated hydrocarbons (e.g., cyclohexane, hexane, etc.), halogenated hydrocarbons (e.g., dichloromethane, 1,2-dichloroethane, etc.), ethers (e.g., THF, dioxane, etc.), ketones (e.g., acetone, methyl ethyl ketone, etc.), nitrites (e.g., acetonitrile, etc.), water, mixed solvents thereof, etc.

The reaction temperature is 0° C. to 190° C., preferably 20° C. to 160° C. The reaction time varies with the kind of compound, and is 0.5 to 90 hours.

The compound (XXVIII) thus obtained can be used in the next step as the crude product, or after purifying it by a conventional method (e.g., chromatography, recrystallization, etc.

Route 14

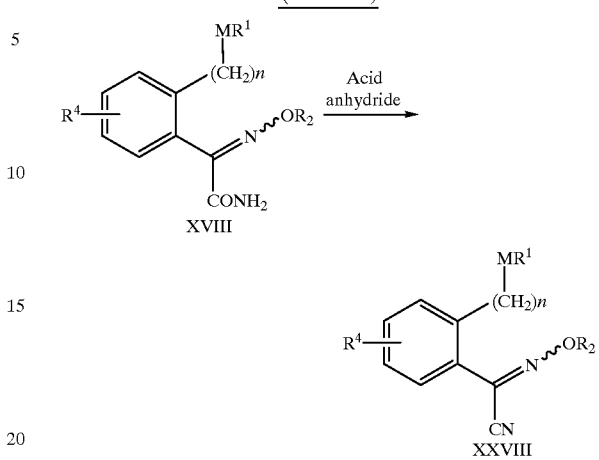

wherein each symbol is as defined above.

The compound of the formula (XXVIII) can be prepared by reacting the compound (XVIII) with an acid anhydride in the presence or absence of a base in the absence of a solvent or in an appropriate solvent (alone or as a mixture) by reference to, for example, J. Goto et al., J. Antibiotics, 37, 557 (1984).

Examples of the acid anhydride to be used include acetic anhydride, trifluoroacetic anhydride, etc. The amount of the acid anhydride to be used is 1 equivalent or more, preferably 1 to 5 equivalents, based on the compound (XVIII).

Examples of the base to be used include amines (e.g., pyridine, etc.), etc. The amount of the base to be used is 1 equivalent or more, preferably 1 to 30 equivalents, based on the compound (XVIII). Examples of the solvent to be used is aromatic hydrocarbons (e.g., toluene, benzene, xylene, etc.), saturated hydrocarbons (e.g., cyclohexane, hexane, etc.), halogenated hydrocarbons (e.g., dichloromethane, 1,2-dichloroethane, etc.), mixed solvents thereof, etc.

The reaction temperature is −30° C. to 160° C., preferably −10° C. to 110° C. The reaction time varies with the kind of compound, and is 0.5 to 90 hours.

The compound (XXVIII) thus obtained can be used in the next step as the crude product, or after purifying it by a conventional method (e.g., chromatography, recrystallization, etc.).

Route 15

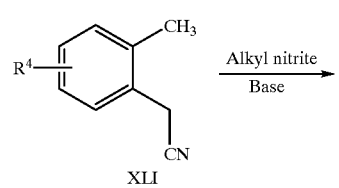

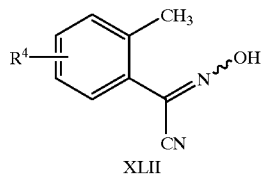

XLII wherein $R^4$ is as defined above.

The compound of the formula (XLII) can be prepared by reacting the compound (XLI) with an alkyl nitrite in the presence of a base in an appropriate solvent (alone or as a mixture) in the presence or absence of a phase-transfer catalyst.

Examples of the alkyl nitrite to be used include methyl nitrite, ethyl nitrite, propyl nitrite, isopropyl nitrite, butyl nitrite, isoamyl nitrite, etc. The amount of the alkyl nitrite to be used is 1 equivalent or more, preferably 1 to 2 equivalents.

Examples of the phase-transfer catalyst to be used include tetra-n-butylammonium chloride, tetra-n-butylammonium bromide, tetra-n-butylammonium hydrogensulfate, tetramethylammonium bromide, benzyltriethylammonium chloride, tris(3,6-dioxaheptyl)amine, etc. The amount of the phase-transfer catalyst to be used is 0.005 to 0.5 equivalent, preferably 0.01 to 0.2 equivalent.

Examples of the base to be used include metal hydroxides (e.g., sodium hydroxide, potassium hydroxide, etc.), metal carbonates (e.g., sodium carbonate, potassium carbonate, etc.), metal alkoxides (e.g., sodium methoxide, sodium ethoxide, potassium tert-butoxide, etc.), etc. The amount of the base to be used is 1 equivalent or more, preferably 1 to 2 equivalents.

Examples of the solvent to be used is N,N-dimethylformamide (DMF), dimethyl sulfoxide (DMSO), aromatic hydrocarbons (e.g., toluene, benzene, xylene, etc.), saturated hydrocarbons (e.g., cyclohexane, hexane, etc.), halogenated hydrocarbons (e.g., dichloromethane, 1,2-dichloroethane, etc.), ethers (e.g., THF, dioxane, etc.), ketones (e.g., acetone, methyl ethyl ketone, etc.), nitrites (e.g., acetonitrile, etc.), alcohols (e.g., methanol, butanol, etc.), water, mixed solvents thereof, etc.

The reaction temperature is −10° C. to 120° C., preferably 0° C. to 80° C. The reaction time varies with the kind of compound, and is 0.5 to 90 hours.

The compound (XLII) or a salt thereof (e.g., sodium salt, potassium salt, etc.) thus obtained can be used in the next step as the reaction mixture or the crude product, or after purifying it by a conventional method (e.g., chromatography, recrystallization, etc.).

The compound (XLI) used as the starting material in this reaction is commercially available from Aldrich.

Route 15 (continued)

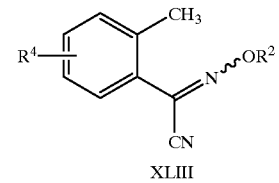

XLIII wherein each symbol is as defined above.

The compound of the formula (XLIII) can be prepared by reacting the compound (XLII) or a salt thereof (e.g., sodium salt, potassium salt, etc.) with the compound (XVII) in the presence or absence of a base in the presence or absence of a phase-transfer catalyst in an appropriate solvent (alone or as a mixture).

The amount of the compound (XVII) to be used in this reaction is 1 equivalent or more, preferably 1 to 2 equivalents, based on the compound (XLII).

Examples of the phase-transfer catalyst to be used include tetra-n-butylammonium chloride, tetra-n-butylammonium bromide, tetra-n-butylammonium hydrogensulfate, tetramethylammonium bromide, benzyltriethylammonium chloride, tris(3,6-dioxaheptyl)amine, etc. The amount of the phase-transfer catalyst to be used is 0.005 to 0.5 equivalent, preferably 0.01 to 0.2 equivalent.

Examples of the base to be used include metal hydroxides (e.g., sodium hydroxide, potassium hydroxide, etc.), metal carbonates (e.g., sodium carbonate, potassium carbonate, etc.), metal alkoxides (e.g., sodium methoxide, sodium ethoxide, potassium tert-butoxide, etc.), etc. The amount of the base to be used is 1 equivalent or more, preferably 1 to 2 equivalents.

Examples of the solvent to be used is N,N-dimethylformamide (DMF), dimethyl sulfoxide (DMSO), aromatic hydrocarbons (e.g., toluene, benzene, xylene, etc.), saturated hydrocarbons (e.g., cyclohexane, hexane, etc.), halogenated hydrocarbons (e.g., dichloromethane, 1,2-dichloroethane, etc.), ethers (e.g., THF, dioxaneketone), ketones (e.g., acetone, methyl ethyl ketone, etc.), nitrites (e.g., acetonitrile, etc.), water, mixed solvents thereof, etc.

The reaction temperature is −20° C. to 140° C., preferably 10° C. to 120° C. The reaction time varies with the kind of compound, and is 0.5 to 90 hours.

The compound (XLIII) thus obtained can be used in the next step as the crude product, or after purifying it by a conventional method (e.g., chromatography, recrystallization, etc.).

Route 15 (continued)

(Scheme 35)

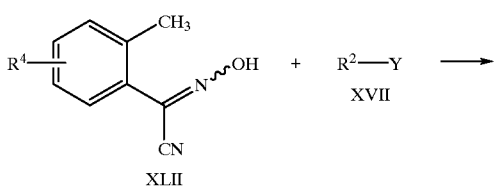

XLII (Scheme 36)

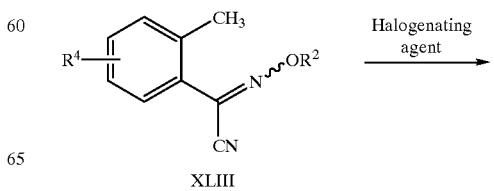

XLIII

-continued

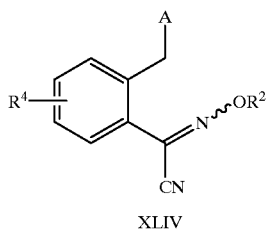

XLIV wherein each symbol is as defined above.

The compound of the formula (XLIV) can be prepared by reacting the compound (XLIII) with a halogenating agent in the presence of a reaction initiator in an appropriate solvent (alone or as a mixture).

Examples of the halogenating agent to be used include halogenated succinimide (e.g., N-chlorosuccinimide, N-bromosuccinimide, etc.), chlorine, and bromine. The amount of the halogenating agent to be used is 1 equivalent or more, preferably 1 to 1.5 equivalent.

Examples of the reaction initiator to be used include peroxides (e.g., benzoyl peroxide, etc.), 2,2'-azobis (isobutyronitrile), etc. The amount of the reaction initiator to be used is 0.01 equivalent or more, preferably 0.03 to 0.3 equivalent.

Examples of the solvent to be used include aromatic hydrocarbons (e.g., benzene, etc.), saturated hydrocarbons (e.g., cyclohexane, hexane, etc.), halogenated hydrocarbons (e.g., carbon tetrachloride, 1,2-dichloroethane, etc.), mixed solvents thereof, etc.

The reaction temperature is 20° C. to 160° C., preferably 50° C. to 120° C. The reaction time varies with the kind of compound, and is 0.1 to 48 hours.

The compound (XLIV) thus obtained can be used in the next step as the crude product, or after purifying it by a conventional method (e.g., chromatography, recrystallization, etc.).

Route 15 (continued)

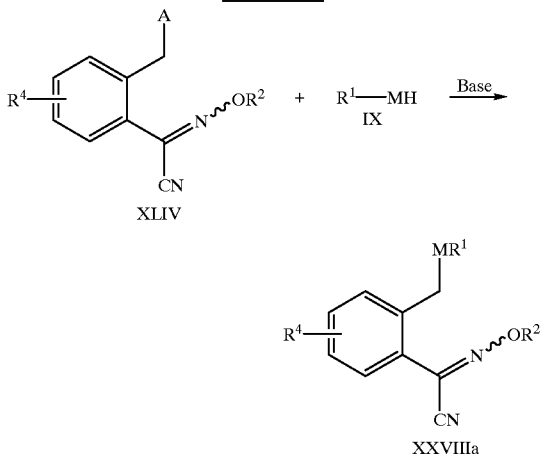

wherein each symbol is as defined above.

The compound of the formula (XXVIIIa) can be prepared by reacting the compound (XLIV) with the compound (IX) in the presence of a base in the presence or absence of a phase-transfer catalyst in the absence of a solvent or in an appropriate solvent (alone or as a mixture).

The amount of the compound (IX) to be used in this reaction is 1 equivalent or more, preferably 1 to 2 equivalents, based on the compound (XLIV).

Examples of the phase-transfer catalyst to be used include tetra-n-butylammonium chloride, tetra-n-butylammonium bromide, tetra-n-butylammonium hydrogensulfate, tetramethylammonium bromide, benzyltriethylammonium chloride, tris(3,6-dioxaheptyl)amine, etc. The amount of the phase-transfer catalyst to be used is 0.005 to 0.5 equivalent, preferably 0.01 to 0.2 equivalent.

Examples of the base to be used include metal hydroxides (e.g., sodium hydroxide, potassium hydroxide, etc.), metal carbonates (e.g., sodium carbonate, potassium carbonate, etc.), metal alkoxides (e.g., sodium methoxide, sodium ethoxide, potassium tert-butoxide, etc.), etc. The amount of the base to be used is 1 equivalent or more, preferably 1 to 2 equivalents.

Examples of the solvent to be used include N,N-dimethylformamide (DMF), dimethyl sulfoxide (DMSO), aromatic hydrocarbons (e.g., toluene, benzene, xylene, etc.), saturated hydrocarbons (e.g., cyclohexane, hexane, etc.), halogenated hydrocarbons (e.g., dichloromethane, 1,2-dichloroethane, etc.), ethers (e.g., THF, dioxane, etc.), ketones (e.g., acetone, methyl ethyl ketone, etc.), nitrites (e.g., acetonitrile, etc.), water, mixed solvents thereof, etc.

The reaction temperature is −30° C. to 150° C., preferably −10° C. to 100° C. The reaction time varies with the kind of compound, and is 0.5 to 80 hours.

The compound (XXVIIIa) thus obtained can be used in the next step as the reaction mixture or the crude product, or after purifying it by a conventional method (e.g., chromatography, recrystallization, etc.).

The compound (XXXIX) which can be used as the starting material in Scheme 31 described above can also be prepared according to the following Route 16.

Route 16

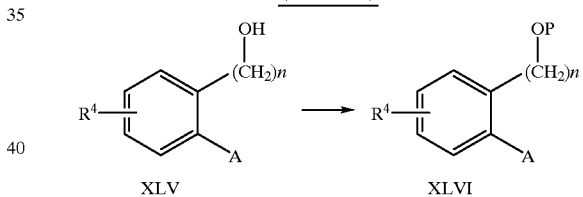

wherein P is a protective group of a hydroxyl group, and the other symbols are as defined above.

The compound (XLVI) can be prepared by protecting the hydroxyl group of the commercially available compound (XLV) with an appropriate protective group.

The hydroxyl group can be protected with a group represented by P by a conventional method for protecting a hydroxyl group described in, for example, T. W. Green, "Protective Groups in Organic Synthesis", p. 1–113, John Willy & Sons (1981); C. B. Reese, "Protective Groups in Organic Chemistry", J. F. McOmie (ed.), p.95–143, Plenum Press (1973), etc.

For example, the compounds (XLVI) protected with tetrahydropyranyl, tetrahydrothiopyranyl, tetrahydrofuranyl, tetrahydrothiofuranyl, 1-ethoxyethyl and 1-methyl-1-methoxyethyl can be prepared by reacting the compound (XLV) with the corresponding olefins in the presence of an acid catalyst in an appropriate solvent or in the absence of a solvent.

The corresponding olefins are 3,4-dihydro-2H-pyran, 2,3-dihydro-4H-thiin, dihydrofuran, dihydrothiofuran, ethyl vinyl ether, and 2-methoxypropene, respectively, and they are commercially available or can be prepared by known methods.

The amount of the olefin to be used is 1 to 3 equivalents, preferably 1 to 2 equivalents, based on the compound (XLV).

Examples of the acid catalyst include hydrogen chloride, phosphorus oxychloride, p-toluenesulfonic acid, p-toluenesulfonic acid pyridine salt, montmorillonite, bistrimethyl sulfate, acetic acid, p-toluenesulfonic acid polyvinyl pyridinium, trifluoroacetic acid, boron trifluoride etherate ($BF_3.OEt_2$) and acidic ion-exchange resins, etc.

When a solvent is used, non-alcoholic solvents can be used. Examples of the solvent include hydrocarbons (e.g., benzene, toluene, xylene, etc.), halogenated hydrocarbons (e.g., chloroform, dichloromethane, etc.), ethers (e.g., diethyl ether, tetrahydrofuran, dioxane, etc.), esters (e.g., ethyl acetate, etc.), N,N-dimethylformamide, mixed solvents thereof, etc.

The reaction temperature is −30° C. to 100° C., preferably 0° C. to 60° C. The reaction time is normally 15 minutes to 24 hours.

The compound (XLVI) protected with a silyl enol type protective group can be obtained by reacting the compound (XLV) with an appropriate silylating agent. In general, it can be obtained by reacting the compound (XLV) with chlorosilane in the presence of a base in an appropriate solvent.

Chlorosilane is commercially available or can be prepared by a known method.

The amount of the chlorosilane to be used is 1 to 5 equivalents, preferably 1 to 2 equivalents, based on the compound (XLV).

Examples of the base to be used include organic bases (e.g., N,N-dimethylaniline, pyridine, triethylamine, imidazole, etc.), metal carbonates (e.g., sodium carbonate, potassium carbonate, etc.), metal hydrides (e.g., sodium hydride, potassium hydride, etc.), metal bicarbonates (e.g., sodium bicarbonate, potassium bicarbonate, etc.), etc. The amount of the base to be used is 1 equivalent or more, preferably 1 to 2 equivalents.

Examples of the solvent to be used include hydrocarbons (e.g., hexane, benzene, toluene, xylene, etc.), halogenated hydrocarbons (e.g., chloroform, dichloromethane, etc.), ethers (e.g., diethyl ether, tetrahydrofuran, dioxane, etc.), ketones (e.g., acetone, methyl ethyl ketone, etc.), nitriles (e.g., acetonitrile, etc.), N,N-dimethylformamide, dimethyl sulfoxide, mixed solvents thereof, etc.

The reaction temperature is −20° C. to 100° C., preferably 0° C. to 60° C.

The reaction time is 5 minutes to 30 hours, preferably 30 minutes to 15 hours.

The compound (XLVI) protected with methoxymethyl or triphenylmethyl and the compound (XLVI) protected with tetrahydrofuranyl or 1-ethoxyethyl described above can be obtained by reacting the compound (XLV) with the corresponding halide in the presence of a base.

The corresponding halides are halomethyl methyl ether, triphenylmethyl halide, 2-halotetrahydrofuran and 1-haloethyl ether, respectively, and they are commercially available or can be prepared by a known method.

Examples of the halide to be used include chlorides, and bromides.

The amount of the halide to be used, the kind of base and solvent, and the reaction conditions, etc., are similar to those in the above reaction of the compound (XLV) with chlorosilane.

Alternatively, the compound (XLVI) protected with methoxymethyl described above can also be obtained by reacting the compound (XLV) with dimethoxymethane in the presence of an appropriate catalyst (e.g., phosphorus pentaoxide, etc.).

The solvent to be used and the reaction conditions are similar to those in the reaction of the compound (XLV) with olefin.

The compound (XLVI) thus obtained can be used in the next step as the reaction mixture or the crude product, or after purifying it by a conventional method (e.g., chromatography, recrystallization, etc.).

Route 16 (continued)

(Scheme 39)

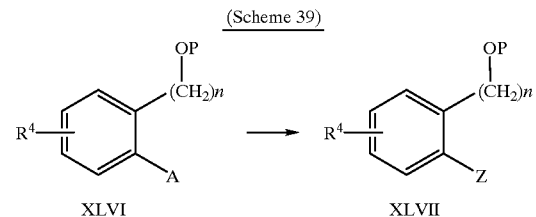

wherein each symbol is as defined above.

The compound (XLVII) can be prepared by reacting the compound (XLVI) with lithium or magnesium in an appropriate solvent.

The amount of the lithium or magnesium to be used is 1 to 4 equivalents, preferably 1 to 2 equivalents, based on the compound (XLVI).

Examples of the solvent to be used include ethers such as dry THF, diethyl ether, dibutyl ether, etc. These solvents can be used alone or as mixtures with other solvents such as hydrocarbons (e.g., toluene, etc.), amines (e.g., triethylamine, etc.), etc.

The reaction temperature is room temperature to 150° C., preferably 40° C. to 100° C.

The reaction time is 10 minutes to 48 hours, preferably 30 minutes to 6 hours.

If necessary, as a reaction activating agent, a small amount of iodine, dibromoethane, ethyl bromide, etc., can be used. The amount thereof is 0.001 to 0.4 equivalent, preferably 0.005 to 0.2 equivalent.

The compound (XLVII) thus obtained can be used in the next step as the reaction mixture or the crude product.

Route 16 (continued)

(Scheme 40)

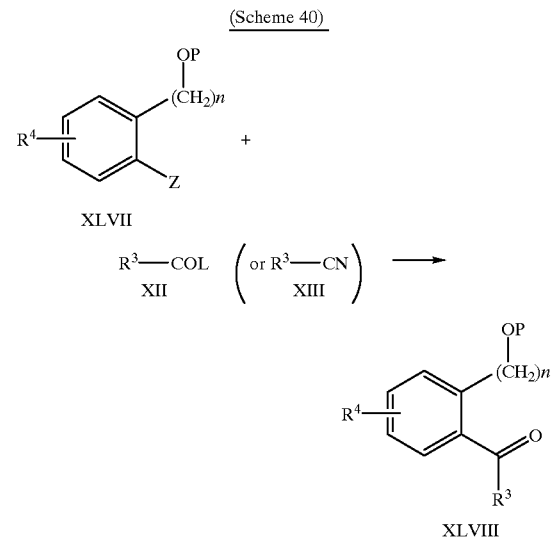

wherein each symbol is as defined above.

The compound of the formula (XLVIII) can be prepared by reacting the compound (XLVII) with the compound (XII) or (XIII) in an appropriate solvent (alone or as a mixture).

The amount of the compound (XII) or (XIII) to be used in this reaction is 1 equivalent or more, preferably 1 to 3 equivalents, based on the compound (XLVII).

Examples of the solvent to be used is aromatic hydrocarbons (e.g., toluene, benzene, xylene, etc.), saturated hydrocarbons (e.g., cyclohexane, hexane, etc.), ethers (e.g., THF, diethyl ether, dioxane, etc.), triethylamine, mixed solvents thereof, etc.

The reaction temperature is −100° C. to 100° C., preferably −80° C. to 40° C.

The reaction time varies with the kind of compound, and is 0.5 to 80 hours.

The compound (XLVIII) thus obtained can be used in the next step as the crude product, or after purifying it by a conventional method (e.g., chromatography, recrystallization, etc.).

Route 16 (continued)

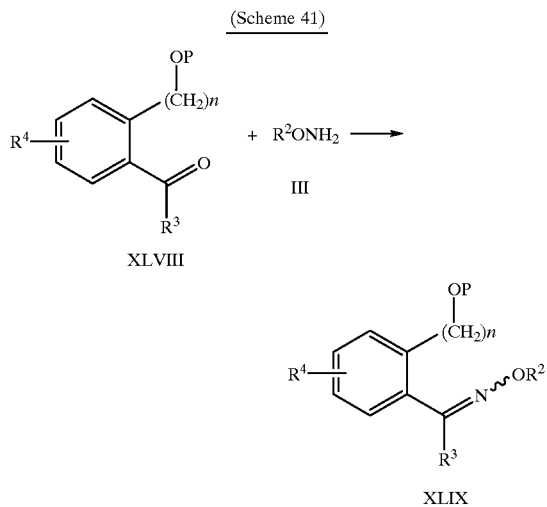

wherein each symbol is as defined above.

The compound (XLIX) can be prepared by reacting the compound (XLVIII) with the compound (III) or a salt thereof in an appropriate solvent.

The amount of the compound (III) to be used is 1 to 4 equivalents, preferably 1 to 2.5 equivalents, based on the compound (XLVIII).

Examples of the salt of the compound (III) include mineral acid salts such as a hydrochloric acid salt, sulfuric acid salt, etc. When the salt is used, it is neutralized with a base for the reaction. Examples of the base to be used include metal hydroxides (e.g., sodium hydroxide, potassium hydroxide, etc.), metal carbonates (e.g., sodium carbonate, potassium carbonate, etc.), metal alkoxides (e.g., sodium methoxide, sodium ethoxide, etc.), etc. The amount of the base to be used is 1 to 3 equivalents, preferably 1 to 2 equivalents, based on the compound (III).

Examples of the solvent to be used is hydrocarbons (e.g., benzene, toluene, xylene, etc.), halogenated hydrocarbons (e.g., chloroform, 1,2-dichloroethane, etc.), ethers (e.g., tetrahydrofuran, dioxane, etc.), alcohols (e.g., methanol, ethanol, n-propanol, isopropanol, etc.), water, mixed solvents thereof, etc.

The reaction temperature is 0° C. to 150° C., preferably 20° C. to 100° C.

The reaction time is normally 15 minutes to 24 hours.

The compound (XLIX) thus obtained can be used in the next step as the reaction mixture or crude product, or after purifying it by a conventional method (e.g., chromatography, recrystallization, etc.).

Route 16 (continued)

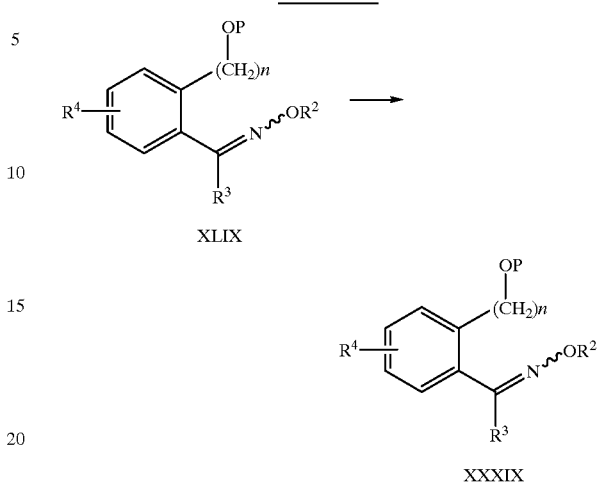

wherein each symbol is as defined above.

The compound (XXXIX) can be obtained by deprotecting the protective group of the hydroxyl group of the compound (XLIX).

The hydroxyl group can be deprotected by a conventional method for deprotecting a protected hydroxyl group described in, e.g., T. W. Green, "Protective Groups in Organic Synthesis", p. 1–113, John Willy & Sons (1981); C. B. Reese, "Protective Groups in Organic Chemistry", J. F. McOmie (ed.), p.95–143, Plenum Press (1973).

For example, the deprotection can be carried out by treating the compound (XLIX) with an acid when the protective group of the hydroxyl group is alkyl (e.g., t-butyl, etc.), alkenyl (e.g., allyl, etc.), aralkyl (e.g., triphenylmethyl, etc.), trialkylsilyl (e.g., t-butyldimethylsilyl, triisopropylsilyl, etc.), alkyldiarylsilyl (e.g., t-butyldiphenylsilyl, etc.), triaralkylsilyl (e.g., tribenzylsilyl, etc.), alkoxyalkyl (e.g., methoxymethyl, 1-ethoxyethyl, 1-methyl-1-methoxyethyl, etc.), alkoxyalkoxyalkyl (e.g., methoxyethoxymethyl, etc.), alkylthioalkyl (e.g., methylthiomethyl, etc.), tetrahydropyranyl (e.g., tetrahydropyran-2-yl, 4-methoxytetrahydropyran-4-yl, etc.), tetrahydrothiopyranyl (e.g., tetrahydrothiopyran-2-yl, etc.), tetrahydrofuranyl (e.g., tetrahydrofuran-2-yl, etc.), tetrahydrothiofuranyl (e.g., tetrahydrothiofuran-2-yl, etc.), aralkyloxyalkyl (e.g., benzyloxymethyl, etc.), etc.

In general, the acid to be used includes, for example, inorganic acids such as hydrohalogenic acids (e.g., hydrochloric acid, hydrobromic acid, hydroiodic acid, etc.) hydrogen halides (e.g., hydrogen chloride, hydrogen bromide, hydrogen iodide, etc.), boric acid, phosphoric acid, sulfuric acid, etc., sulfonic acids (e.g., aliphatic sulfonic acids such as trifluoromethanesulfonic acid, etc., and aromatic sulfonic acids such as toluenesulfonic acid, etc.), carboxylic acids (e.g., acetic acid, trifluoroacetic acid, etc.), silica gel, Lewis acids [e.g., aluminium halides (e.g., aluminium chloride, etc.), zinc chloride, titanium tetrachloride, etc.], etc. One or more suitable acids can be selected from these acids to use them in the reaction.

The amount of the acid to be used is a trace amount to 1 equivalent. Alternatively, a carboxylic acid can be used as a solvent.

Examples of the solvent to be used is hydrocarbons (e.g., benzene, toluene, xylene, etc.), halogenated hydrocarbons (e.g., dichloromethane, 1,2-dichloroethane, etc.), ethers (e.g., tetrahydrofuran, dioxane, etc.), alcohols (e.g., methanol, ethanol, etc.), nitriles (e.g., acetonitrile, etc.), water, mixed solvents thereof, etc.

The reaction temperature is −80° C. to 150° C., preferably −10° C. to 80° C.

The reaction time is 1 minute to 3 hours, preferably 5 minutes to 1 hour.

When the protective group is substituted silyl, for example, the deprotection can be carried out in basic conditions (e.g., sodium hydroxide/water-containing ethanol, etc.) or in the presence of fluoride ion (e.g., n-Bu$_4$N+F−, C$_5$H$_5$N+HF−, etc.).

The compound (XXXIX) thus obtained can be used in the next step as the reaction mixture or crude product.

If necessary, the product can be purified by a conventional method (e.g., column chromatography, recrystallization, etc.).

Route 16 (continued)

(Scheme 43)

XLVIII + R$^2$ONH$_2$ →

III

XXXIX wherein each symbol is as defined above.

The compound (XXXIX) can be prepared by reacting the compound (XLVIII) with the compound (III) or a salt thereof in the presence of a base in an appropriate solvent. The amount of the compound (III) to be used is 1 to 4 equivalents, preferably 1 to 2.5 equivalents, based on the compound (XLVIII).

Examples of the salt of the compound (III) include mineral acid salts such as a hydrochloric acid salt, sulfuric acid salt, etc. When the salt is used, the salt is neutralized with a base for the reaction.

Examples of the base to be used include amines (pyridine, etc.), etc. The amount of the base to be used is 1 to 3 equivalents, preferably 1 to 2 equivalents, based on the salt of the compound (III).

Examples of the solvent to be used is hydrocarbons (e.g., benzene, toluene, xylene, etc.), halogenated hydrocarbons (e.g., chloroform, 1,2-dichloroethane, etc.), ethers (e.g., tetrahydrofuran, dioxane, etc.), alcohols (e.g., methanol, ethanol, n-propanol, isopropanol, etc.), water, mixed solvents thereof, etc.

The reaction temperature is 0° C. to 150° C., preferably 20° C. to 200° C.

The reaction time is normally 15 minutes to 24 hours.

The compound (XXXIX) thus obtained can be used in the next step as the reaction mixture or crude product, or after purifying it by a conventional method (e.g., column chromatography, recrystallization, etc.).

Route 16 (continued)

(Scheme 44)

XLVIII + HONH$_2$ →

L wherein each symbol is as defined above.

The compound (L) can be prepared by reacting the compound (XLVIII) with hydroxylamine or a salt thereof in an appropriate solvent.

The amount of the hydroxylamine to be used is 1 to 4 equivalents, preferably 1 to 2.5 equivalents, based on the compound (XLVIII).

Examples of the salt of hydroxylamine include mineral acid salts such as a hydrochloric acid salt, sulfuric acid salt, etc. When the salt is used, it is neutralized with a base for the reaction. Examples of the base to be used include metal hydroxides (e.g., sodium hydroxide, potassium hydroxide, etc.), metal carbonates (e.g., sodium carbonate, potassium carbonate, etc.), metal alkoxides (e.g., sodium methoxide, sodium ethoxide, etc.), etc. The amount of the base to be used is 1 to 3 equivalents, preferably 1 to 2 equivalents, based on the salt of hydroxylamine.

Examples of the solvent to be used include hydrocarbons (e.g., benzene, toluene, xylene, etc.), halogenated hydrocarbons (e.g., chloroform, 1,2-dichloroethane, etc.), ethers (e.g., tetrahydrofuran, dioxane, etc.), alcohols (e.g., methanol, ethanol, n-propanol, isopropanol, etc.), water, mixed solvents thereof, etc.

The reaction temperature is 0° C. to 150° C., preferably 20° C. to 100° C.

The reaction time is normally 15 minutes to 24 hours.

The compound (L) thus obtained can be used in the next step as the reaction mixture or crude product, or after purifying it by a conventional method (e.g., column chromatography, recrystallization, etc.).

Route 16 (continued)

(Scheme 45)

L + R$^2$—Y →

XVII

-continued

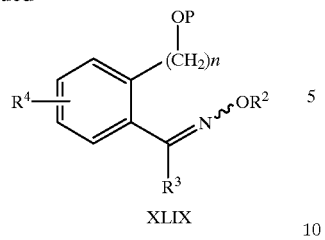

XLIX wherein each symbol is as defined above.

The compound of the formula (XLIX) can be prepared by reacting the compound (L) with the compound (XVII) in the presence of a base in an appropriate solvent (alone or as a mixture). The amount of the compound (XVII) to be used in this reaction is 1 equivalent or more, preferably 1 to 2 equivalents, based on the compound (L).

Examples of the base to be used include metal hydroxides (e.g., sodium hydroxide, potassium hydroxide, etc.), metal carbonates (e.g., sodium carbonate, potassium carbonate, etc.), metal alkoxides (e.g., sodium methoxide, sodium ethoxide, potassium tert-butoxide, etc.), etc. The amount of the base to be used is 1 equivalent or more, preferably 1 to 2 equivalents.

Examples of the solvent to be used include N,N-dimethylformamide (DMF), dimethyl sulfoxide (DMSO), aromatic hydrocarbons (e.g., toluene, benzene, xylene, etc.), saturated hydrocarbons (e.g., cyclohexane, hexane, etc.), halogenated hydrocarbons (e.g., dichloromethane, 1,2-dichloroethane, etc.), ethers (e.g., THF, dioxane, etc.), ketones (e.g., acetone, methyl ethyl ketone, etc.), nitriles (e.g., acetonitrile, etc.), water, mixed solvents thereof, etc.

The reaction temperature is −30° C. to 150° C., preferably −10° C. to 100° C.

The reaction time varies with the kind of compound, and is 0.5 to 90 hours.

The compound (XLIX) thus obtained can be used in the next step as the reaction mixture or crude product, or after purifying it by a conventional method (e.g., chromatography, recrystallization, etc.).

The compound of the formula (II) of the present invention can be prepared according to the following Route 17.

Route 17

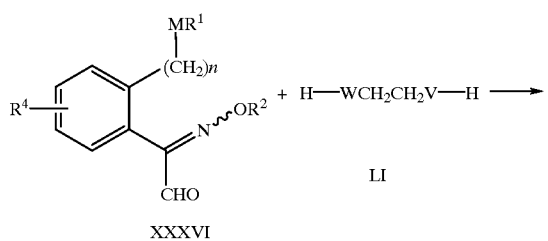

-continued

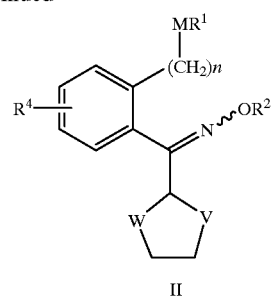

II wherein V is oxygen, sulfur or N-R$^5$, and R$^5$ and the other symbols are as defined above.

The compound of the formula (II) of the present invention can be prepared by reacting the compound (XXXVI) with the compound (LI) or a salt thereof (e.g., hydrochloric acid salt, hydrobromic acid salt, etc.) in the presence or absence of a base, or in the presence or absence of an acid, or in the presence or absence of a metal salt, in the absence of a solvent or in an appropriate solvent (alone or as a mixture) by reference to, e.g., T. W. Green, "Protective Groups in Organic Synthesis", p. 109–151, John Willy & Sons (1981).

The amount of the compound (LI) to be used in this reaction is 1 equivalent or more, preferably 1 to 5 equivalents, based on the compound (XXXVI).

Examples of the base to be used include amines (e.g., triethylamine, etc.), etc. The amount of the base to be used is 1 equivalent or more, preferably 1 to 6 equivalents, based on the compound (XXXVI).

Examples of the acid to be used include inorganic acids (e.g., hydrochloric acid, sulfuric acid, etc.) and sulfonic acids (e.g., p-toluenesulfonic acid, etc.). The amount of the acid to be used is 0.01 to 0.5 equivalent, preferably 0.02 to 0.2 equivalent, based on the compound (XXXVI).

Examples of the metal salt to be used include potassium carbonate, zinc acetate, etc. The amount of the metal salt to be used is 0.01 to 0.5 equivalent, preferably 0.02 to 0.2 equivalent, based on the compound (XXXVI).

Examples of the solvent to be used include N,N-dimethylformamide (DMF), dimethyl sulfoxide (DMSO), aromatic hydrocarbons (e.g., toluene, benzene, xylene, etc.), saturated hydrocarbons (e.g., cyclohexane, hexane, etc.), halogenated hydrocarbons (e.g., dichloromethane, 1,2-dichloroethane, etc.), ethers (e.g., THF, dioxane, etc.), alcohols (e.g., butanol, 2-methoxyethanol, ethylene glycol, glycerol, etc.), mixed solvents thereof, etc.

The reaction temperature is 20° C. to 200° C., preferably 50° C. to 160° C.

The reaction time varies with the kind of compound, and is 0.5 to 90 hours.

If necessary, the desired compound (II) thus obtained can be purified by a conventional method (e.g., chromatography, recrystallization, etc.).

The compound of the formula (Im) of the present invention can be prepared, for example, according to the following Route 18.

Route 18

(Scheme 47)

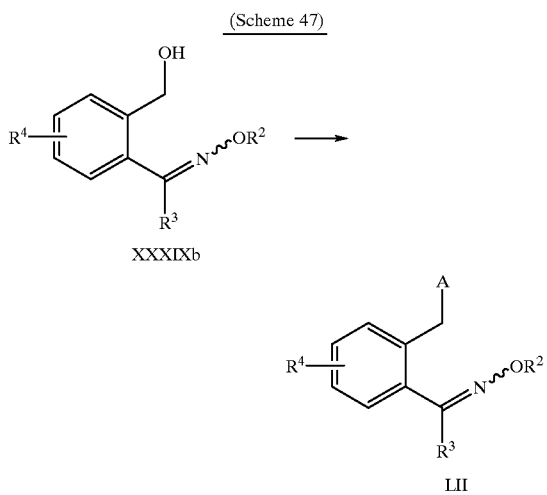

wherein each symbol is as defined above.

The compound of the formula (LII) can be prepared by reacting the compound (XXXIXb) with a halogenating agent in the absence of a solvent or in an appropriate solvent (alone or as a mixture).

Examples of the halogenating agent to be used include thionyl halides (e.g., thionyl chloride, thionyl bromide, etc.), phosphoryl halides (e.g., phosphoryl chloride, phosphoryl bromide, etc.), phosphorus halides (e.g., phosphorus pentachloride, phosphorus trichloride, phosphorus pentabromide, phosphorus tribromide, etc.), phosgene, oxalyl halides (e.g., oxalyl chloride, etc.), triphenylphosphine/carbon tetrachloride, triphenylphosphine/carbon tetrabromide, etc. The amount of the halogenating agent to be used is 1 equivalent or more.

Examples of the solvent to be used include aromatic hydrocarbons (e.g., toluene, benzene, xylene, etc.), saturated hydrocarbons (e.g., cyclohexane, hexane, etc.), halogenated hydrocarbons (e.g., dichloromethane, 1,2-dichloroethane, etc.), nitriles (e.g., acetonitrile, etc.), mixed solvents thereof, etc.

The reaction temperature is $-30°$ C. to $150°$ C., preferably $-10°$ C. to $120°$ C.

The reaction time varies with the kind of compound, and is 0.1 to 48 hours.

The compound (LII) thus obtained can be used in the next step as the crude product, or after purifying it by a conventional method (e.g., column chromatography, recrystallization, etc.).

Route 18 (continued)

(Scheme 48)

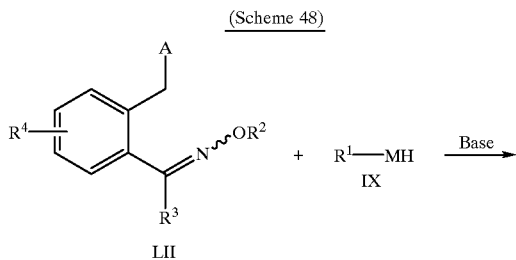

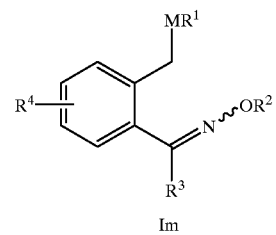

wherein each symbol is as defined above.

The compound of the formula (Im) can be prepared by reacting the compound (LII) with the compound (IX) in the presence of a base in the absence of a solvent or in an appropriate solvent (alone or as a mixture).

The amount of the compound (IX) to be used in this reaction is 1 equivalent or more based on the compound (LII).

Examples of the base to be used include metal hydroxides (e.g., sodium hydroxide, potassium hydroxide, etc.), metal carbonates (e.g., sodium carbonate, potassium carbonate, etc.), metal alkoxides (e.g., sodium methoxide, sodium ethoxide, potassium tert-butoxide, etc.), etc. The amount of the base to be used is 1 equivalent or more.

Examples of the solvent to be used include N,N-dimethylformamide (DMF), dimethyl sulfoxide (DMSO), aromatic hydrocarbons (e.g., toluene, benzene, xylene, etc.), saturated hydrocarbons (e.g., cyclohexane, hexane, etc.), halogenated hydrocarbons (e.g., dichloromethane, 1,2-dichloroethane, etc.), ethers (e.g., THF, dioxane, etc.), ketones (e.g., acetone, methyl ethyl ketone, etc.), nitrites (e.g., acetonitrile, etc.), water, mixed solvents thereof, etc.

The reaction temperature is $-30°$ C. to $150°$ C., preferably $-10°$ C. to $100°$ C. The reaction time varies with the kind of compound, and is 0.5 to 120 hours.

If necessary, the desired compound (Im) thus obtained can be purified by a conventional method (e.g., column chromatography, recrystallization, etc.).

The compound of the formula (I) of the present invention is effective against a wide variety of phytopathogenic fungi on crop plants (e.g., rice, wheat, barley, rye, corn, common millet, millet, buckwheat, soybean, redbean, peanut, etc.), fruit trees (e.g., citrus fruits, grape, apple, pear, peach, etc.), vegetables (e.g., cucumber, eggplant, tomato, pumpkin, kidney bean, etc.), etc., or seeds thereof. It is also effective against phytopathogenic fungi in soil. The compound of the present invention shows potent fungicidal activity particularly against *Pyricularia oryzae, Rhizoctonia solani, Erysinhe graminis, Sphaerotheca fuliginea, Erysiihe cichoracearum, Phytophthora infestans, Pseudoperonospora cubensis, Peronospora manshurica, Plasmopara viticola, Botrytis cinerea* of vegetables, grape, etc., *Pythium aphanidermatum, Sclerotinia sclerotiorum* of buckwheat, soybean, colza, etc., *Corticium rolfsii* of soybean, redbean, potato, peanut, etc., *Pseudocercosporella herpotrichoides*, of cereals, etc. Therefore, the compound (I) of the present invention is useful as fungicides, particularly as agricultural fungicides.

Application of the compound (I) of the present invention may be made to plants by any conventional procedure such as atomizing, scattering or spreading of the active compound. Application may also be made through treatment of seeds of plants, soil where plants grow, soil for seeding, paddy field or water for perfusion with the active compound. Application may be performed before or after the infection with phytopathogenic fungi on plants.

The compound can be used in a conventional formulation form suitable for agricultural fungicides such as solutions, wettable powders, emulsions, suspensions, concentrated liquid preparations, tablets, granules, aerosols, powders, pastes, dusts, etc.

Such formulation form can be prepared in a conventional manner by mixing at least one compound of the present invention with an appropriate solid or liquid carrier(s) and, if necessary, an appropriate adjuvant(s) (e.g., surfactants, spreaders, dispersants, stabilizers, etc.) for improving the dispersibility and other properties of the active ingredient.

Examples of the solid carriers or diluents include botanical materials (e.g., flour, tobacco stalk powder, soybean powder, walnut-shell powder, vegetable powder, saw dust, bran, bark powder, cellulose powder, vegetable extract residue, etc.), fibrous materials (e.g., paper, corrugated cardboard, old rags, etc.), artificial plastic powders, clays (e.g., kaolin, bentonite, fuller's earth, etc.), talc, other inorganic materials (e.g., pyrophyllite, sericite, pumice, sulfur powder, active carbon, etc.), chemical fertilizers (e.g., ammonium sulfate, ammonium phosphate, ammonium nitrate, urea, ammonium chloride, etc.), etc.

Examples of the liquid carriers or diluents include water, alcohols (e.g., methanol, ethanol, etc.), ketones (e.g., acetone, ethyl methyl ketone, etc.), ethers (e.g., diethyl ether, dioxane, cellosolve, tetrahydrofuran, etc.), aromatic hydrocarbons (e.g., benzene, toluene, xylene, methylnaphthalene, etc.), aliphatic hydrocarbons (e.g., gasoline, kerosene, lamp oil, etc.), esters, nitrites, acid amides (e.g., N,N-dimethylformamide, N,N-dimethylacetamide, etc.), halogenated hydrocarbons (e.g., dichloroethane, carbon tetrachloride, etc.), etc.

Examples of the surfactants include alkyl sulfates, alkyl sulfonates, alkylaryl sulfonates, polyethylene glycol ethers, polyhydric alcohol esters, etc.

Examples of the spreaders or dispersants include casein, gelatin, starch powder, carboxymethyl cellulose, gum arabic, alginic acid, lignin, bentonite, molasses, polyvinyl alcohol, pine oil, agar, etc.

Examples of the stabilizers include PAP (a mixture of isopropylphosphate), tricresyl phosphate (TCP), tolu oil, epoxidized oil, surfactants, fatty acids and their esters, etc.

The composition of the present invention may contain other fungicides, insecticides, herbicides or fertilizers in addition to the above ingredients.

In general, the above composition contains at least one compound of the formula (I) of the present invention in a concentration of 0.1 to 95% by weight, preferably 1.0 to 80% by weight. The composition can be used as such or in a diluted form. About 1 g to 5.0 kg/hectare, preferably about 10 g to 10 kg/hectare, of the compound of the present invention is used in a concentration of normally about 1 to 5,000 ppm, preferably about 10 to 1,000 ppm.

EXAMPLES

The following Examples and Test Examples further illustrate the present invention in detail, but are not to be construed to limit the scope thereof. The $^1$H-NMR (CDCl$_3$) data in Examples were determined at 270 MHz in CDCl$_3$ using tetramethylsilane as an internal standard and indicated in δ values (ppm). The coupling constants (J) are indicated in Hz. In the data, s is a singlet, d is a doublet, t is a triplet, q is a quartet, m is a multiplet, brs is a broad singlet.

Example 1

Synthesis of α-ethoxyimino-2-phenoxymethylbenzyl chloride

Dichloroethane (50 ml), thionyl chloride (6.54 g, 0.055 mol) and N,N-dimethylformamide (0.25 ml) were added to 2-phenoxymethylbenzoic acid (11.41 g, 0.05 mol), and the mixture was stirred at 80° C. for 2 hours. After completion of the reaction, the mixture was concentrated under reduced pressure, and the residue was dissolved in dichloromethane (25 ml). The solution was added to a mixture of ethoxyamine hydrochloride (5.85 g, 0.06 mol), pyridine (9.89 g, 0.125 mol) and dry dichloromethane (50 ml) under ice-cooling over 20 minutes, and then the resulting mixture was stirred at room temperature for 2 hours. After completion of the reaction, water (200 ml) was added, adjusted to pH<2 with conc. hydrochloric acid, and extracted with dichloromethane. The dichloromethane layer was dried over anhydrous magnesium sulfate and concentrated under reduced pressure. Acetonitrile (150 ml), triphenylphosphine (20.98 g, 0.08 mol) and carbon tetrachloride (24.61 g, 0.16 mol) were added to the residue, and the mixture was stirred under reflux for 1.5 hours. After completion of the reaction, the mixture was concentrated under reduced pressure, and the residue was purified by silica gel chromatography (ethyl acetate/n-hexane) to give α-ethoxyimino-2-phenoxymethylbenzyl chloride (13.51 g, 93.2%) as a colorless oil.

$^1$H-NMR(CDCl$_3$) δ ppm: 3.14(3H,t,J=6.7), 4.27(2H,q,J=6.7), 5.28(2H,s), 6.93–7.70(9H,m).

Synthesis of 1-(α-ethoxyimino-2-phenoxymethylbenzyl)-1H-1,2,4-triazole

N,N-Dimethylformamide (3 ml) and 60% sodium hydride (0.12 g, 3 mmol) were added to 1H-1,2,4-triazole (0.20 g, 3 mmol), and the mixture was stirred at room temperature for 10 minutes. Then α-ethoxyimno-2-phenoxymethylbenzyl chloride (0.43 g, 1.5 mmol) was added, and the mixture was stirred at 120° C. for 5 hours. After completion of the reaction, ether (100 ml) was added, and the mixture was washed with brine (80 ml) twice. The ether layer was dried over anhydrous magnesium sulfate and concentrated under reduced pressure. The residue was purified by silica gel chromatography (ethyl acetate/n-hexane) and recrystallized from ethyl acetate/n-hexane to give 1-(α-ethoxyimino-2-phenoxymethylbenzyl)-1H-1,2,4-triazole (0.42 g, 86.9%) as colorless crystals. mp. 78.5–80.5° C.

$^1$H-NMR(CDCl$_3$) δ ppm: 1.35(3H,t,J=6.7), 4.30 (2H,q,J=6.7), 4.93(2H,s), 6.76–7.55(9H,m), 7.94(1H,s), 9.14(1H,s).

Example 2

Synthesis of 2-chloromethyl-α-methoxyiminobenzyl chloride

2-Chloromethylbenzoyl chloride (18.90 g, 0.1 mol) was dissolved in dichloromethane (50 ml). The solution was added to a mixture of methoxyamine hydrochloride (12.53 g, 0.15 mol), pyridine (19.78 g, 0.25 mol) and dry dichloromethane (150 ml) under ice-cooling over 1 hour, and then the resulting mixture was stirred at 0° C. for 2 hours. After completion of the reaction, water (300 ml) was added, adjusted to pH<2 with conc. hydrochloric acid, and extracted with dichloromethane. The dichloromethane layer was dried over anhydrous magnesium sulfate and concentrated under reduced pressure. The residue was dissolved in dichloromethane (200 ml), and phosphorus pentachloride (20.82 g, 0.1 mol) was added under ice-cooling over 5 minutes. The mixture was stirred at 0° C. for 1 hour. After completion of the reaction, saturated aqueous sodium bicarbonate solution (400 ml) was added, and the mixture was extracted with dichloromethane. The dichloromethane layer was dried over anhydrous magnesium sulfate, concentrated under reduced pressure, and the residue was purified by silica gel chromatography (ethyl acetate/n-hexane) to give 2-chloromethyl-α-methoxyiminobenzyl chloride (18.15 g, 83.2%) as a colorless oil.

$^1$H-NMR(CDCl$_3$) δ ppm: 4.12 (3H,s), 4.83(2H,s), 7.40–7.62(4H,m).

Synthesis of 2-(3-chlorophenoxymethyl)-α-methoxyiminobenzyl chloride

3-Chlorophenol (3.09 g, 0.024 mol), N,N-dimethylformamide (20 ml) and potassium carbonate (4.15 g, 0.03 mol) were added to 2-chloromethyl-(α-methoxyiminobenzyl chloride (4.36 g, 0.02 mol), and the mixture was stirred at room temperature for 4 days. After completion of the reaction, ether (250 ml) was added, and the mixture was washed with brine (200 ml) twice. The ether layer was dried over anhydrous magnesium sulfate and concentrated under reduced pressure. The residue was purified by silica gel chromatography (ethyl acetate/n-hexane) to give 2-(3-chlorophenoxymethyl)-α-methoxyiminobenzyl chloride (5.66 g, 91.2%) as a colorless oil.

$^1$H-NMR(CDCl$_3$) δ ppm: 4.02 (3H,s), 5.25(2H,s), 6.80–7.70(8H,m).

Synthesis of 1-[2-(3-chlorophenoxymethyl)-α-methoxy-iminobenzyl]imidazole

N,N-Dimethylformamide (3 ml) and 60% sodium hydride (0.16 g, 3.9 mmol) were added to imidazole (0.27 g, 3.9 mmol), and the mixture was stirred at room temperature for 10 minutes. Then, 2-(3-chlorophenoxymethyl)-α-methoxyiminobenzyl chloride (0.40 g, 1.3 mmol) was added, and the mixture was stirred at 110° C. for 2 hours. After completion of the reaction, ether (100 ml) was added, and the mixture was washed with brine (80 ml) twice. The ether layer was dried over anhydrous magnesium sulfate and concentrated under reduced pressure. The residue was purified by silica gel chromatography (ethyl acetate/n-hexane) and recrystallized from ethyl acetate/n-hexane to give 1-[2-(3-chlorophenoxymethyl)-α-methoxyiminobenzyl] imidazole (0.29 g, 65.3%) as colorless crystals. mp. 96.5–97.5° C.

$^1$H-NMR(CDCl$_3$) δ ppm: 3.97(3H,s), 5.00(2H,s), 6.63–7.60(10H,m), 7.98(1H,s).

According to the same manner as that of the synthesis of the intermediate in Example 1 or 2, various compounds of the formula (V) of the present invention, which are intermediates for production of the compound (I), were synthesized. The compounds thus obtained and their physical data are as follows. In the following tables, the physical data of the compounds obtained in Examples 1 and 2 are also listed.

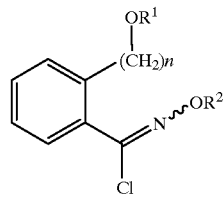

| No | R$^1$ | R$^2$ | n | Physical data |
|---|---|---|---|---|
| V-1 | C$_6$H$_5$ | Me | 0 | $^1$H-NMR(CDCl$_3$) δ ppm: 4.02(3H, s), 6.94–7.55(9H, m) |
| V-2 | C$_6$H$_5$ | Me | 1 | $^1$H-NMR(CDCl$_3$) δ ppm: 4.02(3H, s), 5.28(2H, s), 6.93-7.69(9H, m) |
| V-3 | C$_6$H$_5$ | Et | 1 | $^1$H-NMR(CDCl$_3$) δ ppm: 1.34(3H, t, J=6.7), 4.27(2H, q, J=6.7), 5.28(2H, s), 6.93–7.70(9H, m) |
| V-4 | C$_6$H$_5$ | Allyl | 1 | $^1$H-NMR(CDCl$_3$) δ ppm: 4.69–4.72(2H, m), 5.24–5.38(2H, m), 5.25(2H, s), 5.94–6.08(1H, m), 6.93–7.71(9H, m) |
| V-5 | 2-Cl—C$_6$H$_4$ | Me | 1 | $^1$H-NMR(CDCl$_3$) δ ppm: 4.07(3H, s), 5.37(2H, s), 6.88–7.79(8H, m) |
| V-6 | 3-Cl—C$_6$H$_4$ | Me | 1 | $^1$H-NMR(CDCl$_3$) δ ppm: 4.02(3H, s), 5.25(2H, s), 6.80–7.70(8H, m) |
| V-7 | 4-Cl—C$_6$H$_4$ | Me | 1 | $^1$H-NMR(CDCl$_3$) δ ppm: 4.01(3H, s), 5.24(2H, s), 6.85–7.70(8H, m) |
| V-8 | 2-Me—C$_6$H$_4$ | Me | 1 | $^1$H-NMR(CDCl$_3$) δ ppm: 2.30(3H, s), 4.03(3H, s), 5.23(2H, s), 6.80–7.70(8H, m) |
| V-9 | 4-Me—C$_6$H$_4$ | Me | 1 | $^1$H-NMR(CDCl$_3$) δ ppm: 2.28(3H, s), 4.03(3H, s), 5.25(2H, s), 6.84(2H, d, J=8.5), 7.08(2H, d, J=8.5) |
| V-10 | 2-Et—C$_6$H$_4$ | Me | 1 | $^1$H-NMR(CDCl$_3$) δ ppm: 1.24(3H, t, J=7.3), 2.73(2H, q, J=7.3), 4.05(3H, s), 5.29(2H, s), 6.81–7.70(8H, m) |
| V-11 | 2,5-Me$_2$—C$_6$H$_3$ | Me | 1 | $^1$H-NMR(CDCl$_3$) δ ppm: 2.25(3H, s), 2.30(3H, s), 4.05(3H, s), 5.26(2H, s), 6.65–7.70(7H, m) |
| V-12 | 2,6-Me$_2$—C$_6$H$_3$ | Me | 1 | $^1$H-NMR(CDCl$_3$) δ ppm: 2.28(6H, s), 4.02(3H, s), 5.02(2H, s), 6.93–7.62(6H, m), 7.90(1H, d, J=7.9) |
| V-13 | 2-Cl-pyridin-3-yl | Me | 1 | mp 65–66° C. |

Example 3

Synthesis of 2-(2,5-dimethylphenoxymethyl)phenyl 3-methylisoxazol-5-yl ketone THF (2 ml) and bromoethane (0.1 ml) were added to magnesium (0.49 g, 0.02 mol) in a stream of nitrogen, and the mixture was stirred at 50° C. for 10 minutes. Then, a mixture of 1-bromo-2-(2,5-dimethylphenoxymethyl) benzene (2.91 g, 0.01 mol) and THF (8 ml) was added at 50 to 60° C. over 30 minutes, and the mixture was stirred at 50 to 60° C. for 1 hour. After completion of the reaction, the reaction mixture was added to a mixture of 3-methylisoxazol-5-carbonyl chloride (1.45 g, 0.01 mol) and THF (15 ml) at −70 to −60° C. over 15 minutes, and then the mixture was stirred at −70 to −60° C. for 0.5 hours. After completion of the reaction, saturated aqueous ammonium chloride solution (150 ml) was added, and the mixture was extracted with ether. The ether layer was dried over anhydrous magnesium sulfate and concentrated under reduced pressure, and the residue was purified by silica gel chromatography (ethyl acetate/n-hexane) and recrystallized from n-hexane to give 2-(2,5-dimethylphenoxymethyl)phenyl 3-methylisoxazol-5-yl ketone (0.56 g, 17.4%) as colorless crystals. mp. 106–108° C.

$^1$H-NMR(CDCl$_3$) δ ppm: 2.13(3H,s), 2.28(3H,s), 2.38 (3H,s), 5.28(2H,s), 6.66(1H,s), 6.67(1H,d,J=6.7), 6.72(1H, s), 7.00(1H,d,J=7.9), 7.46–7.83(4H,m).

Synthesis of 2-(2,5-dimethylphenoxymethyl)phenyl 3-methylisoxazol-5-yl ketone O-methyloxime n-Propanol (2 ml) and methoxyamine hydrochloride (0.25 g, 3 mmol) were added to 2-(2,5-dimethylphenoxymethyl) phenyl 3-methylisoxazol-5-yl ketone (0.33 g, 1 mmol), and the mixture was stirred under reflux for 15 hours. After completion of the reaction, water (200 ml) was added, the mixture was extracted with dichloromethane. The dichloromethane layer was dried over anhydrous magnesium sulfate and concentrated under reduced pressure, and the residue was purified by silica gel chromatography (ethyl acetate/ n-hexane) to give isomer A (0.18 g, 51.4%, as colorless crystals) and isomer B (0.15 g, 42.8%, as colorless crystals) of 2-(2,5-dimethylphenoxymethyl)phenyl 3-methylisoxazol-5-yl ketone O-methyloxime. One of the isomers A and B is the E-isomer and the other is Z-isomer.

Isomer A: mp. 113–114° C.

$^1$H-NMR(CDCl$_3$) δ ppm: 2.11(3H,s), 2.25(3H,s) 2.33(3H, s), 4.12(3H,s), 4.98(2H,s), 6.51(1H,s), 6.64(1H,d,J=7.3), 6.91(1H,s), 6.97(1H,d,J=7.3), 7.38–7.62(4H,m).

Isomer B: mp. 107–108° C.

$^1$H-NMR(CDCl$_3$) δ ppm: 2.13(3H,s), 2.24(3H,s), 2.26 (3H,s), 4.04(3H,s), 4.93(2H,s), 5.99(1H,s), 6.53(1H,s), 6.65 (1H,d,J=7.9), 6.99(1H,d,J=7.3), 7.21–7.52(3H,m), 7.68(1H, d,J=7.9).

Example 4

Synthesis of 2-(2,5-dimethylphenoxymethyl)phenyl isoxazol-3-yl ketone

THF (2 ml) and bromoethane (0.1 ml) were added to magnesium (0.49 g, 0.02 mol) in a stream of nitrogen, and the mixture was stirred at 50° C. for 10 minutes. Then, a mixture of 1-bromo-2-(2,5-dimethylphenoxymethyl) benzene (2.91 g, 0.01 mol) and THF (8 ml) was added at 50 to 60° C. over 30 minutes, and the mixture was stirred at 50 to 60° C. for 1 hour. After completion of the reaction, the reaction mixture was added to a mixture of 3-cyanoisoxazole (1.45 g, 0.015 mol) and THF (15 ml) at 20° C. or lower over 15 minutes, and then the mixture was stirred at room temperature for 2 hours. After completion of the reaction, 2N sulfuric acid (200 ml) was added, and the mixture was extracted with ether. The ether layer was dried over anhydrous magnesium sulfate and concentrated under reduced pressure, and the residue was purified by silica gel chromatography (ethyl acetate/n-hexane) and recrystallized from n-hexane to give 2-(2,5-dimethylphenoxymethyl) phenyl isoxazol-3-yl ketone (0.20 g, 6.3%) as colorless crystals. mp. 90.5–92° C.

$^1$H-NMR(CDCl$_3$) δ ppm: 2.16(3H,s), 2.29(3H,s) 5.32 (2H,s), 6.66(1H,s), 6.67(1H,d,J=6.7), 6.86(1H,d,J=1.2), 7.00(1H,d,J=7.3), 7.47(1H,t,J=7.3), 7.60–8.03(3H,m), 8.50 (1H,d,J=1.8).

Synthesis of 2-(2,5-dimethylphenoxymethyl)phenyl isoxazol-3-yl ketone O-methyloxime n-Propanol (2 ml) and methoxyamine hydrochloride (0.50 g, 6 mmol) were added to 2-(2,5-dimethylphenoxymethyl) phenyl isoxazol-3-yl ketone (0.64 g, 2 mmol), and the mixture was stirred under reflux for 17 hours. After completion of the reaction, water (100 ml) was added, the mixture was extracted with dichloromethane. The dichloromethane layer was dried over anhydrous magnesium sulfate and concentrated under reduced pressure, and the residue was purified by silica gel chromatography (benzene/n-hexane) to give 2-(2,5-dimethylphenoxymethyl)phenyl isoxazol-3-yl ketone O-methyloxime (a mixture of isomers A/B) (0.55 g, 81.8%) as colorless crystals. mp. 104–108° C.

$^1$H-NMR(CDCl$_3$) δ ppm: 2.13(2.15) (3H,s) 2.23(2.25) (3H,s), 4.01(4.08)(3H,s), 4.95(5.01)(2H,s), 6.52–7.00(4H, m), 7.29–7.64(4H,m), 8.39(8.45)(1H,d,J=1.8).

Example 5

Synthesis of 2-(2,5-dimethylphenoxymethyl)phenyl 1-methylpyrazol-5-yl ketone

Dichloroethane (20 ml), thionyl chloride (1.31 g, 0.011 mol) and N,N,-dimethylformamide (0.1 ml) were added to 2-(2,5-dimethylphenoxymethyl)benzoic acid (2.56 g, 0.01 mol), and the mixture was stirred under reflux for 2 hours. After completion of the reaction, the reaction mixture was concentrated under reduced pressure to give crude 2-(2,5-dimethylphenoxymethyl)benzoyl chloride. 1.6M n-butyllithium/n-hexane solution (6.25 ml, 0.01 mol) was added to a mixture of 1-methylpyrazole (0.99 g, 0.012 mol) and THF (10 ml) at −70 to −60° C. over 15 minutes, and then the mixture was stirred at −70° C. to room temperature for 1 hour. The reaction mixture was cooled to −70° C., and a solution of the crude 2-(2,5-dimethylphenoxymethyl) benzoyl chloride in THF (10 ml) was added, and the mixture was stirred at −70° C. for 1 hour. After completion of the reaction, IN hydrochloric acid (100 ml) was added, and the mixture was extracted with ether. The ether layer was dried over anhydrous magnesium sulfate and concentrated under reduced pressure, and the residue was purified by silica gel chromatography (ethyl acetate/n-hexane) to give 2-(2,5-dimethylphenoxymethyl)phenyl 1-methylpyrazol-5-yl ketone (0.50 g, 15.6%) as colorless crystals.

mp. 88–89° C.

$^1$H-NMR(CDCl$_3$) δ ppm: 2.04(3H,s), 2.28(3H,s), 4.22 (3H,s), 5.23(2H,s), 6.50(1H,d,J=2.4), 6.65(1H,s), 6.66(1H, d,J=6.7), 6.97(1H,d,J=7.3), 7.38–7.76(4H,m).

Synthesis of 2-(2,5-dimethylphenoxymethyl)phenyl 1-methylpyrazol-5-yl ketone O-ethyloxime n-Propanol (2 ml) and ethoxyamine hydrochloride (0.18 g, 1.8 mmol) were added to 2-(2,5-dimethylphenoxymethyl) phenyl 1-methylpyrazol-5-yl ketone (0.20 g, 0.6 mmol), and the mixture was stirred under reflux for 3 days. After completion of the reaction, water (100 ml) was added, and the mixture was extracted with dichloromethane. The dichloromethane layer was dried over anhydrous magnesium sulfate and concentrated under reduced pressure, and the residue was purified by silica gel chromatography (ethyl acetate/n-hexane) to give isomer A (0.11 g, 50.4%, as colorless crystals) and isomer B (0.10 g, 45.9%, as colorless crystals) of 2-(2,5-dimethylphenoxymethyl)phenyl 1-methylpyrazol-5-yl ketone O-ethyloxime.

Isomer A: mp. 74–76° C.

$^1$H-NMR(CDCl$_3$) δ ppm: 1.30(3H,t,J=7.3), 2.13(3H,s), 2.23(3H,s), 4.13(3H,s), 4.24(2H,q,J=7.3), 4.95(2H,s), 5.92(1H,d,J=2.4), 6.51(1H,s), 6.64(1H,d,J=7.9), 6.99(1H,d,J=7.3), 7.17–7.64(5H,m).

Isomer B: mp. 84–86° C.

$^1$H-NMR(CDCl$_3$) δ ppm: 1.33(3H,t,J=6.7), 2.23(3H,s) 2.29(3H,s), 3.68(3H,s), 4.29(2H,q,J=6.7), 5.14(2H,s), 6.30(1H,d,J=1.8), 6.58(1H,s), 6.68(1H,d,J=7.3), 7.03(1H,d,J=7.3), 7.16–7.47(3H,m), 7.52(1H,d,J=1.8), 7.73(1H,d,J=7.9).

According to the same manner as that of the syntheses of the intermediates in Examples 3 to 5, various compounds of the formula (XIV) of the present invention, which are intermediates for production of the compound (I), were synthesized. The compounds thus obtained and their physical data are as follows. In the following tables, the physical data of the compounds obtained in Examples 3 to 5 are also listed.

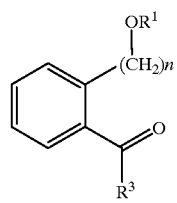

| No | R$^1$ | R$^3$ | n | Physical data |
|---|---|---|---|---|
| XIV-1 | C$_6$H$_5$ | 1-Me-imidazol-2-yl | 0 | $^1$H-NMR(CDCl$_3$) δ ppm: 3.94(3H, s), 6.92–7.30(7H, m), 7.43(1H, td, J=8.6, 1.8), 7.64(1H, dd, J=7.9, 1.8) |
| XIV-2 | 2,5-Me$_2$—C$_6$H$_3$ | 1-Me-imidazol-2-yl | 1 | $^1$H-NMR(CDCl$_3$) δ ppm: 2.07(3H, s), 2.26(3H, s), 4.01(3H, s), 5.23(2H, s), 6.00(1H, s), 6.64(1H, d, J=7.3), 6.97(1H, d, J=7.3), 7.05(1H, s), 7.19(1H, s), 7.40–7.83(4H, m) |
| XIV-3 | C$_6$H$_5$ | Isoxazol-3-yl | 1 | $^1$H-NMR(CDCl$_3$) δ ppm: 5.34(2H, s), 6.85–7.28(6H, m), 7.46(1H, t, J=7.3), 7.61(1H, td, J=7.9, 1.2), 7.74(1H, d, J=7.9), 7.99(1H, dd, J=7.3, 1.2), 8.50(1H, dd, J=1.2) |
| XIV-4 | 2-Me—C$_6$H$_4$ | Isoxazol-3-yl | 1 | $^1$H-NMR(CDCl$_3$) δ ppm: 2.21 (3H, s), 5.34(2H, s), 6.80–7.14(5H, m), 7.44–8.02(4H, m), 8.49(1H, d, J=1.2) |
| XIV-5 | 2,5-Me$_2$—C$_6$H$_3$ | Isoxazol-3-yl | 1 | mp 90.5–92° C. |
| XIV-6 | C$_6$H$_5$ | 5-Me-isoxazol-3-yl | 1 | $^1$H-NMR(CDCl$_3$) δ ppm: 2.49(3H, s), 5.34(2H, s), 6.46(1H, d, J=1.2), 6.88–7.99(9H, m) |
| XIV-7 | 2,5-Me$_2$—C$_6$H$_3$ | 5-Me-isoxazol-3-yl | 1 | $^1$H-NMR(CDCl$_3$) δ ppm: 2.17(3H, s), 2.28(3H, s), 2.49(3H, s), 5.32(2H, s), 6.46(1H, s), 6.66–7.02(3H, m), 7.42–8.00(4H, m) |
| XIV-8 | 2-Me—C$_6$H$_4$ | 3-Me-isoxazol-5-yl | 1 | $^1$H-NMR(CDCl$_3$) δ ppm: 2.18(3H, s), 2.38(3H, s), 5.30(2H, s), 6.71(1H, s), 6.81–7.80(8H, m) |
| XIV-9 | 2,5-Me$_2$—C$_6$H$_3$ | 3-Me-isoxazol-5-yl | 1 | mp 106–108° C. |
| XIV-10 | 2,5-Me$_2$—C$_6$H$_3$ | 2-Isoxazolin-3-yl | 1 | $^1$H-NMR(CDCl$_3$) δ ppm: 2.17(3H, s), 2.31(3H, s), 3.20(2H, t, J=11.0), 4.42(2H, t, J=11.0), 5.20(2H, s), 6.68–7.84(7H, m) |
| XIV-11 | 2,5-Me$_2$—C$_6$H$_3$ | 5,5-Me$_2$-2-isoxazolin-3-yl | 1 | $^1$H-NMR(CDCl$_3$) δ ppm: 1.35(6H, s), 2.16(3H, s), 2.30(3H, s), 2.96(2H, s), 5.22(2H, s), 6.67–7.80(7H, m) |
| XIV-12 | 2,5-Me$_2$—C$_6$H$_3$ | 1-Me-pyrazol-5-yl | 1 | mp 88–89° C. |
| XIV-13 | 2,5-Me$_2$—C$_6$H$_3$ | 2-Furyl | 1 | $^1$H-NMR(CDCl$_3$) δ ppm: 2.10(3H, s), 2.26(3H, s), 5.25(2H, s), 6.55–6.67(3H, m), 6.97(1H, d, J=7.3), 7.06(1H, d, J=3.7), 7.39–7.80(5H, m) |
| XIV-14 | 2,5-Me$_2$—C$_6$H$_3$ | Thiazol-2-yl | 1 | $^1$H-NMR(CDCl$_3$) δ ppm: 2.11(3H, s), 2.27(3H, s), 5.30(2H, s), 6.64(1H, s), 6.65(1H, d, J=2.5), 6.98(1H, d, J=7.9), 7.45–8.10(6H, m) |
| XIV-15 | 2,5-Me$_2$—C$_6$H$_3$ | 3-Me-isothiazol-5-yl | 1 | $^1$H-NMR(CDCl$_3$) δ ppm: 2.07(3H, s), 2.27(3H, s), 2.53(3H, s), 5.25(2H, s), 6.60–7.82(8H, m) |
| XIV-16 | 4-Cl-2-Me—C$_6$H$_3$ | 5-Me-isoxazol-3-yl | 1 | mp 103–104° C. |

-continued

| No | R¹ | R³ | n | Physical data |
|---|---|---|---|---|
| XIV-17 | 3-Me—C₆H₄ | Isoxazol-3-yl | 1 | ¹H-NMR(CDCl₃) δ ppm: 2.30(3H, s), 5.32(2H, s), 6.66–6.77(3H, m), 6.87(1H, s), 7.12(1H, t, J=7.3), 7.46–7.76(3H, m), 8.00(1H, d, J=7.9), 8.50(1H, s) |
| XIV-18 | 4-Me—C₆H₄ | Isoxazol-3-yl | 1 | ¹H-NMR(CDCl₃) δ ppm: 2.26(3H, s), 5.30(2H, s), 6.77(2H, d, J=8.6), 6.86(1H, d, J=1.8), 7.04(2H, d, J=8.6), 7.45–7.98(4H, m), 8.50(1H, d, J=1.8) |
| XIV-19 | 2-Cl—C₆H₄ | Isoxazol-3-yl | 1 | mp 92.0–93.0° C. |
| XIV-20 | 3-Cl—C₆H₄ | Isoxazol-3-yl | 1 | mp 75.0–76.0° C. |
| XIV-21 | 4-Cl—C₆H₄ | Isoxazol-3-yl | 1 | ¹H-NMR(CDCl₃) δ ppm: 5.32(2H, s), 6.80–6.83(2H, m), 6.86(1H, d, J=1.8), 7.19–7.22(2H, m), 7.45–8.02(4H, m), 8.52(1H, d, J=1.2) |
| XIV-22 | 3-CF₃—C₆H₄ | Isoxazol-3-yl | 1 | ¹H-NMR(CDCl₃) δ ppm: 5.38(2H, s), 6.87(1H, d, J=1.8), 7.04–7.75(7H, m), 8.04(1H, d, J=7.9), 8.52(1H, d, J=1.8) |
| XIV-23 | 4-Cl-2-Me—C₆H₃ | Isoxazol-3-yl | 1 | mp 107.0–108.0° C. |
| XIV-24 | 2-Me—C₆H₄ | 5-Me-isoxazol-3-yl | 1 | mp 77.5–78.5° C. |
| XIV-25 | 3-Me—C₆H₄ | 5-Me-isoxazol-3-yl | 1 | ¹H-NMR(CDCl₃) δ ppm: 2.30(3H, s), 2.49(3H, s), 5.32(2H, s), 6.47(1H, d, J=1.2), 6.67–6.85(3H, m), 7.12(1H, t, J=7.3), 7.41–7.98(4H, m) |
| XIV-26 | 4-Me—C₆H₄ | 5-Me-isoxazol-3-yl | 1 | ¹H-NMR(CDCl₃) δ ppm: 2.26(3H, s), 2.49(3H, s), 5.30(2H, s), 6.46(1H, s), 6.77–6.80(2H, m), 7.05(2H, d, J=7.9), 7.40–7.97(4H, m) |
| XIV-27 | 2-Cl—C₆H₄ | 5-Me-isoxazol-3-yl | 1 | mp 93.5–94.5° C. |
| XIV-28 | 3-Cl—C₆H₄ | 5-Me-isoxazol-3-yl | 1 | mp 72.0–73.0° C. |
| XIV-29 | 4-Cl—C₆H₄ | 5-Me-isoxazol-3-yl | 1 | mp 95.0–96.0° C. |
| XIV-30 | 3-CF₃—C₆H₄ | 5-Me-isoxazol-3-yl | 1 | mp 58.5-59.5° C. |
| XIV-31 | 4-Ph—C₆H₄ | 5-Me-isoxazol-3-yl | 1 | mp 116.5–117.5° C. |
| XIV-32 | 2-Me—C₆H₄ | Isoxazol-5-yl | 1 | mp 67.5–68.5° C. |
| XIV-33 | 2,5-Me₂—C₆H₃ | Isoxazol-5-yl | 1 | mp 103.5–105.0° C. |
| XIV-34 | 4-Cl-2-Me—C₆H₃ | Isoxazol-5-yl | 1 | mp 109.5–111.0° C. |
| XIV-35 | C₆H₅ | 3-Me-isoxazol-5-yl | 0 | ¹H-NMR(CDCl₃) δ ppm: 2.30(3H, s), 6.76(1H, s), 6.91(1H, d, J=7.3), 6.99–7.51(7H, m), 7.63(1H, dd, J=7.3, 1.8) |
| XIV-36 | 3-Me—C₆H₄ | 3-Me-isoxazol-5-yl | 1 | mp 68.0–69.0° C. |
| XIV-37 | 2-Cl—C₆H₄ | 3-Me-isoxazol-5-yl | 1 | mp 104.0–105.0° C. |
| XIV-38 | 3-Cl—C₆H₄ | 3-Me-isoxazol-5-yl | 1 | mp 92.5–93.5° C. |
| XIV-39 | 3-CF₃—C₆H₄ | 3-Me-isoxazol-5-yl | 1 | mp 80.5–81.5° C. |
| XIV-40 | 4-Cl-2-Me—C₆H₃ | 3-Me-isoxazol-5-yl | 1 | mp 125.5–126.5° C. |
| XIV-41 | 4-Ph—C₆H₄ | 3-Me-isoxazol-5-yl | 1 | mp 127.0–128.0° C. |
| XIV-42 | C₆H₅ | 1-Me-imidazol-2-yl | 1 | ¹H-NMR(CDCl₃) δ ppm: 4.01(3H, s), 5.24(2H, s), 6.80-6.83(2H, m), 6.91(1H, t, J=7.3), 7.04(1H, s), 7.18–7.81(7H, m) |
| XIV-43 | 2-Me—C₆H₄ | 1-Me-imidazol-2-yl | 1 | ¹H-NMR(CDCl₃) δ ppm: 2.13(3H, s), 4.01(3H, s), 5.25(2H, s), 6.78–6.85(2H, m), 7.05(1H, s), 7.10(1H, d, J=7.3), 7.18(1H, s), 7.39–7.83(4H, m) |
| XIV-44 | 3-Me—C₆H₄ | 1-Me-imidazol-2-yl | 1 | ¹H-NMR(CDCl₃) δ ppm: 2.28(3H, s), 4.01(3H, s), 5.21(2H, s), 6.59–6.74(3H, m), 7.04(1H, s), 7.09(1H, t, J=7.9), 7.18(1H, s), 7.39–7.80(4H, m) |

-continued

| No | R¹ | R³ | n | Physical data |
|---|---|---|---|---|
| XIV-45 | 4-Me—C₆H₄ | 1-Me-imidazol-2-yl | 1 | ¹H-NMR(CDCl₃) δ ppm: 2.25(3H, s), 4.02(3H, s), 5.20(2H, s), 6.69–6.72(2H, m), 6.99–7.02(2H, m), 7.05(1H, s), 7.18(1H, s), 7.38–7.79(4H, m) |
| XIV-46 | 2-Cl—C₆H₄ | 1-Me-imidazol-2-yl | 1 | mp 87.0–88.0° C. |
| XIV-47 | 3-Cl—C₆H₄ | 1-Me-imidazol-2-yl | 1 | ¹H-NMR(CDCl₃) δ ppm: 4.03(3H, s), 5.23(2H, s), 6.70(1H, dd, J=8.6, 1.8), 6.82(1H, t, J=1.8), 6.90(1H, dd, J=7.3, 1.2), 7.06(1H, s), 7.13(1H, t, J=7.9), 7.19(1H, d, J=1.2), 7.40–7.81(3H, m) |
| XIV-48 | 4-Cl—C₆H₄ | 1-Me-imidazol-2-yl | 1 | ¹H-NMR(CDCl₃) δ ppm: 4.03(3H, s), 5.22(2H, s), 6.73–6.78(2H, m), 7.06(1H, s), 7.13–7.59(6H, m), 7.80(1H, dd, J=7.3, 1.2) |
| XIV-49 | 2,4-Cl₂—C₆H₃ | 1-Me-imidazol-2-yl | 1 | mp 141.0–142.0° C. |
| XIV-50 | 3,4-Cl₂—C₆H₃ | 1-Me-imidazol-2-yl | 1 | mp 78.0–79.0° C. |
| XIV-51 | 4-Cl-2-Me—C₆H₃ | 1-Me-imidazol-2-yl | 1 | mp 101.0–102.0° C. |
| XIV-52 | 3-CF₃—C₆H₄ | 1-Me-imidazol-2-yl | 1 | ¹H-NMR(CDCl₃) δ ppm: 4.01(3H, s), 5.28(2H, s), 6.97–7.61(9H, m), 7.80(1H, dd, J=7.9, 1.8) |
| XIV-53 | 2-MeO—C₆H₄ | 1-Me-imidazol-2-yl | 1 | mp 88.0–89.0° C. |
| XIV-54 | 3-MeO—C₆H₄ | 1-Me-imidazol-2-yl | 1 | ¹H-NMR(CDCl₃) δ ppm: 3.74(3H, s), 4.02(3H, s), 5.21(2H, s), 6.38–6.50(3H, m), 7.05(1H, s), 7.11(1H, t, J=7.9), 7.18(1H, s), 7.42–7.79(4H, m) |
| XIV-55 | 4-F—C₆H₄ | 1-Me-imidazol-2-yl | 1 | ¹H-NMR(CDCl₃) δ ppm: 4.03(3H, s), 5.21(2H, s), 6.72–6.95(4H, m), 7.06(1H, s), 7.18(4H, d, J=1.2), 7.42–7.80(4H, m) |
| XIV-56 | 3-i-Pr—C₆H₄ | 1-Me-imidazol-2-yl | 1 | ¹H-NMR(CDCl₃) δ ppm: 1.20(6H, d, J=7.3), 2.83(1H, sept, J=7.3), 4.00(3H, s), 5.21(2H, s), 6.60–6.80(3H, m), 7.03(1H, s), 7.11–7.79(6H, m) |
| XIV-57 | 4-Ph—C₆H₄ | 1-Me-imidazol-2-yl | 1 | ¹H-NMR(CDCl₃) δ ppm: 4.03(3H, s), 5.28(2H, s), 6.87–6.90(2H, m), 7.06(1H, s), 7.19(1H, s), 7.28–7.84(11H, m) |
| XIV-58 | C₆H₅ | 3,5-Me₂-isoxazol-4-yl | 1 | ¹H-NMR(CDCl₃) δ ppm: 2.17(3H, s), 2.25(3H, s), 5.19(2H, s), 6.78–6.82(2H, m), 6.93(1H, t, J=7.3), 7.21–7.67(6H, m) |
| XIV-59 | 2,5-Me₂—C₆H₃ | 3,5-Me₂-isoxazol-4-yl | 1 | mp 109.0–110.5° C. |
| XIV-60 | 2-Me—C₆H₄ | 3-Me-2-isoxazolin-5-yl | 1 | ¹H-NMR(CDCl₃) δ ppm: 2.02(3H, s), 2.32(3H, s), 3.08(1H, m), 3.53–3.62(1H, m), 5.33–5.46(2H, m), 5.69(1H, dd, J=11.6, 6.7), 6.88(1H, s), 6.91(1H, s), 7.15(1H, t, J=8.5), 7.43–8.01(4H, m) |
| XIV-61 | 2,5-Me₂—C₆H₃ | 3-Me-2-isoxazolin-5-yl | 1 | mp 88.0–90.0° C. |
| XIV-62 | C₆H₅ | 4-Me-1,2,3-thiadiazol-5-yl | 1 | ¹H-NMR(CDCl₃) δ ppm: 2.77(3H, s), 5.26(2H, s), 6.76(1H, s), 6.79(1H, d, J=1.2), 6.94(1H, t, J=7.3), 7.21–7.74(6H, m) |
| XIV-63 | 2,5-Me₂—C₆H₃ | 4-Me-1,2,3-thiadiazol-5-yl | 1 | mp 98.5–99.5° C. |
| XIV-64 | 2-Me—C₆H₄ | 5-Me-2-isoxazolin-3-yl | 1 | |
| XIV-65 | C₆H₅ | 5-Me-2-isoxazolin-3-yl | 1 | |
| XIV-66 | 4-Cl—C₆H₄ | 5-Me-2-isoxazolin-3-yl | 1 | |
| XIV-67 | 3-CF₃—C₆H₄ | 5-Me-2-isoxazolin-3-yl | 1 | |
| XIV-68 | 4-Cl-2-Me—C₆H₃ | 5-Me-2-isoxazolin-3-yl | 1 | |
| XIV-69 | 4-Cl—C₆H₄ | 2-Isoxazolin-3-yl | 1 | |
| XIV-70 | 3-CF₃—C₆H₄ | 2-Isoxazolin-3-yl | 1 | |
| XIV-71 | 4-Cl-2-Me—C₆H₃ | 2-Isoxazolin-3-yl | 1 | |
| XIV-72 | 2-Me—C₆H₄ | 2-Isoxazolin-3-yl | 1 | |

-continued

| No | R¹ | R³ | n | Physical data |
|---|---|---|---|---|
| XIV-73 | $C_6H_5$ | 2-Isoxazolin-3-yl | 0 | |
| XIV-74 | $C_6H_5$ | Isoxazol-3-yl | 0 | |

Example 6

Synthesis of 2-(4-chlorophenoxymethyl)phenyl 1-methyl-1H-1,2,4-triazol-5-yl ketone O-methyloxime Dimethylformamide dimethylacetal (0.53 g, 4.5 mmol) was added to 2-(4-chlorophenoxymethyl)-α-methoxyiminophenylacetamide (0.48 g, 1.5 mmol), and the mixture was stirred under reduced pressure (ca. 40 mmHg) at 60° C. for 0.5 hours. After completion of the reaction, the mixture was concentrated under reduced pressure, and a mixture of methylhydrazine (0.08 g, 1.8 mmol) and acetic acid (3 ml) was added to the residue. The mixture was stirred at 90° C. for 1 hour. After completion of the reaction, ether (150 ml) was added, and the mixture was washed with saturated aqueous sodium bicarbonate solution (100 ml) twice. The ether layer was dried over anhydrous magnesium sulfate and concentrated under reduced pressure. The residue was purified by silica gel chromatography (ethyl acetate/n-hexane) and recrystallized from ethyl acetate/n-hexane to give 2-(4-chlorophenoxymethyl)phenyl 1-methyl-1H-1,2,4-triazol-5-yl ketone O-methyloxime (0.31 g, 57.9%) as colorless crystals.

mp. 113–114° C.

$^1$H-NMR(CDCl$_3$) δ ppm: 4.01(3H,s), 4.08(3H,s), 4.91 (2H,s), 6.67–6.70(2H,m), 7.15–7.18(2H,m), 7.26–7.54(4H, m), 7.83(1H,s).

Example 7

Synthesis of 2-(4-chlorophenoxymethyl)-N-hydroxyaminomethylene-α-methoxyiminophenylacetamide N,N-Dimethylformamide dimethylacetal (0.53 g, 4.5 mmol) was added to 2-(4-chlorophenoxymethyl)-α-methoxyiminophenylacetamide (0.48 g, 1.5 mmol), and the mixture was stirred under reduced pressure (ca. 40 mmHg) at 60° C. for 0.5 hours. After completion of the reaction, the mixture was concentrated under reduced pressure, and a mixture of aqueous 50% hydroxylamine solution (0.20 g, 2 mmol) and acetic acid (3 ml) was added to the residue under ice-cooling. The mixture was stirred at room temperature for 1 hour. After completion of the reaction, ethyl acetate (150 ml) was added, and the mixture was washed with saturated aqueous sodium bicarbonate solution (100 ml) twice. The ethyl acetate layer was dried over anhydrous magnesium sulfate and concentrated under reduced pressure. The residue was recrystallized from ethyl acetate/n-hexane to give 2-(4-chlorophenoxymethyl)-N-hydroxyaminomethylene-α-methoxyiminophenylacetamide (0.41 g, 75.6%) as colorless crystals.

mp. 185–186° C. (decomposition)

$^1$H-NMR(CDCl$_3$) δ ppm: 4.00(3H,s), 4.93(2H,s), 6.76–6.80(2H,m), 6.86(1H,d,J=8.5), 7.18–7.22(2H,m), 7.37–7.52(3H,m), 7.70(1H,d,J=10.4), 9.50(1H,d,J=9.8).

Synthesis of 2-(4-chlorophenoxymethyl)phenyl 1,2,4-oxadiazol-5-yl ketone O-methyloxime Dioxane (2 ml) and acetic acid (1.5 ml) were added to 2-(4-chlorophenoxymethyl)-N-hydroxyaminomethylene-α-methoxyiminophenylacetamide (0.36 g, 1 mmol), and the mixture was stirred at 120° C. for 4 hours. After completion of the reaction, ether (150 ml) was added, and the mixture was washed with saturated aqueous sodium bicarbonate solution (100 ml) twice. The ether layer was dried over anhydrous magnesium sulfate and concentrated under reduced pressure, and the residue was purified by silica gel chromatography (ethyl acetate/n-hexane) and recrystallized from ethyl acetate/n-hexane to give 2-(4-chlorophenoxymethyl)phenyl 1,2,4-oxadiazol-5-yl ketone O-methyloxime (0.14 g, 40.8%) as colorless crystals.

mp. 96–97.5° C.

$^1$H-NMR(CDCl$_3$) δ ppm: 4.09(3H,s), 4.94(2H,s), 6.66–6.70(2H,m), 7.14–7.17(2H,m), 7.28–7.60(4H,m), 8.44 (1H,s).

Example 8

Synthesis of 2-(2,5-dimethylphenoxymethyl)phenyl 3-ethyl-1,2,4-oxadiazol-5-yl ketone O-methyloxime Dichloroethane (5 ml), thionyl chloride (0.65 g, 5.5 mmol) and N,N-dimethylformamide (0.05 ml) were added to 2-(2,5-dimethylphenoxymethyl)-α-methoxyiminophenylacetic acid (1.57 g, 5 mmol), and the mixture was stirred under reflux for 2 hours. After completion of the reaction, the mixture was concentrated under reduced pressure, pyridine (3 ml) and 1-hydroxyimino-1-propylamine (0.88 g, 10 mmol) were added to the residue, and the mixture was stirred under reflux for 0.5 hours. After completion of the reaction, ether (150 ml) was added, and the mixture was washed with 1N hydrochloric acid (150 ml) twice. The ether layer was dried over anhydrous magnesium sulfate and concentrated under reduced pressure, and the residue was purified by silica gel chromatography (ethyl acetate/n-hexane) and recrystallized from ethyl acetate/n-hexane to give 2-(2,5-dimethylphenoxymethyl)phenyl 3-ethyl-1,2,4-oxadiazol-5-yl ketone O-methyloxime (0.63 g, 34.5%) as colorless crystals.

mp. 111.5–112.5° C.

$^1$H-NMR(CDCl$_3$) δ ppm: 1.30(3H,t,J=7.3), 2.09(3H,s), 2.25(3H,s), 2.77(2H,q,J=7.3), 4.11(3H,s), 4.95(2H,s), 6.54 (1H,s), 6.65(1H,d,J=7.9), 6.98(1H,d,J=7.3), 7.27–7.66(4H, m).

Example 9

Synthesis of 2-(2,5-dimethylphenoxymethyl)-α-methoxyiminophenylacetohydrazide

Methanol (10 ml), THF (10 ml) and hydrazine monohydrate (1.68 g, 0.03 mol) were added to methyl 2-(2,5-dimethylphenoxymethyl)-α-methoxyiminophenylacetate (3.27 g, 0.01 mol), and the mixture was stirred at room temperature for 3 hours. After completion of the reaction, water (200 ml) was added, and the mixture was extracted with dichloromethane. The dichloromethane layer was dried over anhydrous magnesium sulfate and concentrated under reduced pressure. The residue was recrystallized from ethyl acetate/n-hexane to give 2-(2,5-dimethylphenoxymethyl)-α-methoxyiminophenylacetohydrazide (2.93 g, 89.6%) as colorless crystals.

mp. 124.5–126° C.

¹H-NMR(CDCl₃) δ ppm: 2.18(3H,s), 2.29(3H,s), 3.88 (2H,d,J=4.3), 3.96(3H,s), 4.92(2H,s), 6.61(1H,s), 6.67 (1H, d,J=7.3), 7.01(1H,d,J=7.3), 7.21–7.59(4H,m), 7.76(1H,brs).

Synthesis of 2-(2,5-dimethylphenoxymethyl)phenyl 1,3,4-oxadiazol-2-yl ketone O-methyloxime Ethyl orthoformate (2 ml) was added to 2-(2,5-dimethylphenoxymethyl)-α-methoxyiminophenylacetohydrazide (0.49 g, 1.5 mmol), and the mixture was stirred under reflux for 4 hours. After completion of the reaction, water (100 ml) was added, and the mixture was extracted with dichloromethane. The dichloromethane layer was dried over anhydrous magnesium sulfate and concentrated under reduced pressure. The residue was recrystallized from ethyl acetate/n-hexane to give 2-(2,5-dimethylphenoxymethyl)phenyl 1,3,4-oxadiazol-2-yl ketone O-methyloxime (0.10 g, 19.8%) as colorless crystals.

mp. 134–135° C.

¹H-NMR(CDCl₃) δ ppm: 2.08(3H,s), 2.25(3H,s), 4.08 (3H,s), 4.96(2H,s), 6.54(1H,s), 6.65(1H,d,J=7.3), 6.97(1H, d,J=7.9), 7.32–7.64(4H,m), 8.93(1H,s).

Example 10

Synthesis of α-amino-2-(4-chlorophenoxymethyl)-α-hydroxyiminoacetophenone O-methyloxime 28% sodium methoxide/methanol solution (1.31 g, 6.8 mmol) was added to a mixture of hydroxylamine hydrochloride (0.47 g, 6.8 mmol) and methanol (10 ml) under ice-cooling over 5 minutes. Then, 2-(4-chlorophenoxymethyl)-α-methoxyiminophenylacetonitrile (1.02 g, 3.4 mmol) was added, and the mixture was stirred under reflux for 1.5 hours. After completion of the reaction, water (200 ml) was added, and the mixture was extracted with dichloromethane. The dichloromethane layer was dried over anhydrous magnesium sulfate and concentrated under reduced pressure. The residue was recrystallized from ethyl acetate/n-hexane to give α-amino-2-(4-chlorophenoxymethyl)-α-hydroxyiminoacetophenone O-methyloxime (0.87 g, 76.7%) as colorless crystals.

mp. 200° C. (decomposition)

¹H-NMR(CDCl₃) δ ppm: 3.92(3H,s), 4.93(2H,s), 5.04 (2H,brs), 6.79–6.87(2H,m), 7.15–7.21(3H,m), 7.33–7.52 (3H,m).

Synthesis of 2-(4-chlorophenoxymethyl)phenyl 1,2,4-oxadiazol-3-yl ketone O-methyloxime Ethyl orthoformate (2 ml) was added to α-amino-2-(4-chlorophenoxymethyl)-α-hydroxyiminoacetophenone O-methyloxime (0.40 g, 1.2 mmol), and the mixture was stirred under reflux for 4 hours. After completion of the reaction, toluene (10 ml) was added, and the mixture was concentrated under reduced pressure. The residue was purified by silica gel chromatography (ethyl acetate/n-hexane) and recrystallized from ethyl acetate/n-hexane to give 2-(4-chlorophenoxymethyl)phenyl 1,2,4-oxadiazol-3-yl ketone O-methyloxime (0.36 g, 87.3%) as colorless crystals.

mp. 107–108° C.

¹H-NMR(CDCl₃) δ ppm: 4.08(3H,s), 4.96(2H,s), 6.72–6.75(2H,m), 7.14–7.18(2H,m), 7.28–7.60(4H,m), 8.76 (1H,s).

Example 11

Synthesis of 2-(4-chlorophenoxymethyl)phenyl 5-methyl-1,2,4-oxadiazol-3-yl ketone O-methyloxime Acetic anhydride (2 ml) was added α-amino-2-(4-chlorophenoxymethyl)-α-hydroxyiminoacetophenone O-methyloxime (0.40 g, 1.2 mmol), and the mixture was stirred under reflux for 5 hours. After completion of the reaction, the reaction mixture was concentrated under reduced pressure, ether (100 ml) was added, and the mixture was washed with saturated aqueous sodium bicarbonate solution (50 ml) twice. The ether layer was dried over anhydrous magnesium sulfate and concentrated under reduced pressure. The residue was purified by silica gel chromatography (ethyl acetate/n-hexane) and recrystallized from ethyl acetate/n-hexane to give 2 (4-chlorophenoxymethyl)phenyl 5-methyl-1,2,4-oxadiazol-3-yl ketone O-methyloxime (0.35 g, 81.5%) as colorless crystals.

mp. 125–126° C.

¹H-NMR(CDCl₃) δ ppm: 2.65(3H,s), 4.07(3H,s), 4.96 (2H,S), 6.74–6.77(2H,m), 7.15–7.18(2H,m), 7.26–7.59(4H, m).

Example 12

Synthesis of 2-(2,5-dimethylphenoxymethyl)phenyl 1H-tetrazol-5-yl ketone O-methyloxime Sodium azide (1.30 g, 20 mmol), ammonium chloride (1.07 g, 20 mmol) and N,N-dimethylformamide (10 ml) were added to 2-(2,5-dimethylphenoxymethyl)-α-methoxyiminophenylacetonitrile (0.59 g, 2 mmol), and the mixture was stirred at 115° C. for 9 hours. After completion of the reaction, ethyl acetate (150 ml) was added, and the mixture was washed with saturated brine (100 ml) twice. The ethyl acetate layer was dried over anhydrous magnesium sulfate and concentrated under reduced pressure. The residue was recrystallized from ethyl acetate/n-hexane to give 2-(2,5-dimethylphenoxymethyl)phenyl 1H-tetrazol-5-yl ketone O-methyloxime (0.59 g, 87.4%) as colorless crystals.

mp. 168–170° C.

¹H-NMR(CDCl₃) δ ppm: 2.00(3H,s), 2.25(3H,s), 4.05 (3H,s), 4.95(2H,s), 6.52(1H,s), 6.65(1H,d,J=7.3), 6.96(1H, d,J=7.3), 7.32–7.63(4H,m).

Example 13

Synthesis of 2-(2,5-dimethylphenoxymethyl)phenyl 1-methyl-1H-tetrazol-5-yl ketone O-methyloxime and 2-(2,5-dimethylphenoxymethyl)phenyl 2-methyl-2H-tetrazol-5-yl ketone O-methyloxime N,N-Dimethylformamide (3 ml) and potassium carbonate (0.33 g, 2.4 mmol) were added to 2-(2,5-dimethylphenoxymethyl)phenyl 1H-tetrazol-5-yl ketone O-methyloxime (0.40 g, 1.2 mmol), and the mixture was stirred at room temperature for 5 minutes. Then, dimethyl sulfate (0.23 g, 1.8 mmol) was added under ice-cooling, and the mixture was stirred at room temperature overnight. After completion of the reaction, ether (150 ml) was added, and the mixture was washed with brine (50 ml) twice. The ether layer was dried over anhydrous magnesium sulfate and concentrated under reduced pressure. The residue was purified by silica gel chromatography (ethyl acetate/n-hexane) and recrystallized from ethyl acetate/n-hexane to give 2-(2, 5-dimethylphenoxymethyl)phenyl 1-methyl-1H-tetrazol-5-yl ketone O-methyloxime as colorless crystals (0.16 g, 37.9%) [mp. 115.5–116.5° C.; ¹H-NMR(CDCl₃) δ ppm: 1.97(3H,s), 2.26(3H,s), 4.06(3H,s), 4.13(3H,s), 4.89(2H,s), 6.50(1H,s), 6.65(1H,d,J=7.9), 6.97(1H,d,J=7.9), 7.34–7.58 (4H,m)] and 2-(2,5-dimethylphenoxymethyl)phenyl 2-methyl-2H-tetrazol-5-yl ketone O-methyloxime as colorless crystals (0.08 g, 19.0%) [mp. 131–132° C.; $^1$H-NMR (CDCl$_3$) δ ppm: 2.12(3H,s), 2.24(3H,s), 4.09(3H,s), 4.34 (3H,s), 4.96(2H,s), 6.54(1H,s), 6.64(1H,d,J=7.9), 6.98(1H, d,J=7.3), 7.29–7.53(3H,m), 7.69(1H,d,J=7.3)].

Example 14

Synthesis of 2-(3-chlorophenoxymethyl)phenyl 1-methyl-2-imidazolin-2-yl ketone O-methyloxime Xylene (5 ml) and benzene (5 ml) were added to 2-(3-chlorophenoxymethyl)-α-methoxyiminophenylacetonitrile (1.0 g, 3.3 mmol), N-methylethylenediamine (740 mg, 10 mmol) and zinc acetate dihydrate (100 mg, 0.46 mmol), and the mixture was subjected to azeotropic dehydration and stirred at 140° C. for 18 hours. After allowing the mixture to stand for cooling, ethyl acetate was added to the reaction mixture. The mixture was washed successively with water and saturated brine and dried over anhydrous sodium sulfate, and the solvent was evaporated under reduced pressure. The residue was purified by column chromatography on activated alumina containing water (5%) (ethyl acetate/n-hexane) and column chromatography on silica gel (ethyl acetate/n-hexane) to give isomer A (720 mg, 60%, as an oil) and isomer B (220 mg, 19%, as an oil) of 2-(3-chlorophenoxymethyl)phenyl 1-methyl-2-imidazolin-2-yl ketone O-methyloxime.

Isomer A: $^1$H-NMR(CDCl$_3$) δ ppm: 2.75(3H,s), 3.41(2H, t,J=9.8), 3.92(2H,t,J=9.8), 3.97(3H,s), 5.35(2H,s), 6.84(1H, ddd,J=8.0,2.4,0.9), 6.93(1H,ddd,J=8.0,1.8,0.9), 6.99(1H,dd, J=2.4,1.8), 7.19(1H,t,J=8.0), 7.32–7.44(2H,m), 7.51(1H,dd, J=7.3,1.4), 7.64(1H,d,J=7.0).

Isomer B: $^1$H-NMR(CDCl$_3$) δ ppm: 3.03(3H,s), 3.38(2H, t,J=9.9), 3.77(2H,t,J=9.9), 3.97(3H,s), 4.99(2H,s), 6.83(1H, dd,J=8.5,2.5), 6.91(1H,d,J=7.8), 6.94(1H,brs), 7.16(1H,dd, J=8.3,7.8), 7.23(1H,d,J=7.6), 7.34–7.39(2H,m), 7.49(1H,d, J=6.4).

Example 15

Synthesis of 2-(3-methylphenoxymethyl)phenyl 2-oxazolin-2-yl ketone O-methyloxime Ethylene glycol (2 ml) and benzene (10 ml) were added to 2-(3-methylphenoxymethyl)-α-methoxyiminophenylacetonitrile (1.0 g, 3.6 mmol), 2-aminoethanol (400 mg, 6.6 mmol) and zinc acetate dihydrate (100 mg, 0.46 mmol), and the mixture was subjected to azeotropic dehydration and stirred at 100° C. for 20 hours. After allowing the mixture to stand for cooling, ethyl acetate was added to the reaction mixture. The mixture was washed successively with water and saturated brine and dried over anhydrous sodium sulfate, and the solvent was evaporated under reduced pressure. The residue was purified by column chromatography on silica gel (ethyl acetate/n-hexane) to give 2-(3-methylphenoxymethyl)phenyl 2-oxazolin-2-yl ketone O-methyloxime (280 mg, 24%) as an oil.

$^1$H-NMR(CDCl$_3$) δ ppm: 2.31(3H,s), 4.00(2H,t,J=9.8), 4.03(3H,s), 4.32(2H,t,J=9.8), 5.21(2H,s), 6.72–6.78(3H,m), 7.14(1H,t,J=7.6), 7.31–7.48(3H,m), 7.62(1H,d,J=7.6), Example 16

Synthesis of 2-(2,5-dimethylphenoxymethyl)phenyl 2-thiazolin-2-yl ketone O-methyloxime 2-Aminoethanethiol hydrochloride (2.80 g, 24.6 mmol), zinc acetate dihydrate (600 mg, 2.7 mmol), toluene (12 ml) and triethylamine (3.12 g, 30.8 mmol) were added to 2-(2, 5-dimethylphenoxymethyl)-α-methoxyiminophenylacetonitrile (6.00 g, 20.4 mmol), and the mixture was stirred under reflux for 14 hours. After completion of the reaction, water (100 ml) was added, and the mixture was extracted with ethyl acetate. The ethyl acetate layer was dried over anhydrous sodium sulfate and concentrated under reduced pressure. The residue was purified by silica gel chromatography (ethyl acetate/n-hexane) to give 2-(2,5-dimethylphenoxymethyl)phenyl 2-thiazolin-2-yl ketone O-methyloxime (5.71 g, 79.0%) as crystals.

mp. 79–82° C.

$^1$H-NMR(CDCl$_3$) δ ppm: 2.24(2.23)(3H,s), 2.29(2.28) (3H,s), 3.21(3.27)(2H,t,J=8.6), 4.07(4.02)(3H,s), 4.24(3.36) (2H,t,J=8.6), 5.11(4.93) (2H,s), 6.56–7.63(7H,m).

Example 17

Synthesis of 2-(2,5-dimethylphenoxymethyl)-α-methoxyiminophenylacetaldehyde 1M diisobutylaluminum hydride/toluene solution (5.5 ml, 5.5 mmol) was added dropwise to a mixture of methyl 2-(2,5-dimethylphenoxymethyl)-α-methoxyiminophenylacetate (1.64 g, 5 mmol) and dichloromethane (15 ml) at −70° C. over 0.5 hours, and then the mixture was stirred at −70° C. to room temperature for 3 hours. Methanol (3 ml) was added to the reaction mixture, and the mixture was stirred at room temperature for 1 hour. The precipitated insoluble materials were removed, and the mixture was concentrated under reduced pressure. The residue was purified by silica gel chromatography (ethyl acetate/n-hexane) to 2-(2,5-dimethylphenoxymethyl)-α-methoxyiminophenylacetaldehyde (0.54 g, 36.3%) as a colorless oil.

$^1$H-NMR(CDCl$_3$) δ ppm: 2.16(3H,s), 2.28(3H,s) 4.11(3H, s), 4.86(2H,s), 6.55(1H,s), 6.67(1H,d,J=7.3), 6.99–7.58(5H, m), 9.69(1H,s).

Synthesis of 2-(2,5-dimethylphenoxymethyl)phenyl oxazol-5-yl ketone O-methyloxime p-Toluenesulfonylmethylisocyanide (0.23 g, 1.2 mmol), potassium carbonate (0.18 g, 1.3 mmol) and methanol (2 ml) were added to 2-(2,5-dimethylphenoxymethyl)-α-methoxyiminophenylacetaldehyde (0.30 g, 1 mmol), and the mixture was stirred under reflux for 2 hours. After completion of the reaction, ether (100 ml) was added, and the mixture was washed with brine (80 ml) twice. The ether layer was dried over anhydrous magnesium sulfate and concentrated under reduced pressure. The residue was purified by silica gel chromatography (ethyl acetate/n-hexane) and recrystallized from ethyl acetate/n-hexane to give 2-(2, 5-dimethylphenoxymethyl)phenyl oxazol-5-yl ketone O-methyloxime (0.15 g, 44.6%) as colorless crystals.

mp. 90–91° C.

$^1$H-NMR(CDCl$_3$) δ ppm: 2.12(3H,s), 2.24(3H,s) 4.01 (3H,s), 4.96(2H,s), 6.54(1H,s), 6.65(1H,d,J=7.3), 6.88(1H, s), 6.98(1H,d,J=7.3), 7.24–7.69(4H,m), 7.94(1H,s).

Example 18

Synthesis of 2-(4-chlorobenzyloxy)phenyl 2-oxazolin-2-yl ketone O-methyloxime

Zinc acetate dihydrate (400 mg, 1.8 mmol), ethanolamine (975 mg, 15.9 mmol) and xylene (8 ml) were added to 2-(4-chlorobenzyloxy)-α-methoxyiminophenylacetonitrile (4.00 g, 13.3 mmol), and the mixture was stirred under reflux for 63 hours. After completion of the reaction, water (100 ml) was added, and the mixture was extracted with ethyl acetate. The ethyl acetate layer was dried over sodium sulfate and concentrated under reduced pressure. The residue was purified by silica gel chromatography (ethyl acetate/n-hexane) to give isomer A (1.31 g, 28.6%, as crystals) and isomer B (0.45 g, 9.8%, as crystals) of 2-(4-chlorobenzyloxy)phenyl 2-oxazolin-2-yl ketone O-methyloxime.

Isomer A: mp. 97–100° C.
$^1$H-NMR(CDCl$_3$) δ ppm: 3.73(2H,t,J=7.9), 3.96 (2H,t,J= 7.9), 4.07(3H,s), 5.00(2H,s), 6.92–7.65(8H,m).

Isomer B: mp. 109–112° C.
$^1$H-NMR(CDCl$_3$) δ ppm: 3.92(2H,t,J=9.8), 4.02(3H,s), 4.39(2H,t,J=9.8), 5.07(2H,s), 6.94–7.46(8H,m).

Synthesis of 2-hydroxyphenyl 2-oxazolin-2-yl ketone O-methyloxime

Anisole (152 ml) and aluminium chloride (16.3 g, 122 mmol) were added to 2-(4-chlorobenzyloxy)phenyl 2-oxazolin-2-yl ketone O-methyloxime (19.08 g, 55.3 mmol), and the mixture was stirred under ice-cooling for 1.5 hours. After completion of the reaction, water (100 ml) was added, and the mixture was extracted with ethyl acetate. The ethyl acetate layer was dried over anhydrous sodium sulfate and concentrated under reduced pressure. The residue was purified by silica gel chromatography (ethyl acetate/n-hexane) to give 2-hydroxyphenyl 2-oxazolin-2-yl ketone O-methyloxime (6.82 g, 56%) as an oil.
$^1$H-NMR(CDCl$_3$) δ ppm: 4.07(3H,s), 4.15(2H,t,J=9.5), 4.50(2H,t,J=9.5), 6.85–7.35(5H,m).

Synthesis of 2-(5-trifluoromethyl-2-pyridyloxy) phenyl 2-oxazolin-2-yl ketone O-methyloxime N,N-Dimethylformamide (2.2 ml), potassium carbonate (210 mg, 1.5 mmol) and 2-chloro-5-trifluoromethylpyridine (220 mg, 1.2 mmol) were added to 2-hydroxyphenyl 2-oxazolin-2-yl ketone O-methyloxime (220 mg, 1.0 mmol), and the mixture was stirred at 100° C. for 2.5 hours. After completion of the reaction, aqueous 1N sodiumhydroxide solution NaOH (100 ml) was added, and the mixture was extracted with ether. The ether layer was dried over anhydrous sodium sulfate and concentrated under reduced pressure. The residue was purified by silica gel chromatography (ethyl acetate/n-hexane) to give 2-(5-trifluoromethyl-2-pyridyloxy)phenyl 2-oxazolin-2-yl ketone O-methyloxime (190 mg, 52.1%) as an oil.
$^1$H-NMR(CDCl$_3$) δ ppm: 3.78(2H,t,J=9.8), 3.98(3H,s), 4.16(2H,t,J=9.8), 6.94–7.87(6H,m), 8.43(1H,brs).

Example 19

Synthesis of 5-chloro-2-(4-chlorobenzyloxy)-α-methoxyiminophenylacetonitrile

Dimethyl sulfoxide (3 ml) and 95% sodium cyanide (0.31 g, 6 mmol) were added to 5-chloro-2-(4-chlorobenzyloxy)-α-methoxyiminobenzyl chloride (1.03 g, 3 mmol), and the mixture was stirred at 100° C. for 4 hours. After completion of the reaction, ethyl acetate (150 ml) was added, and the mixture was washed with saturated brine (100 ml) twice. The ethyl acetate layer was dried over anhydrous magnesium sulfate and concentrated under reduced pressure. The residue was purified by silica gel chromatography (ethyl acetate/n-hexane) to give 5-chloro-2-(4-chlorobenzyloxy)-α-methoxyiminophenylacetonitrile (0.92 g, 91.5%) as crystals.
$^1$H-NMR(CDCl$_3$) δ ppm: 4.20(3H,s), 5.15(2H,s), 6.90–7.41(6H,m), 7.52(1H,d,J=2.4).

Synthesis of 5-chloro-2-(4-chlorobenzyloxy)phenyl 5-methyl-1,2,4-oxadiazol-3-yl ketone O-methyloxime 28% sodium methoxide/methanol solution (1.04 g, 5.4 mmol) was added to a mixture of hydroxylamine hydrochloride (0.38 g, 5.4 mmol) and methanol (6 ml) under ice-cooling over 5 minutes. Then, 5-chloro-2-(4-chlorobenzyloxy)-α-methoxyiminophenylacetonitrile (0.91 g, 2.7 mmol) was added, and the mixture was stirred under reflux for 1.5 hours. After completion of the reaction, water (100 ml) was added, and the mixture was extracted with dichloromethane. The dichloromethane layer was dried over anhydrous magnesium sulfate and concentrated under reduced pressure to give α-amino-5-chloro-2-(4-chlorobenzyloxy)-α-hydroxyiminoacetophenone O-methyloxime as a crude product.

Acetic anhydride (2 ml) was added to the crude product, and the mixture was stirred under reflux for 2 hours. After completion of the reaction, the mixture was concentrated under reduced pressure, ethyl acetate (100 ml) was added, and the mixture was washed with saturated aqueous sodium bicarbonate solution (80 ml) twice. The ethyl acetate layer was dried over anhydrous magnesium sulfate and concentrated under reduced pressure. The residue was purified by silica gel chromatography (ethyl acetate/n-hexane) and recrystallized from ethyl acetate/n-hexane to give 5-chloro-2-(4-chlorobenzyloxy)phenyl 5-methyl-1,2,4-oxadiazol-3-yl ketone O-methyloxime (0.35 g, 33.0%) as colorless crystals.

mp. 127–128.5° C.
$^1$H-NMR(CDCl$_3$) δ ppm: 2.38(3H,s), 4.12(3H,s), 4.85 (2H,s), 6.84–7.61(7H,m).

Synthesis of 5-chloro-2-hydroxyphenyl 5-methyl-1, 2,4-oxadiazol-3-yl ketone O-methyloxime Aluminium chloride (0.27 g, 2 mmol) was added to a mixture of 5-chloro-2-(4-chlorobenzyloxy)phenyl 5-methyl-1,2,4-oxadiazol-3-yl ketone O-methyloxime (0.39 g, 1 mmol) and anisole (3 ml) under ice-cooling, and the mixture was stirred at the same temperature for 1 hour. After completion of the reaction, aqueous sodium bicarbonate solution (100 ml) was added, and the mixture was extracted with ethyl acetate. The ethyl acetate layer was dried over anhydrous magnesium sulfate and concentrated under reduced pressure. The residue was purified by silica gel chromatography (ethyl acetate/n-hexane) to give 5-chloro-2-hydroxyphenyl 5-methyl-1,2,4-oxadiazol-3-yl ketone O-methyloxime (0.22 g, 82.2%) as colorless crystals. A part of the crystals was recrystallized from ether/n-hexane to give crystals (mp. 92–93.5° C.).
$^1$H-NMR(CDCl$_3$) δ ppm: 2.75(3H,s), 4.06(3H,s), 6.82–7.27(3H,m), 10.22(1H,s).

Synthesis of 5-chloro-2-(5-trifluoromethyl-2-pyridyloxy)phenyl 5-methyl-1,2,4-oxadiazol-3-yl ketone O-methyloxime N,N-Dimethylformamide (1 ml), potassium carbonate (0.10 g, 0.74 mmol) and 5-trifluoromethyl-2-chloropyridine (0.10 g, 0.56 mmol) were added to 5-chloro-2-hydroxyphenyl 5-methyl-1,2,4-oxadiazol-3-yl ketone O-methyloxime (0.10 g, 0.37 mmol), and the mixture was stirred at 110° C. for 2 hours. After completion of the reaction, ether (100 ml) was added, and the mixture was washed with saturated brine (80 ml) twice. The ether layer was dried over anhydrous magnesium sulfate and concentrated under reduced pressure. The residue was purified by silica gel chromatography (ethyl acetate/n-hexane) to give 5-chloro-2-(5-trifluoromethyl-2-pyridyloxy)phenyl 5-methyl-1,2,4-oxadiazol-3-yl ketone O-methyloxime (0.14 g, 91.7%) as a colorless oil.

$^1$H-NMR(CDCl$_3$) δ ppm: 2.46(3H,s), 4.03(3H,s), 6.77 (1H,d,J=9.2), 7.16(1H,d,J=9.2), 7.44–7.86(3H,m), 8.36(1H, d,J=1.8).

Example 20

Synthesis of 2-(2,5-dimethylphenoxymethyl)-α-methoxyiminophenylacetonitrile

Dimethyl sulfoxide (2 ml) and 95% sodium cyanide (0.21 g, 0.004 mol) were added to 2-(2,5-dimethylphenoxymethyl)-α-methoxyiminobenzyl chloride (0.60 g, 0.002 mol), and the mixture was stirred at 110° C. for 2 hours. After completion of the reaction, ether (100 ml) was added, and the mixture was washed with water twice, dried over anhydrous magnesium sulfate and concentrated under reduced pressure. The residue was purified by silica gel chromatography (ethyl acetate/n-hexane) to give 2-(2,5-dimethylphenoxymethyl)-α-methoxyiminophenylacetonitrile (0.45 g, 76.4%) as colorless crystals.

$^1$H-NMR(CDCl$_3$) δ ppm: 2.24(s,3H), 2.30(s,3H), 4.13(s, 3H), 5.26(s,2H), 6.62–7.76(m,7H).

Example 21

Synthesis 2-(4-chlorophenoxymethyl)-α-methoxyiminophenylacetonitrile

Trifluoroacetic anhydride (3.15 g, 15 mmol) was added to a mixture of 2-(4-chlorophenoxymethyl)-α-methoxyiminophenylacetamide (1.19 g, 6 mmol) and pyridine (12 ml) under ice-cooling over 20 minutes, and the mixture was stirred at room temperature for 2 hours. After completion of the reaction, ether (150 ml) was added, and the mixture was washed with 1N hydrochloric acid (150 ml), water (100 ml) and saturated aqueous sodium bicarbonate solution (100 ml). The ether layer was dried over anhydrous magnesium sulfate and concentrated under reduced pressure. The residue was purified by silica gel chromatography (ethyl acetate/n-hexane) to give 2-(4-chlorophenoxymethyl)-α-methoxyiminophenylacetonitrile (1.57 g, 87.0%) as colorless crystals.

mp. 69–71° C.

$^1$H-NMR(CDCl$_3$) δ ppm: 4.02(3H,s), 4.99(2H,s), 6.86–6.89(2H,m), 7.23–7.26(2H,m), 7.36–7.56(4H,m).

Example 22

Synthesis of α-methoxyimino-2-methylphenylacetonitrile

85% potassium hydroxide (4.0 g, 61 mmol) and 2-methylphenylacetonitrile (6.6 g, 50 mmol) were added to toluene (33 ml), and the mixture was ice-cooled. Methanol (6.6 ml) was added dropwise, and then butyl nitrite (7.0 ml, 60 mmol) was added dropwise while maintaining the temperature of the mixture at 25 to 35° C. The resulting mixture was stirred under ice-cooling for 3 hours. After allowing the mixture to stand at room temperature overnight, water was added to the reaction mixture, and the resulting potassium salt of α-hydroxyimino-2-methylphenylacetonitrile was extracted. Water was added to the extract to a volume of 100 ml. Toluene (50 ml) and tetrabutylammonium bromide (800 mg, 2.5 mmol) were added, and dimethyl sulfate (5.7 ml, 60 mmol) was added under ice-cooling in 4 divided portions. The mixture was stirred at room temperature for additional 30 minutes, and then the organic layer was separated, washed successively with aqueous 1N sodium hydroxide solution and saturated brine and dried over anhydrous sodium sulfate, and the solvent was evaporated under reduced pressure. The residue was purified by silica gel chromatography (ethyl acetate/n-hexane) to give two geometrical isomers A (6.0 g, 69%, as an oil) and B (1.2 g, 14%, as an oil) of α-methoxyimino-2-methylphenylacetonitrile.

Isomer A: $^1$H-NMR(CDCl$_3$) δ ppm: 2.51(3H,s), 4.20 (3H,s), 7.25–7.36(3H,m), 7.54(1H,d,J=7.9).

Isomer B: $^1$H-NMR(CDCl$_3$) δ ppm: 2.31(3H,s), 4.06 (3H,s), 7.25–7.39(4H,m).

Synthesis of 2-bromomethyl-α-methoxyiminophenylacetonitrile

Benzene (80 ml) was added to (-methoxyimino-2-methylphenylacetonitrile (isomer A)(4.0 g, 23 mmol) and N-bromosuccinimide (4.9 g, 28 mmol), and the mixture was heated under reflux for 1 hour in the presence of 2,2'-azobis (isobutyronitrile) (190 mg, 1.2 mmol) as a radical initiator. After allowing the mixture to stand for cooling, n-hexane (100 ml) was added, and the mixture was allowed to stand overnight, and the resulting insoluble materials were filtered off. The filtrate was concentrated to dryness under reduced pressure and purified by column chromatography on silica gel (ethyl acetate/n-hexane) to give 2-bromomethyl-α-methoxyiminophenyl-acetonitrile (4.4 g, 76%) as an oil.

$^1$H-NMR(CDCl$_3$) δ ppm: 4.30(3H,s), 4.79(2H,s), 7.42–7.50(3H,m), 7.66–7.69(1H,m).

Synthesis of 2-(3-chlorophenoxymethyl)-α-methoxyiminophenylacetonitrile

2-Bromomethyl-α-methoxyiminophenylacetonitrile (5.0 g, 20 mmol) and 3-chlorophenol (3.0 g, 23 mmol) were dissolved in N,N-dimethylformamide (25 ml), and the mixture was stirred at room temperature for 2 hours in the presence of potassium carbonate (3.3 g, 24 mmol). After completion of the reaction, diethyl ether (ca. 100 ml) was added to the reaction mixture, and the mixture was washed successively with water and saturated brine. The organic layer was dried over anhydrous sodium sulfate and concentrated to dryness under reduced pressure. The residue was purified by column chromatography on silica gel (ethyl acetate/n-hexane) and crystallized from diethyl ether/n-hexane to give 2-(3-chlorophenoxymethyl)-α-methoxyiminophenylacetonitrile (3.7 g, 62%) as colorless crystals.

mp. 62–63° C.

$^1$H-NMR(CDCl$_3$) δ ppm: 4.11(3H,s), 5.25(2H,s), 6.82 (1H,d,J=8.3), 6.95–6.97(2H,m), 7.21(1H,t,J=8.3), 7.45–7.53 (2H,m), 7.67(1H,d,J=7.3), 7.75(1H,dd,J=7.3,1.5).

Example 23

Synthesis of 1-bromo-2-(2-tetrahydropyranyloxymethyl)benzene

Pyridinium p-toluenesulfonate (0.30 g, 0.0012 mol) was added to a solution of 2-bromobenzylalcohol (25 g, 0.134 mol) in dichloromethane (100 ml), and the mixture was stirred at room temperature. 3,4-Dihydro-2H-pyran (16.86 g, 0.20 mol) was added thereto. The mixture was stirred at room temperature for 2 hours. Then, saturated aqueous sodium bicarbonate solution (200 ml) was added, and the mixture was extracted with dichloromethane (200 ml). After drying over anhydrous magnesium sulfate, the solvent was evaporated to give the desired 1-bromo-2-(2-tetrahydropyranyloxymethyl)benzene (36.00 g, yield: 99.3%) as an oil.

$^1$H-NMR(CDCl$_3$) δ ppm: 1.45–1.80(6H,m), 3.45–3.55 (1H,m), 3.80–3.90(1H,m), 4.52(1H,d,J=15.0), 4.80(1H,m), 4.90(1H,d,J=15.0), 7.16(1H,t,J=7.3), 7.31(1H,t,J=7.3), 7.51 (1H,d,J=7.3), 7.54(1H,d,J=7.3).

Example 24

Synthesis of 2-(2-tetrahydropyranyloxymethyl) phenyl 3-methylisoxazol-5-yl ketone Magnesium (0.73 g, 0.03 mol) and bromoethane (0.2 ml) were added to a mixture of 1-bromo-2-(2-tetrahydropyranyloxymethyl)benzene (5.42 g, 0.02 mol) and THF (50 ml) under an atmosphere of nitrogen gas, and the resulting mixture was stirred at 50 to 60° C. for 1 hour to prepare Grignard reagent. The Grignard reagent was added dropwise to a mixture of N-methoxy-3, N-dimethyl-5-isoxazolcarboxamide (3.40 g, 0.02 mol) and THF (40 ml). The mixture was stirred at −60° C. to room temperature for 1 hour, water (200 ml) was added, and the mixture was extracted with ether (200 ml). The extract was dried over anhydrous magnesium sulfate and concentrated under reduced pressure. The residue was purified by silica gel chromatography (ethyl acetate/n-hexane) to give 2-(2-tetrahydropyranyloxymethyl)phenyl 3-methylisoxazol-5-yl ketone (4.09 g, yield: 67.9%) as a colorless oil.

$^1$H-NMR(CDCl$_3$) δ ppm: 1.41–1.74(6H,m), 2.39(3H,s), 3.45–3.51(1H,m), 3.75–3.83(1H,m), 4.59–4.60(1H,m), 4.71 (1H,d,J=12.8), 4.94(1H,d,J=12.8), 6.69(1H,S), 7.38–7.63 (4H,m).

Example 25

Synthesis of 2-hydroxymethylphenyl 3-methylisoxazol-5-yl ketone O-methyloxime

Methanol (25 ml), methoxyamine hydrochloride (2.17 g, 0.026 mol) and pyridine (2.1 ml, 0.026 mol) were added to 2-(2-tetrahydropyranyloxymethyl)phenyl 3-methylisoxazol-5-yl ketone (4.09 g, 0.013 mol), and the mixture was stirred under reflux for 3 hours. After completion of the reaction, half-saturated brine (200 ml) was added, and the mixture was extracted with dichloromethane (100 ml) twice. The extracts were dried over anhydrous magnesium sulfate and concentrated under reduced pressure. The residue was purified by silica gel chromatography (ethyl acetate/n-hexane) to give isomer A (0.63 g, yield: 19.7%, as a colorless oil) and isomer B (1.62 g, yield: 50.7%, as a colorless oil) of 2-hydroxymethylphenyl 3-methylisoxazol-5-yl ketone O-methyloxime.

Isomer A: $^1$H-NMR(CDCl$_3$) δ ppm: 2.39 (3H,s) 2.74(1H, t,J=6.7), 4.17(3H,s), 4.54(2H,d,J=6.7), 7.02(1H,s), 7.33–7.55(4H,m).

Isomer B: $^1$H-NMR(CDCl$_3$) δ ppm: 1.89(1H,t,J=6.1), 2.28(3H,s), 4.03(3H,s), 4.52(2H,d,J=6.1), 6.05(1H,s), 7.17–7.62(4H,m).

Example 26

Synthesis of 2-(3-chloro-5-trifluoromethyl-2-pyridyloxymethyl)phenyl 3-methylisoxazol-5-yl ketone O-methyloxime THF (7.5 ml), 2,3-dichloro-5-trifluoromethylpyridine (0.81 g, 3.75 mmol) and 60% sodium hydride (0.12 g, 3.0 mmol) were added to 2-hydroxymethylphenyl 3-methylisoxazol-5-yl ketone O-methyloxime (0.62 g, 2.5 mmol) under ice-cooling, and the mixture was stirred at room temperature overnight. Water (100 ml) was added to the reaction mixture, and the mixture was extracted with ether (150 ml). The extract was dried over anhydrous magnesium sulfate and concentrated under reduced pressure. The residue was purified by silica gel chromatography (ethyl acetate/n-hexane) to give isomer A (0.29 g, yield: 27.2%) and isomer B (0.76 g, yield: 71.4%) of 2-(3-chloro-5-trifluoromethyl-2-pyridyloxymethyl)phenyl 3-methylisoxazol-5-yl ketone O-methyloxime.

Isomer A: mp. 77–79° C., $^1$H-NMR(CDCl$_3$) δ ppm: 2.37(3H,s), 4.14(3H,s), 5.45(2H,s), 6.97(1H,s), 7.36–7.63 (4H,m), 7.79(1H,d,J=2.4), 8.09(1H,d,J=2.4).

Isomer B: $^1$H-NMR(CDCl$_3$) δ ppm: 2.28(3H,s), 4.04(3H, s), 5.33(2H,s), 6.01(1H,s), 7.20–7.65(4H,m), 7.80(1H,d,J= 2.2), 8.08(1H,d,J=2.2).

Example 27

Synthesis of 2-(2,5-dimethylphenoxymethyl)phenyl thiazolidin-2-yl ketone O-methyloxime Toluene (3 ml), butanol (3 ml), cysteamine hydrochloride (0.34 g, 3.0 mmol) and triethylamine (0.42 ml, 3 =mol) were added to 2-(2,5-dimethylphenoxymethyl)-α-methoxyiminophenylacetoaldehyde (0.45 g, 1.5 mmol), and the mixture was stirred at room temperature for 1 hour. After completion of the reaction, half-saturated brine (100 ml) was added, and the mixture was extracted with dichloromethane (50 ml) twice. The extracts were dried over anhydrous magnesium sulfate and concentrated under reduced pressure. The residue was purified by silica gel chromatography (ethyl acetate/n-hexane) to give 2-(2,5-dimethylphenoxymethyl)phenyl thiazolidin-2-yl ketone O-methyloxime (0.49 g, yield 91.6%) as a colorless oil.

$^1$H-NMR(CDCl$_3$) δ ppm: 2.28(6H,s), 2.40(1H,brs), 2.81–3.06(3H,m), 3.38–3.55(1H,m), 3.87(3H,s), 4.85–5.50 (3H,m), 6.67–7.64(7H,m).

Example 28

Synthesis of 2-(2,5-dimethylphenoxymethyl)phenyl 1,3-dioxolan-2-yl ketone O-methyloxime Benzene (4 ml), ethylene glycol (0.12 g, 2.0 mmol) and p-toluenesulfonic acid monohydrate (0.01 g, 0.05 mmol) were added to 2-(2,5-dimethylphenoxymethyl)-α-methoxyiminophenylacetaldehyde (0.3 g, 1.0 mmol), and the mixture was subjected to azeotropic dehydration for 2 hours. After completion of the reaction, half-saturated brine (100 ml) was added, and the mixture was extracted with dichloromethane (50 ml) twice. The extracts were dried over anhydrous magnesium sulfate and concentrated under reduced pressure. The residue was purified by silica gel chromatography (ethyl acetate/n-hexane) to give 2-(2,5-dimethylphenoxymethyl)phenyl 1,3-dioxolan-2-yl ketone O-methyloxime (0.30 g, yield 87.9%) as colorless crystals. mp 136–137° C.

$^1$H-NMR(CDCl$_3$) δ ppm: 2.28(3H,m), 2.29(3H,s), 3.59–3.85(4H,m), 3.92(3H,s), 5.04(1H,s), 5.09(1H,s), 5.63 (1H,s), 6.66–7.62(7H,m).

Example 29

Synthesis of 1-bromo-2-(1-ethoxyethyl) oxymethylbenzene

Pyridinium p-toluenesulfonate (0.50 g, 0.002 mol) was added to a mixture of 2-bromobenzylalcohol (18.70 g, 0.1 mol), dichloromethane (150 ml) and ethyl vinyl ether (14.42 g, 0.2 mol) under ice-cooling, and the mixture was stirred at room temperature for 3 hours. After completion of the reaction, half-saturated aqueous sodium bicarbonate solution (300 ml) was added, and the mixture was extracted with dichloromethane (100 ml) twice. The extracts were dried over anhydrous magnesium sulfate and concentrated under reduced pressure to give 1-bromo-2-(1-ethoxyethyl) oxymethylbenzene (25.44 g, yield: 98.2%) as a colorless oil.

¹H-NMR(CDCl₃) δ ppm: 1.22(3H,t,J=7.3), 1.41 (3H,t,J= 5.5), 3.49–3.77(2H,m), 4.59(1H,d,J=12.8), 4.70 (1H,d,J= 12.8), 4.87(1H,q,J=5.5), 7.11–7.55(4H,m).

Example 30

Synthesis of 2-(1-ethoxyethyl)oxymethylphenyl 5-methylisoxazol-3-yl ketone

A mixture of 1-bromo-2-(1-ethoxyethyl)oxymethylbenzene (12.96 g, 0.05 mol) and THF (45 ml) was added to a mixture of magnesium (1.82 g, 0.075 mol) and bromoethane (0.2 ml) and THF (5 ml) at 45 to 55° C. under an atmosphere of nitrogen gas, and the resulting mixture was stirred at 50 to 55° C. for 1 hour to prepare a Grignard reagent. The Grignard reagent was added dropwise to a mixture of N-methoxy-5, N-dimethyl-3-isoxazolcarboxamide (5.62 g, 0.033 mol) and THF (40 ml) cooled to −50° C. The mixture was stirred at −60° C. to room temperature for 1 hour, water (200 ml) was added, and the mixture was extracted with ether (200 ml). The extract was dried over anhydrous magnesium sulfate and concentrated under reduced pressure. The residue was purified by silica gel chromatography (ethyl acetate/n-hexane) to give 2-(1-ethoxyethyl)oxymethylphenyl 5-methylisoxazol-3-yl ketone (8.61 g, yield: 90.2%) as a colorless oil.

¹H-NMR(CDCl₃) δ ppm: 1.16(3H,t,J=6.7), 1.27 (3H,d,J= 5.5), 2.52(3H,s), 3.43–3.65(2H,m), 4.68–4.92(3H,m), 6.50 (1H,s), 7.36–7.84(4H,m).

Example 31

Synthesis of 2-(1-ethoxyethyl)oxymethylphenyl 5-methylisoxazol-3-yl ketone O-methyloxime 2-(1-Ethoxyethyl)oxymethylphenyl 5-methylisoxazol-3-yl ketone (4.34 g, 0.015 mol) was added to a mixture of methanol (30 ml), methoxyamine hydrochloride (2.51 g, 0.03 mol) and 28% sodium methylate/methanol solution (7.23 g, 0.0375 mol), and the mixture was stirred under reflux for 3 hours. After completion of the reaction, half-saturated brine (200 ml) was added, and the mixture was extracted with dichloromethane (100 ml) twice. The extracts were dried over anhydrous magnesium sulfate and concentrated under reduced pressure. The residue was purified by silica gel chromatography (ethyl acetate/n-hexane) to give 2-(1-ethoxyethyl)oxymethylphenyl 5-methylisoxazol-3-yl ketone O-methyloxime (4.32 g, yield: 90.5%) as a colorless oil.

¹H-NMR(CDCl₃) δ ppm: 1.11–1.26(6H,m), 2.47(2.43) (3H,s), 3.39–3.60(2H,m), 4.08(3.97)(3H,s), 4.11–4.70(3H,m), 6.61(6.37)(1H,s), 7.19–7.56(4H,m).

Example 32

Synthesis of 2-hydroxymethylphenyl 5-methylisoxazol-3-yl ketone O-methyloxime

Methanol (26 ml) and pyridinium p-toluenesulfonate (0.33 g, 0.0013 mol) were added to 2-(1-ethoxyethyl)oxymethylphenyl 5-methylisoxazol-3-yl ketone O-methyloxime (4.14 g, 0.013 mol), and the mixture was stirred under reflux for 0.5 hour. After completion of the reaction, half-saturated brine (300 ml) was added, and the mixture was extracted with dichloromethane (100 ml) twice. The extracts were dried over anhydrous magnesium sulfate and concentrated under reduced pressure. The residue was purified by silica gel chromatography (ethyl acetate/n-hexane) to give 2-hydroxymethylphenyl 5-methylisoxazol-3-yl ketone O-methyloxime (2.95 g, yield: 92.1%) as a colorless oil.

¹H-NMR(CDCl₃) δ ppm: 2.43(3.18) (1H,t,J=6.7), 2.44 (2.50)(3H,s), 3.99(4.11)(3H,s), 4.47(4.57)(2H,d,J=6.7), 6.44 (6.62)(1H,s), 7.19–7.60(4H,m).

Example 33

Synthesis of 2-(5-chloro-3-trifluoromethyl-2-pyridyloxymethyl)phenyl 5-methylisoxazol-3-yl ketone O-methyloxime THF (3 ml), 2,5-dichloro-3-trifluoromethylpyridine (0.32 g, 1.5 mmol) and 60% sodium hydride (0.05 g, 1.2 mmol) were added to 2-hydroxymethylphenyl 5-methylisoxazol-3-yl ketone O-methyloxime (0.25 g, 1.0 mmol) under ice-cooling, and the mixture was stirred at room temperature overnight. Water (100 ml) was added to the reaction mixture, and the mixture was extracted with ether (150 ml). The extract was dried over anhydrous magnesium sulfate and concentrated under reduced pressure. The residue was purified by silica gel chromatography (ethyl acetate/n-hexane) to give 2-(5-chloro-3-trifluoromethyl-2-pyridyloxymethyl)phenyl 5-methylisoxazol-3-yl ketone O-methyloxime (0.41 g, yield: 96.3%) as colorless crystals.

mp. 120–121° C. (ether/n-hexane)

¹H-NMR(CDCl₃) δ ppm: 2.45(3H,s), 3.99(3H,s), 5.34 (2H,s), 6.39(1H,s), 7.23–7.64(2H,m), 7.79(1H,d,J=2.5), 8.06(1H,d,J=2.5).

Example 34

Synthesis of 2-chloromethylphenyl 3-methylisoxazol-5-yl ketone O-methyloxime

Benzene (5 ml) and thionyl chloride (0.36 g, 3.0 mmol) were added to 2-hydroxymethylphenyl 3-methylisoxazol-5-yl ketone O-methyloxime (0.62 g, 2.5 mmol), and the mixture was stirred at room temperature for 2 hours. After completion of the reaction, the solvent was evaporated under reduced pressure. The residue was purified by silica gel chromatography (ethyl acetate/n-hexane) to give 2-chloromethylphenyl 3-methylisoxazol-5-yl ketone O-methyloxime (0.26 g, yield: 39.3%) as a colorless oil.

¹H-NMR(CDCl₃) δ ppm: 2.29(3H,s), 4.04(3H,s), 4.47 (2H,s), 6.05(1H,s), 7.18–7.60(4H,m).

Example 35

Synthesis of 2-(3,4-dichloro-α-methylbenzylideneaminooxymethyl)phenyl 3-methylisoxazol-5-yl ketone O-methyloxime N,N-Dimethylformamide (3 ml), 3,4-dichloroacetophenone oxime (0.31 g, 1.5 mmol) and potassium carbonate (0.28 g, 2.0 mmol) were added to 2-chloromethylphenyl 3-methylisoxazol-5-yl ketone O-methyloxime (0.26 g, 1.0 mmol), and the mixture was stirred at 60° C. for 2 hours. Water (100 ml) was added to the reaction mixture, and the mixture was extracted with ether (150 ml). The extract was dried over anhydrous magnesium sulfate and concentrated under reduced pressure. The residue was purified by silica gel chromatography (ethyl acetate/n-hexane) to give 2-(3,4-dichloro-α-methylbenzylideneaminooxymethyl)phenyl 3-methylisoxazol-5-yl ketone O-methyloxime (0.37 g, yield: 85.6%) as colorless crystals.

¹H-NMR(CDCl₃) δ ppm: 2.01(3H,s), 2.21(3H,s), 4.04 (3H,s), 5.13(2H,s), 5.96(1H,s), 7.20–7.64(7H,m). mp. 84–85° C.

Example 36

Synthesis of 2-[(α-methyl-3-trifluoromethylbenzylidene)aminooxymethyl]-α-methoxyiminophenylacetaldehyde 1M diisobutylaluminum hydride/toluene solution (11 ml, 16.5 mmol) was added dropwise to a mixture of methyl 2-[(α-methyl-3-trifluoromethylbenzylidene) aminooxymethyl]-α-methoxyiminophenylacetate (4.83 g, 11.8 mmol) and dichloromethane (47 ml) at −65° C. or lower over 4 minutes, and the mixture was stirred at −78° C. to room temperature for 3 hours. Methanol (7 ml) was added to the reaction mixture, and the mixture was stirred at room temperature for 1 hour. The precipitated insoluble materials were removed, and the remaining mixture was concentrated under reduced pressure. The residue was purified by silica gel chromatography (ethyl acetate/n-hexane) to give 2-[(α-methyl-3-trifluoromethylbenzylidene)aminooxymethyl]-α-methoxyiminophenylacetaldehyde (2.11 g, 47.3%) as a colorless oil.

$^1$H-NMR(CDCl$_3$) δ ppm: 2.19(3H,s), 4.11(3H,s), 5.09 (2H,s), 7.09–7.12(1H,m), 7.36–7.52(4H,m), 7.59(1H,d,J=7.9), 7.77(1H,d,J=7.9), 7.85(1H,s), 9.70(1H,s).

Example 37

Synthesis of 2-[(α-methyl-3-trifluoromethyl-benzylidene)aminooxymethyl]phenyl thiazolidin-2-yl ketone O-methyloxime Toluene (2.5 ml), butanol (2.5 ml), cysteamine hydrochloride (0.29 g, 2.54 mmol) and triethylamine (0.26 g, 2.54 mmol) were added to 2-[(α-methyl-3-trifluoromethylbenzylidene)aminooxymethyl]-α-methoxyiminophenylacetaldehyde (0.48 g, 1.27 mmol), and the mixture was stirred at room temperature for 1 hour. After completion of the reaction, half-saturated brine (100 ml) was added, and the mixture was extracted with dichloromethane (50 ml) twice. The extracts were dried over anhydrous magnesium sulfate and concentrated under reduced pressure. The residue was purified by silica gel chromatography (ethyl acetate/n-hexane) to give 2-[(α-methyl-3-trifluoromethylbenzylidene)aminooxymethyl]phenyl thiazolidin-2-yl ketone O-methyloxime (0.52 g, yield 93.6%) as a colorless oil.

$^1$H-NMR(CDCl$_3$) δ ppm: 2.39(3H,s), 2.75–3.10(3H,m) 3.50(2H,m), 3.86(3H,s), 5.20–5.30(2H,m), 5.45(1H,m), 7.37–7.61(6H,m), 7.82(1H,d,J=7.9), 7.91(1H,s).

According to the same manner as that in Examples 24 and 30, various compounds of the formula (XLVIII), which are intermediates for production of the compound (I), were synthesized. The compounds thus obtained and their physical data are as follows. In the following tables, the physical data of the compounds (XLVIII-7) and (XLVIII-4) obtained in Examples 24 and 30, respectively, are also listed.

| No | R$^3$ | R$^4$ | P | Physical data |
|---|---|---|---|---|
| XLVIII-1 | Isoxazol-3-yl | H | Tetrahydropyranyl | |
| XLVIII-2 | Isoxazol-3-yl | H | 1-C$_2$H$_5$OC$_2$H$_4$ | $^1$H-NMR(CDCl$_3$) δ ppm: 1.16(3H, t, J=7.3), 1.26(3H, d, J=5.5), 3.40–3.65(2H, m), 4.70–4.93(3H, m), 6.89(1H, d, J=1.8), 7.37–7.87(4H, m), 8.53(1H, J=1.8) |
| XLVIII-3 | 5-Me-isoxazol-3-yl | H | Tetrahydropyranyl | |
| XLVIII-4 | 5-Me-isoxazol-3-yl | H | 1-C$_2$H$_5$OC$_2$H$_4$ | $^1$H-NMR(CDCl$_3$) δ ppm: 1.16(3H, t, J=6.7), 1.27(3H, d, J=5.5), 2.52(3H, s), 3.43–3.65(2H, m), 4.68–4.92(3H, m), 6.50(1H, s), 7.36–7.84(4H, m). |
| XLVIII-5 | Isoxazol-5-yl | H | Tetrahydropyranyl | |
| XLVIII-6 | Isoxazol-5-yl | H | 1-C$_2$H$_5$OC$_2$H$_4$ | |
| XLVIII-7 | 3-Me-isoxazol-5-yl | H | Tetrahydropyranyl | $^1$H-NMR(CDCl$_3$) δ ppm: 1.41–1.74 (6H, m), 2.39(3H, s), 3.45-3.51(1H, m), 3.75–3.83(1H, m), 4.59–4.60 (1H, m), 4.71(1H, d, J=12.8), 4.94 (1H, d, J=12.8), 6.69(1H, s), 7.38–7.63(4H, m). |
| XLVIII-8 | 3-Me-isoxazol-5-yl | H | 1-C$_2$H$_5$OC$_2$H$_4$ | $^1$H-NMR(CDCl$_3$) δ ppm: 1.16(3H, t, J=7.3), 1.25(3H, d, J=5.5), 2.40(3H, s), 3.42–3.61(2H, m), 4.68–4.88(3H, m), 6.70(1H, s), 7.37–7.66(4H, m) |
| XLVIII-9 | 1,3,4-Oxadiazol-2-yl | H | Tetrahydropyranyl | |
| XLVIII-10 | 1,3,4-Oxadiazol-2-yl | H | 1-C$_2$H$_5$OC$_2$H$_4$ | |
| XLVIII-11 | 1-Me-imidazol-2-yl | H | Tetrahydropyranyl | |
| XLVIII-12 | 1-Me-imidazol-2-yl | H | 1-C$_2$H$_5$OC$_2$H$_4$ | |
| XLVIII-13 | 2-Isoxazolin-3-yl | H | Tetrahydropyranyl | |
| XLVIII-14 | 2-Isoxazolin-3-yl | H | 1-C$_2$H$_5$OC$_2$H$_4$ | |
| XLVIII-15 | 5-Me-2-isoxazolin-3-yl | H | Tetrahydropyranyl | |
| XLVIII-16 | 5-Me-2-isoxazolin-3-yl | H | 1-C$_2$H$_5$OC$_2$H$_4$ | |
| XLVIII-17 | 2-Furyl | H | Tetrahydropyranyl | |
| XLVIII-18 | 2-Furyl | H | 1-C$_2$H$_5$OC$_2$H$_4$ | |
| XLVIII-19 | 5-Me-1,2,4-oxadiazol-3-yl | H | Tetrahydropyranyl | |
| XLVIII-20 | 5-Me-1,2,4-oxadiazol-3-yl | H | 1-C$_2$H$_5$OC$_2$H$_4$ | |

According to the same manner as that in Examples described above, various compounds of the formula (I) were synthesized. The compounds thus obtained and their physical data are as follows. In the following tables, the physical data of the compounds obtained in the above Examples are also listed. "No." represents a compound number. When the product is obtained as a mixture of isomers A/B, the δ values of either isomer are indicated in the parentheses.

The basic structures of the compound (I) in the tables are as follows:

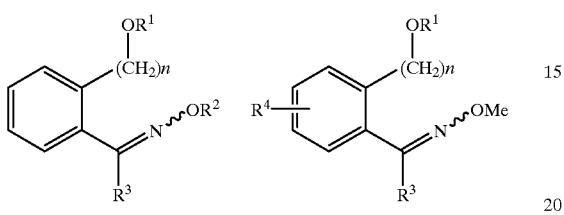

Comp. No. 1~2100          Comp. No. 2101~2320

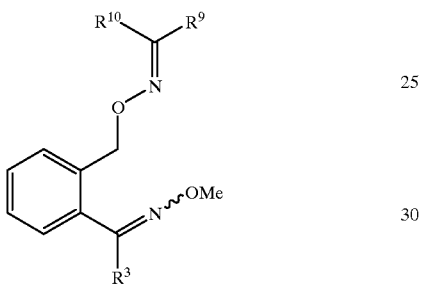

Comp. No. 2321~3140

| No | R$^1$ | R$^2$ | R$^3$ | n | Physical data |
|---|---|---|---|---|---|
| 1 | C$_6$H$_5$ | Me | Imidazol-1-yl | 1 | mp 66–67.5° C. |
| 2 | 2-F—C$_6$H$_4$ | Me | Imidazol-1-yl | 1 | |
| 3 | 3-F—C$_6$H$_4$ | Me | Imidazol-1-yl | 1 | |
| 4 | 4-F—C$_6$H$_4$ | Me | Imidazol-1-yl | 1 | |
| 5 | 2-Cl—C$_6$H$_4$ | Me | Imidazol-1-yl | 1 | mp 79.5–80.5° C. |
| 6 | 3-Cl—C$_6$H$_4$ | Me | Imidazol-1-yl | 1 | mp 96.5–97.5° C. |
| 7 | 4-Cl—C$_6$H$_4$ | Me | Imidazol-1-yl | 1 | mp 88–88.5° C. |
| 8 | 2-Br—C$_6$H$_4$ | Me | Imidazol-1-yl | 1 | |
| 9 | 3-Br—C$_6$H$_4$ | Me | Imidazol-1-yl | 1 | |
| 10 | 4-Br—C$_6$H$_4$ | Me | Imidazol-1-yl | 1 | |
| 11 | 3-I—C$_6$H$_4$ | Me | Imidazol-1-yl | 1 | |
| 12 | 4-I—C$_6$H$_4$ | Me | Imidazol-1-yl | 1 | |
| 13 | 2-Me—C$_6$H$_4$ | Me | Imidazol-1-yl | 1 | $^1$H-NMR(CDCl$_3$)δppm: 2.16(3H, s), 3.99(3H, s), 4.98(2H, s), 6.68–7.66 (10H, m), 7.96(1H, s) |
| 14 | 3-Me—C$_6$H$_4$ | Me | Imidazol-1-yl | 1 | |
| 15 | 4-Me—C$_6$H$_4$ | Me | Imidazol-1-yl | 1 | mp 58–65° C. |
| 16 | 2-Et—C$_6$H$_4$ | Me | Imidazol-1-yl | 1 | $^1$H-NMR(CDCl$_3$)δ ppm: 1.16(3H, t, J = 7.3), 2.60(2H, q, J = 7.3), 3.99(3H, s), 4.98 (2H, s), 6.69–7.67 (10H, m), 7.96(1H, s) |
| 17 | 3-Et—C$_6$H$_4$ | Me | Imidazol-1-yl | 1 | |
| 18 | 4-Et—C$_6$H$_4$ | Me | Imidazol-1-yl | 1 | |
| 19 | 2-MeO—C$_6$H$_4$ | Me | Imidazol-1-yl | 1 | |
| 20 | 3-MeO—C$_6$H$_4$ | Me | Imidazol-1-yl | 1 | |
| 21 | 4-MeO—C$_6$H$_4$ | Me | Imidazol-1-yl | 1 | |
| 22 | 2-CF$_3$—C$_6$H$_4$ | Me | Imidazol-1-yl | 1 | |
| 23 | 3-CF$_3$—C$_6$H$_4$ | Me | Imidazol-1-yl | 1 | |

-continued

| No | R¹ | R² | R³ | n | Physical data |
|---|---|---|---|---|---|
| 24 | 4-CF₃—C₆H₄ | Me | Imidazol-1-yl | 1 | |
| 25 | 2,3-F₂—C₆H₃ | Me | Imidazol-1-yl | 1 | |
| 26 | 2,4-F₂—C₆H₃ | Me | Imidazol-1-yl | 1 | |
| 27 | 2,5-F₂—C₆H₃ | Me | Imidazol-1-yl | 1 | |
| 28 | 2,6-F₂—C₆H₃ | Me | Imidazol-1-yl | 1 | |
| 29 | 3,4-F₂—C₆H₃ | Me | Imidazol-1-yl | 1 | |
| 30 | 3,5-F₂—C₆H₃ | Me | Imidazol-1-yl | 1 | |
| 31 | 2,3-Cl₂—C₆H₃ | Me | Imidazol-1-yl | 1 | |
| 32 | 2,4-Cl₂—C₆H₃ | Me | Imidazol-1-yl | 1 | |
| 33 | 2,5-Cl₂—C₆H₃ | Me | Imidazol-1-yl | 1 | |
| 34 | 2,6-Cl₂—C₆H₃ | Me | Imidazol-1-yl | 1 | |
| 35 | 3,4-Cl₂—C₆H₃ | Me | Imidazol-1-yl | 1 | |
| 36 | 3,5-Cl₂—C₆H₃ | Me | Imidazol-1-yl | 1 | |
| 37 | 2,3-Me₂—C₆H₃ | Me | Imidazol-1-yl | 1 | |
| 38 | 2,4-Me₂—C₆H₃ | Me | Imidazol-1-yl | 1 | |
| 39 | 2,5-Me₂—C₆H₃ | Me | Imidazol-1-yl | 1 | $^1$H-NMR(CDCl₃) δ ppm: 2.11 (3H, s), 2.26 (3H, s), 3.99(3H, s), 4.96 (2H, s), 6.52(1H, s), 6.66 (1H, d, J = 7.3), 6.98–7.66 (7H, m), 7.96(1H, s) |
| 40 | 2,6-Me₂—C₆H₃ | Me | Imidazol-1-yl | | $^1$H-NMR(CDCl₃)δ ppm: 2.17(6H, s), 4.01 (3H, s), 4.78(2H, s), 6.89–7.85 (9H, m), 8.04(1H, s) |
| 41 | 3,4-Me₂—C₆H₃ | Me | Imidazol-1-yl | 1 | |
| 42 | 3,5-Me₂—C₆H₃ | Me | Imidazol-1-yl | 1 | |
| 43 | 2-Cl-4-Me—C₆H₃ | Me | Imidazol-1-yl | 1 | |
| 44 | 2-Cl-5-Me—C₆H₃ | Me | Imidazol-1-yl | 1 | |
| 45 | 4-Cl-2-Me—C₆H₃ | Me | Imidazol-1-yl | 1 | |
| 46 | 4-Cl-3-Me—C₆H₃ | Me | Imidazol-1-yl | 1 | |
| 47 | 2,3,5-Me₃—C₆H₂ | Me | Imidazol-1-yl | 1 | |
| 48 | 3-Ph—C₆H₄ | Me | Imidazol-1-yl | 1 | |
| 49 | 4-Ph—C₆H₄ | Me | Imidazol-1-yl | 1 | |
| 50 | 2-i-Pr—C₆H₄ | Me | Imidazol-1-yl | 1 | |
| 51 | 3-i-Pr—C₆H₄ | Me | Imidazol-1-yl | 1 | |
| 52 | 4-i-Pr—C₆H₄ | Me | Imidazol-1-yl | 1 | |
| 53 | 3-t-Bu—C₆H₄ | Me | Imidazol-1-yl | 1 | |
| 54 | 4-t-Bu—C₆H₄ | Me | Imidazol-1-yl | 1 | |
| 55 | 3-i-PrO—C₆H₄ | Me | Imidazol-1-yl | 1 | |
| 56 | 4-i-PrO—C₆H₄ | Me | Imidazol-1-yl | 1 | |
| 57 | 2-Cl-pyridin-3-yl | Me | Imidazol-1-yl | 1 | mp 107.5–108.5° C. |
| 58 | 4-MeS—C₆H₄ | Me | Imidazol-1-yl | 1 | |
| 59 | Pyridin-3-yl | Me | Imidazol-1-yl | 1 | |
| 60 | 2,4,5-Cl₃—C₆H₂ | Me | Imidazol-1-yl | 1 | |
| 61 | C₆H₅ | Et | Imidazol-1-yl | 1 | $^1$H-NMR(CDCl₃)δ ppm: 1.30(3H, t, J = 6.7), 4.21(2H, q, J = 6.7), 5.02(2H, s), 6.78–7.64 (11H, m), 8.04(1H, s) |
| 62 | 2-F—C₆H₄ | Et | Imidazol-1-yl | 1 | |
| 63 | 3-F—C₆H₄ | Et | Imidazol-1-yl | 1 | |
| 64 | 4-F—C₆H₄ | Et | Imidazol-1-yl | 1 | |
| 65 | 2-Cl—C₆H₄ | Et | Imidazol-1-yl | 1 | |
| 66 | 3-Cl—C₆H₄ | Et | Imidazol-1-yl | 1 | |
| 67 | 4-Cl—C₆H₄ | Et | Imidazol-1-yl | 1 | |
| 68 | 2-Br—C₆H₄ | Et | Imidazol-1-yl | 1 | |
| 69 | 3-Br—C₆H₄ | Et | Imidazol-1-yl | 1 | |
| 70 | 4-Br—C₆H₄ | Et | Imidazol-1-yl | 1 | |
| 71 | 3-I—C₆H₄ | Et | Imidazol-1-yl | 1 | |
| 72 | 2-Me—C₆H₄ | Et | Imidazol-1-yl | 1 | |
| 73 | 3-Me—C₆H₄ | Et | Imidazol-1-yl | 1 | |
| 74 | 4-Me—C₆H₄ | Et | Imidazol-1-yl | 1 | |
| 75 | 2-Et—C₆H₄ | Et | Imidazol-1-yl | 1 | |
| 76 | 3-Et—C₆H₄ | Et | Imidazol-1-yl | 1 | |

-continued

| No | R¹ | R² | R³ | n | Physical data |
|---|---|---|---|---|---|
| 77 | 4-Et—C₆H₄ | Et | Imidazol-1-yl | 1 | |
| 78 | 2-MeO—C₆H₄ | Et | Imidazol-1-yl | 1 | |
| 79 | 3-MeO—C₆H₄ | Et | Imidazol-1-yl | 1 | |
| 80 | 4-MeO—C₆H₄ | Et | Imidazol-1-yl | 1 | |
| 81 | C₆H₅ | Allyl | Imidazol-1-yl | 1 | $^1$H-NMR(CDCl₃) δppm: 4.63–4.66(2H, m), 5.02(2H, 2), 5.20–5.33 (2H, m), 5.86–6.01 (1H, m), 6.77–7.64 (11H, m), 8.03(1H, s) |
| 82 | 2-F—C₆H₄ | Allyl | Imidazol-1-yl | 1 | |
| 83 | 3-F—C₆H₄ | Allyl | Imidazol-1-yl | 1 | |
| 84 | 4-F—C₆H₄ | Allyl | Imidazol-1-yl | 1 | |
| 85 | 2-Cl—C₆H₄ | Allyl | Imidazol-1-yl | 1 | |
| 86 | 3-Cl—C₆H₄ | Allyl | Imidazol-1-yl | 1 | |
| 87 | 4-Cl—C₆H₄ | Allyl | Imidazol-1-yl | 1 | |
| 88 | 2-Br—C₆H₄ | Allyl | Imidazol-1-yl | 1 | |
| 89 | 3-Br—C₆H₄ | Allyl | Imidazol-1-yl | 1 | |
| 90 | 4-Br—C₆H₄ | Allyl | Imidazol-1-yl | 1 | |
| 91 | 3-I—C₆H₄ | Allyl | Imidazol-1-yl | 1 | |
| 92 | 2-Me—C₆H₄ | Allyl | Imidazol-1-yl | 1 | |
| 93 | 3-Me—C₆H₄ | Allyl | Imidazol-1-yl | 1 | |
| 94 | 4-Me—C₆H₄ | Allyl | Imidazol-1-yl | 1 | |
| 95 | 2-Et—C₆H₄ | Allyl | Imidazol-1-yl | 1 | |
| 96 | 3-Et—C₆H₄ | Allyl | Imidazol-1-yl | 1 | |
| 97 | 4-Et—C₆H₄ | Allyl | Imidazol-1-yl | 1 | |
| 98 | 2-MeO—C₆H₄ | Allyl | Imidazol-1-yl | 1 | |
| 99 | 3-MeO—C₆H₄ | Allyl | Imidazol-1-yl | 1 | |
| 100 | 4-MeO—C₆H₄ | Allyl | Imidazol-1-yl | 1 | |
| 101 | C₆H₅ | Me | 1-Me-imidazol-2-yl | 1 | Isomer A: $^1$H-NMR (CDCl₃)δ ppm: 3.85(3H, s), 4.93(2H, s), 6.80–7.57(11H, m) Isomer B: $^1$H-NMR (CDCl₃)δ ppm: 3.51(3H, s), 3.99(3H, s), 4.91(2H, s), 6.83–7.57(11H, m) |
| 102 | 2-F—C₆H₄ | Me | 1-Me-imidazol-2-yl | 1 | |
| 103 | 3-F—C₆H₄ | Me | 1-Me-imidazol-2-yl | 1 | |
| 104 | 4-F—C₆H₄ | Me | 1-Me-imidazol-2-yl | 1 | Isomer A: mp99.5–100.5° C. Isomer B: mp114.5–115.520 C. |
| 105 | 2-Cl—C₆H₄ | Me | 1-Me-imidazol-2-yl | 1 | Isomer A: $^1$H-NMR (CDCl₃)δ ppm: 3.91(3H, s), 3.96(3H, s), 5.04(2H, s), 6.81–7.65(10H, m) Isomer B: mp146.5–147.5° C. |
| 106 | 3-Cl—C₆H₄ | Me | 1-Me-imidazol-2-yl | 1 | Isomer A: $^1$H-NMR (CDCl₃)δ ppm: 3.88(3H, s), 3.96(3H, s), 4.94(2H, s), 6.69–7.54(10H, m) Isomer B: $^1$H-NMR (CDCl₃)δ ppm: 3.53(3H, s), 4.00(3H, s), 4.94(2H, s), 6.74–7.55(10H, m) |
| 107 | 4-Cl—C₆H₄ | Me | 1-Me-imidazol-2-yl | 1 | Isomer A: mp122.0–123.0° C. Isomer B: mp144.5–145.5° C. |
| 108 | 2-Br—C₆H₄ | Me | 1-Me-imidazol-2-yl | 1 | |
| 109 | 3-Br—C₆H₄ | Me | 1-Me-imidazol-2-yl | 1 | |
| 110 | 4-Br—C₆H₄ | Me | 1-Me-imidazol-2-yl | 1 | |
| 111 | 3-I—C₆H₄ | Me | 1-Me-imidazol-2-yl | 1 | |

-continued

| No | R¹ | R² | R³ | n | Physical data |
|---|---|---|---|---|---|
| 112 | 2-Me—C₆H₄ | Me | 1-Me-imidazol-2-yl | 1 | Isomer A: $^1$H-NMR (CDCl$_3$)δ ppm: 2.18(3H, s), 3.85(3H, s), 3.96(3H, s), 4.93(2H, s), 6.73–7.60(10H, m) Isomer B: mp126.0–127.0° C. |
| 113 | 3-Me—C₆H₄ | Me | 1-Me-imidazol-2-yl | 1 | Isomer A: mp88.0–91.0° C. Isomer B: $^1$H-NMR (CDCl$_3$)δ ppm: 2.31 (3H, s), 3.51 (3H, s), 4.01(3H, s), 4.89(2H, s), 6.63–7.65(10H, m) |
| 114 | 4-Me—C₆H₄ | Me | 1-Me-imidazol-2-yl | 1 | Isomer A: mp105.5–106.5° C. Isomer B: mp118.5–119.5° C. |
| 115 | 2-Et—C₆H₄ | Me | 1-Me-imidazol-2-yl | 1 | |
| 116 | 3-Et—C₆H₄ | Me | 1-Me-imidazol-2-yl | 1 | |
| 117 | 4-Et—C₆H₄ | Me | 1-Me-imidazol-2-yl | 1 | |
| 118 | 2-MeO—C₆H₄ | Me | 1-Me-imidazol-2-yl | 1 | Isomer A: $^1$H-NMR (CDCl$_3$)δ ppm: 3.85(3H, s), 3.91(3H, s), 3.96(3H, s), 5.04(2H, s), 6.74–7.65(10H, m) Isomer B: mp108.5–109.5° C. |
| 119 | 3-MeO—C₆H₄ | Me | 1-Me-imidazol-2-yl | 1 | Isomer A: $^1$H-NMR (CDCl$_3$)δ ppm: 3.74(3H, s), 3.85(3H, s), 3.95(3H, s), 4.91(2H, s), 6.38–7.56(10H, m) Isomer B: $^1$H-NMR (CDCl$_3$)δ ppm: 3.52(3H, s), 3.77(3H, s), 4.00(3H,s), 4.89(2H, s), 6.44–7.56(10H, m) |
| 120 | 4-MeO—C₆H₄ | Me | 1-Me-imidazol-2-yl | 1 | |
| 121 | 2-CF₃—C₆H₄ | Me | 1-Me-imidazol-2-yl | 1 | |
| 122 | 3-CF₃—C₆H₄ | Me | 1-Me-imidazol-2-yl | 1 | Isomer A: $^1$H-NMR (CDCl$_3$)δ ppm: 3.86(3H, s), 4.99(2H, s), 6.92–7.54(10H, m) Isomer B: mp106.0–107.0° C. |
| 123 | 4-CF₃—C₆H₄ | Me | 1-Me-imidazol-2-yl | 1 | |
| 124 | 2,4-F₂—C₆H₃ | Me | 1-Me-imidazol-2-yl | 1 | |
| 125 | 2,5-F₂—C₆H₃ | Me | 1-Me-imidazol-2-yl | 1 | |
| 126 | 2,6-F₂—C₆H₃ | Me | 1-Me-imidazol-2-yl | 1 | |
| 127 | 3,4-F₂—C₆H₃ | Me | 1-Me-imidazol-2-yl | 1 | |
| 128 | 3,5-F₂—C₆H₃ | Me | 1-Me-imidazol-2-yl | 1 | |
| 129 | 2,3-Cl₂—C₆H₃ | Me | 1-Me-imidazol-2-yl | 1 | |
| 130 | 2,4-Cl₂—C₆H₃ | Me | 1-Me-imidazol-2-yl | 1 | Isomer A: mp115.0–116.0° C. Isomer B: mp157.5–158.5° C. |
| 131 | 2,5-Cl₂—C₆H₃ | Me | 1-Me-imidazol-2-yl | 1 | Isomer A: $^1$H-NMR (CDCl$_3$)δ ppm: 3.94(3H, s), 3.98(3H, s), 5.04(2H, s), 6.82–7.65(9H, m) Isomer B: mp128.5–130.0° C. |

-continued

| No | R¹ | R² | R³ | n | Physical data |
|---|---|---|---|---|---|
| 132 | 3,4-Cl₂—C₆H₃ | Me | 1-Me-imidazol-2-yl | 1 | Isomer A: ¹H-NMR (CDCl₃)δ ppm: 3.91(3H, s), 3.96(3H, s), 4.94(2H, s), 6.67–7.65(9H, m) Isomer B: mp124.5–125.5° C. |
| 133 | 3,5-Cl₂—C₆H₃ | Me | 1-Me-imidazol-2-yl | 1 | |
| 134 | 2,3-Me₂C₆H₃ | Me | 1-Me imidazol-2-yl | 1 | |
| 135 | 2,4-Me₂—C₆H₃ | Me | 1-Me-imidazol-2-yl | 1 | |
| 136 | 2,5-Me₂—C₆H₃ | Me | 1-Me-imidazol-2-yl | 1 | Isomer A: ¹H-NMR CDCl₃)δ ppm: 2.13(3H, s), 2.24(3H, s), 3.86(3H, s), 3.97(3H, s), 4.92(2H, s), 6.55(1H, s), 6.63(1H, d, J = 7.9), 6.91(1H, s), 6.98(1H, d, J = 7.9), 7.26(1 H, s), 7.29–7.60(4H, m) Isomer B: ¹H-NMR (CDCl₃)δ ppm: 2.21(3H, s), 2.29(3H, s), 3.49(3H, s), 4.03(3H, s), 4.92(2H, s), 6.53(1H, s), 6.67(1H, d, J = 7.3), 6.95(1H, d, J = 1.2), 7.01(1H, d, 7.3), 7.17(1H, d, J = 1.2), 7.30–7.65(4H, m) |
| 137 | 3,4-Me₂—C₆H₃ | Me | 1-Me-imidazol-2-yl | 1 | |
| 138 | 3,5-Me₂—C₆H₃ | Me | 1-Me-imidazol-2-yl | 1 | |
| 139 | 2-Cl-4-Me—C₆H₃ | Me | 1-Me-imidazol-2-yl | 1 | |
| 140 | 2-Cl-5-Me—C₆H₃ | Me | 1-Me-imidazol-2-yl | 1 | |
| 141 | 4-Cl-2-Me—C₆H₃ | Me | 1-Me-imidazol-2-yl | 1 | Isomer A: mp87.0–88.0° C. Isomer B: mp134.0–135.0° C. |
| 142 | 4-Cl-3-C₆H₃ | Me | 1-Me-imidazol-2-yl | 1 | |
| 143 | 3-Ph—C₆H₄ | Me | 1-Me-imidazol-2-yl | 1 | |
| 144 | 4-Ph—C₆H₄ | Me | 1-Me-imidazol-2-yl | 1 | Isomer A: ¹H-NMR (CDCl₃)δ ppm: 3.87(3H, s). 3.97(3H, s), 4.98(2H, s), 6.88–7.64(15H, m) Isomer B: mp141.5–142.5° C. |
| 145 | 3-i-PrO—C₆H₄ | Me | 1-Me-imidazol-2-yl | 1 | |
| 146 | 3-i-Pr—C₆H₄ | Me | 1-Me-imidazol-2-yl | 1 | Isomer A: ¹H-NMR (CDCl₃)δ ppm: 1.20(6H, d, J = 7.3), 2.83(1H, sept, J = 7.3), 3.82(3H, s), 3.96(3H, s), 4.91(2H, s), 6.61–7.57(10H, m) Isomer B: ¹H-NMR (CDCl₃)δ ppm: 1.23(6H, d, J = 7.3), 2.86(1H, sept, J = 7.3), 3.50(3H, s), 4.00(3H, s), 4.88(2H, s), 6.64–7.58(10H, m) |
| 147 | 4-i-Pr—C₆H₄ | Me | 1-Me-imidazol-2-yl | 1 | |
| 148 | 3-t-Bu—C₆H₄ | Me | 1-Me-imidazol-2-yl | 1 | |
| 149 | 2-MeS—C₆H₄ | Me | 1-Me-imidazol-2-yl | 1 | |

-continued

| No | R¹ | R² | R³ | n | Physical data |
|---|---|---|---|---|---|
| 150 | 4-MeS—C₆H₄ | Me | 1-Me-imidazol-2-yl | 1 | |
| 151 | 2,3,6-F₃—C₆H₂ | Me | 1-Me-imidazol-2-yl | 1 | |
| 152 | 2,4,5-Cl₃—C₆H₂ | Me | 1-Me-imidazol-2-yl | 1 | |
| 153 | 3-PhO—C₆H₄ | Me | 1-Me-imidazol-2-yl | 1 | |
| 154 | 3,4,5-(MeO)₃—C₆H₂ | Me | 1-Me-imidazol-2-yl | 1 | |
| 155 | 2,3,5-Me₃—C₆H₂ | Me | 1-Me-imidazol-2-yl | 1 | |
| 156 | 3,4,5-Me₃—C₆H₂ | Me | 1-Me-imidazol-2-yl | 1 | |
| 157 | C₆F₅ | Me | 1-Me-imidazol-2-yl | 1 | |
| 158 | 4-Cl-3-Et—C₆H₃ | Me | 1-Me-imidazol-2-yl | 1 | |
| 159 | 3-EtO—C₆H₄ | Me | 1-Me-imidazol-2-yl | 1 | |
| 160 | 4-EtO—C₆H₄ | Me | 1-Me-imidazol-2-yl | 1 | |
| 161 | C₆H₅ | Me | 1-Me-imidazol-2-yl | 0 | ¹H-NMR(CDCl₃) δ ppm: 3.48(3H, s), 4.02(3H, s), 6.67–7.36 (10H, m), 7.75(1H, dd, J = 7.3, 1.8) |
| 162 | 4-F—C₆H₄ | Me | 1-Me-imidazol-2-yl | 0 | |
| 163 | 3-Cl—C₆H₄ | Me | 1-Me-imidazol-2-yl | 0 | |
| 164 | 4-Cl—C₆H₄ | Me | 1-Me-imidazol-2-yl | 0 | |
| 165 | 3-Me—C₆H₄ | Me | 1-Me-imidazol-2-yl | 0 | |
| 166 | 4-Me—C₆H₄ | Me | 1-Me-imidazol-2-yl | 0 | |
| 167 | 4-Et—C₆H₄ | Me | 1-Me-imidazol-2-yl | 0 | |
| 168 | 4-NO₂—C₆H₄ | Me | 1-Me-imidazol-2-yl | 0 | |
| 169 | 3,4-Cl₂—C₆H₃ | Me | 1-Me-imidazol-2-yl | 0 | |
| 170 | 3,5-Cl₂—C₆H₃ | Me | 1-Me-imidazol-2-yl | 0 | |
| 171 | 3,4-Me₂—C₆H₃ | Me | 1-Me-imidazol-2-yl | 0 | |
| 172 | 3,5-Me₂—C₆H₃ | Me | 1-Me-imidazol-2-yl | 0 | |
| 173 | 3-PhO—C₆H₄ | Me | 1-Me-imidazol-2-yl | 0 | |
| 174 | 4-Cl-3-Et—C₆H₃ | Me | 1-Me-imidazol-2-yl | 0 | |
| 175 | 3-EtO—C₆H₄ | Me | 1-Me-imidazol-2-yl | 0 | |
| 176 | 3-CF₃—C₆H₄ | Me | 1-Me-imidazol-2-yl | 0 | |
| 177 | 4-CF₃—C₆H₄ | Me | 1-Me-imidazol-2-yl | 0 | |
| 178 | 3-i-PrO—C₆H₄ | Me | 1-Me-imidazol-2-yl | 0 | |
| 179 | 3-i-Pr—C₆H₄ | Me | 1-Me-imidazol-2-yl | 0 | |
| 180 | 4-Cl-3-Me—C₆H₃ | Me | 1-Me-imidazol-2-yl | 0 | |
| 181 | Pyridin-2-yl | Me | 1-Me-imidazol-2-yl | 1 | |
| 182 | Pyridin-3-yl | Me | 1-Me-imidazol-2-yl | 1 | |
| 183 | 5-Cl-pyridin-2-yl | Me | 1-Me-imidazol-2-yl | 1 | |
| 184 | 3-Cl-pyridin-2-yl | Me | 1-Me-imidazol-2-yl | 1 | |

-continued

| No | R¹ | R² | R³ | n | Physical data |
|---|---|---|---|---|---|
| 185 | 6-Cl pyridin-2-yl | Me | 1-Me-imidazol-2-yl | 1 | |
| 186 | 2-Cl-pyridin-3-yl | Me | 1-Me-imidazol-2-yl | 1 | |
| 187 | 5-CF₃-pyridin-2-yl | Me | 1-Me-imidazol-2-yl | 1 | |
| 188 | 3-CF₃-pyridin-2-yl | Me | 1-Me-imidazol-2-yl | 1 | |
| 189 | 6-CF₃-3-Cl-pyridin-2-yl | Me | 1-Me-imidazol-2-yl | 1 | |
| 190 | 5-CF₃-3-Cl-pyridin-2-yl | Me | 1-Me-imidazol-2-yl | 1 | |
| 191 | Benzo-thiazol-2-yl | Me | 1-Me-imidazol-2-yl | 1 | |
| 192 | Benzo-xazol-2-yl | Me | 1-Me-imidazol-2-yl | 1 | |
| 193 | Quinolin-2-yl | Me | 1-Me-imidazol-2-yl | 1 | |
| 194 | 5-CF₃-1,3,4-thiadiazol-2-yl | Me | 1-Me-imidazol-2-yl | 1 | |
| 195 | Pyrimidin-2-yl | Me | 1-Me-imidazol-2-yl | 1 | |
| 196 | 5-Cl-6-Me-pyrimidin-4-yl | Me | 1-Me-imidazol-2-yl | 1 | |
| 197 | 5-Et-6-Me-pyrimidin-4-yl | Me | 1-Me-imidazol-2-yl | 1 | |
| 198 | 6-Cl-pyrazin-2-yl | Me | 1-Me-imidazol-2-yl | 1 | |
| 199 | 3,6-Me₂-pyrazin-2-yl | Me | 1-Me-imidazol-2-yl | 1 | |
| 200 | 5-Me-isoxazol-3-yl | Me | 1-Me-imidazol-2-yl | 1 | |
| 201 | C₆H₅ | Me | 5-Me-imidazol-1-yl | 1 | ¹H-NMR(CDCl₃) δ ppm: 1.95(3H, s), 3.92 (3H, s), 5.18(2H, s), 6.86–7.71(11H, m) |
| 202 | 2-F—C₆H₄ | Me | 5-Me-imidazol-1-yl | 1 | |
| 203 | 3-F—C₆H₄ | Me | 5-Me-imidazol-1-yl | 1 | |
| 204 | 4-F—C₆H₄ | Me | 5-Me-imidazol-1-yl | 1 | |
| 205 | 2-Cl—C₆H₄ | Me | 5-Me-imidazol-1-yl | 1 | ¹H-NMR(CDCl₃) δ ppm: 1.94(3H, d, J = 1.2), 3.96(3H, s), 5.24(2H, s), 6.86–7.82(10H, m) |
| 206 | 3-Cl—C₆H₄ | Me | 5-Me-imidazol-1-yl | 1 | ¹H-NMR(CDCl₃) δ ppm: 1.96(3H, s), 3.93(3H, s), 5.18(2H, s), 6.79–7.67(10H, m) |
| 207 | 4-Cl—C₆H₄ | Me | 5-Me-imidazol-1-yl | 1 | ¹H-NMR(CDCl₃) δ ppm: 1.94(3H, s), 3.92(3H, s), 5.13(2H, s), 6.82–7.66(10H, m) |
| 208 | 2-Me—C₆H₄ | Me | 5-Me-imidazol-1-yl | 1 | |

-continued

| No | R¹ | R² | R³ | n | Physical data |
|---|---|---|---|---|---|
| 209 | 3-Me—C₆H₄ | Me | 5-Me-imidazol-1-yl | 1 | |
| 210 | 4-Me—C₆H₄ | Me | 5-Me-imidazol-1-yl | 1 | |
| 211 | 2-MeO—C₆H₄ | Me | 5-Me-imidazol-1-yl | 1 | |
| 212 | 3-MeO—C₆H₄ | Me | 5-Me-imidazol-1-yl | 1 | |
| 213 | 4-MeO—C₆H₄ | Me | 5-Me-imidazol-1-yl | 1 | |
| 214 | 2,5-Me₂—C₆H₃ | Me | 5-Me-imidazol-1-yl | 1 | |
| 215 | C₆H₅ | Et | 5-Me-imidazol-1-yl | 1 | ¹H-NMR(CDCl₃) δ ppm: 1.28(3H, t, J = 7.3), 1.96(3H, s), 4.19(2H, q, J = 7.3), 5.20(2H, s), 6.86–7.72(11H, m) |
| 216 | 4-Cl—C₆H₄ | Et | 5-Me-imidazol-1-yl | 1 | |
| 217 | 4-Me—C₆H₄ | Et | 5-Me-imidazol-1-yl | 1 | |
| 218 | C₆H₅ | Allyl | 5-Me-imidazol-1-yl | 1 | |
| 219 | 4-Cl—C₆H₄ | Allyl | 5-Me-imidazol-1-yl | 1 | |
| 220 | 4-Me—C₆H₄ | Allyl | 5-Me-imidazol-1-yl | 1 | |
| 221 | C₆H₅ | Me | 4-Me-imidazol-1-yl | 1 | ¹H-NMR(CDCl₃) δ ppm: 2.19(3H, s), 3.95(3H, s), 5.00(2H, s), 6.79–7.63(10H, m), 7.90(1H, s) |
| 222 | 2-F—C₆H₄ | Me | 4-Me-imidazol-1-yl | 1 | |
| 223 | 3-F—C₆H₄ | Me | 4-Me-imidazol-1-yl | 1 | |
| 224 | 4-F—C₆H₄ | Me | 4-Me-imidazol-1-yl | 1 | |
| 225 | 2-Cl—C₆H₄ | Me | 4-Me-imidazol-2-yl | 1 | ¹H-NMR(CDCl₃) δ ppm: 2.18(3H, d, J = 1.2), 3.99(3H, s), 5.05(2H, s), 6.77–7.72(9H, m), 7.90(1H, d, J = 1.2) |
| 226 | 3-Cl—C₆H₄ | Me | 4-Me-imidazol-1-yl | 1 | ¹H-NMR(CDCl₃) 2.19(3H, s), 3.96(3H, s), 4.99(2H, s), 6.95–7.59(9H, m), 7.88(1H, d, J = 1.2) |
| 227 | 4-Cl—C₆H₄ | Me | 4-Me-imidazol-1-yl | 1 | ¹H-NMR(CDCl₃) δ ppm: 2.18(3H, s), 3.95(3H, s), 4.97(2H, s), 6.70–7.59(9H, m), 7.88(1H, d, J = 1.2) |
| 228 | 2-Me—C₆H₄ | Me | 4-Me-imidazol-1-yl | 1 | |
| 229 | 3-Me—C₆H₄ | Me | 4-Me-imidazol-1-yl | 1 | |
| 230 | 4-Me—C₆H₄ | Me | 4-Me-imidazol-1-yl | 1 | |
| 231 | 2-MeO—C₆H₄ | Me | 4-Me-imidazol-1-yl | 1 | |
| 232 | 3-MeO—C₆H₄ | Me | 4-Me-imidazol-1-yl | 1 | |
| 233 | 4-MeO—C₆H₄ | Me | 4-Me-imidazol-1-yl | 1 | |
| 234 | 2,5-Me₂—C₆H₃ | Me | 4-Me-imidazol-1-yl | 1 | |
| 235 | C₆H₅ | Et | 4-Me-imidazol-1-yl | 1 | ¹H-NMR(CDCl₃)δ ppm: 1.30(3H, t, J = 7.3), 2.19(3H, s), 4.21(2H, q, J = 7.3), 5.02(2H, s), 6.78–7.63(10H, m), 7.96(1H, s) |

-continued

| No | R¹ | R² | R³ | n | Physical data |
|---|---|---|---|---|---|
| 236 | 4-Cl—C₆H₄ | Et | 4-Me-imidazol-1-yl | 1 | |
| 237 | 4-Me—C₆H₄ | Et | 4-Me-imidazol-1-yl | 1 | |
| 238 | C₆H₅ | Allyl | 4-Me-imidazol-1-yl | 1 | |
| 239 | 4-Cl—C₆H₄ | Allyl | 4-Me-imidazol-1-yl | 1 | |
| 240 | 4-Me—C₆H₄ | Allyl | 4-Me-imidazol-1-yl | 1 | |
| 241 | C₆H₅ | Me | 2-Me-imidazol-1-yl | 1 | ¹H-NMR(CDCl₃) δ ppm: 2.21 (3H, s), 3.93(3H, s), 5.18(2H, s), 6.89–7.71(11H, m) |
| 242 | 2-F—C₆H₄ | Me | 2-Me-imidazol-1-yl | 1 | |
| 243 | 3-F—C₆H₄ | Me | 2-Me-imidazol-1-yl | 1 | |
| 244 | 4-F—C₆H₄ | Me | 2-Me-imidazol-1-yl | 1 | |
| 245 | 2-Cl—C₆H₄ | Me | 2-Me-imidazol-1-yl | 1 | |
| 246 | 3-Cl—C₆H₄ | Me | 2-Me-imidazol-1-yl | 1 | |
| 247 | 4-Cl—C₆H₄ | Me | 2-Me-imidazol-1-yl | 1 | |
| 248 | 2-Me—C₆H₄ | Me | 2-Me-imidazol-1-yl | 1 | |
| 249 | 3-Me—C₆H₄ | Me | 2-Me-imidazol-1-yl | 1 | |
| 250 | 4-Me—C₆H₄ | Me | 2-Me-imidazol-1-yl | 1 | |
| 251 | 2-MeO—C₆H₄ | Me | 2-Me-imidazol-1-yl | 1 | |
| 252 | 3-MeO—C₆H₄ | Me | 2-Me-imidazol-1-yl | 1 | |
| 253 | 4-MeO—C₆H₄ | Me | 2-Me-imidazol-1-yl | 1 | |
| 254 | 2,5-Me₂—C₆H₃ | Me | 2-Me-imidazol-1-yl | 1 | |
| 255 | C₆H₅ | Et | 2-Me-imidazol-1-yl | 1 | |
| 256 | 4-Cl—C₆H₄ | Et | 2-Me-imidazol-1-yl | 1 | |
| 257 | 4-Me—C₆H₄ | Et | 2-Me-imidazol-1-yl | 1 | |
| 258 | C₆H₅ | Allyl | 2-Me-imidazol-1-yl | 1 | |
| 259 | 4-Cl—C₆H₄ | Allyl | 2-Me-imidazol-1-yl | 1 | |
| 260 | 4-Me—C₆H₄ | Allyl | 2-Me-imidazol-1-yl | 1 | |
| 261 | C₆H₅ | Me | 1H-1,2,4-Triazol-1-yl | 1 | mp 86–87° C. |
| 262 | 2-F—C₆H₄ | Me | 1 H-1,2,4-Triazol-1-yl | 1 | |
| 263 | 3-F—C₆H₄ C₆H₄ | Me | 1-H-1,2,4-Triazol-1-yl | 1 | |
| 264 | 4-F—C₆H₄ | Me | 1H-1,2,4-Triazol-1-yl | 1 | |
| 265 | 2-Cl—C₆H₄ | Me | 1H-1,2,4-Triazol-1-yl | 1 | mp 101.5–102.5° C. |
| 266 | 3-Cl—C₆H₄ | Me | 1H-1,2,4-Triazol-1-yl | 1 | ¹H-NMR(CDCl₃) δ ppm: 4.06(3H, s), 4.94(2H, s), 6.63–7.65(8H, m), 7.96(1H, s), 9.12(1H, s) |
| 267 | 4-Cl—C₆H₄ | Me | 1H-1,2,4-Triazol-1-yl | 1 | mp 101–102° C. |
| 268 | 2-Me—C₆H₄ | Me | 1H-1,2,4-Triazol-1-yl | 1 | |
| 269 | 3-Me—C₆H₄ | Me | 1H-1,2,4-Triazol-1-yl | 1 | |
| 270 | 4-Me—C₆H₄ | Me | 1H-1,2,4-Triazol-1-yl | 1 | mp 98.5–99.5° C. |
| 271 | 2-MeO—C₆H₄ | Me | 1H-1,2,4-Triazol-1-yl | 1 | |

-continued

| No | R¹ | R² | R³ | n | Physical data |
|---|---|---|---|---|---|
| 272 | 3-MeO—C₆H₄ | Me | 1H-1,2,4-Triazol-1-yl | 1 | |
| 273 | 4-MeO—C₆H₄ | Me | 1H-1,2,4-Triazol-1-yl | 1 | |
| 274 | 2,5-Me₂—C₆H₃ | Me | 1H-1,2,4-Triazol-1-yl | 1 | mp 96–98° C. |
| 275 | C₆H₅ | Et | 1H-1,2,4-Triazol-1-yl | 1 | mp 78.5–80.5° C. |
| 276 | 4-Cl—C₆H₄ | Et | 1H-1,2,4-Triazol-1-yl | 1 | |
| 277 | 4-Me—C₆H₄ | Et | 1H-1,2,4-Triazol-1-yl | 1 | |
| 278 | C₆H₅ | Allyl | 1H-1,2,4-Triazol-1-yl | 1 | ¹H-NMR(CDCl₃)δ ppm: 4.74(2H, m), 4.94(2H, s), 5.25–5.37(2H, m), 5.91–6.06(1H, m), 6.76–7.59(9H, m), 7.96(1H, s), 9.13 (1H, s) |
| 279 | 4-Cl—C₆H₄ | Allyl | 1H-1,2,4-Triazol-1-yl | 1 | |
| 280 | 4-Me—C₆H₄ | Allyl | 1H-1,2,4-Triazol-1-yl | 1 | |
| 281 | C₆H₅ | Me | Pyrazol-1-yl | 1 | ¹H-NMR(CDCl₃) δ ppm: 4.02(3H, s), 4.78(2H, s), 6.40(1H, dd, J = 3.1, 1.8), 6.78–7.62 (10H, m), 8.42(1H, d, J = 2.4) |
| 282 | 2-F—C₆H₄ | Me | Pyrazol-1-yl | 1 | |
| 283 | 3-F—C₆H₄ | Me | Pyrazol-1-yl | 1 | |
| 284 | 4-F—C₆H₄ | Me | Pyrazol-1-yl | 1 | |
| 285 | 2-Cl—C₆H₄ | Me | Pyrazol-1-yl | 1 | mp 90–91° C. |
| 286 | 3-Cl—C₆H₄ | Me | Pyrazol-1-yl | 1 | ¹H-NMR(CDCl₃) δ ppm: 4.26(3H, s), 4.78 (2H, s), 6.42–7.62(10H, m), 8.45(1H, d, J = 2.4) |
| 287 | 4-Cl—C₆H₄ | Me | Pyrazol-1-yl | 1 | mp 94–95° C. |
| 288 | 2-Me—C₆H₄ | Me | Pyrazol-1-yl | 1 | |
| 289 | 3-Me—C₆H₄ | Me | Pyrazol-1-yl | 1 | |
| 290 | 4-Me—C₆H₄ | Me | Pyrazol-1-yl | 1 | mp 82–83° C. |
| 291 | 2-Cl-pyridin-3-yl | Me | Pyrazol-1-yl | 1 | mp 87.5–88.5° C. |
| 292 | 3-MeO—C₆H₄ | Me | Pyrazol-1-yl | 1 | |
| 293 | 4-MeO—C₆H₄ | Me | Pyrazol-1-yl | 1 | |
| 294 | 2,5-Me₂—C₆H₃ | Me | Pyrazol-1-yl | 1 | mp 78–80° C. |
| 295 | C₆H₅ | Et | Pyrazol-1-yl | 1 | ¹H-NMR(CDCl₃) δ ppm: 1.36(3H, t, J = 6.7), 4.27(2H, q, J = 6.7), 4.79(2H, s), 6.40–7.61(11H, m), 8.48(1H, d, J = 3.1) |
| 296 | 4-Cl—C₆H₄ | Et | Pyrazol-1-yl | 1 | |
| 297 | 4-Me—C₆H₄ | Et | Pyrazol-1-yl | 1 | |
| 298 | C₆H₅ | Allyl | Pyrazol-1-yl | 1 | ¹H-NMR(CDCl₃) δ ppm: 4.73(2H, m), 4.80(2H, s), 5.23–5.38(2H, m), 5.96–6.10(1H, m), 6.40–7.62(11H, m), 8.48(1H, d, J = 2.4) |
| 299 | 4-Cl—C₆H₄ | Allyl | Pyrazol | 1 | |
| 300 | C₆H₅ | Me | Pyrazol-1-yl | 0 | ¹H-NMR(CDCl₃) δ ppm: 4.03(3H, s), 6.34(1H, t, J = 2.9), 6.82–7.63(10H, m), 8.37(1H, d, J = 2.9) |

-continued

| No | R¹ | R² | R³ | n | Physical data |
|---|---|---|---|---|---|
| 301 | C₆H₅ | Me | Isoxazol-3-yl | 1 | ¹H-NMR(CDCl₃) δ ppm: 4.06(3.99)(3H, s), 5.05(4.96)(2H, s), 6.73–7.61(10H, m), 8.46(8.39)(1H,d, J = 1.8) |
| 302 | 2-F—C₆H₄ | Me | Isoxazol-3-yl | 1 | |
| 303 | 3-F—C₆H₄ | Me | Isoxazol-3-yl | 1 | |
| 304 | 4-F—C₆H₄ | Me | Isoxazol-3-yl | 1 | |
| 305 | 2-Cl—C₆H₄ | Me | Isoxazol-3-yl | 1 | ¹H-NMR(CDCl₃) δ ppm: 4.08(4.01) (3H, s), 5.14(5.12)(2H, s), 6.76–7.68(9H, m), 8.46(8.40)(1H, d, J = 1.8) |
| 306 | 3-Cl—C₆H₄ | Me | Isoxazol-3-yl | 1 | ¹H-NMR(CDCl₃) δ 4ppm: 4.07 (4.01)(3H, s), 5.04(4.95)(2H, s), 6.70–7.56(9H, m), 8.48(8.40) (1H, d, J = 1.8) |
| 307 | 4-Cl—C₆H₄ | Me | Isoxazol-3-yl | 1 | ¹H-NMR(CDCl₃) δ ppm: 4.06(3.99) (3H, s), 5.03(4.94)(3H, s), 6.72–7.56(9H, m), 8.47(8.39)(1H, d, J = 1.8) |
| 308 | 2-Br—C₆H₄ | Me | Isoxazol-3-yl | 1 | |
| 309 | 3-Br—C₆H₄ | Me | Isoxazol-3-yl | 1 | |
| 310 | 4-Br—C₆H₄ | Me | Isoxazol-3-yl | 1 | |
| 311 | 3-I—C₆H₄ | Me | Isoxazol-3-yl | 1 | |
| 312 | 2-Me—C₆H₄ | Me | Isoxazol-3-yl | 1 | ¹H-NMR(CDCl₃) δ ppm: 2.20(2.17)(3H, s), 4.07(4.00)(3H, s), 5.03(4.97)(2H, s), 6.68–7.64(9H, m), 8.44(8.39) (1H, d, J = 1.8) |
| 313 | 3-Me—C₆H₄ | Me | Isoxazol-3-yl | 1 | ¹H-NMR(CDCl₃) δ ppm: 2.29(2.27)(3H, s), 4.07(4.00)(3H, s), 5.03(4.95)(2H, s), 6.62–7.61(9H, m), 8.47(8.39) (1H, d, J = 1.8) |
| 314 | 4-Me—C₆H₄ | Me | Isoxazol-3-yl | 1 | ¹H-NMR(CDCl₃) δ ppm: 2.25(3H, s), 4.06(3.99)(3H, s), 5.01 (4.93)(2H, s), 6.70–7.60(9H, m), 8.46(8.39) (1H, d, J = 1.8) |
| 315 | 2-Et—C₆H₄ | Me | Isoxazol-3-yl | 1 | |
| 316 | 3-Et—C₆H₄ | Me | Isoxazol-3-yl | 1 | |
| 317 | 4-Et—C₆H₄ | Me | Isoxazol-3-yl | 1 | |
| 318 | 2-MeO—C₆H₄ | Me | Isoxazol-3-yl | 1 | |
| 319 | 3-MeO—C₆H₄ | Me | Isoxazol-3-yl | 1 | |
| 320 | 4-MeO—C₆H₄ | Me | Isoxazol-3-yl | 1 | |
| 321 | 2-CF₃—C₆H₄ | Me | Isoxazol-3-yl | 1 | |
| 322 | 3-CF₃—C₆H₄ | Me | Isoxazol-3-yl | 1 | ¹H-NMR(CDCl₃) δ ppm: 4.05(3.98)(3H, s), 5.10(5.01)(2H, s), 6.74(1H, d, J = 1.8), 6.94–7.57(8H, m), 8.47(8.40)(1H, d, J = 1.8) |
| 323 | 4-CF₃—C₆H₄ | Me | Isoxazol-3-yl | 1 | |

-continued

| No | R¹ | R² | R³ | n | Physical data |
|---|---|---|---|---|---|
| 324 | 2,4-F₂—C₆H₃ | Me | Isoxazol-3-yl | 1 | |
| 325 | 2,5-F₂—C₆H₃ | Me | Isoxazol-3-yl | 1 | |
| 326 | 2,6-F₂—C₆H₃ | Me | Isoxazol-3-yl | 1 | |
| 327 | 3,4-F₂—C₆H₃ | Me | Isoxazol-3-yl | 1 | |
| 328 | 3,5-F₂—C₆H₃ | Me | Isoxazol-3-yl | 1 | |
| 329 | 2,3-Cl₂—C₆H₃ | Me | Isoxazol-3-yl | 1 | |
| 330 | 2,4-Cl₂—C₆H₃ | Me | Isoxazol-3-yl | 1 | |
| 331 | 2,5-Cl₂—C₆H₃ | Me | Isoxazol-3-yl | 1 | |
| 332 | 3,4-Cl₂—C₆H₃ | Me | Isoxazol-3-yl | 1 | |
| 333 | 3,5-Cl₂—C₆H₃ | Me | Isoxazol-3-yl | 1 | |
| 334 | 2,3-Me₂—C₆H₃ | Me | Isoxazol-3-yl | 1 | |
| 335 | 2,4-Me₂—C₆H₃ | Me | Isoxazol-3-yl | 1 | |
| 336 | 2,5-Me₂—C₆H₃ | Me | Isoxazol-3-yl | 1 | mp 104–108° C. |
| 337 | 3,4-Me₂—C₆H₃ | Me | Isoxazol-3-yl | 1 | |
| 338 | 3,5-Me₂—C₆H₃ | Me | Isoxazol-3-yl | 1 | |
| 339 | 2-Cl-4-Me—C₆H₃ | Me | Isoxazol-3-yl | 1 | |
| 340 | 2-Cl-5-Me—C₆H₃ | Me | Isoxazol-3-yl | 1 | |
| 341 | 4-Cl-2-Me—C₆H₃ | Me | Isoxazol-3-yl | 1 | ¹H-NMR(CDCl₃) δ ppm: 2.16(2.13)(3H, s), 4.07(3.99)(3H, s), 5.01(4.95)(2H, s), 6.59–7.58(8H, m), 8.45(8.40) (1H, d, J = 1.8) |
| 342 | 4-Cl-3-Me—C₆H₃ | Me | Isoxazol-3-yl | 1 | |
| 343 | 3-Ph—C₆H₄ | Me | Isoxazol-3-yl | 1 | |
| 344 | 4-Ph—C₆H₄ | Me | Isoxazol-3-yl | 1 | |
| 345 | 3-i-PrO—C₆H₄ | Me | Isoxazol-3-yl | 1 | |
| 346 | 3-i-Pr—C₆H₄ | Me | Isoxazol-3-yl | 1 | |
| 347 | 4-i-Pr—C₆H₄ | Me | Isoxazol-3-yl | 1 | |
| 348 | 3-t-Bu—C₆H₄ | Me | Isoxazol-3-yl | 1 | |
| 349 | 2-MeS—C₆H₄ | Me | Isoxazol-3-yl | 1 | |
| 350 | 4-MeS—C₆H₄ | Me | Isoxazol-3-yl | 1 | |
| 351 | 2,3,6-F₃—C₆H₂ | Me | Isoxazol-3-yl | 1 | |
| 352 | 2,4,5-Cl₃—C₆H₂ | Me | Isoxazol-3-yl | 1 | |
| 353 | 3-PhO—C₆H₄ | Me | Isoxazol-3-yl | 1 | |
| 354 | 3,4,5-(MeO)₃—C₆H₂ | Me | Isoxazol-3-yl | 1 | |
| 355 | 2,3,5-Me₃—C₆H₂ | Me | Isoxazol-3-yl | 1 | |
| 356 | 3,4,5-Me₃—C₆H₂ | Me | Isoxazol-3-yl | 1 | |
| 357 | C₆F₅ | Me | Isoxazol-3-yl | 1 | |
| 358 | 4-Cl-3-Et—C₆H₃ | Me | Isoxazol-3-yl | 1 | |
| 359 | 3-EtO—C₆H₄ | Me | Isoxazol-3-yl | 1 | |
| 360 | 4-EtO—C₆H₄ | Me | Isoxazol-3-yl | 1 | |
| 361 | C₆H₅ | Me | Isoxazol-3-yl | 0 | |
| 362 | 4-F—C₆H₄ | Me | Isoxazol-3-yl | 0 | |
| 363 | 3-Cl—C₆H₄ | Me | Isoxazol-3-yl | 0 | |
| 364 | 4-Cl—C₆H₄ | Me | Isoxazol-3-yl | 0 | |
| 365 | 3-Me—C₆H₄ | Me | Isoxazol-3-yl | 0 | |
| 366 | 4-Me—C₆H₄ | Me | Isoxazol-3-yl | 0 | |
| 367 | 4-Et—C₆H₄ | Me | Isoxazol-3-yl | 0 | |
| 368 | 4-NO₂—C₆H₄ | Me | Isoxazol-3-yl | 0 | |
| 369 | 3,4-Cl₂—C₆H₃ | Me | Isoxazol-3-yl | 0 | |
| 370 | 3,5-Cl₂—C₆H₃ | Me | Isoxazol-3-yl | 0 | |
| 371 | 3,4-Me₂—C₆H₃ | Me | Isoxazol-3-yl | 0 | |
| 372 | 3,5-Me₂—C₆H₃ | Me | Isoxazol-3-yl | 0 | |
| 373 | 3-PhO—C₆H₄ | Me | Isoxazol-3-yl | 0 | |
| 374 | 4-Cl-3-Et—C₆H₃ | Me | Isoxazol-3-yl | 0 | |
| 375 | 3-EtO—C₆H₄ | Me | Isoxazol-3-yl | 0 | |
| 376 | 3-CF₃—C₆H₄ | Me | Isoxazol-3-yl | 0 | |
| 377 | 4-CF₃—C₆H₄ | Me | Isoxazol-3-yl | 0 | |
| 378 | 3-i-PrO—C₆H₄ | Me | Isoxazol-3-yl | 0 | |
| 379 | 3-i-Pr—C₆H₄ | Me | Isoxazol-3-yl | 0 | |
| 380 | 4-Cl-3-Me—C₆H₃ | Me | Isoxazol-3-yl | 0 | |
| 381 | pyridin-2-yl | Me | Isoxazol-3-yl | 1 | |
| 382 | pyridin-3-yl | Me | Isoxazol-3-yl | 1 | |
| 383 | 5-Cl-pyridin-2-yl | Me | Isoxazol-3-yl | 1 | |

-continued

| No | R¹ | R² | R³ | n | Physical data |
|---|---|---|---|---|---|
| 384 | 3-Cl-pyridin-2-yl | Me | Isoxazol-3-yl | 1 | |
| 385 | 6-Cl-pyridin-2-yl | Me | Isoxazol-3-yl | 1 | |
| 386 | 2-Cl-pyridin-3-yl | Me | Isoxazol-3-yl | 1 | |
| 387 | 5-$CF_3$-pyridin-2-yl | Me | Isoxazol-3-yl | 1 | $^1$H-NMR(CDCl$_3$) δ ppm: 3.98(3H, s), 5.32(2H, s), 6.63(1H, d, J = 8.5), 6.73(1H, d, J = 1.8), 7.27–7.71(5H, m), 8.30(1H, s), 8.39(1H, d, J = 1.8) |
| 388 | 3-$CF_3$-pyridin-2-yl | Me | Isoxazol-3-yl | 1 | mp 125–126.5° C. |
| 389 | 6-$CF_3$-3-Cl-pyridin-2-yl | Me | Isoxazol-3-yl | 1 | |
| 390 | 5-$CF_3$-3-Cl-pyridin-2-yl | Me | Isoxazol-3-yl | 1 | $^1$H-NMR(CDCl$_3$) δ ppm: 4.00(3H, s), 5.41(2H, s), 6.76(1H, d, J = 1.8), 7.27–7.78(5H, m), 8.15(1H, s), 8.46(1H, d, J = 1.8) |
| 391 | Benzothiazol-2-yl | Me | Isoxazol-3-yl | 1 | |
| 392 | Benzoxazol-2-yl | Me | Isoxazol-3-yl | 1 | |
| 393 | Quinolin-2-yl | Me | Isoxazol-3-yl | 1 | |
| 394 | 5-$CF_3$-1,3,4-thiadiazol-2-yl | Me | Isoxazol-3-yl | 1 | |
| 395 | pyrimidin-2-yl | Me | Isoxazol-3-yl | 1 | |
| 396 | 5-Cl-6-Me-pyrimidin-4-yl | Me | Isoxazol-3-yl | 1 | |
| 397 | 5-Et-6-Me-pyrimidin-4-yl | Me | Isoxazol-3-yl | 1 | |
| 398 | 6-Cl-pyrazin-2-yl | Me | Isoxazol-3-yl | 1 | |
| 399 | 3,6-Me$_2$-pyrazin-2-yl | Me | Isoxazol-3-yl | 1 | |
| 400 | 5-Me-isoxazol-3-yl | Me | Isoxazol-3-yl | 1 | |
| 401 | $C_6H_5$ | Me | 5-Me-isoxazol-3-yl | 1 | $^1$H-NMR(CDCl$_3$) δ ppm: 2.43(3H, s), 3.97(4.04)(3H, s), 4.96(5.06)(2H, s), 6.35(6.55)(1H, s), 6.83–7.60(9H, m) |
| 402 | 2-F—$C_6H_4$ | Me | 5-Me-isoxazol-3-yl | 1 | |
| 403 | 3-F—$C_6H_4$ | Me | 5-Me-isoxazol-3-yl | 1 | |
| 404 | 4-F—$C_6H_4$ | Me | 5-Me-isoxazol-3-yl | 1 | |

-continued

| No | R¹ | R² | R³ | n | Physical data |
|---|---|---|---|---|---|
| 405 | 2-Cl—C₆H₄ | Me | 5-Me-isoxazol-3-yl | 1 | ¹H-NMR(CDCl₃) δ ppm: 2.44(3H, s), 4.07(3.98)(3H, s), 5.15(5.06)(2H, s), 6.38 (6.57)(1H, s), 6.78–7.66(8H, m) |
| 406 | 3-Cl—C₆H₄ | Me | 5-Me-isoxazol-3-yl | 1 | mp111.0–123.0° C. |
| 407 | 4-Cl—C₆H₄ | Me | 5-Me-isoxazol-3-yl | 1 | mp74.0–85.0° C. |
| 408 | 2-Br—C₆H₄ | Me | 5-Me-isoxazol-3-yl | 1 | |
| 409 | 3-Br—C₆H₄ | Me | 5-Me-isoxazol-3-yl | 1 | |
| 410 | 4-Br—C₆H₄ | Me | 5-Me-isoxazol-3-yl | 1 | |
| 411 | 3-I—C₆H₄ | Me | 5-Me-isoxazol-3-yl | 1 | |
| 412 | 2-Me—C₆H₄ | Me | 5-Me-isoxazol-3-yl | 1 | ¹H-NMR(CDCl₃) δ ppm: 2.20 (2.22)(3H, s), 2.42(2.42)(3H, s), 3.98(4.06)(3H, s), 4.97(5.04)(2H, s), 6.35(6.53)(1H, s), 6.69–7.63(8H, m) |
| 413 | 3-Me—C₆H₄ | Me | 5-Me-isoxazol-3-yl | 1 | mp92.0–93.0° C. |
| 414 | 4-Me—C₆H₄ | Me | 5-Me-isoxazol-3-yl | 1 | mp104.0–105.5° C. |
| 415 | 2-Et—C₆H₄ | Me | 5-Me-isoxazol-3-yl | 1 | |
| 416 | 3-Et—C₆H₄ | Me | 5-Me-isoxazol-3-yl | 1 | |
| 417 | 4-Et—C₆H₄ | Me | 5-Me-isoxazol-3-yl | 1 | |
| 418 | 2-MeO—C₆H₄ | Me | 5-Me-isoxazol-3-yl | 1 | |
| 419 | 3-MeO—C₆H₄ | Me | 5-Me-isoxazol-3-yl | 1 | |
| 420 | 4-MeO—C₆H₄ | Me | 5-Me-isoxazol-3-yl | 1 | |
| 421 | 2-CF₃—C₆H₄ | Me | 5-Me-isoxazol-3-yl | 1 | |
| 422 | 3-CF₃—C₆H₄ | Me | 5-Me-isoxazol-3-yl | 1 | ¹H-NMR(CDCl₃) δ ppm: 2.43(2.44) (3H, s), 4.03(3.97)(3H, s), 5.00(5.09)(2H, s), 6.35(1H, s), 6,56(6.57) (1H, s), 7.00–7.64 (7H, m) |
| 423 | 4-CF₃—C₆H₄ | Me | 5-Me-isoxazol-3-yl | 1 | |
| 424 | 2,4-F₂-C₆H₃ | Me | 5-Me-isoxazol-3-yl | 1 | |
| 425 | 2,5-F₂-C₆H₃ | Me | 5-Me-isoxazol-3-yl | 1 | |
| 426 | 2,6-F₂-C₆H₃ | Me | 5-Me-isoxazol-3-yl | 1 | |
| 427 | 3,4-F₂-C₆H₃ | Me | 5-Me-isoxazol-3-yl | 1 | |
| 428 | 3,5-F₂-C₆H₃ | Me | 5-Me-isoxazol-3-yl | 1 | |
| 429 | 2,3-Cl₂-C₆H₃ | Me | 5-Me-isoxazol-3-yl | 1 | |
| 430 | 2,4-Cl₂-C₆H₃ | Me | 5-Me-isoxazol-3-yl | 1 | |
| 431 | 2,5-Cl₂-C₆H₃ | Me | 5-Me-isoxazol-3-yl | 1 | |
| 432 | 3,4-Cl₂-C₆H₃ | Me | 5-Me-isoxazol-3-yl | 1 | |
| 433 | 3,5-Cl₂-C₆H₃ | Me | 5-Me-isoxazol-3-yl | 1 | |
| 434 | 2,3-Me₂-C₆H₃ | Me | 5-Me-isoxazol-3-yl | 1 | |
| 435 | 2,4-Me₂-C₆H₃ | Me | 5-Me-isoxazol-3-yl | 1 | |

-continued

| No | R¹ | R² | R³ | n | Physical data |
|---|---|---|---|---|---|
| 436 | 2,5-Me₂—C₆H₃ | Me | 5-Me-isoxazol-3-yl | 1 | ¹H-NMR(CDCl₃)δ ppm: 2.15(2.16)(3H, s), 2.24(2.25)(3H, s), 2.42(2.43)(3H, s), 3.99(4.07)(3H, s), 4.95(5.01)(2H, s), 6.36–7.64(8H, m) |
| 437 | 3,4-Me₂—C₆H₃ | Me | 5-Me-isoxazol-3-yl | 1 | |
| 438 | 3,5-Me₂—C₆H₃ | Me | 5-Me-isoxazol-3-yl | 1 | |
| 439 | 2-Cl-4-Me—C₆H₃ | Me | 5-Me-isoxazol-3-yl | 1 | |
| 440 | 2-Cl-5-Me—C₆H₃ | Me | 5-Me-isoxazol-3-yl | 1 | |
| 441 | 4-Cl-2-Me—C₆H₃ | Me | 5-Me-isoxazol-3-yl | 1 | mp79–83° C. |
| 442 | 4-Cl-3-Me—C₆H₃ | Me | 5-Me-isoxazol-3-yl | 1 | |
| 443 | 3-Ph—C₆H₄ | Me | 5-Me-isoxazol-3-yl | 1 | |
| 444 | 4-Ph—C₆H₄ | Me | 5-Me-isoxazol-3-yl | 1 | mp105.0–115.0° C. |
| 445 | 3-i-PrO—C₆H₄ | Me | 5-Me-isoxazol-3-yl | 1 | |
| 446 | 3-i-Pr—C₆H₄ | Me | 5-Me-isoxazol-3-yl | 1 | |
| 447 | 4-i-Pr—C₆H₄ | Me | 5-Me-isoxazol-3-yl | 1 | |
| 448 | 3-t-Bu—C₆H₄ | Me | 5-Me-isoxazol-3-yl | 1 | |
| 449 | 2-MeS—C₆H₄ | Me | 5-Me-isoxazol-3-yl | 1 | |
| 449 | 2-MeS—C₆H₄ | Me | 5-Me-isoxazol-3-yl | 1 | |
| 450 | 4-MeS—C₆H₄ | Me | 5-Me-isoxazol-3-yl | 1 | |
| 451 | 2,3,6-F₃—C₆H₂ | Me | 5-Me-isoxazol-3-yl | 1 | |
| 452 | 2,4,5-Cl₃—C₆H₂ | Me | 5-Me-isoxazol-3-yl | 1 | |
| 453 | 3-PhO—C₆H₄ | Me | 5-Me-isoxazol-3-yl | 1 | |
| 454 | 3,4,5-(MeO)₃—C₆H₂ | Me | 5-Me-isoxazol-3-yl | 1 | |
| 455 | 2,3,5-Me₃—C₆H₂ | Me | 5-Me-isoxazol-3-yl | 1 | |
| 456 | 3,4,5-Me₃—C₆H₂ | Me | 5-Me-isoxazol-3-yl | 1 | |
| 457 | C₆F₅ | Me | 5-Me-isoxazol-3-yl | 1 | |
| 458 | 4-Cl-3-Et—C₆H₃ | Me | 5-Me-isoxazol-3-yl | 1 | |
| 459 | 3-EtO—C₆H₄ | Me | 5-Me-isoxazol-3-yl | 1 | |
| 460 | 4-EtO—C₆H₄ | Me | 5-Me-isoxazol-3-yl | 1 | |
| 461 | C₆H₅ | Me | 5-Me-isoxazol-3-yl | 0 | |
| 462 | 4-F—C₆H₄ | Me | 5-Me-isoxazol-3-yl | 0 | |
| 463 | 3-Cl—C₆H₄ | Me | 5-Me-isoxazol-3-yl | 0 | |
| 464 | 4-Cl—C₆H₄ | Me | 5-Me-isoxazol-3-yl | 0 | |
| 465 | 3-Me—C₆H₄ | Me | 5-Me-isoxazol-3-yl | 0 | |
| 466 | 4-Me—C₆H₄ | Me | 5-Me-isoxazol-3-yl | 0 | |
| 467 | 4-Et—C₆H₄ | Me | 5-Me-isoxazol-3-yl | 0 | |
| 468 | 4-NO₂—C₆H₄ | Me | 5-Me-isoxazol-3-yl | 0 | |
| 469 | 3,4-Cl₂—C₆H₃ | Me | 5-Me-isoxazol-3-yl | 0 | |
| 470 | 3,5-Cl₂—C₆H₃ | Me | 5-Me-isoxazol-3-yl | 0 | |

-continued

| No | R¹ | R² | R³ | n | Physical data |
|---|---|---|---|---|---|
| 471 | 3,4-Me₂—C₆H₃ | Me | 5-Me-isoxazol-3-yl | 0 | |
| 472 | 3,5-Me₂—C₆H₃ | Me | 5-Me-isoxazol-3-yl | 0 | |
| 473 | 3-PhO—C₆H₄ | Me | 5-Me-isoxazol-3-yl | 0 | |
| 474 | 4-Cl-3-Et—C₆H₃ | Me | 5-Me-isoxazol-3-yl | 0 | |
| 475 | 3-EtO—C₆H₄ | Me | 5-Me-isoxazol-3-yl | 0 | |
| 476 | 3-CF₃—C₆H₄ | Me | 5-Me-isoxazol-3-yl | 0 | |
| 477 | 4-CF₃—C₆H₄ | Me | 5-Me-isoxazol-3-yl | 0 | |
| 478 | 3-i-PrO—C₆H₄ | Me | 5-Me-isoxazol-3-yl | 0 | |
| 479 | 3-i-Pr—C₆H₄ | Me | 5-Me-isoxazol-3-yl | 0 | |
| 480 | 4-Cl-3-Me—C₆H₃ | Me | 5-Me-isoxazol-3-yl | 0 | |
| 481 | Pyridin-2-yl | Me | 5-Me-isoxazol-3-yl | 1 | |
| 482 | Pyridin-3-yl | Me | 5-Me-isoxazol-3-yl | 1 | |
| 483 | 5-Cl-pyridin-2-yl | Me | 5-Me-isoxazol-3-yl | 1 | |
| 484 | 3-Cl-pyridin-2-yl | Me | 5-Me-isoxazol-3-yl | 1 | $^1$H-NMR(CDCl₃)δ ppm: 2.42(3H, s), 3.97(3H, s), 5.35 (2H, s), 6.35(1H, s), 6.76–6.81(1H, m), 7.24–7.93(6H, m). |
| 485 | 6-Cl-pyridin-2-yl | Me | 5-Me-isoxazol-3-yl | 1 | |
| 486 | 2-Cl-pyridin-3-yl | Me | 5-Me-isoxazol-3-yl | 1 | |
| 487 | 5-CF₃-pyridin-2-yl | Me | 5-Me-isoxazol- | 1 | $^1$H-NMR(CDCl₃)δ ppm: 2.43(3H, s), 3.96 (3H, s), 5.32(2H, s), 6.34(1H, d, J = 1.2), 6.67(1H, d, J = 8.5), 7.24–7.72 (5H, m), 8.31(1H, s) |
| 488 | 3-CF₃-pyridin-2-yl | Me | 5-Me-isoxazol-3-yl | 1 | |
| 489 | 6-CF₃-3-Cl-pryidin-2-yl | Me | 5-Me-isoxazol-3-yl | 1 | |
| 490 | 5-CF₃-3-Cl-pyridin-2-yl | Me | 5-Me-isoxazol-3-yl | 1 | $^1$H-NMR(CDCl₃)δ ppm: 2.43(3H, s), 3.97 (3H, s), 5.40(2H, s), 6.37(1H, s), 7.25–8.17(6H, m). |
| 491 | Benzo-thiazol-2-yl | Me | 5-Me-isoxazol-3-yl | 1 | |
| 492 | Benzo-xazol-2-yl | Me | 5-Me-isoxazol-3-yl | 1 | |
| 493 | Quinolin-2-yl | Me | 5-Me-isoxazol-3-yl | 1 | |
| 494 | 5-CF₃-1,3,4-thia-diazol-2-yl | Me | 5-Me-isoxazol-3-yl | 1 | |
| 495 | Pyrimidin-2-yl | Me | 5-Me-isoxazol-3-yl | 1 | |

-continued

| No | R¹ | R² | R³ | n | Physical data |
|---|---|---|---|---|---|
| 496 | 5-Cl-6-Me-pyrimidin-4-yl | Me | 5-Me-isoxazol-3-yl | 1 | |
| 497 | 5-Et-6-Me-pyrimidin-4-yl | Me | 5-Me-isoxazol-3-yl | 1 | |
| 498 | 6-Cl-pyrazin-2-yl | Me | 5-Me-isoxazol-3-yl | 1 | |
| 499 | 3,6-Me₂-pyrazin-2-yl | Me | 5-Me-isoxazol-3-yl | 1 | |
| 500 | 5-Me-isoxazol-3-yl | Me | 5-Me- | 1 | |
| 501 | C₆H₅ | Me | Isoxazol-5-yl | 1 | |
| 502 | 2-F—C₆H₄ | Me | Isoxazol-5-yl | 1 | |
| 503 | 3-F—C₆H₄ | Me | Isoxazol-5-yl | 1 | |
| 504 | 4-F—C₆H₄ | Me | Isoxazol-5-yl | 1 | |
| 505 | 2-Cl—C₆H₄ | Me | Isoxazol-5-yl | 1 | |
| 506 | 3-Cl—C₆H₄ | Me | Isoxazol-5-yl | 1 | |
| 507 | 4-Cl—C₆H₄ | Me | Isoxazol-5-yl | 1 | Isomer A: ¹H-NMR (CDCl₃)δ ppm: 4.11(3H, s), 4.99 (2H, s), 6.68–6.73 (2H, m), 7.11(1H, d, J = 1.8), 7.14–7.18(2H, m), 7.40–7.57(4H, m), 8.34(1H, d, J = 1.8) Isomer B: ¹H-NMR (CDCl₃)δ ppm: 4.03(3H, s), 4.92 (2H, s), 6.21(1H, d, J = 1.8), 6.68–6.74(2H, m), 7.13–7.23 (3H, m), 7.41–7.61(3H, m), 8.24(1H, d, J = 1.8) |
| 508 | 2-Br—C₆H₄ | Me | Isoxazol-5-yl | 1 | |
| 509 | 3-Br—C₆H₄ | Me | Isoxazol-5-yl | 1 | |
| 510 | 4-Br—C₆H₄ | Me | Isoxazol-5-yl | 1 | |
| 511 | 3-I—C₆H₄ | Me | Isoxazol-5-yl | 1 | |
| 512 | 2-Me—C₆H₄ | Me | Isoxazol-5-yl | 1 | Isomer A: mp71.5–72.5° C. Isomer B: mp68.0–69.0° C. |
| 513 | 3-Me—C₆H₄ | Me | Isoxazol-5-yl | 1 | |
| 514 | 4-Me—C₆H₄ | Me | Isoxazol-5-yl | 1 | |
| 515 | 2-Et—C₆H₄ | Me | Isoxazol-5-yl | 1 | |
| 516 | 3-Et—C₆H₄ | Me | Isoxazol-5-yl | 1 | |
| 517 | 4-Et—C₆H₄ | Me | Isoxazol-5-yl | 1 | |
| 518 | 2-MeO—C₆H₄ | Me | Isoxazol-5-yl | 1 | |
| 519 | 3-MeO—C₆H₄ | Me | Isoxazol-5-yl | 1 | |
| 520 | 4-MeO—C₆H₄ | Me | Isoxazol-5-yl | 1 | |
| 521 | 2-CF₃—C₆H₄ | Me | Isoxazol-5-yl | 1 | |
| 522 | 3-CF₃—C₆H₄ | Me | Isoxazol-5-yl | 1 | Isomer A: ¹H-NMR (CDCl₃)δ ppm: 4.10(3H, s), 5.07(2H, s), 6.91–7.02(2H, m), 7.11 (1H, d, J = 1.8), 7.15–7.59(6H, m), 8.34(1H, d, J = 1.8) Isomer B: ¹H-NMR (CDCl₃)δ ppm: 4.03(3H, s), 4.99(2H, s), 6.22(1H, d, J = 1.8), 6.92–7.62(8H, m), 8.24 (1H, d, J = 1.8) |
| 523 | 4-CF₃—C₆H₄ | Me | Isoxazol-5-yl | 1 | |
| 524 | 2,4-F₂—C₆H₃ | Me | Isoxazol-5-yl | 1 | |
| 525 | 2,5-F₂—C₆H₃ | Me | Isoxazol-5-yl | 1 | |
| 526 | 2,6-F₂—C₆H₃ | Me | Isoxazol-5-yl | 1 | |
| 527 | 3,4-F₂—C₆H₃ | Me | Isoxazol-5-yl | 1 | |
| 528 | 3,5-F₂—C₆H₃ | Me | Isoxazol-5-yl | 1 | |

-continued

| No | R¹ | R² | R³ | n | Physical data |
|---|---|---|---|---|---|
| 529 | 2,3-Cl₂—C₆H₃ | Me | Isoxazol-5-yl | 1 | |
| 530 | 2,4-Cl₂—C₆H₃ | Me | Isoxazol-5-yl | 1 | |
| 531 | 2,5-Cl₂—C₆H₃ | Me | Isoxazol-5-yl | 1 | |
| 532 | 3,4-Cl₂—C₆H₃ | Me | Isoxazol-5-yl | 1 | |
| 533 | 3,5-Cl₂—C₆H₃ | Me | Isoxazol-5-yl | 1 | |
| 534 | 2,3-Me₂—C₆H₃ | Me | Isoxazol-5-yl | 1 | |
| 535 | 2,4-Me₂—C₆H₃ | Me | Isoxazol-5-yl | 1 | |
| 536 | 2,5-Me₂—C₆H₃ | Me | Isoxazol-5-yl | 1 | Isomer A: mp137.5–138.5° C. Isomer B: mp93.0–94.5° C. |
| 537 | 3,4-Me₂—C₆H₃ | Me | Isoxazol-5-yl | 1 | |
| 538 | 3,5-Me₂—C₆H₃ | Me | Isoxazol-5-yl | 1 | |
| 539 | 2-Cl-4-Me—C₆H₃ | Me | Isoxazol-5-yl | 1 | |
| 540 | 2-Cl-5-Me—C₆H₃ | Me | Isoxazol-5-yl | 1 | |
| 541 | 4-Cl-2-Me—C₆H₃ | Me | Isoxazol-5-yl | 1 | Isomer A: mp84.0–85.0° C. Isomer B: ¹H-NMR (CDCl₃)δ ppm: 4.93(2H, s), 6.20(1H, d, J = 1.8), 6.62(1H, d, J = 8.5), 6.99–7.63(6H, m), 8.22(1H, d, J = 1.8) |
| 542 | 4-Cl-2-Me—C₆H₃ | Me | Isoxazol-5-yl | 1 | |
| 543 | 3-Ph—C₆H₃ | Me | Isoxazol-5-yl | 1 | |
| 544 | 4-Ph—C₆H₄ | Me | Isoxazol-5-yl | 1 | |
| 545 | 3-i-Pro-C₆H₄ | Me | Isoxazol-5-yl | 1 | |
| 546 | 3-i-Pr—C₆H₄ | Me | Isoxazol-5-yl | 1 | |
| 547 | 4-i-Pr—C₆H₄ | Me | Isoxazol-5-yl | 1 | |
| 548 | 3-t-Bu—C₆H₄ | Me | Isoxazol-5-yl | 1 | |
| 549 | 2-MeS—C₆H₄ | Me | Isoxazol-5-yl | 1 | |
| 550 | 4-MeS—C₆H₄ | Me | Isoxazol-5-yl | 1 | |
| 551 | 2,3,6-F₃—C₆H₂ | Me | Isoxazol-5-yl | 1 | |
| 552 | 2,4,5-Cl₃—C₆H₂ | Me | Isoxazol-5-yl | 1 | |
| 553 | 3-PhO—C₆H₄ | Me | Isoxazol-5-yl | 1 | |
| 554 | 3,4,5-(MeO)₃—C₆H₂ | Me | Isoxazol-5-yl | 1 | |
| 555 | 2,3,5-Me₃—C₆H₂ | Me | Isoxazol-5-yl | 1 | |
| 556 | 3,4,5-Me₃—C₆H₂ | Me | Isoxazol-5-yl | 1 | |
| 557 | C₆F₅ | Me | Isoxazol-5-yl | 1 | |
| 558 | 4-Cl-3-Et—C₆H₃ | Me | Isoxazol-5-yl | 1 | |
| 559 | 3-EtO—C₆H₄ | Me | Isoxazol-5-yl | 1 | |
| 560 | 4-EtO—C₆H₄ | Me | Isoxazol-5-yl | 1 | |
| 561 | C₆H₅ | Me | Isoxazol-5-yl | 0 | |
| 562 | 4-F—C₆H₄ | Me | Isoxazol-5-yl | 0 | |
| 563 | 3-Cl—C₆H₄ | Me | Isoxazol-5-yl | 0 | |
| 564 | 4-Cl—C₆H₄ | Me | Isoxazol-5-yl | 0 | |
| 565 | 3-Me—C₆H₄ | Me | Isoxazol-5-yl | 0 | |
| 566 | 4-Me—C₆H₄ | Me | Isoxazol-5-yl | 0 | |
| 567 | 4-Et—C₆H₄ | Me | Isoxazol-5-yl | 0 | |
| 568 | 4-NO₂—C₆H₄ | Me | Isoxazol-5-yl | 0 | |
| 569 | 3,4-Cl₂—C₆H₃ | Me | Isoxazol-5-yl | 0 | |
| 570 | 3,5-Cl₂—C₆H₃ | Me | Isoxazol-5-yl | 0 | |
| 571 | 3,4-Me₂—C₆H₃ | Me | Isoxazol-5-yl | 0 | |
| 572 | 3,5-Me₂—C₆H₃ | Me | Isoxazol-5-yl | 0 | |
| 573 | 3-PhO—C₆H₄ | Me | Isoxazol-5-yl | 0 | |
| 574 | 4-Cl-3-Et—C₆H₃ | Me | Isoxazol-5-yl | 0 | |
| 575 | 3-EtO—C₆H₄ | Me | Isoxazol-5-yl | 0 | |
| 576 | 3-CF₃—C₆H₄ | Me | Isoxazol-5-yl | 0 | |
| 577 | 4-CF₃—C₆H₄ | Me | Isoxazol-5-yl | 0 | |
| 578 | 3-i-PrO—C₆H₄ | Me | Isoxazol-5-yl | 0 | |
| 579 | 3-i-Pr—C₆H₄ | Me | Isoxazol-5-yl | 0 | |
| 580 | 4-Cl-3-Me—C₆H₃ | Me | Isoxazol-5-yl | 0 | |
| 581 | Pyridin-2-yl | Me | Isoxazol-5-yl | 1 | |

-continued

| No | R¹ | R² | R³ | n | Physical data |
|---|---|---|---|---|---|
| 582 | Pyridin-3-yl | Me | Isoxazol-5-yl | 1 | |
| 583 | 5-Cl-pyridin-2-yl | Me | Isoxazol-5-yl | 1 | |
| 584 | 3-Cl-pyridin-2-yl | Me | Isoxazol-5-yl | 1 | |
| 585 | 6-Cl-pyridin-2-yl | Me | Isoxazol-5-yl | 1 | |
| 586 | 2-Cl-pyridin-3-yl | Me | Isoxazol-5-yl | 1 | |
| 587 | 5-CF₃-pyridin-2-yl | Me | Isoxazol-5-yl | 1 | |
| 588 | 5-CF₃-pyridin-2-yl | Me | Isoxazol-5-yl | 1 | |
| 589 | 6-CF₃-3-Cl-pyridin-2-yl | Me | Isoxazol-5-yl | 1 | |
| 590 | 5-CF₃-3-Cl-pyridin-2-yl | Me | Isoxazol-5-yl | 1 | |
| 591 | Benzothazol-2-yl | Me | Isoxazol-5-yl | 1 | |
| 592 | Benzoxazol-2-yl | Me | Isoxazol-5-yl | 1 | |
| 593 | Quinolin-2-yl | Me | Isoxazol-5-yl | 1 | |
| 594 | 5-CF₃-1,3,4-thiadiazol-2-yl | Me | Isoxazol-5-yl | 1 | |
| 595 | Pyrimidin-2-yl | Me | Isoxazol-5-yl | 1 | |
| 596 | 5-Cl-6-Me-pyrimidin-4-yl | Me | Isoxazol-5-yl | 1 | |
| 597 | 5-Et-6-Me-pyrimidin-4-yl | Me | Isoxazol-5-yl | 1 | |
| 598 | 6-Cl-Pyrazin-2-yl | Me | Isoxazol-5-yl | 1 | |
| 599 | 3,6-Me₂-Pyrazin-2-yl | Me | Isoxazol-5-yl- | 1 | |
| 600 | 5-Me-isoxazol-3-yl | Me | Isoxazol-5-yl | 1 | |
| 601 | C₆H₅ | Me | 3-M3-isoazol-5-yl | 1 | Isomer A: mp99.0–100.0° C. Isomer B: ¹H-NMR (CDCl₃)δ ppm: 2.27(3H, s), 4.02(3H, s), 4.95(2H, s), 5.99(1H, s), 6.80–7.65(9H, m) |
| 602 | 2-F—C₆H₄ | Me | 3-Me-isoxazol-5-yl | 1 | |
| 603 | 3-F—C₆H₄ | Me | 3-Me-isoxazol-5-yl | 1 | |
| 604 | 4-F—C₆H₄ | Me | 3-Me-isoxazol-5-yl | 1 | |

-continued

| No | R¹ | R² | R³ | n | Physical data |
|---|---|---|---|---|---|
| 605 | 2-Cl—C₆H₄ | Me | 3-Me-isoxazol-5-yl | 1 | Isomer A: mp87.0–88.0° C.<br>Isomer B: ¹H-NMR (CDCl₃)δ ppm: 2.27(3H, s), 4.04(3H, s), 5.01(2H, s), 6.02(1H, s), 6.81–7.74(8H, m) |
| 606 | 3-Cl—C₆H₄ | Me | 3-Me-isoxazol-5-yl | 1 | Isomer A: ¹H-NMR (CDCl₃)δ ppm: 2.35(3H, s), 4.10(3H, s), 5.00(2H, s), 6.66–6.91 (3H, m), 6.94(1H, s), 7.10–7.57(5H, m).<br>Isomer B: ¹H-NMR (CDCl₃)δ ppm: 2.28(3H, s), 4.03(3H, s), 4.94(2H, s), 6.01(1H, s), 6.68–7.65(8H, m) |
| 607 | 4-Cl—C₆H₄ | Me | 3-Me-isoxazol-5-yl | 1 | Isomer A: mp110.0–111.0° C.<br>Isomer B: ¹H-NMR (CDCl₃)δ ppm: 2.27(3H, s), 4.01(3H, s), 4.92(2H, s), 5.99(1H, s), 6.71–7.60(8H, m) |
| 608 | 2-Br—C₆H₄ | Me | 3-Me-isoxazol-5-yl | 1 | |
| 609 | 3-Br—C₆H₄ | Me | 3-Me-isoxazol-5-yl | 1 | |
| 610 | 4-Br—C₆H₄ | Me | 3-Me-isoxazol-5-yl | 1 | |
| 611 | 3-I—C₆H₄ | Me | 3-Me-isoxazol-5-yl | 1 | |
| 612 | 2-Me—C₆H₄ | Me | 3-Me-isoxazol-5-yl | 1 | Isomer A: mp80.0–81.0° C.<br>Isomer B: ¹H-NMR (CDCl₃)δ ppm: 2.17(3H, s), 2.26(3H, s), 4.03(3H, s), 4.93(2H, s), 5.98(1H, s), 6.71–7.68 (8H, m) |
| 613 | 3-Me—C₆H₄ | Me | 3-Me-isoxazol-5-yl | 1 | Isomer A: mp109.0–110.0° C.<br>Isomer B: mp94.5–95.5° C. |
| 614 | 4-Me—C₆H₄ | Me | 3-Me-isoxazol-5-yl | 1 | Isomer A: mp126.0–127.0° C.<br>Isomer B: ¹H-NMR (CDCl₃)δ ppm: 2.25(3H, s), 2.27(3H, s), 4.02(3H, s), 4.92(2H, s), 5.99(1H, s), 6.70–7.64(8H, m) |
| 615 | 2-Et—C₆H₄ | Me | 3-Me-isoxazol-5-yl | 1 | |
| 616 | 3-Et—C₆H₄ | Me | 3-Me-isoxazol-5-yl | 1 | |
| 617 | 4-Et—C₆H₄ | Me | 3-Me-isoxazol-5-yl | 1 | |
| 618 | 2-MeO—C₆H₄ | Me | 3-Me-isoxazol-5-yl | 1 | |
| 619 | 3-MeO—C₆H₄ | Me | 3-Me-isoxazol-5-yl | 1 | |
| 620 | 4-MeO—C₆H₄ | Me | 3-Me-isoxazol-5-yl | 1 | |
| 621 | 2-CF₃—C₆H₄ | Me | 3-Me-isoxazol-5-yl | 1 | |
| 622 | 3-CF₃—C₆H₄ | Me | 3-Me-isoxazol-5-yl | 1 | Isomer A: ¹H-NMR (CDCl₃)δ ppm: 2.34(3H, s), 4.08(3H, s), 5.05(2H, s), 6.92(1H, s), 6.94–7.57(8H, m)<br>Isomer B: ¹H-NMR (CDCl₃)δ ppm: 2.27(3H, s), 4.02(3H, s), 4.99(2H, s), 6.01(1H, s), 6.96–7.61(8H, m) |

-continued

| No | R¹ | R² | R³ | n | Physical data |
|---|---|---|---|---|---|
| 623 | 4-CF₃—C₆H₄ | Me | 3-Me-isoxazol-5-yl | 1 | |
| 624 | 2,4-F₂—C₆H₃ | Me | 3-Me-isoxazol-5-yl | 1 | |
| 625 | 2,5-F₂—C₆H₃ | Me | 3-Me-isoxazol-5-yl | 1 | |
| 626 | 2,6-F₂—C₆H₃ | Me | 3-Me-isoxazol-5-yl | 1 | |
| 627 | 3,4-F₂—C₆H₃ | Me | 3-Me-isoxazol-5-yl | 1 | |
| 628 | 3,5-F₂—C₆H₃ | Me | 3-Me-isoxazol-5-yl | 1 | |
| 629 | 2,3-Cl₂—C₆H₃ | Me | 3-Me-isoxazol-5-yl | 1 | |
| 630 | 2,4-Cl₂—C₆H₃ | Me | 3-Me-isoxazol-5-yl | 1 | |
| 631 | 2,5-Cl₂—C₆H₃ | Me | 3-Me-isoxazol-5-yl | 1 | |
| 632 | 3,4-Cl₂—C₆H₃ | Me | 3-Me-isoxazol-5-yl | 1 | |
| 633 | 3,5-Cl₂—C₆H₃ | Me | 3-Me-isoxazol-5-yl | 1 | |
| 634 | 2,3-Me₂—C₆H₃ | Me | 3-Me-isoxazol-5-yl | 1 | |
| 635 | 2,4-Me₂—C₆H₃ | Me | 3-Me-isoxazol-5-yl | 1 | |
| 636 | 2,5-Me₂—C₆H₃ | Me | 3-Me-isoxazol-5-yl | 1 | Isomer A: mp113–114° C. Isomer B: mp107–108° C. |
| 637 | 3,4-Me₂—C₆H₃ | Me | 3-Me-isoxazol-5-yl | 1 | |
| 638 | 3,5-Me₂—C₆H₃ | Me | 3-Me-isoxazol-5-yl | 1 | |
| 639 | 2-Cl-4-Me—C₆H₃ | Me | 3-Me-isoxazol-5-yl | 1 | |
| 640 | 2-Cl-5-Me—C₆H₃ | Me | 3-Me-isoxazol-5-yl | 1 | |
| 641 | 4-Cl-2-Me—C₆H₃ | Me | 3-Me-isoxazol-5-yl | 1 | Isomer A: mp76.5–77.5° C. Isomer B: ¹H-NMR (CDCl₃)δ ppm: 2.12(3H, s), 2.26(3H, s), 4.03(3H, s), 4.93(2H, s), 5.97(1H, s), 6.62(1H, d, J = 8.5), 6.99–7.62(6H, m) |
| 642 | 4-Cl-3-Me—C₆H₃ | Me | 3-Me-isoxazol-5-yl | 1 | |
| 643 | 3-Ph—C₆H₄ | Me | 3-Me-isoxazol-5-yl | 1 | |
| 644 | 4-Ph—C₆H₄ | Me | 3-Me-isoxazol-5-yl | 1 | Isomer A: mp130.5–131.5° C. Isomer B: mp102.5–103.5° C. |
| 645 | 3-i-PrO—C₆H₄ | Me | 3-Me-isoxazol-5-yl | 1 | |
| 646 | 3-i-Pr—C₆H₄ | Me | 3-Me-isoxazol-5-yl | 1 | |
| 647 | 4-i-Pr—C₆H₄ | Me | 3-Me-isoxazol-5-yl | 1 | |
| 648 | 3-t-Bu—C₆H₄ | Me | 3-Me-isoxazol-5-yl | 1 | |
| 649 | 2-MeS—C₆H₄ | Me | 3-Me-isoxazol-5-yl | 1 | |
| 650 | 4-MeS—C₆H₄ | Me | 3-Me-isoxazol-5-yl | 1 | |
| 651 | 2,3,6-F₃—C₆H₂ | Me | 3-Me isoxazol-5-yl | 1 | |
| 652 | 2,4,5-Cl₃—C₆H₂ | Me | 3-Me-isoxazol-5-yl | 1 | |
| 653 | 3-PhO—C₆H₄ | Me | 3-Me-isoxazol-5-yl | 1 | |
| 654 | 3,4,5-(MeO)₃—C₆H₂ | Me | 3-Me-isoxazol-5-yl | 1 | |
| 655 | 2,3,5-Me₃—C₆H₂ | Me | 3-Me-isoxazol-5-yl | 1 | |

-continued

| No | R¹ | R² | R³ | n | Physical data |
|---|---|---|---|---|---|
| 656 | 3,4,5-Me₃—C₆H₂ | Me | 3-Me-isoxazol-5-yl | 1 | |
| 657 | C₆F₅ | Me | 3-Me-isoxazol-5-yl | 1 | |
| 658 | 4-Cl-3-Et—C₆H₃ | Me | 3-Me-isoxazol-5-yl | 1 | |
| 659 | 3-EtO—C₆H₄ | Me | 3-Me-isoxazol-5-yl | 1 | |
| 660 | 4-EtO—C₆H₄ | Me | 3-Me-isoxazol-5-yl | 1 | |
| 661 | C₆H₅ | Me | 3-Me-isoxazol-5-yl | 0 | Isomer A: mp100.0–105.5° C. Isomer B: ¹H-NMR (CDCl₃)δ ppm: 2.28(3H, s), 3.94(3H, s), 6.17(1H, s), 6.92–7.41(9H, m) |
| 662 | 4-F—C₆H₄ | Me | 3-Me-isoxazol-5-yl | 0 | |
| 663 | 3-Cl—C₆H₄ | Me | 3-Me-isoxazol-5-yl | 0 | |
| 664 | 4-Cl—C₆H₄ | Me | 3-Me-isoxazol-5-yl | 0 | |
| 665 | 3-Me—C₆H₄ | Me | 3-Me-isoxazol-5-yl | 0 | |
| 666 | 4-Me—C₆H₄ | Me | 3-Me-isoxazol-5-yl | 0 | |
| 667 | 4-Et—C₆H₄ | Me | 3-Me-isoxazol-5-yl | 0 | |
| 668 | 4-NO₂—C₆H₄ | Me | 3-Me-isoxazol-5-yl | 0 | |
| 669 | 3,4-Cl₂—C₆H₃ | Me | 3-Me-isoxazol-5-yl | 0 | |
| 670 | 3,5-Cl₂—C₆H₃ | Me | 3-Me-isoxazol-5-yl | 0 | |
| 671 | 3,4-Me₂—C₆H₃ | Me | 3-Me-isoxazol-5-yl | 0 | |
| 672 | 3,5-Me₂—C₆H₃ | Me | 3-Me-isoxazol-5-yl | 0 | |
| 673 | 3-PhO—C₆H₃ | Me | 3-Me-isoxazol-5-yl | 0 | |
| 674 | 4-Cl-3-Et—C₆H₃ | Me | 3-Me-isoxazol-5-yl | 0 | |
| 675 | 3-EtO—C₆H₄ | Me | 3-Me-isoxazol-5-yl | 0 | |
| 676 | 3-CF₃—C₆H₄ | Me | 3-Me-isoxazol-5-yl | 0 | |
| 677 | 4-CF₃—C₆H₄ | Me | 3-Me-isoxazol-5-yl | 0 | |
| 678 | 3-i-PrO—C₆H₄ | Me | 3-Me-isoxazol-5-yl | 0 | |
| 679 | 3-i-Pr—C₆H₄ | Me | 3-Me-isoxazol-5-yl | 0 | |
| 680 | 4-Cl-3-Me—C₆H₃ | Me | 3-Me-isoxazol-5-yl | 0 | |
| 681 | Pyridin-2-yl | Me | 3-Me-isoxazol-5-yl | 1 | |
| 682 | Pyridin-3-yl | Me | 3-Me-isoxazol-5-yl | 1 | |
| 683 | 5-Cl-pyridin-2-yl | Me | 3-Me-isoxazol-5-yl | 1 | |
| 684 | 3-Cl-pyridin-2-yl | Me | 3-Me-isoxazol-5-yl | 1 | |
| 685 | 6-Cl-pyridin-2-yl | Me | 3-Me-isoxazol-5-yl | 1 | |
| 686 | 2-Cl-pyridin-3-yl | Me | 3-Me-isoxazol-5-yl | 1 | |

-continued

| No | R¹ | R² | R³ | n | Physical data |
|---|---|---|---|---|---|
| 687 | 5-CF₃-pyridin-2-yl | Me | 3-Me-isoxazol-5-yl | 1 | Isomer A: mp88.0–90.0° C. Isomer B: ¹H-NMR (CDCl₃)δ ppm: 2.28(3H, s), 4.01(3H, s), 5.32(2H, s), 6.00(1H, s), 6.64(1H, d, J = 9.2), 7.22–7.73(5H, m), 8.30 (1H, d, J = 1.2) |
| 688 | 3-CF₃-pyridin-2-yl | Me | 3-Me-isoxazol-5-yl | 1 | |
| 689 | 6-CF₃-3-Cl-pyridin-2-yl | Me | 3-Me-isoxazol-5-yl | 1 | |
| 690 | 5-CF₃-3-Cl-pyridin-2-yl | Me | 3-Me-isoxazol-5-yl | 1 | Isomer A: mp77.0–79.0° C. Isomer B: ¹H-NMR CDCl₃)δ ppm: 2.27(3H, s), 4.03(3H, s), 5.39(2H, s), 6.02(1H, s), 7.22–7.67(4H, m), 7.79(1H, d, J = 1.8), 8.17(1H, d, J = 1.8) |
| 691 | Benzothiazol-2-yl | Me | 3-Me-isoxazol-5-yl | 1 | |
| 692 | Benzoxazol-2-yl | Me | 3-Me-isoxazol-5-yl | 1 | |
| 693 | Quinolin-2-yl | Me | 3-Me-isoxazol-5-yl | 1 | |
| 694 | 5-CF₃-1,3,4-thiadiazol-2-yl | Me | 3-Me-isoxazol-5-yl | 1 | |
| 695 | Pyrimidin-2-yl | Me | 3-Me-isoxazol-5-yl | 1 | |
| 696 | 5-Cl-6-Me-pyrimidin-4-yl | Me | 3-Me-isoxazol-5-yl | 1 | |
| 697 | 5-Et-6-Me-pyrimidin-4-yl | Me | 3-Me-isoxazol-5-yl | 1 | |
| 698 | 6-Cl-pyrazin-2-yl | Me | 3-Me-isoxazol-5-yl | 1 | |
| 699 | 3,6-Me₂-pyrazin- | Me | 3-Me-isoxazol-5-yl | 1 | |
| 700 | 5-Me-isoxazol-3-yl | Me | 3-Me-isoxazol-5-yl | 1 | |
| 701 | C₆H₅ | Me | 1,3,4-Oxadiazol-2-yl | 1 | mp88.0–89.0° C. |
| 702 | 2-F—C₆H₄ | Me | 1,3,4-Oxadiazol-2-yl | 1 | |
| 703 | 3-F—C₆H₄ | Me | 1,3,4-Oxadiazol-2-yl | 1 | |
| 704 | 4-F—C₆H₄ | Me | 1,3,4-Oxadiazol-2-yl | 1 | |
| 705 | 2-Cl—C₆H₄ | Me | 1,3,4-Oxadiazol-2-yl | 1 | mp120.0–121.0° C. |
| 706 | 3-Cl—C₆H₄ | Me | 1,3,4-Oxadiazol-2-yl | 1 | mp97.0–98.0° C. |
| 707 | 4-Cl—C₆H₄ | Me | 1,3,4-Oxadiazol-2-yl | 1 | mp120–122° C. |
| 708 | 2-Br—C₆H₄ | Me | 1,3,4-Oxadiazol-2-yl | 1 | |
| 709 | 3-Br—C₆H₄ | Me | 1,3,4-Oxadiazol-2-yl | 1 | |
| 710 | 4-Br—C₆H₄ | Me | 1,3,4-Oxadiazol-2-yl | 1 | |

-continued

| No | R¹ | R² | R³ | n | Physical data |
|---|---|---|---|---|---|
| 711 | 3-I—C₆H₄ | Me | 1,3,4-Oxa-diazol-2-yl | 1 | |
| 712 | 2-Me—C₆H₄ | Me | 1,3,4-Oxa-diazol-2-yl | 1 | mp 95–96.5° C. |
| 713 | 3-Me—C₆H₄ | Me | 1,3,4-Oxa-diazol-2-yl | 1 | mp78.5–79.5° C. |
| 714 | 4-Me—CH₄ | Me | 1,3,4-Oxa-diazol-2-yl | 1 | |
| 715 | 2-Et—C₆H₄ | Me | 1,3,4-Oxa-diazol-2-yl | 1 | |
| 716 | 3-Et—C₆H₄ | Me | 1,3,4-Oxa-diazol-2-yl | 1 | ¹H-NMR(CDCl₃) δ ppm: 1.14(3H, t, J = 7.3), 2.56(2H, q, J = 7.3), 4.08(3H, s), 4.99(2H, s), 6.73–7.65(8H, m), 8.43(1H, s) |
| 717 | 4-Et—C₆H₄ | Me | 1,3,4-Oxa-diazol-2-yl | 1 | |
| 718 | 2-MeO—C₆H₄ | Me | 1,3,4-Oxa-diazol-2-yl | 1 | mp85.0–86.5° C. |
| 719 | 3-MeO—C₆H₄ | Me | 1,3,4-Oxa-diazol-2-yl | 1 | |
| 720 | 4-MeO—C₆H₄ | Me | 1,3,4-Oxa-diazol-2-yl | 1 | |
| 721 | 2-CF₃—C₆H₄ | Me | 1,3,4-Oxa-diazol-2-yl | 1 | |
| 722 | 3-CF₃—C₆H₄ | Me | 1,3,4-Oxa-diazol-2-yl | 1 | ¹H-NMR(CDCl₃) δ ppm: 4.06(3H, s), 5.03(2H, s), 6.92–7.59(8H, m), 8.44(1H, s) |
| 723 | 4-CF₃—C₆H₄ | Me | 1,3,4-Oxa-diazol-2-yl | 1 | |
| 724 | 2,4-F₂—C₆H₃ | Me | 1,3,4-Oxa-diazol-2-yl | 1 | |
| 725 | 2,5-F₂—C₆H₃ | Me | 1,3,4-Oxa-diazol-2-yl | 1 | |
| 726 | 2,6-F₂—C₆H₃ | Me | 1,3,4-Oxa-diazol-2-yl | 1 | |
| 727 | 3,4-F₂—C₆H₃ | Me | 1,3,4-Oxa-diazol-2-yl | 1 | |
| 728 | 3,5-F₂—C₆H₃ | Me | 1,3,4-Oxa-diazol-2-yl | 1 | |
| 729 | 2,3-Cl₂—C₆H₃ | Me | 1,3,4-Oxa-diazol-2-yl | 1 | |
| 730 | 2,4-Cl₂—C₆H₃ | Me | 1,3,4-Oxa-diazol-2-yl | 1 | |
| 731 | 2,5-Cl₂—C₆H₃ | Me | 1,3,4-Oxa-diazol-2-yl | 1 | mp152.0–153.0° C. |
| 732 | 3,4-Cl₂—C₆H₃ | Me | 1,3,4-Oxa-diazol-2-yl | 1 | ¹H-NMR(CDCl₃) δ ppm: 4.08(3H, s), 4.96(2H, s), 6.63(1H, dd, J = 2.4, 8.5), 6.89(1H, d, J = 3.1), 7.24–7.57(5H, m), 8.46(1H, s) |
| 733 | 3,5-Cl₂—C₆H₃ | Me | 1,3,4-Oxa-diazol-2-yl | 1 | |
| 734 | 2,3-Me₂—C₆H₃ | Me | 1,3,4-Oxa-diazol-2-yl | 1 | |
| 735 | 2,4-Me₂—C₆H₃ | Me | 1,3,4-Oxa-diazol-2-yl | 1 | |
| 736 | 2,5-Me₂—C₆H₃ | Me | 1,3,4-Oxa-diazol-2-yl | 1 | mp134–135° C. |
| 737 | 3,4-Me₂—C₆H₃ | Me | 1,3,4-Oxa-diazol-2-yl | 1 | |
| 738 | 3,5-Me₂—C₆H₃ | Me | 1,3,4-Oxa-diazol-2-yl | 1 | |
| 739 | 2-Cl-4-Me—C₆H₃ | Me | 1,3,4-Oxa-diazol-2-yl | 1 | |
| 740 | 2-Cl-5-Me—C₆H₃ | Me | 1,3,4-Oxa-diazol-2-yl | 1 | |
| 741 | 4-Cl-2-Me—C₆H₃ | Me | 1,3,4-Oxa-diazol-2-yl | 1 | mp85.5–86.5° C. |
| 742 | 4-Cl-3-Me—C₆H₃ | Me | 1,3,4-Oxa-diazol-2-yl | 1 | |

-continued

| No | R¹ | R² | R³ | n | Physical data |
|---|---|---|---|---|---|
| 743 | 3-Ph—C₆H₄ | Me | 1,3,4-Oxadiazol-2-yl | 1 | |
| 744 | 4-Ph—C₆H₄ | Me | 1,3,4-Oxadiazol-2-yl | 1 | |
| 745 | 3-i-PrO—C₆H₄ | Me | 1,3,4-Oxadiazol-2-yl | 1 | |
| 746 | 3-i-Pr—C₆H₄ | Me | 1,3,4-Oxadiazol-2-yl | 1 | |
| 747 | 4-i-Pr—C₆H₄ | Me | 1,3,4-Oxadiazol-2-yl | 1 | |
| 748 | 3-t-Bu—C₆H₄ | Me | 1,3,4-Oxadiazol-2-yl | 1 | |
| 749 | 2-MeS—C₆H₄ | Me | 1,3,4-Oxadiazol-2-yl | 1 | |
| 750 | 4-MeS—C₆H₄ | Me | 1,3,4-Oxadiazol-2-yl | 1 | |
| 751 | 2,3,6-F₃—C₆H₂ | Me | 1,3,4-Oxadiazol-2-yl | 1 | |
| 752 | 2,4,5-Cl₃—C₆H₂ | Me | 1,3,4-Oxadiazol-2-yl | 1 | |
| 753 | 3-PhO—C₆H₄ | Me | 1,3,4-Oxadiazol-2-yl | 1 | |
| 754 | 3,4,5-(MeO)₃—C₆H₂ | Me | 1,3,4-Oxadiazol-2-yl | 1 | |
| 755 | 2,3,5-Me₃—C₆H₂ | Me | 1,3,4-Oxadiazol-2-yl | 1 | |
| 756 | 3,4,5-Me₃—C₆H₂ | Me | 1,3,4-Oxadiazol-2-yl | 1 | |
| 757 | C₆F₅ | Me | 1,3,4-Oxadiazol-2-yl | 1 | |
| 758 | 4-Cl-3-Et—C₆H₃ | Me | 1,3,4-Oxadiazol-2-yl | 1 | |
| 759 | 3-EtO—C₆H₄ | Me | 1,3,4-Oxadiazol-2-yl | 1 | |
| 760 | 4-EtO—C₆H₄ | Me | 1,3,4-Oxadiazol-2-yl | 1 | |
| 761 | C₆H₅ | Me | 1,3,4-Oxadiazol-2-yl | 0 | |
| 762 | 4-F—C₆H₄ | Me | 1,3,4-Oxadiazol-2-yl | 0 | |
| 763 | 3-Cl—C₆H₄ | Me | 1,3,4-Oxadiazol-2-yl | 0 | |
| 764 | 4-Cl—C₆H₄ | Me | 1,3,4-Oxadiazol-2-yl | 0 | |
| 765 | 3-Me—C₆H₄ | Me | 1,3,4-Oxadiazol-2-yl | 0 | |
| 766 | 4-Me—C₆H₄ | Me | 1,3,4-Oxadiazol-2-yl | 0 | |
| 767 | 4-Et—C₆H₄ | Me | 1,3,4-Oxadiazol-2-yl | 0 | |
| 768 | 4-NO₂—C₆H₄ | Me | 1,3,4-Oxadiazol-2-yl | 0 | |
| 769 | 3,4-Cl₂—C₆H₃ | Me | 1,3,4-Oxadiazol-2-yl | 0 | |
| 770 | 3,5-Cl₂—C₆H₃ | Me | 1,3,4-Oxadiazol-2-yl | 0 | |
| 771 | 3,4-Me₂—C₆H₃ | Me | 1,3,4-Oxadiazol-2-yl | 0 | |
| 772 | 3,5-Me₂—C₆H₃ | Me | 1,3,4-Oxadiazol-2-yl | 0 | |
| 773 | 3-PhO—C₆H₄ | Me | 1,3,4-Oxadiazol-2-yl | 0 | |
| 774 | 4-Cl-3-Et—C₆H₃ | Me | 1,3,4-Oxadiazol-2-yl | 0 | |
| 775 | 3-EtO—C₆H₄ | Me | 1,3,4-Oxadiazol-2-yl | 0 | |
| 776 | 3-CF₃—C₆H₄ | Me | 1,3,4-Oxadiazol-2-yl | 0 | |
| 777 | 4-CF₃—C₆H₄ | Me | 1,3,4-Oxadiazol-2-yl | 0 | |
| 778 | 3-i-PrO—C₆H₄ | Me | 1,3,4-Oxadiazol-2-yl | 0 | |
| 779 | 3-i-Pr—C₆H₄ | Me | 1,3,4-Oxadiazol-2-yl | 0 | |
| 780 | 4-Cl-3-Me—C₆H₃ | Me | 1,3,4-Oxadiazol-2-yl | 0 | |

-continued

| No | R¹ | R² | R³ | n | Physical data |
|---|---|---|---|---|---|
| 781 | Pyridin-2-yl | Me | 1,3,4-Oxadiazol-2-yl | 1 | |
| 782 | Pyridin-3-yl | Me | 1,3,4-Oxadiazol-2-yl | 1 | |
| 783 | 5-Cl-pyridin-2-yl | Me | 1,3,4-Oxadiazol-2-yl | 1 | |
| 784 | 3-Cl-pyridin-2-yl | Me | 1,3,4-Oxadiazol-2-yl | 1 | |
| 785 | 6-Cl-pyridin-2-yl | Me | 1,3,4-Oxadiazol-2-yl | 1 | |
| 786 | 2-Cl-pyridin-3-yl | Me | 1,3,4-Oxadiazol-2-yl | 1 | |
| 787 | 5-$CF_3$-pyridin-2-yl | Me | 1,3,4-Oxadiazol-2-yl | 1 | |
| 788 | 3-$CF_3$-pyridin-2-yl | Me | 1,3,4-Oxadiazol-2-yl | 1 | |
| 789 | 6-$CF_3$-3-Cl-pyridin-2-yl | Me | 1,3,4-Oxadiazol-1-yl | 1 | |
| 790 | 5-$CF_3$-3-Cl-pyridin-2-yl | Me | 1,3,4-Oxadiazol-2-yl | 1 | |
| 791 | Benzothiazol-2-yl | Me | 1,3,4-Oxadiazol-2-yl | 1 | |
| 792 | Benzoxazol-2-yl | Me | 1,3,4-Oxadiazol-2-yl | 1 | |
| 793 | Quinolin-2-yl | Me | 1,3,4-Oxadiazol-2-yl | 1 | |
| 794 | 5-$CF_3$-1,3,4-thiadiazol-2-yl | Me | 1,3,4-Oxadiazol-2-yl | 1 | |
| 795 | Pyrimidin-2-yl | Me | 1,3,4-Oxadiazol-2-yl | 1 | |
| 796 | 5-Cl-6-Me-pyrimidin-4-yl | Me | 1,3,4-Oxadiazol-2-yl | 1 | |
| 797 | 5-Et-6-Me-pyrimidin-4-yl | Me | 1,3,4-Oxadiazol-2-yl | 1 | |
| 798 | 6-Cl-pyrazin-2-yl | Me | 1,3,4-Oxadiazol-2-yl | 1 | |
| 799 | 3,6-$Me_2$-pyrazin-2-yl | Me | 1,3,4-Oxadiazol-2-yl | 1 | |
| 800 | 5-Me-isoxazol-3-yl | Me | 1,3,4-Oxadiazol-2-yl | 1 | |
| 801 | $C_6H_5$ | Me | 1,2,4-Oxadiazol-3-yl | 1 | mp 70.5–71.5° C. |
| 802 | 2-F—$C_6H_4$ | Me | 1,2,4-Oxadiazol-3-yl | 1 | |
| 803 | 3-F—$C_6H_4$ | Me | 1,2,4-Oxadiazol-3-yl | 1 | |
| 804 | 4-F—$C_6H_4$ | Me | 1,2,4-Oxadiazol-3-yl | 1 | |
| 805 | 2-Cl—$C_6H_4$ | Me | 1,2,4-Oxadiazol-3-yl | 1 | mp 139.0–140.0° C. |
| 806 | 3-Cl—$C_6H_4$ | Me | 1,2,4-Oxadiazol-3-yl | 1 | |
| 807 | 4-Cl—$C_6H_4$ | Me | 1,2,4-Oxadiazol-3-yl | 1 | mp 107–108° C. |
| 808 | 2-Br—$C_6H_4$ | Me | 1,2,4-Oxadiazol-3-yl | 1 | |
| 809 | 3-Br—$C_6H_4$ | Me | 1,2,4-Oxadiazol-3-yl | 1 | |
| 810 | 4-Br—$C_6H_4$ | Me | 1,2,4-Oxadiazol-3-yl | 1 | |
| 811 | 3-I—$C_6H_4$ | Me | 1,2,4-Oxadiazol-3-yl | 1 | |
| 812 | 2-Me—$C_6H_4$ | Me | 1,2,4-Oxadiazol-3-yl | 1 | mp 79–80° C. |
| 813 | 3-Me—$C_6H_4$ | Me | 1,2,4-Oxadiazol-3-yl | 1 | |
| 814 | 4-Me—$C_6H_4$ | Me | 1,2,4-Oxadiazol-3-yl | 1 | mp 92.5–93.5° C. |

-continued

| No | R¹ | R² | R³ | n | Physical data |
|---|---|---|---|---|---|
| 815 | 2-Et—C$_6$H$_4$ | Me | 1,2,4-Oxadiazol-3-yl | 1 | |
| 816 | 3-Et—C$_6$H$_4$ | Me | 1,2,4-Oxadiazol-3-yl | 1 | |
| 817 | 4-Et—C$_6$H$_4$ | Me | 1,2,4-Oxadiazol-3-yl | 1 | |
| 818 | 2-MeO—C$_6$H$_4$ | Me | 1,2,4-Oxadiazol-3-yl | 1 | |
| 819 | 3-MeO—C$_6$H$_4$ | Me | 1,2,4-Oxadiazol-3-yl | 1 | |
| 820 | 4-MeO—C$_6$H$_4$ | Me | 1,2,4-Oxadiazol-3-yl | 1 | |
| 821 | 2-CF$_3$—C$_6$H$_4$ | Me | 1,2,4-Oxadiazol-3-yl | 1 | |
| 822 | 3-CF$_3$—C$_6$H$_4$ | Me | 1,2,4-Oxadiazol-3-yl | 1 | |
| 823 | 4-CF$_3$—C$_6$H$_4$ | Me | 1,2,4-Oxadiazol-3-yl | 1 | |
| 824 | 2,4-F$_2$—C$_6$H$_3$ | Me | 1,2,4-Oxadiazol-3-yl | 1 | |
| 825 | 2,5-F$_2$—C$_6$H$_3$ | Me | 1,2,4-Oxadiazol-3-yl | 1 | |
| 826 | 2,6-F$_2$—C$_6$H$_3$ | Me | 1,2,4-Oxadiazol-3-yl | 1 | |
| 827 | 3,4-F$_2$—C$_6$H$_3$ | Me | 1,2,4-Oxadiazol-3-yl | 1 | |
| 828 | 3,5-F$_2$—C$_6$H$_3$ | Me | 1,2,4-Oxadiazol-3-yl | 1 | |
| 829 | 2,3-Cl$_2$—C$_6$H$_3$ | Me | 1,2,4-Oxadiazol-3-yl | 1 | |
| 830 | 2,4-Cl$_2$—C$_6$H$_3$ | Me | 1,2,4-Oxadiazol-3-yl | 1 | |
| 831 | 2,5-Cl$_2$—C$_6$H$_3$ | Me | 1,2,4-Oxadiazol-3-yl | 1 | |
| 832 | 3,4-Cl$_2$—C$_6$H$_3$ | Me | 1,2,4-Oxadiazol-3-yl | 1 | |
| 833 | 3,5-Cl$_2$—C$_6$H$_3$ | Me | 1,2,4-Oxadiazol-3-yl | 1 | |
| 834 | 2,3-Me$_2$—C$_6$H$_3$ | Me | 1,2,4-Oxadiazol-3-yl | 1 | |
| 835 | 2,4-Me$_2$—C$_6$H$_3$ | Me | 1,2,4-Oxadiazol-3-yl | 1 | |
| 836 | 2,5-Me$_2$—C$_6$H$_3$ | Me | 1,2,4-Oxadiazol-3-yl | 1 | Isomer A: mp 116.5–117.5° C. Isomer B: mp 69–71° C. |
| 837 | 3,4-Me$_2$—C$_6$H$_3$ | Me | 1,2,4-Oxadiazol-3-yl | 1 | |
| 838 | 3,5-Me$_2$—C$_6$H$_3$ | Me | 1,2,4-Oxadiazol-3-yl | 1 | |
| 839 | 2-Cl-4-Me—C$_6$H$_3$ | Me | 1,2,4-Oxadiazol-3-yl | 1 | |
| 840 | 2-Cl-5-Me—C$_6$H$_3$ | Me | 1,2,4-Oxadiazol-3-yl | 1 | |
| 841 | 4-Cl-2-Me—C$_6$H$_3$ | Me | 1,2,4-Oxadiazol-3-yl | 1 | mp 127–128° C. |
| 842 | 4-Cl-3-Me—C$_6$H$_3$ | Me | 1,2,4-Oxadiazol-3-yl | 1 | |
| 843 | 3-Ph—C$_6$H$_4$ | Me | 1,2,4-Oxadiazol-3-yl | 1 | |
| 844 | 4-Ph—C$_6$H$_4$ | Me | 1,2,4-Oxadiazol-3-yl | 1 | mp 147.5–148.5° C. |
| 845 | 3-i-PrO—C$_6$H$_4$ | Me | 1,2,4-Oxadiazol-3-yl | 1 | |
| 846 | 3-i-Pr—C$_6$H$_4$ | Me | 1,2,4-Oxadiazol-3-yl | 1 | |
| 847 | 4-i-Pr—C$_6$H$_4$ | Me | 1,2,4-Oxadiazol-3-yl | 1 | |
| 848 | 3-t-Bu—C$_6$H$_4$ | Me | 1,2,4-Oxadiazol-3-yl | 1 | |
| 849 | 2-MeS—C$_6$H$_4$ | Me | 1,2,4-Oxadiazol-3-yl | 1 | |
| 850 | 4-MeS—C$_6$H$_4$ | Me | 1,2,4-Oxadiazol-3-yl | 1 | |
| 851 | 2,3,6-F$_3$—C$_6$H$_2$ | Me | 1,2,4-Oxadiazol-3-yl | 1 | |

-continued

| No | R¹ | R² | R³ | n | Physical data |
|---|---|---|---|---|---|
| 852 | 2,4,5-Cl₃—C₆H₂ | Me | 1,2,4-Oxadiazol-3-yl | 1 | |
| 853 | 3-PhO—C₆H₄ | Me | 1,2,4-Oxadiazol-3-yl | 1 | |
| 854 | 3,4,5-(MeO)₃—C₆H₂ | Me | 1,2,4-Oxadiazol-3-yl | 1 | |
| 855 | 2,3,5-Me₃—C₆H₂ | Me | 1,2,4-Oxadiazol-3-yl | 1 | |
| 856 | 3,4,5-Me₃—C₆H₂ | Me | 1,2,4-Oxadiazol-3-yl | 1 | |
| 857 | C₆H₅ | Me | 1,2,4-Oxadiazol-3-yl | 1 | |
| 858 | 4-Cl-3-Et—C₆H₃ | Me | 1,2,4-Oxadiazol-3-yl | 1 | |
| 859 | 3-EtO—C₆H₄ | Me | 1,2,4-Oxadiazol-3-yl | 1 | |
| 860 | 4-EtO—C₆H₄ | Me | 1,2,4-Oxadiazol-3-yl | 1 | |
| 861 | C₆H₅ | Me | 1,2,4-Oxadiazol-3-yl | 0 | |
| 862 | 4-F—C₆H₄ | Me | 1,2,4-Oxadiazol-3-yl | 0 | |
| 863 | 3-Cl—C₆H₄ | Me | 1,2,4-Oxadiazol-3-yl | 0 | |
| 864 | 4-Cl—C₆H₄ | Me | 1,2,4-Oxadiazol-3-yl | 0 | |
| 865 | 3-Me—C₆H₄ | Me | 1,2,4-Oxadiazol-3-yl | 0 | |
| 866 | 4-Me—C₆H₄ | Me | 1,2,4-Oxadiazol-3-yl | 0 | |
| 867 | 4-Et—C₆H₄ | Me | 1,2,4-Oxadiazol-3-yl | 0 | |
| 868 | 4-NO₂—C₆H₄ | Me | 1,2,4-Oxadiazol-3-yl | 0 | |
| 869 | 3,4-Cl₂—C₆H₃ | Me | 1,2,4-Oxadiazol-3-yl | 0 | |
| 870 | 3,5-Cl₂—C₆H₃ | Me | 1,2,4-Oxadiazol-3-yl | 0 | |
| 871 | 3,4-Me₂—C₆H₃ | Me | 1,2,4-Oxadiazol-3-yl | 0 | |
| 872 | 3,5-Me₂—C₆H₃ | Me | 1,2,4-Oxadiazol-3-yl | 0 | |
| 873 | 3-PhO—C₆H₄ | Me | 1,2,4-Oxadiazol-3-yl | 0 | |
| 874 | 4-Cl-3-Et—C₆H₃ | Me | 1,2,4-Oxadiazol-3-yl | 0 | |
| 875 | 3-EtO—C₆H₄ | Me | 1,2,4-Oxadiazol-3-yl | 0 | |
| 876 | 3-CF₃—C₆H₄ | Me | 1,2,4-Oxadiazol-3-yl | 0 | |
| 877 | 4-CF₃—C₆H₄ | Me | 1,2,4-Oxadiazol-3-yl | 0 | |
| 878 | 3-i-PrO—C₆H₄ | Me | 1,2,4-Oxadiazol-3-yl | 0 | |
| 879 | 3-i-Pr—C₆H₄ | Me | 1,2,4-Oxadiazol-3-yl | 0 | |
| 880 | 4-Cl-3-Me—C₆H₃ | Me | 1,2,4-Oxadiazol-3-yl | 0 | |
| 881 | Pyridin-2-yl | Me | 1,2,4-Oxadiazol-3-yl | 1 | |
| 882 | Pyridin-3-yl | Me | 1,2,4-Oxadiazol-3-yl | 1 | |
| 883 | 5-Cl-pyridin-2-yl | Me | 1,2,4-Oxadiazol-3-yl | 1 | |
| 884 | 3-Cl-pyridin-2-yl | Me | 1,2,4-Oxadiazol-3-yl | 1 | |
| 885 | 6-Cl-pyridin-2-yl | Me | 1,2,4-Oxadiazol-3-yl | 1 | |
| 886 | 2-Cl-pyridin-3-yl | Me | 1,2,4-Oxadiazol-3-yl | 1 | mp 177–178.5° C. |
| 887 | 5-CF₃-pyridin-2-yl | Me | 1,2,4-Oxadiazol-3-yl | 1 | |
| 888 | 3-CF₃-pyridin-2-yl | Me | 1,2,4-Oxadiazol-3-yl | 1 | |
| 889 | 6-CF₃-3-Cl-pyridin-2-yl | Me | 1,2,4-Oxadiazol-3-yl | 1 | |

-continued

| No | R¹ | R² | R³ | n | Physical data |
|---|---|---|---|---|---|
| 890 | 5-CF₃-3-Cl-pyridin-2-yl | Me | 1,2,4-Oxadiazol-3-yl | 1 | |
| 891 | Benzothiazol-2-yl | Me | 1,2,4-Oxadiazol-3-yl | 1 | |
| 892 | Benzoxazol-2-yl | Me | 1,2,4-Oxadiazol-3-yl | 1 | |
| 893 | Quinolin-2-yl | Me | 1,2,4-Oxadiazol-3-yl | 1 | |
| 894 | 5-CF₃-1,3,4-thiadiazol-2-yl | Me | 1,2,4-Oxadiazol-3-yl | 1 | |
| 895 | Pyrimidin-2-yl | Me | 1,2,4-Oxadiazol-3-yl | 1 | |
| 896 | 5-Cl-6-Me-pyrimidin-4-yl | Me | 1,2,4-Oxadiazol-3-yl | 1 | |
| 897 | 5-Et-6-Me-pyrimidin-4-yl | Me | 1,2,4-Oxadiazol-3-yl | 1 | |
| 898 | 6-Cl-pyrazin-2-yl | Me | 1,2,4-Oxadiazol-3-yl | 1 | |
| 899 | 3,6-Me₂-pyrazin-2-yl | Me | 1,2,4-Oxadiazol-3-yl | 1 | |
| 900 | 5-Me-isoxazol-3-yl | Me | 1,2,4-Oxadiazol-3-yl | 1 | |
| 901 | C₆H₅ | Me | 5-Me-1,2,4-oxadiazol-3-yl | 1 | ¹H-NMR(CDCl₃) δ ppm: 2.64(3H, s), 4.07(3H, s), 4.98(2H, s), 6.82–6.94(2H, m), 7.18–7.63(7H, m) |
| 902 | 2-F—C₆H₄ | Me | 5-Me-1,2,4-oxadiazol-3-yl | 1 | |
| 903 | 3-F—C₆H₄ | Me | 5-Me-1,2,4-oxadiazol-3-yl | 1 | |
| 904 | 4-F—C₆H₄ | Me | 5-Me-1,2,4-oxadiazol-3-yl | 1 | |
| 905 | 2-Cl—C₆H₄ | Me | 5-Me-1,2,4-oxadiazol-3-yl | 1 | mp 88.5–89.5° C. |
| 906 | 3-Cl—C₆H₄ | Me | 5-Me-1,2,4-oxadiazol-3-yl | 1 | |
| 907 | 4-Cl—C₆H₄ | Me | 5-Me-1,2,4-oxadiazol-3-yl | 1 | mp 125–126° C. |
| 908 | 2-Br—C₆H₄ | Me | 5-Me-1,2,4-oxadiazol-3-yl | 1 | |
| 909 | 3-Br—C₆H₄ | Me | 5-Me-1,2,4-oxadiazol-3-yl | 1 | |
| 910 | 4-Br—C₆H₄ | Me | 5-Me-1,2,4-oxadiazol-3-yl | 1 | |
| 911 | 3-I—C₆H₄ | Me | 5-Me-1,2,4-oxadiazol-3-yl | 1 | |
| 912 | 2-Me—C₆H₄ | Me | 5-Me-1,2,4-oxadiazol-3-yl | 1 | mp 86–87.5° C. |
| 913 | 3-Me—C₆H₄ | Me | 5-Me-1,2,4-oxadiazol-3-yl | 1 | |
| 914 | 4-Me—C₆H₄ | Me | 5-Me-1,2,4-oxadiazol-3-yl | 1 | mp 92.5–93.5° C. |
| 915 | 2-Et—C₆H₄ | Me | 5-Me-1,2,4-oxadiazol-3-yl | 1 | |
| 916 | 3-Et—C₆H₄ | Me | 5-Me-1,2,4-oxadiazol-3-yl | 1 | |
| 917 | 4-Et—C₆H₄ | Me | 5-Me-1,2,4-oxadiazol-3-yl | 1 | |
| 918 | 2-MeO—C₆H₄ | Me | 5-Me-1,2,4-oxadiazol-3-yl | 1 | |
| 919 | 3-MeO—C₆H₄ | Me | 5-Me-1,2,4-oxadiazol-3-yl | 1 | |
| 920 | 4-MeO—C₆H₄ | Me | 5-Me-1,2,4-oxadiazol-3-yl | 1 | |
| 921 | 2-CF₃—C₆H₄ | Me | 5-Me-1,2,4-oxadiazol-3-yl | 1 | |
| 922 | 3-CF₃—C₆H₄ | Me | 5-Me-1,2,4-oxadiazol-3-yl | 1 | |
| 923 | 4-CF₃—C₆H₄ | Me | 5-Me-1,2,4-oxadiazol-3-yl | 1 | |
| 924 | 2,4-F₂—C₆H₃ | Me | 5-Me-1,2,4-oxadiazol-3-yl | 1 | |
| 925 | 2,5-F₂—C₆H₃ | Me | 5-Me-1,2,4-oxadiazol-3-yl | 1 | |

-continued

| No | R¹ | R² | R³ | n | Physical data |
|---|---|---|---|---|---|
| 926 | 2,6-F₂—C₆H₃ | Me | 5-Me-1,2,4-oxadiazol-3-yl | 1 | |
| 927 | 3,4-F₂—C₆H₃ | Me | 5-Me-1,2,4-oxadiazol-3-yl | 1 | |
| 928 | 3,5-F₂—C₆H₃ | Me | 5-Me-1,2,4-oxadiazol-3-yl | 1 | |
| 929 | 2,3-Cl₂—C₆H₃ | Me | 5-Me-1,2,4-oxadiazol-3-yl | 1 | |
| 930 | 2,4-Cl₂—C₆H₃ | Me | 5-Me-1,2,4-oxadiazol-3-yl | 1 | |
| 931 | 2,5-Cl₂—C₆H₃ | Me | 5-Me-1,2,4-oxadiazol-3-yl | 1 | |
| 932 | 3,4-Cl₂—C₆H₃ | Me | 5-Me-1,2,4-oxadiazol-3-yl | 1 | |
| 933 | 3,5-Cl₂—C₆H₃ | Me | 5-Me-1,2,4-oxadiazol-3-yl | 1 | |
| 934 | 2,3-Me₂—C₆H₃ | Me | 5-Me-1,2,4-oxadiazol-3-yl | 1 | |
| 935 | 2,4-Me₂—C₆H₃ | Me | 5-Me-1,2,4-oxadiazol-3-yl | 1 | |
| 936 | 2,5-Me₂—C₆H₃ | Me | 5-Me-1,2,4-oxadiazol-3-yl | 1 | Isomer A: mp 98–100° C. Isomer B: mp 130–131.5° C. |
| 937 | 3,4-Me₂—C₆H₃ | Me | 5-Me-1,2,4-oxadiazol-3-yl | 1 | |
| 938 | 3,5-Me₂—C₆H₃ | Me | 5-Me-1,2,4-oxadiazol-3-yl | 1 | |
| 939 | 2-Cl-4-Me—C₆H₃ | Me | 5-Me-1,2,4-oxadiazol-3-yl | 1 | |
| 940 | 2-Cl-5-Me—C₆H₃ | Me | 5-Me-1,2,4-oxadiazol-3-yl | 1 | |
| 941 | 4-Cl-2-Me—C₆H₃ | Me | 5-Me-1,2,4-oxadiazol-3-yl | 1 | mp 115–116° C. |
| 942 | 4-Cl-3-Me—C₆H₃ | Me | 5-Me-1,2,4-oxadiazol-3-yl | 1 | |
| 943 | 3-Ph—C₆H₄ | Me | 5-Me-1,2,4-oxadiazol-3-yl | 1 | |
| 944 | 4-Ph—C₆H₄ | Me | 5-Me-1,2,4-oxadiazol-3-yl | 1 | mp 124.5–125.5° C. |
| 945 | 3-i-PrO—C₆H₄ | Me | 5-Me-1,2,4-oxadiazol-3-yl | 1 | |
| 946 | 3-i-Pr—C₆H₄ | Me | 5-Me-1,2,4-oxadiazol-3-yl | 1 | |
| 947 | 4-i-Pr—C₆H₄ | Me | 5-Me-1,2,4-oxadiazol-3-yl | 1 | |
| 948 | 3-t-Bu—C₆H₄ | Me | 5-Me-1,2,4-oxadiazol-3-yl | 1 | |
| 949 | 2-MeS—C₆H₄ | Me | 5-Me-1,2,4-oxadiazol-3-yl | 1 | |
| 950 | 4-MeS—C₆H₄ | Me | 5-Me-1,2,4-oxadiazol-3-yl | 1 | |
| 951 | 2,3,6-F₃—C₆H₂ | Me | 5-Me-1,2,4-oxadiazol-3-yl | 1 | |
| 952 | 2,4,5-Cl₃—C₆H₂ | Me | 5-Me-1,2,4-oxadiazol-3-yl | 1 | |
| 953 | 3-PhO—C₆H₄ | Me | 5-Me-1,2,4-oxadiazol-3-yl | 1 | |
| 954 | 3,4,5-(MeO)₃—C₆H₂ | Me | 5-Me-1,2,4-oxadiazol-3-yl | 1 | |
| 955 | 2,3,5-Me₃—C₆H₂ | Me | 5-Me-1,2,4-oxadiazol-3-yl | 1 | |
| 956 | 3,4,5-Me₃—C₆H₂ | Me | 5-Me-1,2,4-oxadiazol-3-yl | 1 | |
| 957 | C₆H₅ | Me | 5-Me-1,2,4-oxadiazol-3-yl | 1 | |
| 958 | 4-Cl-3-Et—C₆H₃ | Me | 5-Me-1,2,4-oxadiazol-3-yl | 1 | |
| 959 | 3-EtO—C₆H₄ | Me | 5-Me-1,2,4-oxadiazol-3-yl | 1 | |
| 960 | 4-EtO—C₆H₄ | Me | 5-Me-1,2,4-oxadiazol-3-yl | 1 | |
| 961 | C₆H₅ | Me | 5-Me-1,2,4-oxadiazol-3-yl | 0 | |
| 962 | 4-F—C₆H₄ | Me | 5-Me-1,2,4-oxadiazol-3-yl | 0 | |

-continued

| No | R¹ | R² | R³ | n | Physical data |
|---|---|---|---|---|---|
| 963 | 3-Cl—C₆H₄ | Me | 5-Me-1,2,4-oxadiazol-3-yl | 0 | |
| 964 | 4-Cl—C₆H₄ | Me | 5-Me-1,2,4-oxadiazol-3-yl | 0 | |
| 965 | 3-Me—C₆H₄ | Me | 5-Me-1,2,4-oxadiazol-3-yl | 0 | |
| 966 | 4-Me—C₆H₄ | Me | 5-Me-1,2,4-oxadiazol-3-yl | 0 | |
| 967 | 4-Et—C₆H₄ | Me | 5-Me-1,2,4-oxadiazol-3-yl | 0 | |
| 968 | 4-NO₂—C₆H₄ | Me | 5-Me-1,2,4-oxadiazol-3-yl | 0 | |
| 969 | 3,4-Cl₂—C₆H₃ | Me | 5-Me-1,2,4-oxadiazol-3-yl | 0 | |
| 970 | 3,5-Cl₂—C₆H₃ | Me | 5-Me-1,2,4-oxadiazol-3-yl | 0 | |
| 971 | 3,4-Me₂—C₆H₃ | Me | 5-Me-1,2,4-oxadiazol-3-yl | 0 | |
| 972 | 3,5-Me₂—C₆H₃ | Me | 5-Me-1,2,4-oxadiazol-3-yl | 0 | |
| 973 | 3-PhO—C₆H₄ | Me | 5-Me-1,2,4-oxadiazol-3-yl | 0 | |
| 974 | 4-Cl-3-Et—C₆H₃ | Me | 5-Me-1,2,4-oxadiazol-3-yl | 0 | |
| 975 | 3-EtO—C₆H₄ | Me | 5-Me-1,2,4-oxadiazol-3-yl | 0 | |
| 976 | 3-CF₃-C₆H₄ | Me | 5-Me-1,2,4-oxadiazol-3-yl | 0 | |
| 977 | 4-CF₃-C₆H₄ | Me | 5-Me-1,2,4-oxadiazol-3-yl | 0 | |
| 978 | 3-i-PrO—C₆H₄ | Me | 5-Me-1,2,4-oxadiazol-3-yl | 0 | |
| 979 | 3-i-Pr—C₆H₄ | Me | 5-Me-1,2,4-oxadiazol-3-yl | 0 | |
| 980 | 4-Cl-3-Me—C₆H₃ | Me | 5-Me-1,2,4-oxadiazol-3-yl | 0 | |
| 981 | Pyridin-2-yl | Me | 5-Me-1,2,4-oxadiazol-3-yl | 1 | |
| 982 | Pyridin-3-yl | Me | 5-Me-1,2,4-oxadiazol-3-yl | 1 | |
| 983 | 5-Cl-pyridin-2-yl | Me | 5-Me-1,2,4-oxadiazol-3-yl | 1 | |
| 984 | 3-Cl-pyridin-2-yl | Me | 5-Me-1,2,4-oxadiazol-3-yl | 1 | |
| 985 | 6-Cl-pyridin-2-yl | Me | 5-Me-1,2,4-oxadiazol-3-yl | 1 | |
| 986 | 2-Cl-pyridin-3-yl | Me | 5-Me-1,2,4-oxadiazol-3-yl | 1 | mp 82.5–84.5° C. |
| 987 | 5-CF₃-pyridin-2-yl | Me | 5-Me-1,2,4-oxadiazol-3-yl | 1 | |
| 988 | 3-CF₃-pyridin-2-yl | Me | 5-Me-1,2,4-oxadiazol-3-yl | 1 | |
| 989 | 6-CF₃-3-Cl-pyridin-2-yl | Me | 5-Me-1,2,4-oxadiazol-3-yl | 1 | |
| 990 | 5-CF₃-3-Cl-pyridin-2-yl | Me | 5-Me-1,2,4-oxadiazol-3-yl | 1 | |
| 991 | Benzothiazol-2-yl | Me | 5-Me-1,2,4-oxadiazol-3-yl | 1 | |
| 992 | Benzoxazol-2-yl | Me | 5-Me-1,2,4-oxadiazol-3-yl | 1 | |
| 993 | Quinolin-2-yl | Me | 5-Me-1,2,4-oxadiazol-3-yl | 1 | |
| 994 | 5-CF₃-1,3,4-thiadiazol-2-yl | Me | 5-Me-1,2,4-oxadiazol-3-yl | 1 | |
| 995 | Pyrimidin-2-yl | Me | 5-Me-1,2,4-oxadiazol-3-yl | 1 | |
| 996 | 5-Cl-6-Me-pyrimidin-4-yl | Me | 5-Me-1,2,4-oxadiazol-3-yl | 1 | |
| 997 | 5-Et-6-Me-pyrimidin-4-yl | Me | 5-Me-1,2,4-oxadiazol-3-yl | 1 | |
| 998 | 6-Cl-pyrazin-2-yl | Me | 5-Me-1,2,4-oxadiazol-3-yl | 1 | |
| 999 | 3,6-Me₂-pyrazin-2-yl | Me | 5-Me-1,2,4-oxadiazol-3-yl | 1 | |
| 1000 | 5-Me-isoxazol-3-yl | Me | 5-Me-1,2,4-oxadiazol-3-yl | 1 | |

-continued

| No | R¹ | R² | R³ | n | Physical data |
|---|---|---|---|---|---|
| 1001 | C₆H₅ | Me | 1-Me-1H-tetrazol-5-yl | 1 | mp 83.0–84.5° C. |
| 1002 | 2-F—C₆H₄ | Me | 1-Me-1H-tetrazol-5-yl | 1 | |
| 1003 | 3-F—C₆H₄ | Me | 1-Me-1H-tetrazol-5-yl | 1 | |
| 1004 | 4-F—C₆H₄ | Me | 1-Me-1H-tetrazol-5-yl | 1 | |
| 1005 | 2-Cl—C₆H₄ | Me | 1-Me-1H-tetrazol-5-yl | 1 | mp 118–119° C. |
| 1006 | 3-Cl—C₆H₄ | Me | 1-Me-1H-tetrazol-5-yl | 1 | |
| 1007 | 4-Cl—C₆H₄ | Me | 1-Me-1H-tetrazol-5-yl | 1 | mp 95–96° C. |
| 1008 | 2-Br—C₆H₄ | Me | 1-Me-1H-tetrazol-5-yl | 1 | |
| 1009 | 3-Br—C₆H₄ | Me | 1-Me-1H-tetrazol-5-yl | 1 | |
| 1010 | 4-Br—C₆H₄ | Me | 1-Me-1H-tetrazol-5-yl | 1 | |
| 1011 | 3-I—C₆H₄ | Me | 1-Me-1H-tetrazol-5-yl | 1 | |
| 1012 | 2-Me—C₆H₄ | Me | 1-Me-1H-tetrazol-5-yl | 1 | mp 111–112° C. |
| 1013 | 3-Me—C₆H₄ | Me | 1-Me-1H-tetrazol-5-yl | 1 | |
| 1014 | 4-Me—C₆H₄ | Me | 1-Me-1H-tetrazol-5-yl | 1 | mp 138.5–139.5° C. |
| 1015 | 2-Et—C₆H₄ | Me | 1-Me-1H-tetrazol-5-yl | 1 | |
| 1016 | 3-Et—C₆H₄ | Me | 1-Me-1H-tetrazol-5-yl | 1 | |
| 1017 | 4-Et—C₆H₄ | Me | 1-Me-1H-tetrazol-5-yl | 1 | |
| 1018 | 2-MeO—C₆H₄ | Me | 1-Me-1H-tetrazol-5-yl | 1 | |
| 1019 | 3-MeO—C₆H₄ | Me | 1-Me-1H-tetrazol-5-yl | 1 | |
| 1020 | 4-MeO—C₆H₄ | Me | 1-Me-1H-tetrazol-5-yl | 1 | |
| 1021 | 2-CF₃—C₆H₄ | Me | 1-Me-1H-tetrazol-5-yl | 1 | |
| 1022 | 3-CF₃—C₆H₄ | Me | 1-Me-1H-tetrazol-5-yl | 1 | $^1$H-NMR(CDCl₃) δ ppm: 4.03(3H, s), 4.21(3H, s), 4.99(2H, s), 6.82–7.53(8H, m) |
| 1023 | 4-CF₃—C₆H₄ | Me | 1-Me-1H-tetrazol-5-yl | 1 | |
| 1024 | 2,4-F₂—C₆H₃ | Me | 1-Me-1H-tetrazol-5-yl | 1 | |
| 1025 | 2,5-F₂—C₆H₃ | Me | 1-Me-1H-tetrazol-5-yl | 1 | |
| 1026 | 2,6-F₂—C₆H₃ | Me | 1-Me-1H-tetrazol-5-yl | 1 | |
| 1027 | 3,4-F₂—C₆H₃ | Me | 1-Me-1H-tetrazol-5-yl | 1 | |
| 1028 | 3,5-F₂—C₆H₃ | Me | 1-Me-1H-tetrazol-5-yl | 1 | |
| 1029 | 2,3-Cl₂—C₆H₃ | Me | 1-Me-1H-tetrazol-5-yl | 1 | |
| 1030 | 2,4-Cl₂—C₆H₃ | Me | 1-Me-1H-tetrazol-5-yl | 1 | |
| 1031 | 2,5-Cl₂—C₆H₃ | Me | 1-Me-1H-tetrazol-5-yl | 1 | |
| 1032 | 3,4-Cl₂—C₆H₃ | Me | 1-Me-1H-tetrazol-5-yl | 1 | mp 127–127.5° C. |
| 1033 | 3,5-Cl₂—C₆H₃ | Me | 1-Me-1H-tetrazol-5-yl | 1 | |
| 1034 | 2,3-Me₂—C₆H₃ | Me | 1-Me-1H-tetrazol-5-yl | 1 | |
| 1035 | 2,4-Me₂—C₆H₃ | Me | 1-Me-1H-tetrazol-5-yl | 1 | |
| 1036 | 2,5-Me₂—C₆H₃ | Me | 1-Me-1H-tetrazol-5-yl | 1 | mp 115.5–116.5° C. |

-continued

| No | R¹ | R² | R³ | n | Physical data |
|---|---|---|---|---|---|
| 1037 | 3,4-Me₂—C₆H₃ | Me | 1-Me-1H-tetrazol-5-yl | 1 | |
| 1038 | 3,5-Me₂—C₆H₃ | Me | 1-Me-1H-tetrazol-5-yl | 1 | |
| 1039 | 2-Cl-4-Me—C₆H₃ | Me | 1-Me-1H-tetrazol-5-yl | 1 | |
| 1040 | 2-Cl-5-Me—C₆H₃ | Me | 1-Me-1H-tetrazol-5-yl | 1 | |
| 1041 | 4-Cl-2-Me—C₆H₃ | Me | 1-Me-1H-tetrazol-5-yl | 1 | mp 126.5–127.5° C. |
| 1042 | 4-Cl-3-Me—C₆H₃ | Me | 1-Me-1H-tetrazol-5-yl | 1 | |
| 1043 | 3-Ph—C₆H₄ | Me | 1-Me-1H-tetrazol-5-yl | 1 | |
| 1044 | 4-Ph—C₆H₄ | Me | 1-Me-1H-tetrazol-5-yl | 1 | mp 130.5–131.5° C. |
| 1045 | 3-i-PrO—C₆H₄ | Me | 1-Me-1H-tetrazol-5-yl | 1 | |
| 1046 | 3-i-Pr—C₆H₄ | Me | 1-Me-1H-tetrazol-5-yl | 1 | |
| 1047 | 4-i-Pr—C₆H₄ | Me | 1-Me-1H-tetrazol-5-yl | 1 | |
| 1048 | 3-t-Bu—C₆H₄ | Me | 1-Me-1H-tetrazol-5-yl | 1 | |
| 1049 | 2-MeS—C₆H₄ | Me | 1-Me-1H-tetrazol-5-yl | 1 | |
| 1050 | 4-MeS—C₆H₄ | Me | 1-Me-1H-tetrazol-5-yl | 1 | |
| 1051 | 2,3,6-F₃—C₆H₂ | Me | 1-Me-1H-tetrazol-5-yl | 1 | |
| 1052 | 2,4,5-Cl₃—C₆H₂ | Me | 1-Me-1H-tetrazol-5-yl | 1 | |
| 1053 | 3-PhO—C₆H₄ | Me | 1-Me-1H-tetrazol-5-yl | 1 | |
| 1054 | 3,4,5-(MeO)₃—C₆H₂ | Me | 1-Me-1H-tetrazol-5-yl | 1 | |
| 1055 | 2,3,5-Me₃—C₆H₂ | Me | 1-Me-1H-tetrazol-5-yl | 1 | |
| 1056 | 3,4,5-Me₃—C₆H₂ | Me | 1-Me-1H-tetrazol-5-yl | 1 | |
| 1057 | C₆H₅ | Me | 1-Me-1H-tetrazol-5-yl | 1 | |
| 1058 | 4-Cl-3-Et—C₆H₃ | Me | 1-Me-1H-tetrazol-5-yl | 1 | |
| 1059 | 3-EtO—C₆H₄ | Me | 1-Me-1H-tetrazol-5-yl | 1 | |
| 1060 | 4-EtO—C₆H₄ | Me | 1-Me-1H-tetrazol-5-yl | 1 | |
| 1061 | C₆H₅ | Me | 1-Me-1H-tetrazol-5-yl | 0 | |
| 1062 | 4-F—C₆H₄ | Me | 1-Me-1H-tetrazol-5-yl | 0 | |
| 1063 | 3-Cl—C₆H₄ | Me | 1-Me-1H-tetrazol-5-yl | 0 | |
| 1064 | 4-Cl—C₆H₄ | Me | 1-Me-1H-tetrazol-5-yl | 0 | |
| 1065 | 3-Me—C₆H₄ | Me | 1-Me-1H-tetrazol-5-yl | 0 | |
| 1066 | 4-Me—C₆H₄ | Me | 1-Me-1H-tetrazol-5-yl | 0 | |
| 1067 | 4-Et—C₆H₄ | Me | 1-Me-1H-tetrazol-5-yl | 0 | |
| 1068 | 4-NO₂—C₆H₄ | Me | 1-Me-1H-tetrazol-5-yl | 0 | |
| 1069 | 3,4-Cl₂—C₆H₃ | Me | 1-Me-1H-tetrazol-5-yl | 0 | |
| 1070 | 3,5-Cl₂—C₆H₃ | Me | 1-Me-1H-tetrazol-5-yl | 0 | |
| 1071 | 3,4-Me₂—C₆H₃ | Me | 1-Me-1H-tetrazol-5-yl | 0 | |
| 1072 | 3,5-Me₂—C₆H₃ | Me | 1-Me-1H-tetrazol-5-yl | 0 | |
| 1073 | 3-PhO—C₆H₄ | Me | 1-Me-1H-tetrazol-5-yl | 0 | |
| 1074 | 4-Cl-3-Et—C₆H₃ | Me | 1-Me-1H-tetrazol-5-yl | 0 | |

-continued

| No | R¹ | R² | R³ | n | Physical data |
|---|---|---|---|---|---|
| 1075 | 3-EtO—C₆H₄ | Me | 1-Me-1H-tetrazol-5-yl | 0 | |
| 1076 | 3-CF₃—C₆H₄ | Me | 1-Me-1H-tetrazol-5-yl | 0 | |
| 1077 | 4-CF₃—C₆H₄ | Me | 1-Me-1H-tetrazol-5-yl | 0 | |
| 1078 | 3-i-PrO—C₆H₄ | Me | 1-Me-1H-tetrazol-5-yl | 0 | |
| 1079 | 3-i-Pr—C₆H₄ | Me | 1-Me-1H-tetrazol-5-yl | 0 | |
| 1080 | 4-Cl-3-Me—C₆H₃ | Me | 1-Me-1H-tetrazol-5-yl | 0 | |
| 1081 | Pyridin-2-yl | Me | 1-Me-1H-tetrazol-5-yl | 1 | |
| 1082 | Pyridin-3-yl | Me | 1-Me-1H-tetrazol-5-yl | 1 | |
| 1083 | 5-Cl-pyridin-2-yl | Me | 1-Me-1H-tetrazol-5-yl | 1 | |
| 1084 | 3-Cl-pyridin-2-yl | Me | 1-Me-1H-tetrazol-5-yl | 1 | |
| 1085 | 6-Cl-pyridin-2-yl | Me | 1-Me-1H-tetrazol-5-yl | 1 | |
| 1086 | 2-Cl-pyridin-3-yl | Me | 1-Me-1H-tetrazol-5-yl | 1 | |
| 1087 | 5-CF₃-pyridin-2-yl | Me | 1-Me-1H-tetrazol-5-yl | 1 | |
| 1088 | 3-CF₃-pyridin-2-yl | Me | 1-Me-1H-tetrazol-5-yl | 1 | |
| 1089 | 6-CF₃-3-Cl-pyridin-2-yl | Me | 1-Me-1H-tetrazol-5-yl | 1 | |
| 1090 | 5-CF₃-3-Cl-pyridin-2-yl | Me | 1-Me-1H-tetrazol-5-yl | 1 | |
| 1091 | Benzothiazol-2-yl | Me | 1-Me-1H-tetrazol-5-yl | 1 | |
| 1092 | Benzoxazol-2-yl | Me | 1-Me-1H-tetrazol-5-yl | 1 | |
| 1093 | Quinolin-2-yl | Me | 1-Me-1H-tetrazol-5-yl | 1 | |
| 1094 | 5-CF₃-1,3,4-thiadiazol-2-yl | Me | 1-Me-1H-tetrazol-5-yl | 1 | |
| 1095 | Pyrimidin-2-yl | Me | 1-Me-1H-tetrazol-5-yl | 1 | |
| 1096 | 5-Cl-6-Me-pyrimidin-4-yl | Me | 1-Me-1H-tetrazol-5-yl | 1 | |
| 1097 | 5-Et-6-Me-pyrimidin-4-yl | Me | 1-Me-1H-tetrazol-5-yl | 1 | |
| 1098 | 6-Cl-pyrazin-2-yl | Me | 1-Me-1H-tetrazol-5-yl | 1 | |
| 1099 | 3,6-Me₂-pyrazin-2-yl | Me | 1-Me-1H-tetrazol-5-yl | 1 | |
| 1100 | 5-Me-isoxazol-3-yl | Me | 1-Me-1H-tetrazol-5-yl | 1 | |
| 1101 | C₆H₅ | Me | 1-Me-2-imidazolin-2-yl | 1 | ¹H-NMR(CDCl₃) δ ppm: 2.75(3H, s), 3.40(2H, t, J = 9.8), 3.92(2H, t, J = 9.8), 3.97(3H, s), 5.37(2H, s), 6.93–6.98(3H, m), 7.25–7.35(3H, m), 7.40(1H, t, J = 7.5), 7.52(1H, d, J = 7.5), 7.68(1H, d, J = 7.5) |
| 1102 | 2-F—C₆H₄ | Me | 1-Me-2-imidazolin-2-yl | 1 | |
| 1103 | 3-F—C₆H₄ | Me | 1-Me-2-imidazolin-2-yl | 1 | |
| 1104 | 4-F—C₆H₄ | Me | 1-Me-2-imidazolin-2-yl | 1 | |
| 1105 | 2-CF₃—C₆H₄ | Me | 1-Me-2-imidazolin-2-yl | 1 | |

-continued

| No | R¹ | R² | R³ | n | Physical data |
|---|---|---|---|---|---|
| 1106 | 3-CF₃—C₆H₄ | Me | 1-Me-2-imidazolin-2-yl | 1 | |
| 1107 | 4-CF₃—C₆H₄ | Me | 1-Me-2-imidazolin-2-yl | 1 | |
| 1108 | 2-Br—C₆H₄ | Me | 1-Me-2-imidazolin-2-yl | 1 | |
| 1109 | 3-Br—C₆H₄ | Me | 1-Me-2-imidazolin-2-yl | 1 | |
| 1110 | 4-Br—C₆H₄ | Me | 1-Me-2-imidazolin-2-yl | 1 | |
| 1111 | 3-I—C₆H₄ | Me | 1-Me-2-imidazolin-2-yl | 1 | |
| 1112 | 2-Me—C₆H₄ | Me | 1-Me-2-imidazolin-2-yl | 1 | $^1$H-NMR(CDCl₃) δ ppm: 2.33(3H, s), 2.74(3H, s), 3.40(2H, t, J = 9.8), 3.93(2H, t, J = 9.8), 4.02(3H, s), 5.38(2H, s), 6.82–6.88(2H, m), 7.31–7.35(2H, m), 7.33(1H, t, J = 7.7), 7.41(1H, t, J = 7.7), 7.51(1H, d, J = 7.7) 7.76(1H, d, J = 7.7) |
| 1113 | 3-Me—C₆H₄ | Me | 1-Me-2-imidazolin-2-yl | 1 | $^1$H-NMR(CDCl₃) δ ppm: 2.32(3H, s), 2.75(3H, s), 3.40(2H, t, J = 9.8), 3.92(2H, t, J = 9.8), 3.90(3H, s), 5.35(2H, s), 6.75–6.80(3H, m), 7.16(1H, t, J = 7.6), 7.30–7.43(2H, m), 7.51(1H, dd, J = 7.6, 1.5), 7.68(1H, d, J = 7.6) |
| 1114 | 4-Me—C₆H₄ | Me | 1-Me-2-imidazolin-2-yl | 1 | $^1$H-NMR(CDCl₃) δ ppm: 2.28(3H, s), 2.75(3H, s), 3.40(2H, t, J = 9.8), 3.92(2H, t, J = 9.8), 3.98(3H, s), 5.34(2H, s), 6.85(2H, d, J = 8.5), 7.07(2H, d, J = 8.5), 7.29–7.42(2H, m), 7.51(1H, dd, J = 7.6, 1.5), 7.67(1H, d, J = 7.6) |
| 1115 | 2-Et—C₆H₄ | Me | 1-Me-2-imidazolin-2-yl | 1 | |
| 1116 | 3-Et—C₆H₄ | Me | 1-Me-2-imidazolin-2-yl | 1 | |
| 1117 | 4-Et—C₆H₄ | Me | 1-Me-2-imidazolin-2-yl | 1 | |
| 1118 | 2-MeO—C₆H₄ | Me | 1-Me-2-imidazolin-2-yl | 1 | |
| 1119 | 3-MeO—C₆H₄ | Me | 1-Me-2-imidazolin-2-yl | 1 | |
| 1120 | 4-MeO—C₆H₄ | Me | 1-Me-2-imidazolin-2-yl | 1 | |

-continued

| No | R¹ | R² | R³ | n | Physical data |
|---|---|---|---|---|---|
| 1121 | 2-Cl—C₆H₄ | Me | 1-Me-2-imidazolin-2-yl | 1 | ¹H-NMR(CDCl₃) δ ppm: 2.75(3H, s), 3.41(2H, t, J = 9.8), 3.93(2H, t, J = 9.8), 4.02(3H, s), 5.47(2H, s), 6.86–6.93(2H, m), 7.18(1H, ddd, J = 8.5, 7.6, 1.5), 7.31–7.45(3H, m), 7.49(1H, dd, J = 7.6, 1.5), 7.81(1H, d, J = 7.6) |
| 1122 | 3-Cl—C₆H₄ | Me | 1-Me-2-imidazolin-2-yl | 1 | Isomer A: ¹H-NMR(CDCl₃) δ ppm: 2.75(3H, s), 3.41(2H, t, J = 9.8), 3.92(2H, t, J = 9.8), 3.97(3H, s), 5.35(2H, s), 6.84–6.99(3H, m), 7.19(1H, t, J = 8.0), 7.32–7.44(2H, m), 7.51(1H, dd, J = 7.3, 1.4), 7.64(1H, d, J = 7.0) Isomer B: ¹H-NMR(CDCl₃) δ ppm: 3.03(3H, s), 3.38(2H, t, J = 9.9), 3.77(2H, t, J = 9.9), 3.97(3H, s), 4.99(2H, s), 6.83–7.16(4H, m), 7.23(1H, d, J = 7.6), 7.34–7.39(2H, m), 7.49(1H, d, J = 6.4) |
| 1123 | 4-Cl—C₆H₄ | Me | 1-Me-2-imidazolin-2-yl | 1 | mp 53–56° C. |
| 1124 | 2,4-F₂—C₆H₃ | Me | 1-Me-2-imidazolin-2-yl | 1 | |
| 1125 | 2,5-F₂—C₆H₃ | Me | 1-Me-2-imidazolin-2-yl | 1 | |
| 1126 | 2,6-F₂—C₆H₃ | Me | 1-Me-2-imidazolin-2-yl | 1 | |
| 1127 | 3,4-F₂—C₆H₃ | Me | 1-Me-2-imidazolin-2-yl | 1 | |
| 1128 | 3,5-F₂—C₆H₃ | Me | 1-Me-2-imidazolin-2-yl | 1 | |
| 1129 | 2,3-Cl₂—C₆H₃ | Me | 1-Me-2-imidazolin-2-yl | 1 | |
| 1130 | 2,4-Cl₂—C₆H₃ | Me | 1-Me-2-imidazolin-2-yl | 1 | |
| 1131 | 2,5-Cl₂—C₆H₃ | Me | 1-Me-2-imidazolin-2-yl | 1 | |
| 1132 | 3,4-Cl₂—C₆H₃ | Me | 1-Me-2-imidazolin-2-yl | 1 | |
| 1133 | 3,5-Cl₂—C₆H₃ | Me | 1-Me-2-imidazolin-2-yl | 1 | |
| 1134 | 2,3-Me₂—C₆H₃ | Me | 1-Me-2-imidazolin-2-yl | 1 | |
| 1135 | 2,4-Me₂—C₆H₃ | Me | 1-Me-2-imidazolin-2-yl | 1 | |

-continued

| No | R¹ | R² | R³ | n | Physical data |
|---|---|---|---|---|---|
| 1136 | 2,5-Me₂—C₆H₃ | Me | 1-Me-2-imidazolin-2-yl | 1 | mp 88–90° C. |
| 1137 | 3,4-Me₂—C₆H₃ | Me | 1-Me-2-imidazolin-2-yl | 1 | |
| 1138 | 3,5-Me₂—C₆H₃ | Me | 1-Me-2-imidazolin-2-yl | 1 | |
| 1139 | 2-Cl-4-Me—C₆H₃ | Me | 1-Me-2-imidazolin-2-yl | 1 | |
| 1140 | 2-Cl-5-Me—C₆H₃ | Me | 1-Me-2-imidazolin-2-yl | 1 | |
| 1141 | 4-Cl-2-Me—C₆H₃ | Me | 1-Me-2-imidazolin-2-yl | 1 | |
| 1142 | 4-Cl-3-Me—C₆H₃ | Me | 1-Me-2-imidazolin-2-yl | 1 | |
| 1143 | 3-Ph—C₆H₃ | Me | 1-Me-2-imidazolin-2-yl | 1 | |
| 1144 | 4-Ph—C₆H₄ | Me | 1-Me-2-imidazolin-2-yl | 1 | |
| 1145 | 3-i-PrO—C₆H₄ | Me | 1-Me-2-imidazolin-2-yl | 1 | |
| 1146 | 3-i-Pr—C₆H₄ | Me | 1-Me-2-imidazolin-2-yl | 1 | |
| 1147 | 4-i-Pr—C₆H₄ | Me | 1-Me-2-imidazolin-2-yl | 1 | |
| 1148 | 3-t-Bu—C₆H₄ | Me | 1-Me-2-imidazolin-2-yl | 1 | |
| 1149 | 2-MeS—C₆H₄ | Me | 1-Me-2-imidazolin-2-yl | 1 | |
| 1150 | 4-MeS—C₆H₄ | Me | 1-Me-2-imidazolin-2-yl | 1 | |
| 1151 | 2,3,6-F₃—C₆H₂ | Me | 1-Me-2-imidazolin-2-yl | 1 | |
| 1152 | 2,4,5-Cl₃—C₆H₂ | Me | 1-Me-2-imidazolin-2-yl | 1 | |
| 1153 | 3-PhO—C₆H₄ | Me | 1-Me-2-imidazolin-2-yl | 1 | |
| 1154 | 3,4,5-(MeO)₃—C₆H₂ | Me | 1-Me-2-imidazolin-2-yl | 1 | |
| 1155 | 2,3,5-Me₃—C₆H₂ | Me | 1-Me-2-imidazolin-2-yl | 1 | |
| 1156 | 3,4,5-Me₃—C₆H₂ | Me | 1-Me-2-imidazolin-2-yl | 1 | |
| 1157 | C₆F₅ | Me | 1-Me-2-imidazolin-2-yl | 1 | |
| 1158 | 4-Cl-3-Et—C₆H₃ | Me | 1-Me-2-imidazolin-2-yl | 1 | |
| 1159 | 3-EtO—C₆H₄ | Me | 1-Me-2-imidazolin-2-yl | 1 | |
| 1160 | 4-EtO—C₆H₄ | Me | 1-Me-2-imidazolin-2-yl | 1 | |

-continued

| No | R¹ | R² | R³ | n | Physical data |
|---|---|---|---|---|---|
| 1161 | C₆H₅ | Me | 1-Me-2-imidazolin-2-yl | 0 | ¹H-NMR(CDCl₃) δ ppm: 2.80(2.91)(3H, s), 3.03(3.14)(2H, s), 3.53(3.61)(2H, t, J = 9.8), 4.05(3.95) (3H, s), 6.96–7.72(9H, m) |
| 1162 | 4-F—C₆H₄ | Me | 1-Me-2-imidazolin-2-yl | 0 | |
| 1163 | 3-Cl—C₆H₄ | Me | 1-Me-2-imidazolin-2-yl | 0 | |
| 1164 | 4-Cl—C₆H₄ | Me | 1-Me-2-imidazolin-2-yl | 0 | |
| 1165 | 3-Me—C₆H₄ | Me | 1-Me-2-imidazolin-2-yl | 0 | |
| 1166 | 4-Me—C₆H₄ | Me | 1-Me-2-imidazolin-2-yl | 0 | |
| 1167 | 4-Et—C₆H₄ | Me | 1-Me-2-imidazolin-2-yl | 0 | |
| 1168 | 4-NO₂-C₆H₄ | Me | 1-Me-2-imidazolin-2-yl | 0 | |
| 1169 | 3,4-Cl₂-C₆H₃ | Me | 1-Me-2-imidazolin-2-yl | 0 | |
| 1170 | 3,5-Cl₂-C₆H₃ | Me | 1-Me-2-imidazolin-2-yl | 0 | |
| 1171 | 3,4-Me₂-C₆H₃ | Me | 1-Me-2-imidazolin-2-yl | 0 | |
| 1172 | 3,5-Me₂-C₆H₃ | Me | 1-Me-2-imidazolin-2-yl | 0 | |
| 1173 | 3-PhO—C₆H₄ | Me | 1-Me-2-imidazolin-2-yl | 0 | |
| 1174 | 4-Cl-3-Et—C₆H₃ | Me | 1-Me-2-imidazolin-2-yl | 0 | |
| 1175 | 3-EtO—C₆H₄ | Me | 1-Me-2-imidazolin-2-yl | 0 | |
| 1176 | 3-CF₃—C₆H₄ | Me | 1-Me-2-imidazolin-2-yl | 0 | |
| 1177 | 4-CF₃—C₆H₄ | Me | 1-Me-2-imidazolin-2-yl | 0 | |
| 1178 | 3-i-PrO—C₆H₄ | Me | 1-Me-2-imidazolin-2-yl | 0 | |
| 1179 | 3-i-Pr—C₆H₄ | Me | 1-Me-2-imidazolin-2-yl | 0 | |
| 1180 | 4-Cl-3-Me—C₆H₃ | Me | 1-Me-2-imidazolin-2-yl | 0 | |
| 1181 | Pyridin-2-yl | Me | 1-Me-2-imidazolin-2-yl | 1 | |
| 1182 | Pyridin-3-yl | Me | 1-Me-2-imidazolin-2-yl | 1 | |
| 1183 | 5-Cl-pyridin-2-yl | Me | 1-Me-2-imidazolin-2-yl | 1 | |
| 1184 | 3-Cl-pyridin-2-yl | Me | 1-Me-2-imidazolin-2-yl | 1 | |

| No | R¹ | R² | R³ | n | Physical data |
|---|---|---|---|---|---|
| 1185 | 6-Cl-pyridin-2-yl | Me | 1-Me-2-imidazolin-2-yl | 1 | |
| 1186 | 2-Cl-pyridin-3-yl | Me | 1-Me-2-imidazolin-2-yl | 1 | |
| 1187 | 5-CF₃-pyridin-2-yl | Me | 1-Me-2-imidazolin-2-yl | 1 | |
| 1188 | 3-CF₃-pyridin-2-yl | Me | 1-Me-2-imidazolin-2-yl | 1 | |
| 1189 | 6-CF₃-3-Cl-pyridin-2-yl | Me | 1-Me-2-imidazolin-2-yl | 1 | |
| 1190 | 5-CF₃-3-Cl-pyridin-2-yl | Me | 1-Me-2-imidazolin-2-yl | 1 | |
| 1191 | Benzothiazol-2-yl | Me | 1-Me-2-imidazolin-2-yl | 1 | |
| 1192 | Benzoxazol-2-yl | Me | 1-Me-2-imidazolin-2-yl | 1 | |
| 1193 | Quinolin-2-yl | Me | 1-Me-2-imidazolin-2-yl | 1 | |
| 1194 | 5-CF₃-1,3,4-thiadiazol-2-yl | Me | 1-Me-2-imidazolin-2-yl | 1 | |
| 1195 | Pyrimidin-2-yl | Me | 1-Me-2-imidazolin-2-yl | 1 | |
| 1196 | 5-Cl-6-Me-pyrimidin-4-yl | Me | 1-Me-2-imidazolin-2-yl | 1 | |
| 1197 | 5-Et-6-Me-pyrimidin-4-yl | Me | 1-Me-2-imidazolin-2-yl | 1 | |
| 1198 | 6-Cl-pyrazin-2-yl | Me | 1-Me-2-imidazolin-2-yl | 1 | |
| 1199 | 3,6-Me₂-pyrazin-2-yl | Me | 1-Me-2-imidazolin-2-yl | 1 | |
| 1200 | 5-Me-isoxazol-3-yl | Me | 1-Me-2-imidazolin-2-yl | 1 | |
| 1201 | C₆H₅ | Me | 2-Isoxazolin-3-yl | 1 | |
| 1202 | 2-F—C₆H₄ | Me | 2-Isoxazolin-3-yl | 1 | |
| 1203 | 3-F—C₆H₄ | Me | 2-Isoxazolin-3-yl | 1 | |
| 1204 | 4-F—C₆H₄ | Me | 2-Isoxazolin-3-yl | 1 | |
| 1205 | 2-Cl—C₆H₄ | Me | 2-Isoxazolin-3-yl | 1 | |
| 1206 | 3-Cl—C₆H₄ | Me | 2-Isoxazolin-3-yl | 1 | |
| 1207 | 4-Cl—C₆H₄ | Me | 2-Isoxazolin-3-yl | 1 | |
| 1208 | 2-Br—C₆H₄ | Me | 2-Isoxazolin-3-yl | 1 | |
| 1209 | 3-Br—C₆H₄ | Me | 2-Isoxazolin-3-yl | 1 | |
| 1210 | 4-Br—C₆H₄ | Me | 2-Isoxazolin-3-yl | 1 | |
| 1211 | 3-I—C₆H₄ | Me | 2-Isoxazolin-3-yl | 1 | |
| 1212 | 2-Me—C₆H₄ | Me | 2-Isoxazolin-3-yl | 1 | |
| 1213 | 3-Me—C₆H₄ | Me | 2-Isoxazolin-3-yl | 1 | |
| 1214 | 4-Me—C₆H₄ | Me | 2-Isoxazolin-3-yl | 1 | |

-continued

| No | R¹ | R² | R³ | n | Physical data |
|---|---|---|---|---|---|
| 1215 | 2-Et—C₆H₄ | Me | 2-Isoxazolin-3-yl | 1 | |
| 1216 | 3-Et—C₆H₄ | Me | 2-Isoxazolin-3-yl | 1 | |
| 1217 | 4-Et—C₆H₄ | Me | 2-Isoxazolin-3-yl | 1 | |
| 1218 | 2-MeO—C₆H₄ | Me | 2-Isoxazolin-3-yl | 1 | |
| 1219 | 3-MeO—C₆H₄ | Me | 2-Isoxazolin-3-yl | 1 | |
| 1220 | 4-MeO—C₆H₄ | Me | 2-Isoxazolin-3-yl | 1 | |
| 1221 | 2-CF₃—C₆H₄ | Me | 2-Isoxazolin-3-yl | 1 | |
| 1222 | 3-CF₃—C₆H₄ | Me | 2-Isoxazolin-3-yl | 1 | |
| 1223 | 4-CF₃—C₆H₄ | Me | 2-Isoxazolin-3-yl | 1 | |
| 1224 | 2,4-F₂—C₆H₃ | Me | 2-Isoxazolin-3-yl | 1 | |
| 1225 | 2,5-F₂—C₆H₃ | Me | 2-Isoxazolin-3-yl | 1 | |
| 1226 | 2,6-F₂—C₆H₃ | Me | 2-Isoxazolin-3-yl | 1 | |
| 1227 | 3,4-F₂—C₆H₃ | Me | 2-Isoxazolin-3-yl | 1 | |
| 1228 | 3,5-F₂—C₆H₃ | Me | 2-Isoxazolin-3-yl | 1 | |
| 1229 | 2,3-Cl₂—C₆H₃ | Me | 2-Isoxazolin-3-yl | 1 | |
| 1230 | 2,4-Cl₂—C₆H₃ | Me | 2-Isoxazolin-3-yl | 1 | |
| 1231 | 2,5-Cl₂—C₆H₃ | Me | 2-Isoxazolin-3-yl | 1 | |
| 1232 | 3,4-Cl₂—C₆H₃ | Me | 2-Isoxazolin-3-yl | 1 | |
| 1233 | 3,5-Cl₂—C₆H₃ | Me | 2-Isoxazolin-3-yl | 1 | |
| 1234 | 2,3-Me₂—C₆H₃ | Me | 2-Isoxazolin-3-yl | 1 | |
| 1235 | 2,4-Me₂—C₆H₃ | Me | 2-Isoxazolin-3-yl | 1 | |
| 1236 | 2,5-Me₂—C₆H₃ | Me | 2-Isoxazolin-3-yl | 1 | $^1$H-NMR(CDCl₃) δ ppm: 2.17–2.29(6H, m), 3.24–3.38(2H, m), 3.95(4.00)(3H, s), 4.28(4.44)(2H, t, J = 10.4), 4.93–5.06(2H, m), 6.59–7.58(7H, m) |
| 1237 | 3,4-Me₂—C₆H₃ | Me | 2-Isoxazolin-3-yl | 1 | |
| 1238 | 3,5-Me₂—C₆H₃ | Me | 2-Isoxazolin-3-yl | 1 | |
| 1239 | 2-Cl-4-Me—C₆H₃ | Me | 2-Isoxazolin-3-yl | 1 | |
| 1240 | 2-Cl-5-Me—C₆H₃ | Me | 2-Isoxazolin-3-yl | 1 | |
| 1241 | 4-Cl-2-Me—C₆H₃ | Me | 2-Isoxazolin-3-yl | 1 | |
| 1242 | 4-Cl-3-Me—C₆H₃ | Me | 2-Isoxazolin-3-yl | 1 | |
| 1243 | 3-Ph—C₆H₄ | Me | 2-Isoxazolin-3-yl | 1 | |
| 1244 | 4-Ph—C₆H₄ | Me | 2-Isoxazolin-3-yl | 1 | |
| 1245 | 3-i-PrO—C₆H₄ | Me | 2-Isoxazolin-3-yl | 1 | |
| 1246 | 3-i-Pr—C₆H₄ | Me | 2-Isoxazolin-3-yl | 1 | |
| 1247 | 4-i-Pr—C₆H₄ | Me | 2-Isoxazolin-3-yl | 1 | |
| 1248 | 3-t-Bu—C₆H₄ | Me | 2-Isoxazolin-3-yl | 1 | |
| 1249 | 2-MeS—C₆H₄ | Me | 2-Isoxazolin-3-yl | 1 | |

-continued

| No | R¹ | R² | R³ | n | Physical data |
|---|---|---|---|---|---|
| 1250 | 4-MeS—C₆H₄ | Me | 2-Isoxazolin-3-yl | 1 | |
| 1251 | 2,3,6-F₃—C₆H₂ | Me | 2-Isoxazolin-3-yl | 1 | |
| 1252 | 2,4,5-Cl₃—C₆H₂ | Me | 2-Isoxazolin-3-yl | 1 | |
| 1253 | 3-PhO—C₆H₄ | Me | 2-Isoxazolin-3-yl | 1 | |
| 1254 | 3,4,5-(MeO)₃—C₆H₂ | Me | 2-Isoxazolin-3-yl | 1 | |
| 1255 | 2,3,5-Me₃—C₆H₂ | Me | 2-Isoxazolin-3-yl | 1 | |
| 1256 | 3,4,5-Me₃—C₆H₂ | Me | 2-Isoxazolin-3-yl | 1 | |
| 1257 | C₆F₅ | Me | 2-Isoxazolin-3-yl | 1 | |
| 1258 | 4-Cl-3-Et—C₆H₃ | Me | 2-Isoxazolin-3-yl | 1 | |
| 1259 | 3-EtO—C₆H₄ | Me | 2-Isoxazolin-3-yl | 1 | |
| 1260 | 4-EtO—C₆H₄ | Me | 2-Isoxazolin-3-yl | 1 | |
| 1261 | C₆H₅ | Me | 2-Isoxazolin-3-yl | 0 | |
| 1262 | 4-F—C₆H₄ | Me | 2-Isoxazolin-3-yl | 0 | |
| 1263 | 3-Cl—C₆H₄ | Me | 2-Isoxazolin-3-yl | 0 | |
| 1264 | 4-Cl—C₆H₄ | Me | 2-Isoxazolin-3-yl | 0 | |
| 1265 | 3-Me—C₆H₄ | Me | 2-Isoxazolin-3-yl | 0 | |
| 1266 | 4-Me—C₆H₄ | Me | 2-Isoxazolin-3-yl | 0 | |
| 1267 | 4-Et—C₆H₄ | Me | 2-Isoxazolin-3-yl | 0 | |
| 1268 | 4-NO₂—C₆H₄ | Me | 2-Isoxazolin-3-yl | 0 | |
| 1269 | 3,4-Cl₂—C₆H₃ | Me | 2-Isoxazolin-3-yl | 0 | |
| 1270 | 3,5-Cl₂—C₆H₃ | Me | 2-Isoxazolin-3-yl | 0 | |
| 1271 | 3,4-Me₂—C₆H₃ | Me | 2-Isoxazolin-3-yl | 0 | |
| 1272 | 3,5-Me₂—C₆H₃ | Me | 2-Isoxazolin-3-yl | 0 | |
| 1273 | 3-PhO—C₆H₄ | Me | 2-Isoxazolin-3-yl | 0 | |
| 1274 | 4-Cl-3-Et—C₆H₃ | Me | 2-Isoxazolin-3-yl | 0 | |
| 1275 | 3-EtO—C₆H₄ | Me | 2-Isoxazolin-3-yl | 0 | |
| 1276 | 3-CF₃—C₆H₄ | Me | 2-Isoxazolin-3-yl | 0 | |
| 1277 | 4-CF₃—C₆H₄ | Me | 2-Isoxazolin-3-yl | 0 | |
| 1278 | 3-i-PrO—C₆H₄ | Me | 2-Isoxazolin-3-yl | 0 | |
| 1279 | 3-i-Pr—C₆H₄ | Me | 2-Isoxazolin-3-yl | 0 | |
| 1280 | 4-Cl-3-Me—C₆H₃ | Me | 2-Isoxazolin-3-yl | 0 | |
| 1281 | Pyridin-2-yl | Me | 2-Isoxazolin-3-yl | 1 | |
| 1282 | Pyridin-3-yl | Me | 2-Isoxazolin-3-yl | 1 | |
| 1283 | 5-Cl-pyridin-2-yl | Me | 2-Isoxazolin-3-yl | 1 | |
| 1284 | 3-Cl-pyridin-2-yl | Me | 2-Isoxazolin-3-yl | 1 | |
| 1285 | 6-Cl-pyridin-2-yl | Me | 2-Isoxazolin-3-yl | 1 | |
| 1286 | 2-Cl-pyridin-3-yl | Me | 2-Isoxazolin-3-yl | 1 | |
| 1287 | 5-CF₃-pyridin-2-yl | Me | 2-Isoxazolin-3-yl | 1 | |

-continued

| No | R¹ | R² | R³ | n | Physical data |
|---|---|---|---|---|---|
| 1288 | 3-CF₃-pyridin-2-yl | Me | 2-Isoxazolin-3-yl | 1 | |
| 1289 | 6-CF₃-3-Cl-pyridin-2-yl | Me | 2-Isoxazolin-3-yl | 1 | |
| 1290 | 5-CF₃-3-Cl-pyridin-2-yl | Me | 2-Isoxazolin-3-yl | 1 | |
| 1291 | Benzothiazol-2-yl | Me | 2-Isoxazolin-3-yl | 1 | |
| 1292 | Benzoxazol-2-yl | Me | 2-Isoxazolin-3-yl | 1 | |
| 1293 | Quinolin-2-yl | Me | 2-Isoxazolin-3-yl | 1 | |
| 1294 | 5-CF₃-1,3,4-thiadiazol-2-yl | Me | 2-Isoxazolin-3-yl | 1 | |
| 1295 | Pyrimidin-2-yl | Me | 2-Isoxazolin-3-yl | 1 | |
| 1296 | 5-Cl-6-Me-pyrimidin-4-yl | Me | 2-Isoxazolin-3-yl | 1 | |
| 1297 | 5-Et-6-Me-pyrimidin-4-yl | Me | 2-Isoxazolin-3-yl | 1 | |
| 1298 | 6-Cl-pyrazin-2-yl | Me | 2-Isoxazolin-3-yl | 1 | |
| 1299 | 3,6-Me₂-pyrazin-2-yl | Me | 2-Isoxazolin-3-yl | 1 | |
| 1300 | 5-Me-isoxazol-3-yl | Me | 2-Isoxazolin-3-yl | 1 | |
| 1301 | $C_6H_5$ | Me | 2-Oxazolin-2-yl | 1 | mp 69–70° C. |
| 1302 | 2-F—$C_6H_4$ | Me | 2-Oxazolin-2-yl | 1 | |
| 1303 | 3-F—$C_6H_4$ | Me | 2-Oxazolin-2-yl | 1 | |
| 1304 | 4-F—$C_6H_4$ | Me | 2-Oxazolin-2-yl | 1 | |
| 1305 | 2-Cl—$C_6H_4$ | Me | 2-Oxazolin-2-yl | 1 | mp 89–90° C. |
| 1306 | 3-Cl—$C_6H_4$ | Me | 2-Oxazolin-2-yl | 1 | mp 82–83° C. |
| 1307 | 4-Cl—$C_6H_4$ | Me | 2-Oxazolin-2-yl | 1 | mp 76–80° C. |
| 1308 | 3-Br—$C_6H_4$ | Me | 2-Oxazolin-2-yl | 1 | |
| 1309 | 4-Br—$C_6H_4$ | Me | 2-Oxazolin-2-yl | 1 | |
| 1310 | 2-Me—$C_6H_4$ | Me | 2-Oxazolin-2-yl | 1 | ¹H-NMR(CDCl₃) δ ppm: 2.30(3H, s), 4.02(2H, t, J = 9.8), 4.05(3H, s), 4.32(2H, t, J = 9.8), 5.25(2H, s), 6.82(1H, d, J = 8.3), 6.86(1H, t, J = 7.6), 7.10–7.16(2H, m), 7.35(1H, t, J = 7.6), 7.41–7.48(2H, m), 7.68(1H, d, J = 7.6) |
| 1311 | 3-Me—$C_6H_4$ | Me | 2-Oxazolin-2-yl | 1 | ¹H-NMR(CDCl₃) δ ppm: 2.31(3H, s), 4.00(2H, t, J = 9.8), 4.03(3H, s), 4.32(2H, t, J = 9.8), 5.21(2H, s), 6.72–6.78(3H, m), 7.14(1H, t, J = 7.6), 7.31–7.48(3H, m), 7.62(1H, d, J = 7.6) |
| 1312 | 4-Me—$C_6H_4$ | Me | 2-Oxazolin-2-yl | 1 | ¹H-NMR(CDCl₃) δ ppm: 2.27(3H, s), 4.00(2H, t, J = 9.6), 4.03(3H, s), 4.31(2H, t, J = 9.6), 5.20(2H, s), 6.84(2H, d, J = 8.6), 7.06(2H, d, J = 8.6), 7.31–7.47(3H, m), 7.62(1H, d, J = 7.6) |

-continued

| No | R¹ | R² | R³ | n | Physical data |
|---|---|---|---|---|---|
| 1313 | 3-Et—C₆H₄ | Me | 2-Oxazolin-2-yl | 1 | |
| 1314 | 2-MeO—C₆H₄ | Me | 2-Oxazolin-2-yl | 1 | |
| 1315 | 3-MeO—C₆H₄ | Me | 2-Oxazolin-2-yl | 1 | |
| 1316 | 4-MeO—C₆H₄ | Me | 2-Oxazolin-2-yl | 1 | |
| 1317 | 4-Et—C₆H₄ | Me | 2-Oxazolin-2-yl | 1 | |
| 1318 | 3-CF₃—C₆H₄ | Me | 2-Oxazolin-2-yl | 1 | |
| 1319 | 4-CF₃—C₆H₄ | Me | 2-Oxazolin-2-yl | 1 | |
| 1320 | 3,5-F₂—C₆H₃ | Me | 2-Oxazolin-2-yl | 1 | |
| 1321 | 2,3-Cl₂—C₆H₃ | Me | 2-Oxazolin-2-yl | 1 | |
| 1322 | 2,4-Cl₂—C₆H₃ | Me | 2-Oxazolin-2-yl | 1 | |
| 1323 | 2,5-Cl₂—C₆H₃ | Me | 2-Oxazolin-2-yl | 1 | |
| 1324 | 3,4-Cl₂—C₆H₃ | Me | 2-Oxazolin-2-yl | 1 | |
| 1325 | 3,5-Cl₂—C₆H₃ | Me | 2-Oxazolin-2-yl | 1 | |
| 1326 | 2,3-Me₂—C₆H₃ | Me | 2-Oxazolin-2-yl | 1 | |
| 1327 | 2,4-Me₂—C₆H₃ | Me | 2-Oxazolin-2-yl | 1 | |
| 1328 | 2,5-Me₂—C₆H₃ | Me | 2-Oxazolin-2-yl | 1 | mp 81–85° C. |
| 1329 | 3,4-Me₂—C₆H₃ | Me | 2-Oxazolin-2-yl | 1 | |
| 1330 | 2-Cl-4-Me—C₆H₃ | Me | 2-Oxazolin-2-yl | 1 | |
| 1331 | 2-Cl-5-Me—C₆H₃ | Me | 2-Oxazolin-2-yl | 1 | |
| 1332 | 4-Cl-3-Me—C₆H₃ | Me | 2-Oxazolin-2-yl | 1 | |
| 1333 | 3-Ph—C₆H₄ | Me | 2-Oxazolin-2-yl | 1 | |
| 1334 | 3-i-PrO—C₆H₄ | Me | 2-Oxazolin-2-yl | 1 | |
| 1335 | 3-PhO—C₆H₄ | Me | 2-Oxazolin-2-yl | 1 | |
| 1336 | 4-Cl-2-Me—C₆H₃ | Me | 2-Oxazolin-2-yl | 1 | |
| 1337 | 4-Cl-3-Et—C₆H₃ | Me | 2-Oxazolin-2-yl | 1 | |
| 1338 | 3-EtO—C₆H₄ | Me | 2-Oxazolin-2-yl | 1 | |
| 1339 | 2-Cl-4-Me—C₆H₃ | Me | 2-Oxazolin-2-yl | 1 | |
| 1340 | 2,4,5-Cl₃—C₆H₂ | Me | 2-Oxazolin-2-yl | 1 | |
| 1341 | C₆H₅ | Me | 2-Oxazolin-2-yl | 0 | Isomer A: ¹H-NMR(CDCl₃) δ ppm: 3.63(2H, t, J = 9.8), 4.08(308(2H, t, J = 9.8), 6.94–7.40(8H, m), 7.69(1H, dd, J = 7.9, 1.9) Isomer B: ¹H-NMR(CDCl₃) δ ppm: 3.91(2H, t, J = 9.8), 3.96(3H, s), 4.37(2H, t, J = 9.8), 6.91–7.37(9H, m) |
| 1342 | 4-F—C₆H₄ | Me | 2-Oxazolin-2-yl | 0 | |
| 1343 | 3-Cl—C₆H₄ | Me | 2-Oxazolin-2-yl | 0 | |

-continued

| No | R¹ | R² | R³ | n | Physical data |
|---|---|---|---|---|---|
| 1344 | 4-Cl—C₆H₄ | Me | 2-Oxazolin-2-yl | 0 | |
| 1345 | 4-Me—C₆H₄ | Me | 2-Oxazolin-2-yl | 0 | |
| 1346 | 3,5-Cl₂—C₆H₃ | Me | 2-Oxazolin-2-yl | 0 | |
| 1347 | 3,4-Me₂—C₆H₃ | Me | 2-Oxazolin-2-yl | 0 | |
| 1348 | 2-Cl-pyridin-3-yl | Me | 2-Oxazolin-2-yl | 1 | |
| 1349 | 5-CF₃-pyridin-2-yl | Me | 2-Oxazolin-2-yl | 1 | |
| 1350 | 5-Cl-pyridin-2-yl | Me | 2-Oxazolin-2-yl | 1 | |
| 1351 | C₆H₅ | Me | 5-Me-2-isoxazolin-3-yl | 1 | |
| 1352 | 2-F—C₆H₄ | Me | 5-Me-2-isoxazolin-3-yl | 1 | |
| 1353 | 3-F—C₆H₄ | Me | 5-Me-2-isoxazolin-3-yl | 1 | |
| 1354 | 4-F—C₆H₄ | Me | 5-Me-2-isoxazolin-3-yl | 1 | |
| 1355 | 2-Cl—C₆H₄ | Me | 5-Me-2-isoxazolin-3-yl | 1 | |
| 1356 | 3-Cl—C₆H₄ | Me | 5-Me-2-isoxazolin-3-yl | 1 | |
| 1357 | 4-Cl—C₆H₄ | Me | 5-Me-2-isoxazolin-3-yl | 1 | |
| 1358 | 3-Br—C₆H₄ | Me | 5-Me-2-isoxazolin-3-yl | 1 | |
| 1359 | 4-Br—C₆H₄ | Me | 5-Me-2-isoxazolin-3-yl | 1 | |
| 1360 | 2-Me—C₆H₄ | Me | 5-Me-2-isoxazolin-3-yl | 1 | |
| 1361 | 3-Me—C₆H₄ | Me | 5-Me-2-isoxazolin-3-yl | 1 | |
| 1362 | 4-Me—C₆H₄ | Me | 5-Me-2-isoxazolin-3-yl | 1 | |
| 1363 | 3-Et—C₆H₄ | Me | 5-Me-2-isoxazolin-3-yl | 1 | |
| 1364 | 2-MeO—C₆H₄ | Me | 5-Me-2-isoxazolin-3-yl | 1 | |
| 1365 | 3-MeO—C₆H₄ | Me | 5-Me-2-isoxazolin-3-yl | 1 | |
| 1366 | 4-MeO—C₆H₄ | Me | 5-Me-2-isoxazolin-3-yl | 1 | |
| 1367 | 4-Et—C₆H₄ | Me | 5-Me-2-isoxazolin-3-yl | 1 | |
| 1368 | 3-CF₃—C₆H₄ | Me | 5-Me-2-isoxazolin-3-yl | 1 | |
| 1369 | 4-CF₃—C₆H₄ | Me | 5-Me-2-isoxazolin-3-yl | 1 | |
| 1370 | 3,5-F₂—C₆H₃ | Me | 5-Me-2-isoxazolin-3-yl | 1 | |
| 1371 | 2,3-Cl₂—C₆H₃ | Me | 5-Me-2-isoxazolin-3-yl | 1 | |
| 1372 | 2,4-Cl₂—C₆H₃ | Me | 5-Me-2-isoxazolin-3-yl | 1 | |
| 1373 | 2,5-Cl₂—C₆H₃ | Me | 5-Me-2-isoxazolin-3-yl | 1 | |
| 1374 | 3,4-Cl₂—C₆H₃ | Me | 5-Me-2-isoxazolin-3-yl | 1 | |
| 1375 | 3,5-Cl₂—C₆H₃ | Me | 5-Me-2-isoxazolin-3-yl | 1 | |
| 1376 | 2,3-Me₂—C₆H₃ | Me | 5-Me-2-isoxazolin-3-yl | 1 | |
| 1377 | 2,4-Me₂—C₆H₃ | Me | 5-Me-2-isoxazolin-3-yl | 1 | |
| 1378 | 2,5-Me₂—C₆H₃ | Me | 5-Me-2-isoxazolin-3-yl | 1 | |
| 1379 | 3,4-Me₂—C₆H₃ | Me | 5-Me-2-isoxazolin-3-yl | 1 | |
| 1380 | 2-Cl-4-Me—C₆H₃ | Me | 5-Me-2-isoxazolin-3-yl | 1 | |
| 1381 | 2-Cl-5-Me—C₆H₃ | Me | 5-Me-2-isoxazolin-3-yl | 1 | |

-continued

| No | R¹ | R² | R³ | n | Physical data |
|---|---|---|---|---|---|
| 1382 | 4-Cl-3-Me—C₆H₃ | Me | 5-Me-2-isoxazolin-3-yl | 1 | |
| 1383 | 3-Ph—C₆H₄ | Me | 5-Me-2-isoxazolin-3-yl | 1 | |
| 1384 | 3-i-PrO—C₆H₄ | Me | 5-Me-2-isoxazolin-3-yl | 1 | |
| 1385 | 3-PhO—C₆H₄ | Me | 5-Me-2-isoxazolin-3-yl | 1 | |
| 1386 | 4-Cl-2-Me—C₆H₃ | Me | 5-Me-2-isoxazolin-3-yl | 1 | |
| 1387 | 4-Cl-3-Et—C₆H₃ | Me | 5-Me-2-isoxazolin-3-yl | 1 | |
| 1388 | 3-EtO—C₆H₄ | Me | 5-Me-2-isoxazolin-3-yl | 1 | |
| 1389 | 2-Cl-4-Me—C₆H₃ | Me | 5-Me-2-isoxazolin-3-yl | 1 | |
| 1390 | 2,4,5-Cl₃—C₆H₂ | Me | 5-Me-2-isoxazolin-3-yl | 1 | |
| 1391 | C₆H₅ | Me | 5-Me-2-isoxazolin-3-yl | 0 | |
| 1392 | 4-F—C₆H₄ | Me | 5-Me-2-isoxazolin-3-yl | 0 | |
| 1393 | 3-Cl—C₆H₄ | Me | 5-Me-2-isoxazolin-3-yl | 0 | |
| 1394 | 4-Cl—C₆H₄ | Me | 5-Me-2-isoxazolin-3-yl | 0 | |
| 1395 | 4-Me—C₆H₄ | Me | 5-Me-2-isoxazolin-3-yl | 0 | |
| 1396 | 3,5-Cl₂—C₆H₃ | Me | 5-Me-2-isoxazolin-3-yl | 0 | |
| 1397 | 3,4-Me₂—C₆H₃ | Me | 5-Me-2-isoxazolin-3-yl | 0 | |
| 1398 | 2-Cl-pyridin-3-yl | Me | 5-Me-2-isoxazolin-3-yl | 1 | |
| 1399 | 5-CF₃-pyridin-2-yl | Me | 5-Me-2-isoxazolin-3-yl | 1 | |
| 1400 | 5-Cl-pyridin-2-yl | Me | 5-Me-2-isoxazolin-3-yl | 1 | |
| 1401 | C₆H₅ | Me | Imidazol-2-yl | 1 | |
| 1402 | 2-F—C₆H₄ | Me | Imidazol-2-yl | 1 | |
| 1403 | 3-F—C₆H₄ | Me | Imidazol-2-yl | 1 | |
| 1404 | 4-F—C₆H₄ | Me | Imidazol-2-yl | 1 | |
| 1405 | 2-Cl—C₆H₄ | Me | Imidazol-2-yl | 1 | |
| 1406 | 3-Cl—C₆H₄ | Me | Imidazol-2-yl | 1 | |
| 1407 | 4-Cl—C₆H₄ | Me | Imidazol-2-yl | 1 | |
| 1408 | 3-Br—C₆H₄ | Me | Imidazol-2-yl | 1 | |
| 1409 | 4-Br—C₆H₄ | Me | Imidazol-2-yl | 1 | |
| 1410 | 2-Me—C₆H₄ | Me | Imidazol-2-yl | 1 | |
| 1411 | 3-Me—C₆H₄ | Me | Imidazol-2-yl | 1 | |
| 1412 | 4-Me—C₆H₄ | Me | Imidazol-2-yl | 1 | |
| 1413 | 3-Et—C₆H₄ | Me | Imidazol-2-yl | 1 | |
| 1414 | 2-MeO—C₆H₄ | Me | Imidazol-2-yl | 1 | |
| 1415 | 3-MeO—C₆H₄ | Me | Imidazol-2-yl | 1 | |
| 1416 | 4-MeO—C₆H₄ | Me | Imidazol-2-yl | 1 | |
| 1417 | 4-Et—C₆H₄ | Me | Imidazol-2-yl | 1 | |
| 1418 | 3-CF₃—C₆H₄ | Me | Imidazol-2-yl | 1 | |
| 1419 | 4-CF₃—C₆H₄ | Me | Imidazol-2-yl | 1 | |
| 1420 | 3,5-F₂—C₆H₃ | Me | Imidazol-2-yl | 1 | |
| 1421 | 2,3-Cl₂—C₆H₃ | Me | Imidazol-2-yl | 1 | |
| 1422 | 2,4-Cl₂—C₆H₃ | Me | Imidazol-2-yl | 1 | |
| 1423 | 2,5-Cl₂—C₆H₃ | Me | Imidazol-2-yl | 1 | |
| 1424 | 3,4-Cl₂—C₆H₃ | Me | Imidazol-2-yl | 1 | |
| 1425 | 3,5-Cl₂—C₆H₃ | Me | Imidazol-2-yl | 1 | |
| 1426 | 2,3-Me₂—C₆H₃ | Me | Imidazol-2-yl | 1 | |
| 1427 | 2,4-Me₂—C₆H₃ | Me | Imidazol-2-yl | 1 | |
| 1428 | 2,5-Me₂—C₆H₃ | Me | Imidazol-2-yl | 1 | mp 153–154° C. |
| 1429 | 3,4-Me₂—C₆H₃ | Me | Imidazol-2-yl | 1 | |
| 1430 | 2-Cl-4-Me—C₆H₃ | Me | Imidazol-2-yl | 1 | |
| 1431 | 2-Cl-5-Me—C₆H₃ | Me | Imidazol-2-yl | 1 | |
| 1432 | 4-Cl-3-Me—C₆H₃ | Me | Imidazol-2-yl | 1 | |
| 1433 | 3-Ph—C₆H₄ | Me | Imidazol-2-yl | 1 | |
| 1434 | 3-i-PrO—C₆H₄ | Me | Imidazol-2-yl | 1 | |
| 1435 | 3-PrO—C₆H₄ | Me | Imidazol-2-yl | 1 | |
| 1436 | 4-Cl-2-Me—C₆H₃ | Me | Imidazol-2-yl | 1 | |
| 1437 | 4-Cl-3-Et—C₆H₃ | Me | Imidazol-2-yl | 1 | |
| 1438 | 3-EtO—C₆H₄ | Me | Imidazol-2-yl | 1 | |
| 1439 | 2-Cl-4-Me—C₆H₃ | Me | Imidazol-2-yl | 1 | |

-continued

| No | R¹ | R² | R³ | n | Physical data |
|---|---|---|---|---|---|
| 1440 | 2,4,5-Cl₃—C₆H₂ | Me | Imidazol-2-yl | 1 | |
| 1441 | C₆H₅ | Me | Imidazol-2-yl | 0 | |
| 1442 | 4-F—C₆H₄ | Me | Imidazol-2-yl | 0 | |
| 1443 | 3-Cl—C₆H₄ | Me | Imidazol-2-yl | 0 | |
| 1444 | 4-Cl—C₆H₄ | Me | Imidazol-2-yl | 0 | |
| 1445 | 4-Me—C₆H₄ | Me | Imidazol-2-yl | 0 | |
| 1446 | 3,5-Cl₂—C₆H₃ | Me | Imidazol-2-yl | 0 | |
| 1447 | 3,4-Me₂—C₆H₃ | Me | Imidazol-2-yl | 0 | |
| 1448 | 2-Cl-pyridin-3-yl | Me | Imidazol-2-yl | 1 | |
| 1449 | 5-CF₃-pyridin-2-yl | Me | Imidazol-2-yl | 1 | |
| 1450 | 5-Cl-pyridin-2-yl | Me | Imidazol-2-yl | 1 | |
| 1451 | C₆H₅ | Me | 2-Imidazolin-2-yl | 1 | mp 91–92° C. |
| 1452 | 2-F—C₆H₄ | Me | 2-Imidazolin-2-yl | 1 | |
| 1453 | 3-F—C₆H₄ | Me | 2-Imidazolin-2-yl | 1 | |
| 1454 | 4-F—C₆H₄ | Me | 2-Imidazolin-2-yl | 1 | |
| 1455 | 2-Cl—C₆H₄ | Me | 2-Imidazolin-2-yl | 1 | mp 121–123° C. |
| 1456 | 3-Cl—C₆H₄ | Me | 2-Imidazolin-2-yl | 1 | ¹H-NMR(CDCl₃) δ ppm: 3.67(4H, brs), 3.95(4.02)(3H, s), 4.97(5.11)2H, s), 6.78–6.81(1H, m), 6.90–6.95(2H, m), 7.13–7.23(2H, m), 7.35–7.41(2H, m), 7.49–7.51(1H, m) |
| 1457 | 4-Cl—C₆H₄ | Me | 2-Imidazolin-2-yl | 1 | mp 113–114° C. |
| 1458 | 3-Br—C₆H₄ | Me | 2-Imidazolin-2-yl | 1 | |
| 1459 | 4-Br—C₆H₄ | Me | 2-Imidazolin-2-yl | 1 | |
| 1460 | 2-Me—C₆H₄ | Me | 2-Imidazolin-2-yl | 1 | mp 96–100° C. |
| 1461 | 3-Me—C₆H₄ | Me | 2-Imidazolin-2-yl | 1 | ¹H-NMR(CDCl₃) δ ppm: 2.31(2.27)(3H, s), 3.66(4H, brs), 4.02(3.94)(3H, s), 5.11(4.95)(2H, s), 6.54–6.76(3H, m), 7.04–7.15(1H, m), 7.21–7.41(3H, m) 7.50–7.53(1H, m) |
| 1462 | 4-Me—C₆H₄ | Me | 2-Imidazolin-2-yl | 1 | mp 89–90° C. |
| 1463 | 3-Et—C₆H₄ | Me | 2-Imidazolin-2-yl | 1 | |
| 1464 | 2-MeO—C₆H₄ | Me | 2-Imidazolin-2-yl | 1 | |
| 1465 | 3-MeO—C₆H₄ | Me | 2-Imidazolin-2-yl | 1 | |
| 1466 | 4-MeO—C₆H₄ | Me | 2-Imidazolin-2-yl | 1 | |
| 1467 | 4-Et—C₆H₄ | Me | 2-Imidazolin-2-yl | 1 | |
| 1468 | 3-CF₃—C₆H₄ | Me | 2-Imidazolin-2-yl | 1 | |
| 1469 | 4-CF₃—C₆H₄ | Me | 2-Imidazolin-2-yl | 1 | |
| 1470 | 3,5-F₂—C₆H₃ | Me | 2-Imidazolin-2-yl | 1 | |
| 1471 | 2,3-Cl₂—C₆H₃ | Me | 2-Imidazolin-2-yl | 1 | |
| 1472 | 2,4-Cl₂—C₆H₃ | Me | 2-Imidazolin-2-yl | 1 | |
| 1473 | 2,5-Cl₂—C₆H₃ | Me | 2-Imidazolin-2-yl | 1 | |

-continued

| No | R¹ | R² | R³ | n | Physical data |
|---|---|---|---|---|---|
| 1474 | 3,4-Cl₂—C₆H₃ | Me | 2-Imidazolin-2-yl | 1 | |
| 1475 | 3,5-Cl₂—C₆H₃ | Me | 2-Imidazolin-2-yl | 1 | |
| 1476 | 2,3-Me₂—C₆H₃ | Me | 2-Imidazolin-2-yl | 1 | |
| 1477 | 2,4-Me₂—C₆H₃ | Me | 2-Imidazolin-2-yl | 1 | |
| 1478 | 2,5-Me₂—C₆H₃ | Me | 2-Imidazolin-2-yl | 1 | mp 97–101° C. |
| 1479 | 3,4-Me₂—C₆H₃ | Me | 2-Imidazolin-2-yl | 1 | |
| 1480 | 2-Cl-4-Me—C₆H₃ | Me | 2-Imidazolin-2-yl | 1 | |
| 1481 | 2-Cl-5-Me—C₆H₃ | Me | 2-Imidazolin-2-yl | 1 | |
| 1482 | 4-Cl-3-Me—C₆H₃ | Me | 2-Imidazolin-2-yl | 1 | |
| 1483 | 3-Ph—C₆H₄ | Me | 2-Imidazolin-2-yl | 1 | |
| 1484 | 3-i-PrO—C₆H₄ | Me | 2-Imidazolin-2-yl | 1 | |
| 1485 | 3-PhO—C₆H₄ | Me | 2-Imidazolin-2-yl | 1 | |
| 1486 | 4-Cl-2-Me—C₆H₃ | Me | 2-Imidazolin-2-yl | 1 | |
| 1487 | 4-Cl-3-Et—C₆H₃ | Me | 2-Imidazolin-2-yl | 1 | |
| 1488 | 3-EtO—C₆H₄ | Me | 2-Imidazolin-2-yl | 1 | |
| 1489 | 2-Cl-4-Me—C₆H₃ | Me | 2-Imidazolin-2-yl | 1 | |
| 1490 | 2,4,5-Cl₃—C₆H₂ | Me | 2-Imidazolin-2-yl | 1 | |
| 1491 | C₆H₅ | Me | 2-Imidazolin-2-yl | 0 | mp 95–99° C. |
| 1492 | 4-F—C₆H₄ | Me | 2-Imidazolin-2-yl | 0 | |
| 1493 | 3-Cl—C₆H₄ | Me | 2-Imidazolin-2-yl | 0 | |
| 1494 | 4-Cl—C₆H₄ | Me | 2-Imidazolin-2-yl | 0 | |
| 1495 | 4-Me—C₆H₄ | Me | 2-Imidazolin-2-yl | 0 | |
| 1496 | 3,5-Cl₂—C₆H₃ | Me | 2-Imidazolin-2-yl | 0 | |
| 1497 | 3,4-Me₂—C₆H₃ | Me | 2-Imidazolin-2-yl | 0 | |
| 1498 | 2-Cl-pyridin-3-yl | Me | 2-Imidazolin-2-yl | 1 | |
| 1499 | 5-CF₃-pyridin-2-yl | Me | 2-Imidazolin-2-yl | 1 | |
| 1500 | 5-Cl-pyridin-2-yl | Me | 2-Imidazolin-2-yl | 1 | |
| 1501 | C₆H₅ | Me | 2-Thiazolin-2-yl | 1 | |
| 1502 | 2-Cl—C₆H₄ | Me | 2-Thiazolin-2-yl | 1 | |
| 1503 | 3-Cl—C₆H₄ | Me | 2-Thiazolin-2-yl | 1 | |
| 1504 | 4-Cl—C₆H₄ | Me | 2-Thiazolin-2-yl | 1 | |
| 1505 | 2-Me—C₆H₄ | Me | 2-Thiazolin-2-yl | 1 | |
| 1506 | 3-Me—C₆H₄ | Me | 2-Thiazolin-2-yl | 1 | |
| 1507 | 4-Me—C₆H₄ | Me | 2-Thiazolin-2-yl | 1 | |
| 1508 | 2-MeO—C₆H₄ | Me | 2-Thiazolin-2-yl | 1 | |
| 1509 | 4-Br—C₆H₄ | Me | 2-Thiazolin-2-yl | 1 | |
| 1510 | 3-CF₃—C₆H₄ | Me | 2-Thiazolin-2-yl | 1 | |
| 1511 | 2-4-Cl₂—C₆H₃ | Me | 2-Thiazolin-2-yl | 1 | |

-continued

| No | R¹ | R² | R³ | n | Physical data |
|---|---|---|---|---|---|
| 1512 | 2,5-Cl$_2$—C$_6$H$_3$ | Me | 2-Thiazolin-2-yl | 1 | |
| 1513 | 2,4-Me$_2$—C$_6$H$_3$ | Me | 2-Thiazolin-2-yl | 1 | |
| 1514 | 2,5-Me$_2$—C$_6$H$_3$ | Me | 2-Thiazolin-2-yl | 1 | mp 79–82° C. |
| 1515 | C$_6$H$_5$ | Me | 2-Thiazolin-2-yl | 0 | $^1$H-NMR(CDCl$_3$) δ ppm: 2.88(3.22)(2H, t, J = 8.0), 3.90 (4.29)(2H, t, J = 8.0), 4.06(3.95)(3H, s), 6.91–7.58(9H, m) |
| 1516 | 4-Cl—C$_6$H$_4$ | Me | 2-Thiazolin-2-yl | 0 | |
| 1517 | 4-Me—C$_6$H$_4$ | Me | 2-Thiazolin-2-yl | 0 | |
| 1518 | 2-Cl-pyridin-3-yl | Me | 2-Thiazolin-2-yl | 1 | |
| 1519 | 5-CF$_3$-pyridin-2-yl | Me | 2-Thiazolin-2-yl | 1 | |
| 1520 | 5-Cl-pyridin-2-yl | Me | 2-Thiazolin-2-yl | 1 | |
| 1521 | C$_6$H$_5$ | Me | Thiazol-2-yl | 1 | |
| 1522 | 2-Cl—C$_6$H$_4$ | Me | Thiazol-2-yl | 1 | |
| 1523 | 3-Cl—C$_6$H$_4$ | Me | Thiazol-2-yl | 1 | |
| 1524 | 4-Cl—C$_6$H$_4$ | Me | Thiazol-2-yl | 1 | |
| 1525 | 2-Me—C$_6$H$_4$ | Me | Thiazol-2-yl | 1 | |
| 1526 | 3-Me—C$_6$H$_4$ | Me | Thiazol-2-yl | 1 | |
| 1527 | 4-Me—C$_6$H$_4$ | Me | Thiazol-2-yl | 1 | |
| 1528 | 2-MeO—C$_6$H$_4$ | Me | Thiazol-2-yl | 1 | |
| 1529 | 4-Br—C$_6$H$_4$ | Me | Thiazol-2-yl | 1 | |
| 1530 | 3-CF$_3$—C$_6$H$_4$ | Me | Thiazol-2-yl | 1 | |
| 1532 | 2,5-Cl$_2$—C$_6$H$_3$ | Me | Thiazol-2-yl | 1 | |
| 1533 | 2,4-Me$_2$—C$_6$H$_3$ | Me | Thiazol-2-yl | 1 | |
| 1534 | 2,5-Me$_2$—C$_6$H$_3$ | Me | Thiazol-2-yl | 1 | mp 112–113.5° C. |
| 1535 | C$_6$H$_5$ | Me | Thiazol-2-yl | 0 | |
| 1536 | 4-Cl—C$_6$H$_4$ | Me | Thiazol-2-yl | 0 | |
| 1537 | 4-Me—C$_6$H$_4$ | Me | Thiazol-2-yl | 0 | |
| 1538 | 2-Cl-pyridin-3-yl | Me | Thiazol-2-yl | 1 | |
| 1539 | 5-CF$_3$-pyridin-2-yl | Me | Thiazol-2-yl | 1 | |
| 1540 | 5-Cl-pyridin-2-yl | Me | Thiazol-2-yl | 1 | |
| 1541 | C$_6$H$_5$ | Me | 1-Me-pyrazol-5-yl | 1 | |
| 1542 | 2-Cl—C$_6$H$_4$ | Me | 1-Me-pyrazol-5-yl | 1 | |
| 1543 | 3-Cl—C$_6$H$_4$ | Me | 1-Me-pyrazol-5-yl | 1 | |
| 1544 | 4-Cl—C$_6$H$_4$ | Me | 1-Me-pyrazol-5-yl | 1 | |
| 1545 | 2-Me—C$_6$H$_4$ | Me | 1-Me-pyrazol-5-yl | 1 | |
| 1546 | 3-Me—C$_6$H$_4$ | Me | 1-Me-pyrazol-5-yl | 1 | |
| 1547 | 4-Me—C$_6$H$_4$ | Me | 1-Me-pyrazol-5-yl | 1 | |
| 1548 | 2-MeO—C$_6$H$_4$ | Me | 1-Me-pyrazol-5-yl | 1 | |
| 1549 | 4-Br—C$_6$H$_4$ | Me | 1-Me-pyrazol-5-yl | 1 | |
| 1550 | 2,5-Me$_2$—C$_6$H$_3$ | Et | 1-Me-pyrazol-5-yl | 1 | Isomer A: mp 74–76° C. Isomer B: mp 84–86° C. |
| 1551 | 2,4-Cl$_2$—C$_6$H$_3$ | Me | 1-Me-pyrazol-5-yl | 1 | |
| 1552 | 2,5-Cl$_2$—C$_6$H$_3$ | Me | 1-Me-pyrazol-5-yl | 1 | |
| 1553 | 2,4-Me$_2$—C$_6$H$_3$ | Me | 1-Me-pyrazol-5-yl | 1 | |

-continued

| No | R¹ | R² | R³ | n | Physical data |
|---|---|---|---|---|---|
| 1554 | 2,5-Me₂—C₆H₃ | Me | 1-Me-pyrazol-5-yl | 1 | Isomer A:<br>¹H-NMR(CDCl₃)<br>δ ppm: 2.12(3H, s),<br>2.24(3H, s),<br>3.98(3H, s),<br>4.12(3H, s),<br>4.93(2H, s),<br>5.92(1H, d, J = 1.8),<br>6.52(1H, s),<br>6.64–7.64(7H, m)<br>Isomer B:<br>mp 108–110° C. |
| 1555 | C₆H₅ | Me | 1-Me-pyrazol-5-yl | 0 | |
| 1556 | 4-Cl—C₆H₄ | Me | 1-Me-pyrazol-5-yl | 0 | |
| 1557 | 4-Me—C₆H₄ | Me | 1-Me-pyrazol-5-yl | 0 | |
| 1558 | 2-Cl-pyridin-3-yl | Me | 1-Me-pyrazol-5-yl | 1 | |
| 1559 | 5-CF₃-pyridin-2-yl | Me | 1-Me-pyrazol-5-yl | 1 | |
| 1560 | 5-Cl-pyridin-2-yl | Me | 1-Me-pyrazol-5-yl | 1 | |
| 1561 | C₆H₅ | Me | 1-Me-1,2,4-triazol-5-yl | 1 | ¹H-NMR(CDCl₃)<br>δ ppm: 4.00(3H, s),<br>4.03(3H, s),<br>4.92(2H, s),<br>6.74–6.94(3H, m),<br>7.18–7.57(5H, m),<br>7.83(1H, s) |
| 1562 | 2-Cl—C₆H₄ | Me | 1-Me-1,2,4-triazol-5-yl | 1 | |
| 1563 | 3-Cl—C₆H₄ | Me | 1-Me-1,2,4-triazol-5-yl | 1 | |
| 1564 | 4-Cl—C₆H₄ | Me | 1-Me-1,2,4-triazol-5-yl | 1 | mp 113–114° C. |
| 1565 | 2-Me—C₆H₄ | Me | 1-Me-1,2,4-triazol-5-yl | 1 | |
| 1566 | 3-Me—C₆H₄ | Me | 1-Me-1,2,4-triazol-5-yl | 1 | |
| 1567 | 4-Me—C₆H₄ | Me | 1-Me-1,2,4-triazol-5-yl | 1 | |
| 1568 | 2-MeO—C₆H₄ | Me | 1-Me-1,2,4-triazol-5-yl | 1 | |
| 1569 | 4-Br—C₆H₄ | Me | 1-Me-1,2,4-triazol-5-yl | 1 | |
| 1570 | 3-CF₃—C₆H₄ | Me | 1-Me-1,2,4-triazol-5-yl | 1 | |
| 1571 | 2,4-Cl₂—C₆H₃ | Me | 1-Me-1,2,4-triazol-5-yl | 1 | |
| 1572 | 2,5-Cl₂—C₆H₃ | Me | 1-Me-1,2,4-triazol-5-yl | 1 | |
| 1573 | 2,4-Me₂—C₆H₃ | Me | 1-Me-1,2,4-triazol-5-yl | 1 | |
| 1574 | 2,5-Me₂—C₆H₃ | Me | 1-Me-1,2,4-triazol-5-yl | 1 | mp 101–102° C. |
| 1575 | C₆H₅ | Me | 1-Me-1,2,4-triazol-5-yl | 0 | ¹H-NMR(CDCl₃)<br>δ ppm: 3.98(6H, s),<br>6.85–7.48(9H, m),<br>7.80(1H, s) |
| 1576 | 4-Cl—C₆H₄ | Me | 1-Me-1,2,4-triazol-5-yl | 0 | |
| 1577 | 4-Me—C₆H₄ | Me | 1-Me-1,2,4-triazol-5-yl | 0 | |
| 1578 | 2-Cl-pyridin-3-yl | Me | 1-Me-1,2,4-triazol-5-yl | 1 | mp 99–100° C. |
| 1579 | 5-CF₃-pyridin-2-yl | Me | 1-Me-1,2,4-triazol-5-yl | 1 | |
| 1580 | 5-Cl-pyridin-2-yl | Me | 1-Me-1,2,4-triazol-5-yl | 1 | |
| 1581 | C₆H₅ | Me | 1,2,4-Oxadiazol-5-yl | 1 | mp 109.0–110.0° C. |
| 1582 | 2-Cl—C₆H₄ | Me | 1,2,4-Oxadiazol-5-yl | 1 | |
| 1583 | 3-Cl—C₆H₄ | Me | 1,2,4-Oxadiazol-5-yl | 1 | |

-continued

| No | R¹ | R² | R³ | n | Physical data |
|---|---|---|---|---|---|
| 1584 | 4-Cl—C₆H₄ | Me | 1,2,4-Oxadiazol-5-yl | 1 | mp 96–97.5° C. |
| 1585 | 2-Me—C₆H₄ | Me | 1,2,4-Oxadiazol-5-yl | 1 | |
| 1586 | 3-Me—C₆H₄ | Me | 1,2,4-Oxadiazol-5-yl | 1 | |
| 1587 | 4-Me—C₆H₄ | Me | 1,2,4-Oxadiazol-5-yl | 1 | |
| 1588 | 2-MeO—C₆H₄ | Me | 1,2,4-Oxadiazol-5-yl | 1 | |
| 1589 | 4-Br—C₆H₄ | Me | 1,2,4-Oxadiazol-5-yl | 1 | |
| 1590 | 2,5-Me₂—C₆H₃ | Me | 3-Et-1,2,4-oxadiazol-5-yl | 1 | mp 111.5–112.5° C. |
| 1591 | 2,4-Cl₂—C₆H₃ | Me | 1,2,4-Oxadiazol-5-yl | 1 | |
| 1592 | 2,5-Cl₂—C₆H₃ | Me | 1,2,4-Oxadiazol-5-yl | 1 | |
| 1593 | 2,4-Me₂—C₆H₃ | Me | 1,2,4-Oxadiazol-5-yl | 1 | |
| 1594 | 2,5-Me₂—C₆H₃ | Me | 1,2,4-Oxadiazol-5-yl | 1 | mp 75–76° C. |
| 1595 | C₆H₅ | Me | 1,2,4-Oxadiazol-5-yl | 0 | mp 115.5–116.5° C. |
| 1596 | 4-Cl—C₆H₄ | Me | 1,2,4-Oxadiazol-5-yl | 0 | |
| 1597 | 4-Me—C₆H₄ | Me | 1,2,4-Oxadiazol-5-yl | 0 | |
| 1598 | 2-Cl-pyridin-3-yl | Me | 1,2,4-Oxadiazol-5-yl | 1 | |
| 1599 | 5-CF₃-pyridin-2-yl | Me | 1,2,4-Oxadiazol-5-yl | 1 | |
| 1600 | 5-Cl-pyridin-2-yl | Me | 1,2,4-Oxadiazol-5-yl | 1 | |
| 1601 | C₆H₅ | Me | 2-Thienyl | 1 | |
| 1602 | 2-Cl—C₆H₄ | Me | 2-Thienyl | 1 | |
| 1603 | 3-Cl—C₆H₄ | Me | 2-Thienyl | 1 | |
| 1604 | 4-Cl—C₆H₄ | Me | 2-Thienyl | 1 | |
| 1605 | 2-Me—C₆H₄ | Me | 2-Thienyl | 1 | |
| 1606 | 3-Me—C₆H₄ | Me | 2-Thienyl | 1 | |
| 1607 | 4-Me—C₆H₄ | Me | 2-Thienyl | 1 | |
| 1608 | 2-MeO—C₆H₄ | Me | 2-Thienyl | 1 | |
| 1609 | 4-Br—C₆H₄ | Me | 2-Thienyl | 1 | |
| 1610 | 3-CF₃—C₆H₄ | Me | 2-Thienyl | 1 | |
| 1611 | 2,4-Cl₂—C₆H₃ | Me | 2-Thienyl | 1 | |
| 1612 | 2,5-Cl₂—C₆H₃ | Me | 2-Thienyl | 1 | |
| 1613 | 2,4-Me₂—C₆H₃ | Me | 2-Thienyl | 1 | |
| 1614 | 2,5-Me₂—C₆H₃ | Me | 2-Thienyl | 1 | Isomer A: mp 81–84° C. Isomer B: mp 106–107° C. |
| 1615 | C₆H₅ | Me | 2-Thienyl | 0 | |
| 1616 | 4-Cl—C₆H₄ | Me | 2-Thienyl | 0 | |
| 1617 | 4-Me—C₆H₄ | Me | 2-Thienyl | 0 | |
| 1618 | 2-Cl-pyridin-3-yl | Me | 2-Thienyl | 1 | |
| 1619 | 5-CF₃-pyridin-2-yl | Me | 2-Thienyl | 1 | |
| 1620 | 5-Cl-pyridin-2-yl | Me | 2-Thienyl | 1 | |
| 1621 | C₆H₅ | Me | 2-Furyl | 1 | |
| 1622 | 2-Cl—C₆H₄ | Me | 2-Furyl | 1 | |
| 1623 | 3-Cl—C₆H₄ | Me | 2-Furyl | 1 | |
| 1624 | 4-Cl—C₆H₄ | Me | 2-Furyl | 1 | |
| 1625 | 2-Me—C₆H₄ | Me | 2-Furyl | 1 | |
| 1626 | 3-Me—C₆H₄ | Me | 2-Furyl | 1 | |
| 1627 | 4-Me—C₆H₄ | Me | 2-Furyl | 1 | |
| 1628 | 2-MeO—C₆H₄ | Me | 2-Furyl | 1 | |
| 1629 | 4-Br—C₆H₄ | Me | 2-Furyl | 1 | |
| 1630 | 3-CF₃—C₆H₄ | Me | 2-Furyl | 1 | |
| 1631 | 2,4-Cl₂—C₆H₃ | Me | 2-Furyl | 1 | |
| 1632 | 2,5-Cl₂—C₆H₃ | Me | 2-Furyl | 1 | |
| 1633 | 2,4-Me₂—C₆H₃ | Me | 2-Furyl | 1 | |
| 1634 | 2,5-Me₂—C₆H₃ | Me | 2-Furyl | 1 | Isomer A: mp 81–82° C. Isomer B: mp 110–112° C. |
| 1635 | C₆H₅ | Me | 2-Furyl | 0 | |
| 1636 | 4-Cl—C₆H₄ | Me | 2-Furyl | 0 | |
| 1637 | 4-Me—C₆H₄ | Me | 2-Furyl | 0 | |
| 1638 | 2-Cl-pyridin-3-yl | Me | 2-Furyl | 1 | |
| 1639 | 5-CF₃-pyridin-2-yl | Me | 2-Furyl | 1 | |
| 1640 | 5-Cl-pyridin-2-yl | Me | 2-Furyl | 1 | |
| 1641 | C₆H₅ | Me | 3-Me-isothiazol-5-yl | 1 | |

-continued

| No | R¹ | R² | R³ | n | Physical data |
|---|---|---|---|---|---|
| 1642 | 2-Cl—C₆H₄ | Me | Isothiazol-5-yl | 1 | |
| 1643 | 3-Cl—C₆H₄ | Me | Isothiazol-5-yl | 1 | |
| 1644 | 4-Cl—C₆H₄ | Me | 3-Me-isothiazol-5-yl | 1 | |
| 1645 | 2-Me—C₆H₄ | Me | 3-Me-isothiazol-5-yl | 1 | |
| 1646 | 3-Me—C₆H₄ | Me | Isothiazol-5-yl | 1 | |
| 1647 | 4-Me—C₆H₄ | Me | Isothiazol-5-yl | 1 | |
| 1648 | 2-MeO—C₆H₄ | Me | Isothiazol-5-yl | 1 | |
| 1649 | 4-Br—C₆H₄ | Me | Isothiazol-5-yl | 1 | |
| 1650 | 3-CF₃—C₆H₄ | Me | Isothiazol-5-yl | 1 | |
| 1651 | 2,4-Cl₂—C₆H₃ | Me | Isothiazol-5-yl | 1 | |
| 1652 | 2,5-Cl₂—C₆H₃ | Me | Isothiazol-5-yl | 1 | |
| 1653 | 2,4-Me₂—C₆H₃ | Me | Isothiazol-5-yl | 1 | |
| 1654 | 2,5-Me₂—C₆H₃ | Me | 3-Me-isothiazol-5-yl | 1 | ¹H-NMR(CDCl₃) δ ppm: 2.06(3H, s), 2.23(3H, s), 2.40(3H, s), 4.21(3H, s), 5.01(2H, s), 6.51(1H, s), 6.60–6.65(1H, m), 6.71(1H, s), 6.96(1H, d, J = 7.9), 7.37–7.71(4H, m) |
| 1655 | C₆H₅ | Me | Isothiazol-5-yl | 0 | |
| 1656 | 4-Cl—C₆H₄ | Me | Isothiazol-5-yl | 0 | |
| 1657 | 4-Me—C₆H₄ | Me | Isothiazol-5-yl | 0 | |
| 1658 | 2-Cl-pyridin-3-yl | Me | Isothiazol-5-yl | 1 | |
| 1659 | 5-CF₃-pyridin-2-yl | Me | Isothiazol-5-yl | 1 | |
| 1660 | 5-Cl-pyridin-2-yl | Me | Isothiazol-5-yl | 1 | |
| 1661 | C₆H₅ | Et | Isoxazol-3-yl | 1 | ¹H—NMR(CDCl₃) δ ppm: 1.35(1.28)(3H, t, J = 7.3), 4.31(4.26)(2H, q, J = 7.3), 5.06(4.98)(2H, s), 6.81–7.60(10H, m), 8.46(8.38)(1H, d, J = 1.8) |
| 1662 | 2-Cl—C₆H₄ | Et | Isoxazol-3-yl | 1 | |
| 1663 | 3-Cl—C₆H₄ | Et | Isoxazol-3-yl | 1 | |
| 1664 | 4-Cl—C₆H₄ | Et | Isoxazol-3-yl | 1 | |
| 1665 | 2-Me—C₆H₄ | Et | Isoxazol-3-yl | 1 | ¹H—NMR(CDCl₃) δ ppm: 1.36(1.28)(3H, t, J = 7.3), 2.20(2.18)(3H, s), 4.23–4.37(2H, m), 5.04(4.98)(2, s), 6.68–7.63(9H, m), 8.44(8.38)(1H, d, J = 1.8) |
| 1666 | 3-Me—C₆H₄ | Et | Isoxazol-3-yl | 1 | |
| 1667 | 2-Me—C₆H₄ | Allyl | Isoxazol-3-yl | 1 | ¹H—NMR(CDCl₃) δ ppm: 2.20(2.17)(3H, s), 4.69–4.78(2H, m), 5.05(4.98)(2H, s), 5.18–5.48(2H, m), 5.92–6.08(1H, m), 6.69–7.63(9H, m), 8.45(8.38)(1H, d, J = 1.8) |
| 1668 | 2-MeO—C₆H₄ | Et | Isoxazol-3-yl | 1 | |
| 1669 | 4-Br—C₆H₄ | Et | Isoxazol-3-yl | 1 | |
| 1670 | 3-CF₃—C₆H₄ | Et | Isoxazol-3-yl | 1 | |
| 1671 | 2,4-Cl₂—C₆H₃ | Et | Isoxazol-3-yl | 1 | |
| 1672 | 2,5-Cl₂—C₆H₃ | Et | Isoxazol-3-yl | 1 | |
| 1673 | 2,4-Me₂—C₆H₃ | Et | Isoxazol-3-yl | 1 | |
| 1674 | 2,5-Me₂—C₆H₃ | Et | Isoxazol-3-yl | 1 | ¹H—NMR(CDCl₃) δ ppm: 1.37(1.29)(3H, t, J = 7.3), 2.16(2.13)(3H, s), 2.25(2.22)(3H, s), 4.23–4.38(2H, m), 5.03(4.96)(2H, s ), 6.53–7.64(8H, m), 8.45(8.39)(1H, d, J = 1.8) |
| 1675 | C₆H₅ | Et | Isoxazol-3-yl | 0 | |
| 1676 | 4-Cl—C₆H₄ | Et | Isoxazol-3-yl | 0 | |
| 1677 | 4-Me—C₆H₄ | Et | Isoxazol-3-yl | 0 | |
| 1678 | 2-Cl-pyridin-3-yl | Et | Isoxazol-3-yl | 1 | |
| 1679 | 5-CF₃-pyridin-2-yl | Et | Isoxazol-3-yl | 1 | |
| 1680 | 5-Cl-pyridin-2-yl | Et | Isoxazol-3-yl | 1 | |
| 1681 | C₆H₅ | Me | 1,3,4-Thiadiazol-2-yl | 1 | |
| 1682 | 2-Cl—C₆H₄ | Me | 1,3,4-Thiadiazol-2-yl | 1 | |
| 1683 | 3-Cl—C₆H₄ | Me | 1,3,4-Thiadiazol-2-yl | 1 | |
| 1684 | 4-Cl—C₆H₄ | Me | 1,3,4-Thiadiazol-2-yl | 1 | |
| 1685 | 2-Me—C₆H₄ | Me | 1,3,4-Thiadiazol-2-yl | 1 | |
| 1686 | 3-Me—C₆H₄ | Me | 1,3,4-Thiadiazol-2-yl | 1 | |
| 1687 | 4-Me—C₆H₄ | Me | 1,3,4-Thiadiazol-2-yl | 1 | |
| 1688 | 2-MeO—C₆H₄ | Me | 1,3,4-Thiadiazol-2-yl | 1 | |
| 1689 | 4-Br—C₆H₄ | Me | 1,3,4-Thiadiazol-2-yl | 1 | |
| 1690 | 3-CF₃—C₆H₄ | Me | 1,3,4-Thiadiazol-2-yl | 1 | |
| 1691 | 2,4-Cl—C₆H₃ | Me | 1,3,4-Thiadiazol-2-yl | 1 | |

-continued

| No | R¹ | R² | R³ | n | Physical data |
|---|---|---|---|---|---|
| 1692 | 2,5-Cl$_2$—C$_6$H$_3$ | Me | 1,3,4-Thiadiazol-2-yl | 1 | |
| 1693 | 2,4-Me$_2$—C$_6$H$_3$ | Me | 1,3,4-Thiadiazol-2-yl | 1 | |
| 1694 | 2,5-Me$_2$—C$_6$H$_3$ | Me | 1,3,4-Thiadiazol-2-yl | 1 | |
| 1695 | C$_6$H$_5$ | Me | 1,3,4-Thiadiazol-2-yl | 0 | |
| 1696 | 4-Cl—C$_6$H$_4$ | Me | 1,3,4-Thiadiazol-2-yl | 0 | |
| 1697 | 4-Me—C$_6$H$_4$ | Me | 1,3,4-Thiadiazol-2-yl | 0 | |
| 1698 | 2-Cl-pyridin-3-yl | Me | 1,3,4-Thiadiazol-2-yl | 1 | |
| 1699 | 5-CF$_3$-pyridin-2-yl | Me | 1,3,4-Thiadiazol-2-yl | 1 | |
| 1700 | 5-Cl-pyridin-2-yl | Me | 1,3,4-Thiadiazol-2-yl | 1 | |
| 1701 | C$_6$H$_5$ | Me | Oxazol-2-yl | 1 | |
| 1702 | 2-Cl—C$_6$H$_4$ | Me | Oxazol-2-yl | 1 | |
| 1703 | 3-Cl—C$_6$H$_4$ | Me | Oxazol-2-yl | 1 | |
| 1704 | 4-Cl—C$_6$H$_4$ | Me | Oxazol-2-yl | 1 | |
| 1705 | 2-Me—C$_6$H$_4$ | Me | Oxazol-2-yl | 1 | |
| 1706 | 3-Me—C$_6$H$_4$ | Me | Oxazol-2-yl | 1 | |
| 1707 | 4-Me—C$_6$H$_4$ | Me | Oxazol-2-yl | 1 | |
| 1708 | 2-MeO—C$_6$H$_4$ | Me | Oxazol-2-yl | 1 | |
| 1709 | 4-Br—C$_6$H$_4$ | Me | Oxazol-2-yl | 1 | |
| 1710 | 3-CF$_3$—C$_6$H$_4$ | Me | Oxazol-2-yl | 1 | |
| 1711 | 2,4-Cl$_2$—C$_6$H$_3$ | Me | Oxazol-2-yl | 1 | |
| 1712 | 2,5-Cl$_2$—C$_6$H$_3$ | Me | Oxazol-2-yl | 1 | |
| 1713 | 2,4-Me$_2$—C$_6$H$_3$ | Me | Oxazol-2-yl | 1 | |
| 1714 | 2,5-Me$_2$—C$_6$H$_3$ | Me | Oxazol-2-yl | 1 | |
| 1715 | C$_6$H$_5$ | Me | Oxazol-2-yl | 0 | |
| 1716 | 4-Cl—C$_6$H$_4$ | Me | Oxazol-2-yl | 0 | |
| 1717 | 4-Me—C$_6$H$_4$ | Me | Oxazol-2-yl | 0 | |
| 1718 | 2-Cl-pyridin-3-yl | Me | Oxazol-2-yl | 1 | |
| 1719 | 5-CF$_3$-pyridin-2-yl | Me | Oxazol-2-yl | 1 | |
| 1720 | 5-Cl-pyridin-2-yl | Me | Oxazol-2-yl | 1 | |
| 1721 | C$_6$H$_5$ | Me | Oxazol-5-yl | 1 | $^1$H—NMR(CDCl$_3$) δ ppm: 4.00(3.85),(3H, s), 4.98(4.97)(2H, s), 6.78–7.66(10H, m), 7.92(1H, s) |
| 1722 | 2-Cl—C$_6$H$_4$ | Me | Oxazol-5-yl | 1 | |
| 1723 | 3-Cl—C$_6$H$_4$ | Me | Oxazol-5-yl | 1 | |
| 1724 | 4-Cl—C$_6$H$_4$ | Me | Oxazol-5-yl | 1 | mp 71–73° C. |
| 1725 | 2-Me—C$_6$H$_4$ | Me | Oxazol-5-yl | 1 | |
| 1726 | 3-Me—C$_6$H$_4$ | Me | Oxazol-5-yl | 1 | |
| 1727 | 4-Me—C$_6$H$_4$ | Me | Oxazol-5-yl | 1 | |
| 1728 | 2-MeO—C$_6$H$_4$ | Me | Oxazol-5-yl | 1 | |
| 1729 | 4-Br—C$_6$H$_4$ | Me | Oxazol-5-yl | 1 | |
| 1730 | 3-CF$_3$—C$_6$H$_4$ | Me | Oxazol-5-yl | 1 | $^1$H—NMR(CDCl$_3$) δ ppm: 3.99(3H, s), 5.01(2H, s), 6.88(1H, s), 6.94–7.62(8H, m), 7.93(1H, s) |
| 1731 | 2,4-Cl$_2$—C$_6$H$_3$ | Me | Oxazol-5-yl | 1 | |
| 1732 | 2,5-Cl$_2$—C$_6$H$_3$ | Me | Oxazol-5-yl | 1 | |
| 1733 | 2,4-Me$_2$—C$_6$H$_3$ | Me | Oxazol-5-yl | 1 | |
| 1734 | 2,5-Me$_2$—C$_6$H$_3$ | Me | Oxazol-5-yl | 1 | mp 90–91° C. |
| 1735 | C$_6$H$_5$ | Me | Oxazol-5-yl | 0 | mp 76.5–77.5° C. |
| 1736 | 4-Cl—C$_6$H$_4$ | Me | Oxazol-5-yl | 0 | |
| 1737 | 4-Me—C$_6$H$_4$ | Me | Oxazol-5-yl | 0 | |
| 1738 | 2-Cl-pyridin-3-yl | Me | Oxazol-5-yl | 1 | |
| 1739 | 5-CF$_3$-pyridin-2-yl | Me | Oxazol-5-yl | 1 | |
| 1740 | 5-Cl-pyridin-2-yl | Me | Oxazol-5-yl | 1 | |
| 1741 | C$_6$H$_5$ | Me | 5,5-Me$_2$-2-isoxazolin-3-yl | 1 | |
| 1742 | 2-Cl—C$_6$H$_4$ | Me | 5,5-Me$_2$-2-isoxazolin-3-yl | 1 | |
| 1743 | 3-Cl—C$_6$H$_4$ | Me | 5,5-Me$_2$-2-isoxazolin-3-yl | 1 | |
| 1744 | 4-Cl—C$_6$H$_4$ | Me | 5,5-Me$_2$-2-isoxazolin-3-yl | 1 | |
| 1745 | 2-Me—C$_6$H$_4$ | Me | 5,5-Me$_2$-2-isoxazolin-3-yl | 1 | |
| 1746 | 3-Me—C$_6$H$_4$ | Me | 5,5-Me$_2$-2-isoxazolin-3-yl | 1 | |
| 1747 | 4-Me—C$_6$H$_4$ | Me | 5,5-Me$_2$-2-isoxazolin-3-yl | 1 | |
| 1748 | 2-MeO—C$_6$H$_4$ | Me | 5,5-Me$_2$-2-isoxazolin-3-yl | 1 | |
| 1749 | 4-Br—C$_6$H$_4$ | Me | 5,5-Me$_2$-2-isoxazolin-3-yl | 1 | |
| 1750 | 2,5-Me$_2$—C$_6$H$_3$ | Et | 5,5-Me$_2$-2-isoxazolin-3-yl | 1 | $^1$H—NMR(CDCl$_3$) δ ppm: 1.25(1.33)(3H, t, J = 7.3), 1.36(1.55)(6H, s), 2.20(2.21)(3H, s), 2.27(2.26) (3H, s), 3.03–3.22(2H, m), 4.15–4.27(2H, m), 4.92–5.08(2H, m), 6.57–7.53(7H, m) |
| 1751 | 2,4-Cl$_2$—C$_6$H$_3$ | Me | 5,5-Me$_2$-2-isoxazolin-3-yl | 1 | |
| 1752 | 2,5-Cl$_2$—C$_6$H$_3$ | Me | 5,5-Me$_2$-2-isoxazolin-3-yl | 1 | |
| 1753 | 2,4-Me$_2$—C$_6$H$_3$ | Me | 5,5-Me$_2$-2-isoxazolin-3-yl | 1 | |
| 1754 | 2,5-Me$_2$—C$_6$H$_3$ | Me | 5,5-Me$_2$-2-isoxazolin-3-yl | 1 | mp 86–89° C. |
| 1755 | C$_6$H$_5$ | Me | 5,5-Me$_2$-2-isoxazolin-3-yl | 0 | |
| 1756 | 4-Cl—C$_6$H$_4$ | Me | 5,5-Me$_2$-2-isoxazolin-3-yl | 0 | |

-continued

| No | R¹ | R² | R³ | n | Physical data |
|---|---|---|---|---|---|
| 1757 | 4-Me—C₆H₄ | Me | 5,5-Me₂-2-isoxazolin-3-yl | 0 | |
| 1758 | 2-Cl-pyridin-3-yl | Me | 5,5-Me₂-2-isoxazolin-3-yl | 1 | |
| 1759 | 5-CF₃-pyridin-2-yl | Me | 5,5-Me₂-2-isoxazolin-3-yl | 1 | |
| 1760 | 5-Cl-pyridin-2-yl | Me | 5,5-Me₂-2-isoxazolin-3-yl | 1 | |
| 1761 | C₆H₅ | Et | 3-Me-isoxazol-5-yl | 1 | |
| 1762 | 2-Cl—C₆H₄ | Et | 3-Me-isoxazol-5-yl | 1 | |
| 1763 | 3-Cl—C₆H₄ | Et | 3-Me-isoxazol-5-yl | 1 | |
| 1764 | 4-Cl—C₆H₄ | Et | 3-Me-isoxazol-5-yl | 1 | Isomer A: ¹H—NMR(CDCl₃) δ ppm: 1.38(3H, t, J = 7.3), 2.16(3H, s), 2.34(3H, s), 4.37(2H, q, J = 7.3), 5.02(2H, s), 6.68–7.63(9H, m) Isomer B: ¹H—NMR(CDCl₃) δ ppm: 1.29(3H, t, J =32 7.3), 2.18(3H, s), 2.26(3H, s), 4.30(2H, q, J = 7.3), 4.97(2H, s), 5.96(1H, s), 6.70–7.67(8H, m) |
| 1765 | 2-Me—C₆H₄ | Et | 3-Me-isoxazol-5-yl | 1 | |
| 1766 | 3-Me—C₆H₄ | Et | 3-Me-isoxazol-5-yl | 1 | |
| 1767 | 4-Me—C₆H₄ | Et | 3-Me-isoxazol-5-yl | 1 | |
| 1768 | 2-MeO—C₆H₄ | Et | 3-Me-isoxazol-5-yl | 1 | |
| 1769 | 4-Br—C₆H₄ | Et | 3-Me-isoxazol-5-yl | 1 | |
| 1770 | 3-CF₃—C₆H₄ | Et | 3-Me-isoxazol-5-yl | 1 | |
| 1771 | 2,4-Cl₂—C₆H₃ | Et | 3-Me-isoxazol-5-yl | 1 | |
| 1772 | 2,5-Cl₂—C₆H₃ | Et | 3-Me-isoxazol-5-yl | 1 | |
| 1773 | 2,4-Me₂—C₆H₃ | Et | 3-Me-isoxazol-5-yl | 1 | |
| 1774 | 2,5-Me₂—C₆H₃ | Et | 3-Me-isoxazol-5-yl | 1 | |
| 1775 | C₆H₅ | Et | 3-Me-isoxazol-5-yl | 0 | |
| 1776 | 4-Cl—C₆H₄ | Et | 3-Me-isoxazol-5-yl | 0 | |
| 1777 | 4-Me—C₆H₄ | Et | 3-Me-isoxazol-5-yl | 0 | |
| 1778 | 2-Cl-pyridin-3-yl | Et | 3-Me-isoxazol-5-yl | 1 | |
| 1779 | 5-CF₃-pyridin-2-yl | Et | 3-Me-isoxazol-5-yl | 1 | |
| 1780 | 5-Cl-pyridin-2-yl | Et | 3-Me-isoxazol-5-yl | 1 | |
| 1781 | C₆H₅ | Et | 1-Me-imidazol-2-yl | 1 | |
| 1782 | 2-Cl—C₆H₄ | Et | 1-Me-imidazol-2-yl | 1 | |
| 1783 | 3-Cl—C₆H₄ | Et | 1-Me-imidazol-2-yl | 1 | |
| 1784 | 4-Cl—C₆H₄ | Et | 1-Me-imidazol-2-yl | 1 | |
| 1785 | 2-Me—C₆H₄ | Et | 1-Me-imidazol-2-yl | 1 | |
| 1786 | 3-Me—C₆H₄ | Et | 1-Me-imidazol-2-yl | 1 | |
| 1787 | 4-Me—C₆H₄ | Et | 1-Me-imidazol-2-yl | 1 | |
| 1788 | 2-MeO—C₆H₄ | Et | 1-Me-imidazol-2-yl | 1 | |
| 1789 | 4-Br—C₆H₄ | Et | 1-Me-imidazol-2-yl | 1 | |
| 1790 | 3-CF₃—C₆H₄ | Et | 1-Me-imidazol-2-yl | 1 | |
| 1791 | 2,4-Cl₂—C₆H₃ | Et | 1-Me-imidazol-2-yl | 1 | |
| 1792 | 2,5-Cl₂—C₆H₃ | Et | 1-Me-imidazol-2-yl | 1 | |
| 1793 | 2,4-Me₂—C₆H₃ | Et | 1-Me-imidazol-2-yl | 1 | |
| 1794 | 2,5-Me₂—C₆H₃ | Et | 1-Me-imidazol-2-yl | 1 | |
| 1795 | C₆H₅ | Et | 1-Me-imidazol-2-yl | 0 | |
| 1796 | 4-Cl—C₆H₄ | Et | 1-Me-imidazol-2-yl | 0 | |
| 1797 | 4-Me—C₆H₄ | Et | 1-Me-imidazol-2-yl | 0 | |
| 1798 | 2-Cl-pyridin-3-yl | Et | 1-Me-imidazol-2-yl | 1 | |
| 1799 | 5-CF₃-pyridin-2-yl | Et | 1-Me-imidazol-2-yl | 1 | |
| 1800 | 5-Cl-pyridin-2-yl | Et | 1-Me-imidazol-2-yl | 1 | |
| 1801 | Pyridin-2-yl | Me | 1-Me-2-imidazolin-2-yl | 0 | |
| 1802 | 5-Cl-pyridin-2-yl | Me | 1-Me-2-imidazolin-2-yl | 0 | |
| 1803 | 3-Cl-pyridin-2-yl | Me | 1-Me-2-imidazolin-2-yl | 0 | |
| 1804 | 6-Cl-pyridin-2-yl | Me | 1-Me-2-imidazolin-2-yl | 0 | |
| 1805 | 3,5-Cl₂-pyridin-2-yl | Me | 1-Me-2-imidazolin-2-yl | 0 | |
| 1806 | 5-CF₃-pyridin-2-yl | Me | 1-Me-2-imidazolin-2-yl | 0 | |
| 1807 | 3-CF₃-pyridin-2-yl | Me | 1-Me-2-imidazolin-2-yl | 0 | |
| 1808 | 6-CF₃-3-Cl-pyridin-2-yl | Me | 1-Me-2-imidazolin-2-yl | 0 | |
| 1809 | 5-CF₃-3-Cl-pyridin-2-yl | Me | 1-Me-2-imidazolin-2-yl | 0 | |
| 1810 | Benzothiazol-2-yl | Me | 1-Me-2-imidazolin-2-yl | 0 | |
| 1811 | Benzoxazol-2-yl | Me | 1-Me-2-imidazolin-2-yl | 0 | |
| 1812 | Quinolin-2-yl | Me | 1-Me-2-imidazolin-2-yl | 0 | |
| 1813 | 5-CF₃-1,3,4-thiadiazol-2-yl | Me | 1-Me-2-imidazolin-2-yl | 0 | |
| 1814 | Pyrimidin-2-yl | Me | 1-Me-2-imidazolin-2-yl | 0 | |
| 1815 | 6-Cl-pyrimidin-4-yl | Me | 1-Me-2-imidazolin-2-yl | 0 | |
| 1816 | 5-Et-6-Me-pyrimidin-2-yl | Me | 1-Me-2-imidazolin-2-yl | 0 | |
| 1817 | 6-Cl-pyrazin-2-yl | Me | 1-Me-2-imidazolin-2-yl | 0 | |
| 1818 | 3,6-Me₂-pyrazin-2-yl | Me | 1-Me-2-imidazolin-2-yl | 0 | |
| 1819 | 3-Ph-isoxazol-5-yl | Me | 1-Me-2-imidazolin-2-yl | 0 | |
| 1820 | 5-Me-isoxazol-3-yl | Me | 1-Me-2-imidazolin-2-yl | 0 | |
| 1821 | Pyridin-2-yl | Me | 2-Oxazolin-2-yl | 0 | |
| 1822 | 5-Cl-pyridin-2-yl | Me | 2-Oxazolin-2-yl | 0 | |
| 1823 | 3-Cl-pyridin-2-yl | Me | 2-Oxazolin-2-yl | 0 | |

-continued

| No | R¹ | R² | R³ | n | Physical data |
|---|---|---|---|---|---|
| 1824 | 6-Cl-pyridin-2-yl | Me | 2-Oxazolin-2-yl | 0 | |
| 1825 | 3,5-Cl₂-pyridin-2-yl | Me | 2-Oxazolin-2-yl | 0 | ¹H—NMR(CDCl₃) δ ppm: 3.97(4.06)(3H, s), 3.86–4.29(4H, m), 6.82–7.91(6H, m) |
| 1826 | 5-CF₃-pyridin-2-yl | Me | 2-Oxazolin-2-yl | 0 | ¹H—NMR(CDCl₃) δ ppm: 3.78(2H, t, J = 9.8), 3.98(3H, s), 4.16(2H, t, J = 9.8), 6.94–7.87(6H, m), 8.43(1H, brs) |
| 1827 | 3-CF₃-pyridin-2-yl | Me | 2-Oxazolin-2-yl | 0 | |
| 1828 | 6-CF₃-3-Cl-pyridin-2-yl | Me | 2-Oxazolin-2-yl | 0 | |
| 1829 | 5-CF₃-3-Cl-pyridin-2-yl | Me | 2-Oxazolin-2-yl | 0 | ¹H—NMR(CDCl₃) δ ppm: 3.92(2H, t, J = 9.8), 3.95(3H, s), 4.28(2H, t, J = 9.8), 7.15–7.95(5H, m), 8.22(1H, brs) |
| 1830 | Benzothiazol-2-yl | Me | 2-Oxazolin-2-yl | 0 | ¹H—NMR(CDCl₃) δ ppm: 3.84(2H, t, J = 9.8), 4.03(3H, s), 4.25(2H, t, J = 9.8), 7.23–7.74(8H, m) |
| 1831 | Benzoxazol-2-yl | Me | 2-Oxazolin-2-yl | 0 | mp 100–103° C. |
| 1832 | Quinolin-2-yl | Me | 2-Oxazolin-2-yl | 0 | |
| 1833 | 5-CF₃-1,3,4-thiadiazol-2-yl | Me | 2-Oxazolin-2-yl | 0 | |
| 1834 | Pyrimidin-2-yl | Me | 2-Oxazolin-2-yl | 0 | |
| 1835 | 6-Cl-pyrimidin-4-yl | Me | 2-Oxazolin-2-yl | 0 | mp 103–105° C. |
| 1836 | 5-Et-6-Me-pyrimidin-2-yl | Me | 2-Oxazolin-2-yl | 0 | |
| 1837 | 6-Cl-pyrazin-2-yl | Me | 2-Oxazolin-2-yl | 0 | |
| 1838 | 3,6-Me₂-pyrazin-2-yl | Me | 2-Oxazolin-2-yl | 0 | |
| 1839 | 3-Ph-isoxazol-5-yl | Me | 2-Oxazolin-2-yl | 0 | |
| 1840 | 5-Me-isoxazol-3-yl | Me | 2-Oxazolin-2-yl | 0 | |
| 1841 | Pyridin-2-yl | Me | 2-Isoxazolin-3-yl | 0 | |
| 1842 | 5-Cl-pyridin-2-yl | Me | 2-Isoxazolin-3-yl | 0 | |
| 1843 | 3-Cl-pyridin-2-yl | Me | 2-Isoxazolin-3-yl | 0 | |
| 1844 | 6-Cl-pyridin-2-yl | Me | 2-Isoxazolin-3-yl | 0 | |
| 1845 | 3,5-Cl₂-pyridin-2-yl | Me | 2-Isoxazolin-3-yl | 0 | |
| 1846 | 5-CF₃-pyridin-2-yl | Me | 2-Isoxazolin-3-yl | 0 | |
| 1847 | 3-CF₃-pyridin-2-yl | Me | 2-Isoxazolin-3-yl | 0 | |
| 1848 | 6-CF₃-3-Cl-pyridin-2-yl | Me | 2-Isoxazolin-3-yl | 0 | |
| 1849 | 5-CF₃-3-Cl-pyridin-2-yl | Me | 2-Isoxazolin-3-yl | 0 | |
| 1850 | Benzothiazol-2-yl | Me | 2-Isoxazolin-3-yl | 0 | |
| 1851 | Benzoxazol-2-yl | Me | 2-Isoxazolin-3-yl | 0 | |
| 1852 | Quinolin-2-yl | Me | 2-Isoxazolin-3-yl | 0 | |
| 1853 | 5-CF₃-1,3,4-thiadiazol-2-yl | Me | 2-Isoxazolin-3-yl | 0 | |
| 1854 | Pyrimidin-2-yl | Me | 2-Isoxazolin-3-yl | 0 | |
| 1855 | 6-Cl-pyrimidin-4-yl | Me | 2-Isoxazolin-3-yl | 0 | |
| 1856 | 5-Et-6-Me-pyrimidin-2-yl | Me | 2-Isoxazolin-3-yl | 0 | |
| 1857 | 6-Cl-pyrazin-2-yl | Me | 2-Isoxazolin-3-yl | 0 | |
| 1858 | 3,6-Me₂-pyrazin-2-yl | Me | 2-Isoxazolin-3-yl | 0 | |
| 1859 | 3-Ph-isoxazol-5-yl | Me | 2-Isoxazolin-3-yl | 0 | |
| 1860 | 5-Me-isoxazol-3-yl | Me | 2-Isoxazolin-3-yl | 0 | |
| 1861 | Pyridin-2-yl | Me | 3-Me-isoxazol-5-yl | 0 | |
| 1862 | 5-Cl-pyridin-2-yl | Me | 3-Me-isoxazol-5-yl | 0 | |
| 1863 | 3-Cl-pyridin-2-yl | Me | 3-Me-isoxazol-5-yl | 0 | |
| 1864 | 6-Cl-pyridin-2-yl | Me | 3-Me-isoxazol-5-yl | 0 | |
| 1865 | 3,5-Cl₂-pyridin-2-yl | Me | 3-Me-isoxazol-5-yl | 0 | |
| 1866 | 5-CF₃-pyridin-2-yl | Me | 3-Me-isoxazol-5-yl | 0 | |
| 1867 | 3-CF₃-pyridin-2-yl | Me | 3-Me-isoxazol-5-yl | 0 | |
| 1868 | 6-CF₃-3-Cl-pyridin-2-yl | Me | 3-Me-isoxazol-5-yl | 0 | |
| 1869 | 5-CF₃-3-Cl-pyridin-2-yl | Me | 3-Me-isoxazol-5-yl | 0 | |
| 1870 | Benzothiazol-2-yl | Me | 3-Me-isoxazol-5-yl | 0 | |
| 1871 | Benzoxazol-2-yl | Me | 3-Me-isoxazol-5-yl | 0 | |
| 1872 | Quinolin-2-yl | Me | 3-Me-isoxazol-5-yl | 0 | |
| 1873 | 5-CF₃-1,3,4-thiadiazol-2-yl | Me | 3-Me-isoxazol-5-yl | 0 | |
| 1874 | Pyrimidin-2-yl | Me | 3-Me-isoxazol-5-yl | 0 | |
| 1875 | 6-Cl-pyrimidin-4-yl | Me | 3-Me-isoxazol-5-yl | 0 | |
| 1876 | 5-Et-6-Me-pyrimidin-2-yl | Me | 3-Me-isoxazol-5-yl | 0 | |
| 1877 | 6-Cl-pyrazin-2-yl | Me | 3-Me-isoxazol-5-yl | 0 | |
| 1878 | 3,6-Me₂-pyrazin-2-yl | Me | 3-Me-isoxazol-5-yl | 0 | |
| 1879 | 3-Ph-isoxazol-5-yl | Me | 3-Me-isoxazol-5-yl | 0 | |
| 1880 | 5-Me-isoxazol-3-yl | Me | 3-Me-isoxazol-5-yl | 0 | |
| 1881 | Pyridin-2-yl | Me | 1-Me-imidazol-2-yl | 0 | |
| 1882 | 5-Cl-pyridin-2-yl | Me | 1-Me-imidazol-2-yl | 0 | |
| 1883 | 3-Cl-pyridin-2-yl | Me | 1-Me-imidazol-2-yl | 0 | |
| 1884 | 6-Cl-pyridin-2-yl | Me | 1-Me-imidazol-2-yl | 0 | |
| 1885 | 3,5-Cl₂-pyridin-2-yl | Me | 1-Me-imidazol-2-yl | 0 | |
| 1886 | 5-CF₃-pyridin-2-yl | Me | 1-Me-imidazol-2-yl | 0 | |
| 1887 | 3-CF₃-pyridin-2-yl | Me | 1-Me-imidazol-2-yl | 0 | |
| 1888 | 6-CF₃-3-Cl-pyridin-2-yl | Me | 1-Me-imidazol-2-yl | 0 | |
| 1889 | 5-CF₃-3-Cl-pyridin-2-yl | Me | 1-Me-imidazol-2-yl | 0 | |

| No | R¹ | R² | R³ | n | Physical data |
|---|---|---|---|---|---|
| 1890 | Benzothiazol-2-yl | Me | 1-Me-imidazol-2-yl | 0 | |
| 1891 | Benzoxazol-2-yl | Me | 1-Me-imidazol-2-yl | 0 | |
| 1892 | Quinolin-2-yl | Me | 1-Me-imidazol-2-yl | 0 | |
| 1893 | 5-CF$_3$-1,3,4-thiadiazol-2-yl | Me | 1-Me-imidazol-2-yl | 0 | |
| 1894 | Pyrimidin-2-yl | Me | 1-Me-imidazol-2-yl | 0 | |
| 1895 | 6-Cl-pyrimidin-4-yl | Me | 1-Me-imidazol-2-yl | 0 | |
| 1896 | 5-Et-6-Me-pyrimidin-2-yl | Me | 1-Me-imidazol-2-yl | 0 | |
| 1897 | 6-Cl-pyrazin-2-yl | Me | 1-Me-imidazol-2-yl | 0 | |
| 1898 | 3,6-Me$_2$-pyrazin-2-yl | Me | 1-Me-imidazol-2-yl | 0 | |
| 1899 | 3-Ph-isoxazol-5-yl | Me | 1-Me-imidazol-2-yl | 0 | |
| 1900 | 5-Me-isoxazol-3-yl | Me | 1-Me-imidazol-2-yl | 0 | |
| 1901 | Pyridin-2-yl | Me | Isoxazol-3-yl | 0 | |
| 1902 | 5-Cl-pyridin-2-yl | Me | Isoxazol-3-yl | 0 | |
| 1903 | 3-Cl-pyridin-2-yl | Me | Isoxazol-3-yl | 0 | |
| 1904 | 6-Cl-pyridin-2-yl | Me | Isoxazol-3-yl | 0 | |
| 1905 | 3,5-Cl$_2$-pyridin-2-yl | Me | Isoxazol-3-yl | 0 | |
| 1906 | 5-CF$_3$-pyridin-2-yl | Me | Isoxazol-3-yl | 0 | |
| 1907 | 3-CF$_3$-pyridin-2-yl | Me | Isoxazol-3-yl | 0 | |
| 1908 | 6-CF$_3$-3-Cl-pyridin-2-yl | Me | Isoxazol-3-yl | 0 | |
| 1909 | 5-CF$_3$-3-Cl-pyridin-2-yl | Me | Isoxazol-3-yl | 0 | |
| 1910 | Benzothiazol-2-yl | Me | Isoxazol-3-yl | 0 | |
| 1911 | Benzoxazol-2-yl | Me | Isoxazol-3-yl | 0 | |
| 1912 | Quinolin-2-yl | Me | Isoxazol-3-yl | 0 | |
| 1913 | 5-CF$_3$-1,3,4-thiadiazol-2-yl | Me | Isoxazol-3-yl | 0 | |
| 1914 | Pyrimidin-2-yl | Me | Isoxazol-3-yl | 0 | |
| 1915 | 6-Cl-pyrimidin-4-yl | Me | Isoxazol-3-yl | 0 | |
| 1916 | 5-Et-6-Me-pyrimidin-2-yl | Me | Isoxazol-3-yl | 0 | |
| 1917 | 6-Cl-pyrazin-2-yl | Me | Isoxazol-3-yl | 0 | |
| 1918 | 3,6-Me$_2$-pyrazin-2-yl | Me | Isoxazol-3-yl | 0 | |
| 1919 | 3-Ph-isoxazol-5-yl | Me | Isoxazol-3-yl | 0 | |
| 1920 | 5-Me-isoxazol-3-yl | Me | Isoxazol-3-yl | 0 | |
| 1921 | Pyridin-2-yl | Me | 5-Me-isoxazol-3-yl | 0 | |
| 1922 | 5-Cl-pyridin-2-yl | Me | 5-Me-isoxazol-3-yl | 0 | |
| 1923 | 3-Cl-pyridin-2-yl | Me | 5-Me-isoxazol-3-yl | 0 | |
| 1924 | 6-Cl-pyridin-2-yl | Me | 5-Me-isoxazol-3-yl | 0 | |
| 1925 | 3,5-Cl$_2$-pyridin-2-yl | Me | 5-Me-isoxazol-3-yl | 0 | |
| 1926 | 5-CF$_3$-pyridin-2-yl | Me | 5-Me-isoxazol-3-yl | 0 | |
| 1927 | 3-CF$_3$-pyridin-2-yl | Me | 5-Me-isoxazol-3-yl | 0 | |
| 1928 | 6-CF$_3$-3-Cl-pyridin-2-yl | Me | 5-Me-isoxazol-3-yl | 0 | |
| 1929 | 5-CF$_3$-3-Cl-pyridin-2-yl | Me | 5-Me-isoxazol-3-yl | 0 | |
| 1930 | Benzothiazol-2-yl | Me | 5-Me-isoxazol-3-yl | 0 | |
| 1931 | Benzoxazol-2-yl | Me | 5-Me-isoxazol-3-yl | 0 | |
| 1932 | Quinolin-2-yl | Me | 5-Me-isoxazol-3-yl | 0 | |
| 1933 | 5-CF$_3$-1,3,4-thiadiazol-2-yl | Me | 5-Me-isoxazol-3-yl | 0 | |
| 1934 | Pyrimidin-2-yl | Me | 5-Me-isoxazol-3-yl | 0 | |
| 1935 | 6-Cl-pyrimidin-4-yl | Me | 5-Me-isoxazol-3-yl | 0 | |
| 1936 | 5-Et-6-Me-pyrimidin-2-yl | Me | 5-Me-isoxazol-3-yl | 0 | |
| 1937 | 6-Cl-pyrazin-2-yl | Me | 5-Me-isoxazol-3-yl | 0 | |
| 1938 | 3,6-Me$_2$-pyrazin-2-yl | Me | 5-Me-isoxazol-3-yl | 0 | |
| 1939 | 3-Ph-isoxazol-5-yl | Me | 5-Me-isoxazol-3-yl | 0 | |
| 1940 | 5-Me-isoxazol-3-yl | Me | 5-Me-isoxazol-3-yl | 0 | |
| 1941 | Pyridin-2-yl | Me | 1,2,4-Oxadiazol-3-yl | 0 | |
| 1942 | 5-Cl-pyridin-2-yl | Me | 1,2,4-Oxadiazol-3-yl | 0 | |
| 1943 | 3-Cl-pyridin-2-yl | Me | 1,2,4-Oxadiazol-3-yl | 0 | |
| 1944 | 6-Cl-pyridin-2-yl | Me | 1,2,4-Oxadiazol-3-yl | 0 | |
| 1945 | 3,5-Cl$_2$-pyridin-2-yl | Me | 1,2,4-Oxadiazol-3-yl | 0 | |
| 1946 | 5-CF$_3$-pyridin-2-yl | Me | 1,2,4-Oxadiazol-3-yl | 0 | |
| 1947 | 3-CF$_3$-pyridin-2-yl | Me | 1,2,4-Oxadiazol-3-yl | 0 | |
| 1948 | 6-CF$_3$-3-Cl-pyridin-2-yl | Me | 1,2,4-Oxadiazol-3-yl | 0 | |
| 1949 | 5-CF$_3$-3-Cl-pyridin-2-yl | Me | 1,2,4-Oxadiazol-3-yl | 0 | |
| 1950 | Benzothiazol-2-yl | Me | 1,2,4-Oxadiazol-3-yl | 0 | |
| 1951 | Benzoxazol-2-yl | Me | 1,2,4-Oxadiazol-3-yl | 0 | |
| 1952 | Quinolin-2-yl | Me | 1,2,4-Oxadiazol-3-yl | 0 | |
| 1953 | 5-CF$_3$-1,3,4-thiadiazol-2-yl | Me | 1,2,4-Oxadiazol-3-yl | 0 | |
| 1954 | Pyrimidin-2-yl | Me | 1,2,4-Oxadiazol-3-yl | 0 | |
| 1955 | 6-Cl-pyrimidin-4-yl | Me | 1,2,4-Oxadiazol-3-yl | 0 | |
| 1956 | 5-Et-6-Me-pyrimidin-2-yl | Me | 1,2,4-Oxadiazol-3-yl | 0 | |
| 1957 | 6-Cl-pyrazin-2-yl | Me | 1,2,4-Oxadiazol-3-yl | 0 | |
| 1958 | 3,6-Me$_2$-pyrazin-2-yl | Me | 1,2,4-Oxadiazol-3-yl | 0 | |
| 1959 | 3-Ph-isoxazol-5-yl | Me | 1,2,4-Oxadiazol-3-yl | 0 | |
| 1960 | 5-Me-isoxazol-3-yl | Me | 1,2,4-Oxadiazol-3-yl | 0 | |
| 1961 | Pyridin-2-yl | Me | 5-Me-1,2,4-oxadiazol-3-yl | 0 | |
| 1962 | 5-Cl-pyridin-2-yl | Me | 5-Me-1,2,4-oxadiazol-3-yl | 0 | |
| 1963 | 3-Cl-pyridin-2-yl | Me | 5-Me-1,2,4-oxadiazol-3-yl | 0 | |
| 1964 | 6-Cl-pyridin-2-yl | Me | 5-Me-1,2,4-oxadiazol-3-yl | 0 | |
| 1965 | 3,5-Cl$_2$-pyridin-2-yl | Me | 5-Me-1,2,4-oxadiazol-3-yl | 0 | |
| 1966 | 5-CF$_3$-pyridin-2-yl | Me | 5-Me-1,2,4-oxadiazol-3-yl | 0 | |

-continued

| No | R¹ | R² | R³ | n | Physical data |
|---|---|---|---|---|---|
| 1967 | 3-CF₃-pyridin-2-yl | Me | 5-Me-1,2,4-oxadiazol-3-yl | 0 | |
| 1968 | 6-CF₃-3-Cl-pyridin-2-yl | Me | 5-Me-1,2,4-oxadiazol-3-yl | 0 | |
| 1969 | 5-CF₃-3-Cl-pyridin-2-yl | Me | 5-Me-1,2,4-oxadiazol-3-yl | 0 | |
| 1970 | Benzothiazol-2-yl | Me | 5-Me-1,2,4-oxadiazol-3-yl | 0 | |
| 1971 | Benzoxazol-2-yl | Me | 5-Me-1,2,4-oxadiazol-3-yl | 0 | |
| 1972 | Quinolin-2-yl | Me | 5-Me-1,2,4-oxadiazol-3-yl | 0 | |
| 1973 | 5-CF₃-1,3,4-thiadiazol-2-yl | Me | 5-Me-1,2,4-oxadiazol-3-yl | 0 | |
| 1974 | Pyrimidin-2-yl | Me | 5-Me-1,2,4-oxadiazol-3-yl | 0 | |
| 1975 | 6-Cl-pyrimidin-4-yl | Me | 5-Me-1,2,4-oxadiazol-3-yl | 0 | |
| 1976 | 5-Et-6-Me-pyrimidin-2-yl | Me | 5-Me-1,2,4-oxadiazol-3-yl | 0 | |
| 1977 | 6-Cl-pyrazin-2-yl | Me | 5-Me-1,2,4-oxadiazol-3-yl | 0 | |
| 1978 | 3,6-Me₂-pyrazin-2-yl | Me | 5-Me-1,2,4-oxadiazol-3-yl | 0 | |
| 1979 | 3-Ph-isoxazol-5-yl | Me | 5-Me-1,2,4-oxadiazol-3-yl | 0 | |
| 1980 | 5-Me-isoxazol-3-yl | Me | 5-Me-1,2,4-oxadiazol-3-yl | 0 | |
| 1981 | Pyridin-2-yl | Me | 1,3,4-Oxadiazol-2-yl | 0 | |
| 1982 | 5-Cl-pyridin-2-yl | Me | 1,3,4-Oxadiazol-2-yl | 0 | |
| 1983 | 3-Cl-pyridin-2-yl | Me | 1,3,4-Oxadiazol-2-yl | 0 | |
| 1984 | 6-Cl-pyridin-2-yl | Me | 1,3,4-Oxadiazol-2-yl | 0 | |
| 1985 | 3,5-Cl₂-pyridin-2-yl | Me | 1,3,4-Oxadiazol-2-yl | 0 | |
| 1986 | 5-CF₃-pyridin-2-yl | Me | 1,3,4-Oxadiazol-2-yl | 0 | |
| 1987 | 3-CF₃-pyridin-2-yl | Me | 1,3,4-Oxadiazol-2-yl | 0 | |
| 1988 | 6-CF₃-3-Cl-pyridin-2-yl | Me | 1,3,4-Oxadiazol-2-yl | 0 | |
| 1989 | 5-CF₃-3-Cl-pyridin-2-yl | Me | 1,3,4-Oxadiazol-2-yl | 0 | |
| 1990 | Benzothiazol-2-yl | Me | 1,3,4-Oxadiazol-2-yl | 0 | |
| 1991 | Benzoxazol-2-yl | Me | 1,3,4-Oxadiazol-2-yl | 0 | |
| 1992 | Quinolin-2-yl | Me | 1,3,4-Oxadiazol-2-yl | 0 | |
| 1993 | 5-CF₃-1,3,4-thiadiazol-2-yl | Me | 1,3,4-Oxadiazol-2-yl | 0 | |
| 1994 | Pyrimidin-2-yl | Me | 1,3,4-Oxadiazol-2-yl | 0 | |
| 1995 | 6-Cl-pyrimidin-4-yl | Me | 1,3,4-Oxadiazol-2-yl | 0 | |
| 1996 | 5-Et-6-Me-pyrimidin-2-yl | Me | 1,3,4-Oxadiazol-2-yl | 0 | |
| 1997 | 6-Cl-pyrazin-2-yl | Me | 1,3,4-Oxadiazol-2-yl | 0 | |
| 1998 | 3,6-Me₂-pyrazin-2-yl | Me | 1,3,4-Oxadiazol-2-yl | 0 | |
| 1999 | 3-Ph-isoxazol-5-yl | Me | 1,3,4-Oxadiazol-2-yl | 0 | |
| 2000 | 5-Me-isoxazol-3-yl | Me | 1,3,4-Oxadiazol-2-yl | 0 | |
| 2001 | C₆H₅ | Me | 2-Me-2H-tetrazol-5-yl | 1 | mp 63.0–66.0° C. |
| 2002 | 2-F—C₆H₄ | Me | 2-Me-2H-tetrazol-5-yl | 1 | |
| 2003 | 3-F—C₆H₄ | Me | 2-Me-2H-tetrazol-5-yl | 1 | |
| 2004 | 4-F—C₆H₄ | Me | 2-Me-2H-tetrazol-5-yl | 1 | |
| 2005 | 2-Cl—C₆H₄ | Me | 2-Me-2H-tetrazol-5-yl | 1 | mp 122–123° C. |
| 2006 | 3-Cl—C₆H₄ | Me | 2-Me-2H-tetrazol-5-yl | 1 | |
| 2007 | 4-Cl—C₆H₄ | Me | 2-Me-2H-tetrazol-5-yl | 1 | mp 120–121.5° C. |
| 2008 | 2-Br—C₆H₄ | Me | 2-Me-2H-tetrazol-5-yl | 1 | |
| 2009 | 3-Br—C₆H₄ | Me | 2-Me-2H-tetrazol-5-yl | 1 | |
| 2010 | 4-Br—C₆H₄ | Me | 2-Me-2H-tetrazol-5-yl | 1 | |
| 2011 | 3-I—C₆H₄ | Me | 2-Me-2H-tetrazol-5-yl | 1 | |
| 2012 | 2-Me—C₆H₄ | Me | 2-Me-2H-tetrazol-5-yl | 1 | mp 118–119° C. |
| 2013 | 3-Me—C₆H₄ | Me | 2-Me-2H-tetrazol-5-yl | 1 | |
| 2014 | 4-Me—C₆H₄ | Me | 2-Me-2H-tetrazol-5-yl | 1 | mp 102.0–103.0° C. |
| 2015 | 2-Et—C₆H₄ | Me | 2-Me-2H-tetrazol-5-yl | 1 | |
| 2016 | 3-Et—C₆H₄ | Me | 2-Me-2H-tetrazol-5-yl | 1 | |
| 2017 | 4-Et—C₆H₄ | Me | 2-Me-2H-tetrazol-5-yl | 1 | |
| 2018 | 2-MeO—C₆H₄ | Me | 2-Me-2H-tetrazol-5-yl | 1 | |
| 2019 | 3-MeO—C₆H₄ | Me | 2-Me-2H-tetrazol-5-yl | 1 | |
| 2020 | 4-MeO—C₆H₄ | Me | 2-Me-2H-tetrazol-5-yl | 1 | |
| 2021 | 2-CF₃—C₆H₄ | Me | 2-Me-2H-tetrazol-5-yl | 1 | |
| 2022 | 3-CF₃—C₆H₄ | Me | 2-Me-2H-tetrazol-5-yl | 1 | |
| 2023 | 4-CF₃—C₆H₄ | Me | 2-Me-2H-tetrazol-5-yl | 1 | |
| 2024 | 2,4-F₂—C₆H₃ | Me | 2-Me-2H-tetrazol-5-yl | 1 | |
| 2025 | 2,5-F₂—C₆H₃ | Me | 2-Me-2H-tetrazol-5-yl | 1 | |
| 2026 | 2,6-F₂—C₆H₃ | Me | 2-Me-2H-tetrazol-5-yl | 1 | |
| 2027 | 3,4-F₂—C₆H₃ | Me | 2-Me-2H-tetrazol-5-yl | 1 | |
| 2028 | 3,5-F₂—C₆H₃ | Me | 2-Me-2H-tetrazol-5-yl | 1 | |
| 2029 | 2,3-Cl₂—C₆H₃ | Me | 2-Me-2H-tetrazol-5-yl | 1 | |
| 2030 | 2,4-Cl₂—C₆H₃ | Me | 2-Me-2H-tetrazol-5-yl | 1 | |
| 2031 | 2,5-Cl₂—C₆H₃ | Me | 2-Me-2H-tetrazol-5-yl | 1 | |
| 2032 | 3,4-Cl₂—C₆H₃ | Me | 2-Me-2H-tetrazol-5-yl | 1 | |
| 2033 | 3,5-Cl₂—C₆H₃ | Me | 2-Me-2H-tetrazol-5-yl | 1 | |
| 2034 | 2,3-Me₂—C₆H₃ | Me | 2-Me-2H-tetrazol-5-yl | 1 | |
| 2035 | 2,4-Me₂—C₆H₃ | Me | 2-Me-2H-tetrazol-5-yl | 1 | |
| 2036 | 2,5-Me₂—C₆H₃ | Me | 2-Me-2H-tetrazol-5-yl | 1 | |
| 2037 | 3,4-Me₂—C₆H₃ | Me | 2-Me-2H-tetrazol-5-yl | 1 | |
| 2038 | 3,5-Me₂—C₆H₃ | Me | 2-Me-2H-tetrazol-5-yl | 1 | |
| 2039 | 2-Cl-4-Me—C₆H₃ | Me | 2-Me-2H-tetrazol-5-yl | 1 | |
| 2040 | 2-Cl-5-Me—C₆H₃ | Me | 2-Me-2H-tetrazol-5-yl | 1 | |
| 2041 | 4-Cl-2-Me—C₆H₃ | Me | 2-Me-2H-tetrazol-5-yl | 1 | |
| 2042 | 4-Cl-3-Me—C₆H₃ | Me | 2-Me-2H-tetrazol-5-yl | 1 | |
| 2043 | 3-Ph—C₆H₄ | Me | 2-Me-2H-tetrazol-5-yl | 1 | |

-continued

| No | R¹ | R² | R³ | n | Physical data |
|---|---|---|---|---|---|
| 2044 | 4-Ph—C₆H₄ | Me | 2-Me-2H-tetrazol-5-yl | 1 | |
| 2045 | 3-i—PrO—C₆H₄ | Me | 2-Me-2H-tetrazol-5-yl | 1 | |
| 2046 | 3-i—Pr—C₆H₄ | Me | 2-Me-2H-tetrazol-5-yl | 1 | |
| 2047 | 4-i—Pr—C₆H₄ | Me | 2-Me-2H-tetrazol-5-yl | 1 | |
| 2048 | 3-t—Bu—C₆H₄ | Me | 2-Me-2H-tetrazol-5-yl | 1 | |
| 2049 | 2-MeS—C₆H₄ | Me | 2-Me-2H-tetrazol-5-yl | 1 | |
| 2050 | 4-MeS—C₆H₄ | Me | 2-Me-2H-tetrazol-5-yl | 1 | |
| 2051 | 2,3,6-F₃—C₆H₂ | Me | 2-Me-2H-tetrazol-5-yl | 1 | |
| 2052 | 2,4,5-Cl₃—C₆H₂ | Me | 2-Me-2H-tetrazol-5-yl | 1 | |
| 2053 | 3-PhO—C₆H₂ | Me | 2-Me-2H-tetrazol-5-yl | 1 | |
| 2054 | 3,4,5-(MeO)₃—C₆H₂ | Me | 2-Me-2H-tetrazol-5-yl | 1 | |
| 2055 | 2,3,5-Me₃—C₆H₂ | Me | 2-Me-2H-tetrazol-5-yl | 1 | |
| 2056 | 3,4,5-Me₃—C₆H₂ | Me | 2-Me-2H-tetrazol-5-yl | 1 | |
| 2057 | C₆F₅ | Me | 2-Me-2H-tetrazol-5-yl | 1 | |
| 2058 | 4-Cl-3-Et—C₆H₃ | Me | 2-Me-2H-tetrazol-5-yl | 1 | |
| 2059 | 3-EtO—C₆H₄ | Me | 2-Me-2H-tetrazol-5-yl | 1 | |
| 2060 | 4-EtO—C₆H₄ | Me | 2-Me-2H-tetrazol-5-yl | 1 | |
| 2061 | C₆H₅ | Me | 2-Me-2H-tetrazol-5-yl | 0 | |
| 2062 | 4-F—C₆H₄ | Me | 2-Me-2H-tetrazol-5-yl | 0 | |
| 2063 | 3-Cl—C₆H₄ | Me | 2-Me-2H-tetrazol-5-yl | 0 | |
| 2064 | 4-Cl—C₆H₄ | Me | 2-Me-2H-tetrazol-5-yl | 0 | |
| 2065 | 3-Me—C₆H₄ | Me | 2-Me-2H-tetrazol-5-yl | 0 | |
| 2066 | 4-Me—C₆H₄ | Me | 2-Me-2H-tetrazol-5-yl | 0 | |
| 2067 | 4-Et—C₆H₄ | Me | 2-Me-2H-tetrazol-5-yl | 0 | |
| 2068 | 4-NO₂—C₆H₄ | Me | 2-Me-2H-tetrazol-5-yl | 0 | |
| 2069 | 3,4-Cl₂—C₆H₃ | Me | 2-Me-2H-tetrazol-5-yl | 0 | |
| 2070 | 3,5-Cl₂—C₆H₃ | Me | 2-Me-2H-tetrazol-5-yl | 0 | |
| 2071 | 3,4-Me₂—C₆H₃ | Me | 2-Me-2H-tetrazol-5-yl | 0 | |
| 2072 | 3,5-Me₂—C₆H₃ | Me | 2-Me-2H-tetrazol-5-yl | 0 | |
| 2073 | 3-PhO—C₆H₄ | Me | 2-Me-2H-tetrazol-5-yl | 0 | |
| 2074 | 4-Cl-3-Et—C₆H₃ | Me | 2-Me-2H-tetrazol-5-yl | 0 | |
| 2075 | 3-EtO—C₆H₄ | Me | 2-Me-2H-tetrazol-5-yl | 0 | |
| 2076 | 3-CF₃—C₆H₄ | Me | 2-Me-2H-tetrazol-5-yl | 0 | |
| 2077 | 4-CF₃—C₆H₄ | Me | 2-Me-2H-tetrazol-5-yl | 0 | |
| 2078 | 3-i—PrO—C₆H₄ | Me | 2-Me-2H-tetrazol-5-yl | 0 | |
| 2079 | 3-i—Pr—C₆H₄ | Me | 2-Me-2H-tetrazol-5-yl | 0 | |
| 2080 | 4-Cl-3-Me—C₆H₃ | Me | 2-Me-2H-tetrazol-5-yl | 0 | |
| 2081 | Pyridin-2-yl | Me | 2-Me-2H-tetrazol-5-yl | 1 | |
| 2082 | Pyridin-3-yl | Me | 2-Me-2H-tetrazol-5-yl | 1 | |
| 2083 | 5-Cl-pyridin-2-yl | Me | 2-Me-2H-tetrazol-5-yl | 1 | |
| 2084 | 3-Cl-pyridin-2-yl | Me | 2-Me-2H-tetrazol-5-yl | 1 | |
| 2085 | 6-Cl-pyridin-2-yl | Me | 2-Me-2H-tetrazol-5-yl | 1 | |
| 2086 | 2-Cl-pyridin-3-yl | Me | 2-Me-2H-tetrazol-5-yl | 1 | |
| 2087 | 5-CF₃-pyridin-3-yl | Me | 2-Me-2H-tetrazol-5-yl | 1 | |
| 2088 | 3-CF₃-pyridin-2-yl | Me | 2-Me-2H-tetrazol-5-yl | 1 | |
| 2089 | 6-CF₃-3-Cl-pyridin-2-yl | Me | 2-Me-2H-tetrazol-5-yl | 1 | |
| 2090 | 5-CF₃-3-Cl-pyridin-2-yl | Me | 2-Me-2H-tetrazol-5-yl | 1 | |
| 2091 | Benzothiazol-2-yl | Me | 2-Me-2H-tetrazol-5-yl | 1 | |
| 2092 | Benzoxazol-2-yl | Me | 2-Me-2H-tetrazol-5-yl | 1 | |
| 2093 | Quinolin-2-yl | Me | 2-Me-2H-tetrazol-5-yl | 1 | |
| 2094 | 5-CF₃-1,3,4-thiadiazol-2-yl | Me | 2-Me-2H-tetrazol-5-yl | 1 | |
| 2095 | Pyrimidin-2-yl | Me | 2-Me-2H-tetrazol-5-yl | 1 | |
| 2096 | 5-Cl-6-Me-pyrimidin-4-yl | Me | 2-Me-2H-tetrazol-5-yl | 1 | |
| 2097 | 5-Et-6-Me-pyrimidin-4-yl | Me | 2-Me-2H-tetrazol-5-yl | 1 | |
| 2098 | 6-Cl-pyrazin-2-yl | Me | 2-Me-2H-tetrazol-5-yl | 1 | |
| 2099 | 3,6-Me₂-prazin-2-yl | Me | 2-Me-2H-tetrazol-5-yl | 1 | |
| 2100 | 5-Me-isoxazol-3-yl | Me | 2-Me-2H-tetrazol-5-yl | 1 | |

| No | R¹ | R³ | R⁴ | n | Physical data |
|---|---|---|---|---|---|
| 2101 | C₆H₅ | 1,2,4-Oxadiazol-3-yl | 5-Cl | 1 | |
| 2102 | 2-Cl—C₆H₄ | 1,2,4-Oxadiazol-3-yl | 5-Cl | 1 | |
| 2103 | 2-Me—C₆H₄ | 1,2,4-Oxadiazol-3-yl | 5-Cl | 1 | |
| 2104 | 2,5-Me₂—C₆H₃ | 1,2,4-Oxadiazol-3-yl | 5-Cl | 1 | |
| 2105 | 4-Cl-2-Me—C₆H₃ | 1,2,4-Oxadiazol-3-yl | 5-Cl | 1 | |
| 2106 | 4-Cl—C₆H₄ | 1,2,4-Oxadiazol-3-yl | 5-Cl | 0 | |
| 2107 | 4-Me—C₆H₄ | 1,2,4-Oxadiazol-3-yl | 5-Cl | 0 | |
| 2108 | C₆H₅ | 1,2,4-Oxadiazol-3-yl | 5-Cl | 0 | |
| 2109 | 5-CF₃-pyridin-2-yl | 1,2,4-Oxadiazol-3-yl | 5-Cl | 1 | |
| 2110 | 5-CF₃-pyridin-2-yl | 1,2,4-Oxadiazol-3-yl | 5-Cl | 0 | |
| 2111 | C₆H₅ | 5-Me-1,2,4-oxadiazol-3-yl | 5-Cl | 1 | |
| 2112 | 2-Cl—C₆H₄ | 5-Me-1,2,4-oxadiazol-3-yl | 5-Cl | 1 | |
| 2113 | 2-Me—C₆H₄ | 5-Me-1,2,4-oxadiazol-3-yl | 5-Cl | 1 | |
| 2114 | 2,5-Me₂—C₆H₃ | 5-Me-1,2,4-oxadiazol-3-yl | 5-Cl | 1 | |
| 2115 | 4-Cl-2-Me—C₆H₃ | 5-Me-1,2,4-oxadiazol-3-yl | 5-Cl | 1 | |
| 2116 | 4-Cl—C₆H₄ | 5-Me-1,2,4-oxadiazol-3-yl | 5-Cl | 0 | |
| 2117 | 4-Me—C₆H₄ | 5-Me-1,2,4-oxadiazol-3-yl | 5-Cl | 0 | |

-continued

| No | R¹ | R² | R³ | n | Physical data |
|---|---|---|---|---|---|
| 2118 | C₆H₅ | 5-Me-1,2,4-oxadiazol-3-yl | 5-Cl | 0 | |
| 2119 | 5-CF₃-pyridin-2-yl | 5-Me-1,2,4-oxadiazol-3-yl | 5-Cl | 1 | |
| 2120 | 5-CF₃-pyridin-2-yl | 5-Me-1,2,4-oxadiazol-3-yl | 5-Cl | 0 | ¹H—NMR(CDCl₃) δ ppm: 2.46(3H, s), 4.03(3H, s), 6.77(1H, d, J = 9.2), 7.16(1H, d, J = 9.2), 7.44–7.86(3H, m), 8.36(1H, d, J = 1.8) |
| 2121 | C₆H₅ | Isoxazol-3-yl | 5-Cl | 1 | |
| 2122 | 2-Cl—C₆H₄ | Isoxazol-3-yl | 5-Cl | 1 | |
| 2123 | 2-Me—C₆H₄ | Isoxazol-3-yl | 5-Cl | 1 | |
| 2124 | 2,5-Me₂—C₆H₃ | Isoxazol-3-yl | 5-Cl | 1 | |
| 2125 | 4-Cl-2-Me—C₆H₃ | Isoxazol-3-yl | 5-Cl | 1 | |
| 2126 | 4-Cl—C₆H₄ | Isoxazol-3-yl | 5-Cl | 0 | |
| 2127 | 4-Me—C₆H₄ | Isoxazol-3-yl | 5-Cl | 0 | |
| 2128 | C₆H₅ | Isoxazol-3-yl | 5-Cl | 0 | |
| 2129 | 5-CF₃-pyridin-2-yl | Isoxazol-3-yl | 5-Cl | 1 | |
| 2130 | 5-CF₃-pyridin-2-yl | Isoxazol-3-yl | 5-Cl | 0 | |
| 2131 | C₆H₅ | 3-Me-isoxazol-5-yl | 5-Cl | 1 | |
| 2132 | 2-Cl—C₆H₄ | 3-Me-isoxazol-5-yl | 5-Cl | 1 | |
| 2133 | 2-Me—C₆H₄ | 3-Me-isoxazol-5-yl | 5-Cl | 1 | |
| 2134 | 2,5-Me₂—C₆H₃ | 3-Me-isoxazol-5-yl | 5-Cl | 1 | |
| 2135 | 4-Cl-2-Me—C₆H₃ | 3-Me-isoxazol-5-yl | 5-Cl | 1 | |
| 2136 | 4-Cl—C₆H₄ | 3-Me-isoxazol-5-yl | 5-Cl | 0 | |
| 2137 | 4-Me—C₆H₄ | 3-Me-isoxazol-5-yl | 5-Cl | 0 | |
| 2138 | C₆H₅ | 3-Me-isoxazol-5-yl | 5-Cl | 0 | |
| 2139 | 5-CF₃-pyridin-2-yl | 3-Me-isoxazol-5-yl | 5-Cl | 1 | |
| 2140 | 5-CF₃-pyridin-2-yl | 3-Me-isoxazol-5-yl | 5-Cl | 0 | |
| 2141 | C₆H₅ | 1-Me-imidazol-2-yl | 5-Cl | 1 | |
| 2142 | 2-Cl—C₆H₄ | 1-Me-imidazol-2-yl | 5-Cl | 1 | |
| 2143 | 2-Me—C₆H₄ | 1-Me-imidazol-2-yl | 5-Cl | 1 | |
| 2144 | 2,5-Me₂—C₆H₃ | 1-Me-imidazol-2-yl | 5-Cl | 1 | |
| 2145 | 4-Cl-2-Me—C₆H₃ | 1-Me-imidazol-2-yl | 5-Cl | 1 | |
| 2146 | 4-Cl—C₆H₄ | 1-Me-imidazol-2-yl | 5-Cl | 0 | |
| 2147 | 4-Me—C₆H₄ | 1-Me-imidazol-2-yl | 5-Cl | 0 | |
| 2148 | C₆H₅ | 1-Me-imidazol-2-yl | 5-Cl | 0 | |
| 2149 | 5-CF₃-pyridin-2-yl | 1-Me-imidazol-2-yl | 5-Cl | 1 | |
| 2150 | 5-CF₃-pyridin-2-yl | 1-Me-imidazol-2-yl | 5-Cl | 0 | |
| 2151 | C₆H₅ | 1-Me-imidazol-2-yl | 5-F | 1 | |
| 2152 | 2-Cl—C₆H₄ | 1-Me-imidazol-2-yl | 5-F | 1 | |
| 2153 | 2-Me—C₆H₄ | 1-Me-imidazol-2-yl | 5-F | 1 | |
| 2154 | 2,5-Me₂—C₆H₃ | 1-Me-imidazol-2-yl | 5-F | 1 | |
| 2155 | 4-Cl-2-Me—C₆H₃ | 1-Me-imidazol-2-yl | 5-F | 1 | |
| 2156 | 4-Cl—C₆H₄ | 1-Me-imidazol-2-yl | 5-F | 0 | |
| 2157 | 4-Me—C₆H₄ | 1-Me-imidazol-2-yl | 5-F | 0 | |
| 2158 | C₆H₅ | 1-Me-imidazol-2-yl | 5-F | 0 | |
| 2159 | 5-CF₃-pyridin-2-yl | 1-Me-imidazol-2-yl | 5-F | 1 | |
| 2160 | 5-CF₃-pyridin-2-yl | 1-Me-imidazol-2-yl | 5-F | 0 | |
| 2161 | C₆H₅ | 1,2,4-Oxadiazol-2-yl | 5-F | 1 | |
| 2162 | 2-Cl—C₆H₄ | 1,2,4-Oxadiazol-2-yl | 5-F | 1 | |
| 2163 | 2-Me—C₆H₄ | 1,2,4-Oxadiazol-2-yl | 5-F | 1 | |
| 2164 | 2,5-Me₂—C₆H₃ | 1,2,4-Oxadiazol-2-yl | 5-F | 1 | |
| 2165 | 4-Cl-2-Me—C₆H₃ | 1,2,4-Oxadiazol-2-yl | 5-F | 1 | |
| 2166 | 4-Cl—C₆H₄ | 1,2,4-Oxadiazol-2-yl | 5-F | 0 | |
| 2167 | 4-Me—C₆H₄ | 1,2,4-Oxadiazol-2-yl | 5-F | 0 | |
| 2168 | C₆H₅ | 1,2,4-Oxadiazol-2-yl | 5-F | 0 | |
| 2169 | 5-CF₃-pyridin-2-yl | 1,2,4-Oxadiazol-2-yl | 5-F | 1 | |
| 2170 | 5-CF₃-pyridin-2-yl | 1,2,4-Oxadiazol-2-yl | 5-F | 0 | |
| 2171 | C₆H₅ | 5-Me-1,2,4-oxadiazol-3-yl | 5-F | 1 | |
| 2172 | 2-Cl—C₆H₄ | 5-Me-1,2,4-oxadiazol-3-yl | 5-F | 1 | |
| 2173 | 2-Me—C₆H₄ | 5-Me-1,2,4-oxadiazol-3-yl | 5-F | 1 | |
| 2174 | 2,5-Me₂—C₆H₃ | 5-Me-1,2,4-oxadiazol-3-yl | 5-F | 1 | |
| 2175 | 4-Cl-2-Me—C₆H₃ | 5-Me-1,2,4-oxadiazol-3-yl | 5-F | 1 | |
| 2176 | 4-Cl—C₆H₄ | 5-Me-1,2,4-oxadiazol-3-yl | 5-F | 0 | |
| 2177 | 4-Me—C₆H₄ | 5-Me-1,2,4-oxadiazol-3-yl | 5-F | 0 | |
| 2178 | C₆H₅ | 5-Me-1,2,4-oxadiazol-3-yl | 5-F | 0 | |
| 2179 | 5-CF₃pyridin-2-yl | 5-Me-1,2,4-oxadiazol-3-yl | 5-F | 1 | |
| 2180 | 5-CF₃pyridin-2-yl | 5-Me-1,2,4-oxadiazol-3-yl | 5-F | 0 | |
| 2181 | C₆H₅ | Isoxazol-3-yl | 5-F | 1 | |
| 2182 | 2-Cl—C₆H₄ | Isoxazol-3-yl | 5-F | 1 | |
| 2183 | 2-Me—C₆H₄ | Isoxazol-3-yl | 5-F | 1 | |
| 2184 | 2,5-Me₂—C₆H₃ | Isoxazol-3-yl | 5-F | 1 | |
| 2185 | 4-Cl-2-Me—C₆H₃ | Isoxazol-3-yl | 5-F | 1 | |
| 2186 | 4-Cl—C₆H₄ | Isoxazol-3-yl | 5-F | 0 | |
| 2187 | 4-Me—C₆H₄ | Isoxazol-3-yl | 5-F | 0 | |
| 2188 | C₆H₅ | Isoxazol-3-yl | 5-F | 0 | |
| 2189 | 5-CF₃-pyridin-2-yl | Isoxazol-3-yl | 5-F | 1 | |
| 2190 | 5-CF₃-pyridin-2-yl | Isoxazol-3-yl | 5-F | 0 | |

-continued

| No | R¹ | R² | R³ | n | Physical data |
|---|---|---|---|---|---|
| 2191 | C₆H₅ | 3-Me-isoxazol-5-yl | 5-F | 1 | |
| 2192 | 2-Cl—C₆H₄ | 3-Me-isoxazol-5-yl | 5-F | 1 | |
| 2193 | 2-Me—C₆H₄ | 3-Me-isoxazol-5-yl | 5-F | 1 | |
| 2194 | 2,5-Me₂—C₆H₃ | 3-Me-isoxazol-5-yl | 5-F | 1 | |
| 2195 | 4-Cl-2-Me—C₆H₃ | 3-Me-isoxazol-5-yl | 5-F | 1 | |
| 2196 | 4-Cl—C₆H₄ | 3-Me-isoxazol-5-yl | 5-F | 0 | |
| 2197 | 4-Me—C₆H₄ | 3-Me-isoxazol-5-yl | 5-F | 0 | |
| 2198 | C₆H₅ | 3-Me-isoxazol-5-yl | 5-F | 0 | |
| 2199 | 5-CF₃-pyridin-2-yl | 3-Me-isoxazol-5-yl | 5-F | 1 | |
| 2200 | 5-CF₃-pyridin-2-yl | 3-Me-isoxazol-5-yl | 5-F | 0 | |
| 2201 | C₆H₅ | 5-Me-1,3,4-oxadiazol-2-yl | H | 1 | |
| 2202 | 2-Cl—C₆H₄ | 5-Me-1,3,4-oxadiazol-2-yl | H | 1 | |
| 2203 | 4-Cl—C₆H₄ | 5-Me-1,3,4-oxadiazol-2-yl | H | 1 | |
| 2204 | 2-Me—C₆H₄ | 5-Me-1,3,4-oxadiazol-2-yl | H | 1 | |
| 2205 | 4-Me—C₆H₄ | 5-Me-1,3,4-oxadiazol-2-yl | H | 1 | |
| 2206 | 3-CF₃—C₆H₄ | 5-Me-1,3,4-oxadiazol-2-yl | H | 1 | |
| 2207 | 2,5-Me₂—C₆H₃ | 5-Me-1,3,4-oxadiazol-2-yl | H | 1 | mp 134.0–139.0° C. |
| 2208 | 4-Cl-2-Me—C₆H₃ | 5-Me-1,3,4-oxadiazol-2-yl | H | 1 | $^1$H—NMR(CDCl₃) δ ppm: 2.12(3H, s), 2.58(3H, s), 4.05(3H, s), 4.97(2H, s), 6.63(1H, s, J = 8.5), 6.99–7.64(6H, m) |
| 2209 | 2,5-Cl₂—C₆H₃ | 5-Me-1,3,4-oxadiazol-2-yl | H | 1 | |
| 2210 | 5-CF₃-pyridin-2-yl | 5-Me-1,3,4-oxadiazol-2-yl | H | 1 | |
| 2211 | C₆H₅ | Thiazolidin-2-yl | H | 1 | |
| 2212 | 2-Cl—C₆H₄ | Thiazolidin-2-yl | H | 1 | |
| 2213 | 4-Cl—C₆H₄ | Thiazolidin-2-yl | H | 1 | |
| 2214 | 2-Me—C₆H₄ | Thiazolidin-2-yl | H | 1 | |
| 2215 | 4-Me—C₆H₄ | Thiazolidin-2-yl | H | 1 | |
| 2216 | 3-CF₃—C₆H₄ | Thiazolidin-2-yl | H | 1 | |
| 2217 | 2,5-Me₂—C₆H₃ | Thiazolidin-2-yl | H | 1 | $^1$H—NMR(CDCl₃) δ ppm: 2.28(6H, s), 2.40(1H, brs), 2.81–3.06(3H, m), 3.38–3.55(1H, m), 3.87(3H, s), 4.85–5.50(3H, m), 6.67–7.64(7H, m) |
| 2218 | 4-Cl-2-Me—C₆H₃ | Thiazolidin-2-yl | H | 1 | |
| 2219 | 2,5-Cl₂—C₆H₃ | Thiazolidin-2-yl | H | 1 | mp 121.0–122.0° C. |
| 2220 | 5-CF₃-pyridin-2-yl | Thiazolidin-2-yl | H | 1 | |
| 2221 | C₆H₅ | 3,5-Me₂-isoxazol-4-yl | H | 1 | $^1$H—NMR(CDCl₃) δ ppm: 2.00(1.96)(3H, s), 2.17(3H, s), 3.94(3.91)(3H, s), 5.19(4.94)(2H, s), 6.83–7.66(9H, m) |
| 2222 | 2-Cl—C₆H₄ | 3,5-Me₂-isoxazol-4-yl | H | 1 | |
| 2223 | 4-Cl—C₆H₄ | 3,5-Me₂-isoxazol-4-yl | H | 1 | |
| 2224 | 2-Me—C₆H₄ | 3,5-Me₂-isoxazol-4-yl | H | 1 | |
| 2225 | 4-Me—C₆H₄ | 3,5-Me₂-isoxazol-4-yl | H | 1 | |
| 2226 | 3-CF₃—C₆H₄ | 3,5-Me₂-isoxazol-4-yl | H | 1 | |
| 2227 | 2,5-Me₂—C₆H₃ | 3,5-Me₂-isoxazol-4-yl | H | 1 | $^1$H—NMR(CDCl₃) δ ppm: 1.95–2.28(12H, m), 3.94(3.99)(3H, s), 4.93(5.18)(2H, s), 6.57–7.71(7H, m) |
| 2228 | 4-Cl-2-Me—C₆H₃ | 3,5-Me₂-isoxazol-4-yl | H | 1 | $^1$H—NMR(CDCl₃) δ ppm: 1.95(1.98)(3H, s), 2.13–2.23(6H, m), 3.93(3.98(*3H, s), 4.91(5.17)(2H, s), 6.65–6.72(2H, m), 7.01–7.66(5H, m) |
| 2229 | 2,5-Cl₂—C₆H₃ | 3,5-Me₂-isoxazol-4-yl | H | 1 | |
| 2230 | 5-CF₃-pyridin-2-yl | 3,5-Me₂-isoxazol-4-yl | H | 1 | |
| 2231 | C₆H₅ | 1,3-Dioxolan-2-yl | H | 1 | |
| 2232 | 2-Cl—C₆H₄ | 1,3-Dioxolan-2-yl | H | 1 | |
| 2233 | 4-Cl—C₆H₄ | 1,3-Dioxolan-2-yl | H | 1 | |
| 2234 | 2-Me—C₆H₄ | 1,3-Dioxolan-2-yl | H | 1 | |
| 2235 | 4-Me—C₆H₄ | 1,3-Dioxolan-2-yl | H | 1 | |
| 2236 | 3-CF₃—C₆H₄ | 1,3-Dioxolan-2-yl | H | 1 | |
| 2237 | 2,5-Me₂—C₆H₃ | 1,3-Dioxolan-2-yl | H | 1 | $^1$H—NMR(CDCl₃) δ ppm: 2.28(3H, s), 2.29(3h, s), 3.59–3.85(4H, m), 3.92(3H, s), 5.04(1H, s), 5.09(1H, s), 5.63(1H, s), 6.66–7.62(7H, m) |
| 2238 | 4-Cl-2-Me—C₆H₃ | 1,3-Dioxolan-2-yl | H | 1 | |
| 2239 | 2,5-Cl₂—C₆H₃ | 1,3-Dioxolan-2-yl | H | 1 | |
| 2240 | 5-CF₃-pyridin-2-yl | 1,3-Dioxolan-2-yl | H | 1 | |
| 2241 | C₆H₅ | 3-Me-2-isoxazolin-5-yl | H | 1 | |
| 2242 | 2-Cl—C₆H₄ | 3-Me-2-isoxazolin-5-yl | H | 1 | |
| 2243 | 4-Cl—C₆H₄ | 3-Me-2-isoxazolin-5-yl | H | 1 | |

-continued

| No | R¹ | R² | R³ | n | Physical data |
|---|---|---|---|---|---|
| 2244 | 2-Me—C₆H₄ | 3-Me-2-isoxazolin-5-yl | H | 1 | ¹H—NMR(CDCl₃) δ ppm: 1.88(3H, s), 2.26(2.27)(3H, s), 2.84–3.38(2H, m), 3.95(3.87)(3H, s), 4.87–5.38(2H, m), 5.74–5.81(1H, m), 6.84–6.89(2H, m), 7.11–7.60(6H, m) |
| 2245 | 4-Me—C₆H₄ | 3-Me-2-isoxazolin-5-yl | H | 1 | |
| 2246 | 3-CF₃—C₆H₄ | 3-Me-2-isoxazolin-5-yl | H | 1 | |
| 2247 | 2,5-Me₂—C₆H₃ | 3-Me-2-isoxazolin-5-yl | H | 1 | ¹H—NMR(CDCl₃) δ ppm: 1.88(3H, s), 2.20(2.22)(3H, s), 2.30(3H, s), 2.84–3.37(2H, m), 3.96(3.88)(3H, s), 4.85–5.35(2H, m), 5.74–5.82(1H, m), 6.67–6.69(2H, m), 7.01(5H, m) |
| 2248 | 4-Cl-2-Me—C₆H₃ | 3-Me-2-isoxazolin-5-yl | H | 1 | |
| 2249 | 2,5-Cl₂—C₆H₃ | 3-Me-2-isoxazolin-5-yl | H | 1 | |
| 2250 | 5-CF₃-pyridin-2-yl | 3-Me-2-isoxazolin-5-yl | H | 1 | |
| 2251 | C₆H₅ | 4-Me-1,2,3-thiadiazol-5-yl | H | 1 | mp 90.5–91.5° C. |
| 2252 | 2-Cl—C₆H₄ | 4-Me-1,2,3-thiadiazol-5-yl | H | 1 | |
| 2253 | 4-Cl—C₆H₄ | 4-Me-1,2,3-thiadiazol-5-yl | H | 1 | |
| 2254 | 2-Me—C₆H₄ | 4-Me-1,2,3-thiadiazol-5-yl | H | 1 | |
| 2255 | 4-Me—C₆H₄ | 4-Me-1,2,3-thiadiazol-5-yl | H | 1 | |
| 2256 | 3-CF₃—C₆H₄ | 4-Me-1,2,3-thiadiazol-5-yl | H | 1 | |
| 2257 | 2,5-Me₂—C₆H₃ | 4-Me-1,2,3-thiadiazol-5-yl | H | 1 | ¹H—NMR(CDCl₃) δ ppm: 2.01(3H, s), 2.14(3H, s), 2.25(3H, s), 4.18(3H, s), 4.98(2H, s), 6.51(1H, s), 6.65(1H, d, J = 7.9), 6.96(1H, d, J = 7.3), 7.24–7.96(4H, m) |
| 2258 | 4-Cl-2-Me—C₆H₃ | 4-Me-1,2,3-thiadiazol-5-yl | H | 1 | |
| 2259 | 2,5-Cl₂—C₆H₃ | 4-Me-1,2,3-thiadiazol-5-yl | H | 1 | |
| 2260 | 5-CF₃-pyridin-2-yl | 4-Me-1,2,3-thiadiazol-5-yl | H | 1 | |
| 2261 | 3,5-Cl₂-pyridin-2-yl | Isoxazol-3-yl | H | 0 | |
| 2262 | 3,5-Cl₂-pyridin-2-yl | Isoxazol-5-yl | H | 0 | |
| 2263 | 3,5-Cl₂-pyridin-2-yl | 5-Me-isoxazol-3-yl | H | 0 | |
| 2264 | 3,5-Cl₂-pyridin-2-yl | 3-Me-isoxazol-5-yl | H | 0 | |
| 2265 | 3,5-Cl₂-pyridin-2-yl | 2-Isoxazolin-3-yl | H | 0 | |
| 2266 | 3,5-Cl₂-pyridin-2-yl | 5-Me-2-isoxazolin-3-yl | H | 0 | |
| 2267 | 3,5-Cl₂-pyridin-2-yl | 3-Me-2-isoxazolin-5-yl | H | 0 | |
| 2268 | 3,5-Cl₂-pyridin-2-yl | 2-Furyl | H | 0 | |
| 2269 | 3,5-Cl₂-pyridin-2-yl | Thiazolidin-2-yl | H | 0 | |
| 2270 | 3,5-Cl₂-pyridin-2-yl | 1-Me-imidazol-2-yl | H | 0 | |
| 2271 | 3,5-Cl₂-pyridin-2-yl | 1,2,4-Oxadiazol-3-yl | H | 0 | |
| 2272 | 3,5-Cl₂-pyridin-2-yl | 5-Me-1,2,4-oxadiazol-3-yl | H | 0 | |
| 2273 | 3,5-Cl₂-pyridin-2-yl | 1,2,4-oxadiazol-5-yl | H | 0 | |
| 2274 | 3,5-Cl₂-pyridin-2-yl | 1,3,4-oxadiazol-2-yl | H | 0 | |
| 2275 | 3,5-Cl₂-pyridin-2-yl | 5-Me-1,3,4-oxadiazol-2-yl | H | 0 | |
| 2276 | 3,5-Cl₂-pyridin-2-yl | Isoxazol-3-yl | H | 1 | mp 136–137° C. |
| 2277 | 3,5-Cl₂-pyridin-2-yl | Isoxazol-5-yl | H | 1 | |
| 2278 | 3,5-Cl₂-pyridin-2-yl | 5-Me-isoxazol-3-yl | H | 1 | ¹H—NMR(CDCl₃) δ ppm: 2.34(3H, s), 3.97((3H, s), 5.32(2H, s), 6.36(1H, s), 7.24–7.85(6H, m). |
| 2279 | 3,5-Cl₂-pyridin-2-yl | 3-Me-isoxazol-5-yl | H | 1 | Isomer A: ¹H—NMR(CDCl₃) δ ppm: 2.35(3H, s), 4.12(3H, s), 5.40(2H, s), 6.95(1H, s), 7.37–7.86(6H, m) Isomer B: ¹H—NMR(CDCl₃) δ ppm: 2.28(3H, s), 4.03(3H, s), 5.30(2H, s), 6.01(1H, s), 7.21–7.86(6H, s) |
| 2280 | 3,5-Cl₂-pyridin-2-yl | 2-Isoxazolin-3-yl | H | 1 | |
| 2281 | 3,5-Cl₂-pyridin-2-yl | 5-Me-2-isoxazolin-3-yl | H | 1 | |
| 2282 | 3,5-Cl₂-pyridin-2-yl | 3-Me-2-isoxazolin-5-yl | H | 1 | |
| 2283 | 3,5-Cl₂-pyridin-2-yl | 2-Furyl | H | 1 | |
| 2284 | 3,5-Cl₂-pyridin-2-yl | Thiazolidin-2-yl | H | 1 | |
| 2285 | 3,5-Cl₂-pyridin-2-yl | 1-Me-imidazol-2-yl | H | 1 | |
| 2286 | 3,5-Cl₂-pyridin-2-yl | 1,2,4-Oxadiazol-3-yl | H | 1 | |
| 2287 | 3,5-Cl₂-pyridin-2-yl | 5-Me-1,2,4-oxadiazol-3-yl | H | 1 | |
| 2288 | 3,5-Cl₂-pyridin-2-yl | 1,2,4-Oxadiazol-5-yl | H | 1 | |
| 2289 | 3,5-Cl₂-pyridin-2-yl | 1,3,4-Oxadiazol-2-yl | H | 1 | |
| 2290 | 3,5-Cl₂-pyridin-2-yl | 5-Me-1,3,4-oxadiazol-2-yl | H | 1 | |
| 2291 | 5-Cl-3-CF₃-pyridin-2-yl | Isoxazol-3-yl | H | 0 | |
| 2292 | 5-Cl-3-CF₃-pyridin-2-yl | Isoxazol-5-yl | H | 0 | |
| 2293 | 5-Cl-3-CF₃-pyridin-2-yl | 5-Me-isoxazol-3-yl | H | 0 | |
| 2294 | 5-Cl-3-CF₃-pyridin-2-yl | 3-Me-isoxazol-5-yl | H | 0 | |
| 2295 | 5-Cl-3-CF₃-pyridin-2-yl | 2-Isoxazolin-3-yl | H | 0 | |
| 2296 | 5-Cl-3-CF₃-pyridin-2-yl | 5-Me-2-isoxazolin-3-yl | H | 0 | |
| 2297 | 5-Cl-3-CF₃-pyridin-2-yl | 3-Me-2-isoxazolin-5-yl | H | 0 | |
| 2298 | 5-Cl-3-CF₃-pyridin-2-yl | 2-Furyl | H | 0 | |

-continued

| No | R¹ | R² | R³ | n | Physical data |
|---|---|---|---|---|---|
| 2299 | 5-Cl-3-CF₃-pyridin-2-yl | Thiazolidin-2-yl | H | 0 | |
| 2300 | 5-Cl-3-CF₃-pyridin-2-yl | 1-Me-imidazol-2-yl | H | 0 | |
| 2301 | 5-Cl-3-CF₃-pyridin-2-yl | 1,2,4-Oxadiazol-3-yl | H | 0 | |
| 2302 | 5-Cl-3-CF₃-pyridin-2-yl | 5-Me-1,2,4-oxadiazol-3-yl | H | 0 | |
| 2303 | 5-Cl-3-CF₃-pyridin-2-yl | 1,2,4-Oxadiazol-5-yl | H | 0 | |
| 2304 | 5-Cl-3-CF₃-pyridin-2-yl | 1,3,4-Oxadiazol-2-yl | H | 0 | |
| 2305 | 5-Cl-3-CF₃-pyridin-2-yl | 5-Me-1,3,4-oxadiazol-2-yl | H | 0 | |
| 2306 | 5-Cl-3-CF₃-pyridin-2-yl | Isoxazol-3-yl | H | 1 | mp 97.5–98.5° C. |
| 2307 | 5-Cl-3-CF₃-pyridin-2-yl | Isoxazol-5-yl | H | 1 | |
| 2308 | 5-Cl-3-CF₃-pyridin-2-yl | 5-Me-isoxazol-3-yl | H | 1 | mp 120–121° C. |
| 2309 | 5-Cl-3-CF₃-pyridin-2-yl | 3-Me-isoxazol-5-yl | H | 1 | Isomer A: ¹H—NMR(CDCl₃) δ ppm: 2.37(3H, s), 4.14(3H, s), 5.45(2H, s), 6.97(1H, s), 7.36–7.63(4H, m), 7.79(1H, d, J = 2.4), 8.09(1H, d, J = 2.4) Isomer B: ¹H—NMR(CDCl₃) δ ppm: 2.28(3H, s), 4.04(3H, s), 5.33(2H, s), 6.01(1H, s), 7.20–7.65(4H, m), 7.80(1H, d, J = 2.4), 8.08(1H, d, J = 2.4) |
| 2310 | 5-Cl-3-CF₃-pyridin-2-yl | 2-Isoxazolin-3-yl | H | 1 | |
| 2311 | 5-Cl-3-CF₃-pyridin-2-yl | 5-Me-2-isoxazolin-3-yl | H | 1 | |
| 2312 | 5-Cl-3-CF₃-pyridin-2-yl | 3-Me-2-isoxazolin-5-yl | H | 1 | |
| 2313 | 5-Cl-3-CF₃-pyridin-2-yl | 2-Furyl | H | 1 | |
| 2314 | 5-Cl-3-CF₃-pyridin-2-yl | Thiazolidin-2-yl | H | 1 | |
| 2315 | 5-Cl-3-CF₃-pyridin-2-yl | 1-Me-imidazol-2-yl | H | 1 | |
| 2316 | 5-Cl-3-CF₃-pyridin-2-yl | 1,2,4-Oxadiazol-3-yl | H | 1 | |
| 2317 | 5-Cl-3-CF₃-pyridin-2-yl | 5-Me-1,2,4-oxadiazol-3-yl | H | 1 | |
| 2318 | 5-Cl-3-CF₃-pyridin-2-yl | 1,2,4-Oxadiazol-5-yl | H | 1 | |
| 2319 | 5-Cl-3-CF₃-pyridin-2-yl | 1,3,4-Oxadiazol-2-yl | H | 1 | |
| 2320 | 5-Cl-3-CF₃-pyridin-2-yl | 5-Me-1,3,4-oxadiazol-2-yl | H | 1 | |

| No | R³ | R⁹ | R¹⁰ | Physical data |
|---|---|---|---|---|
| 2321 | 1-Me-imidazol-2-yl | 2,4-F₂—C₆H₃ | Me | |
| 2322 | 1-Me-imidazol-2-yl | 2,5-F₂—C₆H₃ | Me | |
| 2323 | 1-Me-imidazol-2-yl | 3,4-F₂—C₆H₃ | Me | |
| 2324 | 1-Me-imidazol-2-yl | 3,5-F₂—C₆H₃ | Me | |
| 2325 | 1-Me-imidazol-2-yl | 2,3-Cl₂—C₆H₃ | Me | |
| 2326 | 1-Me-imidazol-2-yl | 2,4-Cl₂—C₆H₃ | Me | |
| 2327 | 1-Me-imidazol-2-yl | 2,5-Cl₂—C₆H₃ | Me | |
| 2328 | 1-Me-imidazol-2-yl | 3,4-Cl₂—C₆H₃ | Me | |
| 2329 | 1-Me-imidazol-2-yl | 3,5-Cl₂—C₆H₃ | Me | |
| 2330 | 1-Me-imidazol-2-yl | 3,4-Me₂—C₆H₃ | Me | |
| 2331 | 1-Me-imidazol-2-yl | 2,4-Me₂—C₆H₃ | Me | |
| 2332 | 1-Me-imidazol-2-yl | 3-Ph—C₆H₄ | Me | |
| 2333 | 1-Me-imidazol-2-yl | 4-Ph—C₆H₄ | Me | |
| 2334 | 1-Me-imidazol-2-yl | Morpholino | Me | |
| 2335 | 1-Me-imidazol-2-yl | 2,6-Me₂morpholino | Me | |
| 2336 | 1-Me-imidazol-2-yl | C₆H₅ | Et | |
| 2337 | 1-Me-imidazol-2-yl | 4-F—C₆H₄ | Et | |
| 2338 | 1-Me-imidazol-2-yl | 4-Cl—C₆H₄ | Et | |
| 2339 | 1-Me-imidazol-2-yl | 4-Me—C₆H₄ | Et | |
| 2340 | 1-Me-imidazol-2-yl | 3,4-Cl₂—C₆H₃ | Et | |
| 2341 | 1H-1,2,4-Triazol-1-yl | C₆H₅ | Me | |
| 2342 | 1H-1,2,4-Triazol-1-yl | 2-F—C₆H₄ | Me | |
| 2343 | 1H-1,2,4-Triazol-1-yl | 3-F—C₆H₄ | Me | |
| 2344 | 1H-1,2,4-Triazol-1-yl | 4-F—C₆H₄ | Me | |
| 2345 | 1H-1,2,4-Triazol-1-yl | 2-Cl—C₆H₄ | Me | |
| 2346 | 1H-1,2,4-Triazol-1-yl | 3-Cl—C₆H₄ | Me | |
| 2347 | 1H-1,2,4-Triazol-1-yl | 4-Cl—C₆H₄ | Me | |
| 2348 | 1H-1,2,4-Triazol-1-yl | 2-Br—C₆H₄ | Me | |
| 2349 | 1H-1,2,4-Triazol-1-yl | 3-Br—C₆H₄ | Me | |
| 2350 | 1H-1,2,4-Triazol-1-yl | 4-Br—C₆H₄ | Me | |
| 2351 | 1H-1,2,4-Triazol-1-yl | 3-I—C₆H₄ | Me | |
| 2352 | 1H-1,2,4-Triazol-1-yl | 2-Me—C₆H₄ | Me | |
| 2353 | 1H-1,2,4-Triazol-1-yl | 3-Me—C₆H₄ | Me | |
| 2354 | 1H-1,2,4-Triazol-1-yl | 4-Me—C₆H₄ | Me | |
| 2355 | 1H-1,2,4-Triazol-1-yl | 3-Et—C₆H₄ | Me | |
| 2356 | 1H-1,2,4-Triazol-1-yl | 4-Et—C₆H₄ | Me | |
| 2357 | 1H-1,2,4-Triazol-1-yl | 3-MeO—C₆H₄ | Me | |
| 2358 | 1H-1,2,4-Triazol-1-yl | 4-MeO—C₆H₄ | Me | |
| 2359 | 1H-1,2,4-Triazol-1-yl | 3-CF₃—C₆H₄ | Me | |
| 2360 | 1H-1,2,4-Triazol-1-yl | 4-CF₃—C₆H₄ | Me | |
| 2361 | 1H-1,2,4-Triazol-1-yl | 2,4-F₂—C₆H₃ | Me | |
| 2362 | 1H-1,2,4-Triazol-1-yl | 2,5-F₂—C₆H₃ | Me | |
| 2363 | 1H-1,2,4-Triazol-1-yl | 3,4-F₂—C₆H₃ | Me | |

-continued

| No | R¹ | R² | R³ | n | Physical data |
|---|---|---|---|---|---|
| 2364 | 1H-1,2,4-Triazol-1-yl | 3,5-F₂—C₆H₃ | Me | | |
| 2365 | 1H-1,2,4-Triazol-1-yl | 2,3-Cl₂—C₆H₃ | Me | | |
| 2366 | 1H-1,2,4-Triazol-1-yl | 2,4-Cl₂—C₆H₃ | Me | | |
| 2367 | 1H-1,2,4-Triazol-1-yl | 2,5-Cl₂—C₆H₃ | Me | | |
| 2368 | 1H-1,2,4-Triazol-1-yl | 3,4-Cl₂—C₆H₃ | Me | | |
| 2369 | 1H-1,2,4-Triazol-1-yl | 3,5-Cl₂—C₆H₃ | Me | | |
| 2370 | 1H-1,2,4-Triazol-1-yl | 3,4-Me₂—C₆H₃ | Me | | |
| 2371 | 1H-1,2,4-Triazol-1-yl | 2,4-Me₂—C₆H₃ | Me | | |
| 2372 | 1H-1,2,4-Triazol-1-yl | 3-Ph—C₆H₄ | Me | | |
| 2373 | 1H-1,2,4-Triazol-1-yl | 4-Ph—C₆H₄ | Me | | |
| 2374 | 1H-1,2,4-Triazol-1-yl | Morpholino | Me | | |
| 2375 | 1H-1,2,4-Triazol-1-yl | 2,6-Me₂-morpholino | Me | | |
| 2376 | 1H-1,2,4-Triazol-1-yl | C₆H₅ | Et | | |
| 2377 | 1H-1,2,4-Triazol-1-yl | 4-F—C₆H₄ | Et | | |
| 2378 | 1H-1,2,4-Triazol-1-yl | 4-Cl—C₆H₄ | Et | | |
| 2379 | 1H-1,2,4-Triazol-1-yl | 4-Me—C₆H₄ | Et | | |
| 2380 | 1H-1,2,4-Triazol-1-yl | 3,4-Cl₂—C₆H₃ | Et | | |
| 2381 | Isoxazol-3-yl | C₆H₅ | Me | | |
| 2382 | Isoxazol-3-yl | 2-F—C₆H₄ | Me | | |
| 2383 | Isoxazol-3-yl | 3-F—C₆H₄ | Me | | |
| 2384 | Isoxazol-3-yl | 4-F—C₆H₄ | Me | | |
| 2385 | Isoxazol-3-yl | 2-Cl—C₆H₄ | Me | | |
| 2386 | Isoxazol-3-yl | 3-Cl—C₆H₄ | Me | | |
| 2387 | Isoxazol-3-yl | 4-Cl—C₆H₄ | Me | | ¹H—NMR(CDCl₃) δ ppm: 2.04(3H, s), 4.00(3H, s), 5.13(2H, s), 6.74(1H, d, J = 1.7), 7.25–7.55(8H, m), 8.36(1H, d, J = 1.7) |
| 2388 | Isoxazol-3-yl | 2-Br—C₆H₄ | Me | | |
| 2389 | Isoxazol-3-yl | 3-Br—C₆H₄ | Me | | |
| 2390 | Isoxazol-3-yl | 4-Br—C₆H₄ | Me | | |
| 2391 | Isoxazol-3-yl | 3-I—C₆H₄ | Me | | |
| 2392 | Isoxazol-3-yl | 2-Me—C₆H₄ | Me | | |
| 2393 | Isoxazol-3-yl | 3-Me—C₆H₄ | Me | | |
| 2394 | Isoxazol-3-yl | 4-Me—C₆H₄ | Me | | ¹H-NMR(CDCl₃)δ ppm: 2.05(3H, s), 2.34(3H, s), 4.00(3H, s), 5.13(2H, s), 6.73(1H, d, J=1.7), 7.11–7.57(8H, m), 8.35(1H, d, J=1.7) |
| 2395 | Isoxazol-3-yl | 3-Et—C₆H₄ | Me | | |
| 2396 | Isoxazol-3-yl | 4-Et—C₆H₄ | Me | | |
| 2397 | Isoxazol-3-yl | 3-MeO—C₆H₄ | Me | | |
| 2398 | Isoxazol-3-yl | 4-MeO—C₆H₄ | Me | | ¹H-NMR(CDCl₃)δ ppm: 2.05(3H, s), 3.81(3H, s), 4.00(3H, s), 5.12(2H, s), 6.73(1H, d, J=1.7), 6.82–6.86(2H, m), 7.25–7.56(6H, m), 8.35(1H, d, J=1.7) |
| 2399 | Isoxazol-3-yl | 3-CF₃—C₆H₄ | Me | | ¹H-NMR(CDCl₃)δ ppm: 2.07(3H, s), 4.00(3H, s), 5.17(2H, s), 6.74(1H, d, J=1.7), 7.26–7.74(7H, m), 7.82(1H, s), 8.36(1H, d, J=1.7) |
| 2400 | Isoxazol-3-yl | 4-CF₃—C₆H₄ | Me | | ¹H-NMR(CDCl₃)δ ppm: 2.07(3H, s), 4.00(3H, s), 5.16(2H, s), 6.74(1H, d, J=1.8), 7.26–7.67(8H, m), 8.36(1H, d, J=1.8) |
| 2401 | Isoxazol-3-yl | 2,4-F₂—C₆H₃ | Me | | |
| 2403 | Isoxazol-3-yl | 2,5-F₂—C₆H₃ | Me | | |
| 2403 | Isoxazol-3-yl | 3,4-F₂—C₆H₃ | Me | | |
| 2404 | Isoxazol-3-yl | 3,5-F₂—C₆H₃ | Me | | |
| 2405 | Isoxazol-3-yl | 2,3-Cl₂—C₆H₃ | Me | | |
| 2406 | Isoxazol-3-yl | 2,4-Cl₂—C₆H₃ | Me | | |
| 2407 | Isoxazol-3-yl | 2,5-Cl₂—C₆H₃ | Me | | |
| 2408 | Isoxazol-3-yl | 3,4-Cl₂—C₆H₃ | Me | | ¹H-NMR(CDCl₃)δ ppm: 2.01(3H, s), 4.00(3H, s), 5.14(2H, s), 6.75(1H, d, J=1.7), 7.25–7.65(7H, m), 8.36(1H, d, J=1.7) |
| 2409 | Isoxazol-3-yl | 3,5-Cl₂—C₆H₃ | Me | | |
| 2410 | Isoxazol-3-yl | 3,4-Me₂—C₆H₃ | Me | | |
| 2411 | Isoxazol-3-yl | 2,4-Me₂—C₆H₃ | Me | | |
| 2412 | Isoxazol-3-yl | 3-Ph—C₆H₄ | Me | | |
| 2413 | Isoxazol-3-yl | 4-Ph—C₆H₄ | Me | | |
| 2414 | Isoxazol-3-yl | Morpholino | Me | | |
| 2415 | Isoxazol-3-yl | 2,6-Me₂—morpholino | Me | | |
| 2416 | Isoxazol-3-yl | C₆H₅ | Et | | |
| 2417 | Isoxazol-3-yl | 4-F—C₆H₄ | Et | | |
| 2418 | Isoxazol-3-yl | 4-Cl—C₆H₄ | Et | | |
| 2419 | Isoxazol-3-yl | 4-Me—C₆H₄ | Et | | |
| 2420 | Isoxazol-3-yl | 3,4-Cl₂—C₆H₃ | Et | | |

-continued

| No | R¹ | R² | R³ | n | Physical data |
|---|---|---|---|---|---|
| 2421 | 5-Me-isoxazol-3-yl | $C_6H_5$ | Me | | |
| 2422 | 5-Me-isoxazol-3-yl | 2-F—$C_6H_4$ | Me | | |
| 2423 | 5-Me-isoxazol-3-yl | 3-F—$C_6H_4$ | Me | | |
| 2424 | 5-Me-isoxazol-3-yl | 4-F—$C_6H_4$ | Me | | |
| 2425 | 5-Me-isoxazol-3-yl | 2-Cl—$C_6H_4$ | Me | | |
| 2426 | 5-Me-isoxazol-3-yl | 3-Cl—$C_6H_4$ | Me | | |
| 2427 | 5-Me-isoxazol-3-yl | 4-Cl—$C_6H_4$ | Me | | |
| 2428 | 5-Me-isoxazol-3-yl | 2-Br—$C_6H_4$ | Me | | |
| 2429 | 5-Me-isoxazol-3-yl | 3-Br—$C_6H_4$ | Me | | |
| 2430 | 5-Me-isoxazol-3-yl | 4-Br—$C_6H_4$ | Me | | |
| 2431 | 5-Me-isoxazol-3-yl | 3-I—$C_6H_4$ | Me | | |
| 2432 | 5-Me-isoxazol-3-yl | 2-Me—$C_6H_4$ | Me | | |
| 2433 | 5-Me-isoxazol-3-yl | 3-Me—$C_6H_4$ | Me | | |
| 2434 | 5-Me-isoxazol-3-yl | 4-Me—$C_6H_4$ | Me | | |
| 2435 | 5-Me-isoxazol-3-yl | 3-Et—$C_6H_4$ | Me | | |
| 2436 | 5-Me-isoxazol-3-yl | 4-Et—$C_6H_4$ | Me | | |
| 2437 | 5-Me-isoxazol-3-yl | 3-MeO—$C_6H_4$ | Me | | |
| 2438 | 5-Me-isoxazol-3-yl | 4-MeO—$C_6H_4$ | Me | | |
| 2439 | 5-Me-isoxazol-3-yl | 3-$CF_3$—$C_6H_4$ | Me | | ¹H-NMR(CDCl₃)δ ppm: 2.11(3H, s), 2.40(3H, s) 3.98(3H, s), 5.17(2H, s), 6.35(1H, d, J=0.7), 7.24–7.76(7H, m), 7.83(1H, s) |
| 2440 | 5-Me-isoxazol-3-yl | 4-$CF_3$—$C_6H_4$ | Me | | |
| 2441 | 5-Me-isoxazol-3-yl | 2,4-$F_2$—$C_6H_3$ | Me | | |
| 2442 | 5-Me-isoxazol-3-yl | 2,5-$F_2$—$C_6H_3$ | Me | | |
| 2443 | 5-Me-isoxazol-3-yl | 3,4-$F_2$—$C_6H_3$ | Me | | |
| 2444 | 5-Me-isoxazol-3-yl | 3,5-$F_2$—$C_6H_3$ | Me | | |
| 2445 | 5-Me-isoxazol-3-yl | 2,3-$Cl_2$—$C_6H_3$ | Me | | |
| 2446 | 5-Me-isoxazol-3-yl | 2,4-$Cl_2$—$C_6H_3$ | Me | | |
| 2447 | 5-Me-isoxazol-3-yl | 2,5-$Cl_2$—$C_6H_3$ | Me | | |

-continued

| No | R¹ | R² | R³ | n | Physical data |
|---|---|---|---|---|---|
| 2448 | 5-Me-isoxazol-3-yl | 3,4-Cl$_2$—C$_6$H$_3$ | Me | | ¹H-NMR(CDCl$_3$)δ ppm: 2.05(3H, s), 2.47(3H, s)3.98(3H, s), 5.14(2H, s), 6.35(1H, s), 7.23–7.53(6H, m), 7.66(1H, d, J=1.7) |
| 2449 | 5-Me-isoxazol-3-yl | 3,5-Cl$_2$—C$_6$H$_3$ | Me | | |
| 2450 | 5-Me-isoxazol-3-yl | 3,4-Me$_2$—C$_6$H$_3$ | Me | | |
| 2451 | 5-Me-isoxazol-3-yl | 2,4-Me$_2$—C$_6$H$_3$ | Me | | |
| 2452 | 5-Me-isoxazol-3-yl | 3-Ph—C$_6$H$_4$ | Me | | |
| 2453 | 5-Me-isoxazol-3-yl | 4-Ph—C$_6$H$_4$ | Me | | |
| 2454 | 5-Me-isoxazol-3-yl | Morpholino | Me | | |
| 2455 | 5-Me-isoxazol-3-yl | 2,6-Me$_2$-morpholino | Me | | |
| 2456 | 5-Me-isoxazol-3-yl | C$_6$H$_5$ | Et | | |
| 2457 | 5-Me-isoxazol-3-yl | 4-F—C$_6$H$_4$ | Et | | |
| 2458 | 5-Me-isoxazol-3-yl | 4-Cl—C$_6$H$_4$ | Et | | |
| 2459 | 5-Me-isoxazol-3-yl | 4-Me—C$_6$H$_4$ | Et | | |
| 2460 | 5-Me-isoxazol-3-yl | 3,4-Cl$_2$—C$_6$H$_3$ | Et | | |
| 2461 | Isoxazol-5-yl | C$_6$H$_5$ | Me | | |
| 2462 | Isoxazol-5-yl | 2-F—C$_6$H$_4$ | Me | | |
| 2463 | Isoxazol-5-yl | 3-F—C$_6$H$_4$ | Me | | |
| 2464 | Isoxazol-5-yl | 4-F—C$_6$H$_4$ | Me | | |
| 2465 | Isoxazol-5-yl | 2-Cl—C$_6$H$_4$ | Me | | |
| 2466 | Isoxazol-5-yl | 3-Cl—C$_6$H$_4$ | Me | | |
| 2467 | Isoxazol-5-yl | 4-Cl—C$_6$H$_4$ | Me | | |
| 2468 | Isoxazol-5-yl | 2-Br—C$_6$H$_4$ | Me | | |
| 2469 | Isoxazol-5-yl | 3-Br—C$_6$H$_4$ | Me | | |
| 2470 | Isoxazol-5-yl | 4-Br—C$_6$H$_4$ | Me | | |
| 2471 | Isoxazol-5-yl | 3-I—C$_6$H$_4$ | Me | | |
| 2472 | Isoxazol-5-yl | 2-Me—C$_6$H$_4$ | Me | | |
| 2473 | Isoxazol-5-yl | 3-Me—C$_6$H$_4$ | Me | | |
| 2474 | Isoxazol-5-yl | 4-Me—C$_6$H$_4$ | Me | | |
| 2475 | Isoxazol-5-yl | 3-Et—C$_6$H$_4$ | Me | | |
| 2476 | Isoxazol-5-yl | 4-Et—C$_6$H$_4$ | Me | | |
| 2477 | Isoxazol-5-yl | 3-MeO—C$_6$H$_4$ | Me | | |
| 2478 | Isoxazol-5-yl | 4-MeO—C$_6$H$_4$ | Me | | |
| 2479 | Isoxazol-5-yl | 3-CF$_3$—C$_6$H$_4$ | Me | | |
| 2480 | Isoxazol-5-yl | 4-CF$_3$—C$_6$H$_4$ | Me | | |
| 2481 | Isoxazol-5-yl | 2,4-F$_2$—C$_6$H$_3$ | Me | | |
| 2482 | Isoxazol-5-yl | 2,5-F$_2$—C$_6$H$_3$ | Me | | |
| 2483 | Isoxazol-5-yl | 3,4-F$_2$—C$_6$H$_3$ | Me | | |
| 2484 | Isoxazol-5-yl | 3,5-F$_2$—C$_6$H$_3$ | Me | | |
| 2485 | Isoxazol-5-yl | 2,3-Cl$_2$—C$_6$H$_3$ | Me | | |
| 2486 | Isoxazol-5-yl | 2,4-Cl$_2$—C$_6$H$_3$ | Me | | |
| 2487 | Isoxazol-5-yl | 2,5-Cl$_2$—C$_6$H$_3$ | Me | | |
| 2488 | Isoxazol-5-yl | 3,4-Cl$_2$—C$_6$H$_3$ | Me | | |
| 2489 | Isoxazol-5-yl | 3,5-Cl$_2$—C$_6$H$_3$ | Me | | |
| 2490 | Isoxazol-5-yl | 3,4-Me$_2$—C$_6$H$_3$ | Me | | |
| 2491 | Isoxazol-5-yl | 2,4-Me$_2$—C$_6$H$_3$ | Me | | |
| 2492 | Isoxazol-5-yl | 3-Ph—C$_6$H$_4$ | Me | | |
| 2493 | Isoxazol-5-yl | 4-Ph—C$_6$H$_4$ | Me | | |
| 2494 | Isoxazol-5-yl | Morpholino | Me | | |
| 2495 | Isoxazol-5-yl | 2,6-Me$_2$-morpholino | Me | | |
| 2496 | Isoxazol-5-yl | C$_6$H$_5$ | Et | | |
| 2497 | Isoxazol-5-yl | 4-F—C$_6$H$_4$ | Et | | |
| 2498 | Isoxazol-5-yl | 4-Cl—C$_6$H$_4$ | Et | | |
| 2499 | Isoxazol-5-yl | 4-Me—C$_6$H$_4$ | Et | | |
| 2500 | Isoxazol-5-yl | 3,4-Cl$_2$—C$_6$H$_3$ | Et | | |
| 2501 | 3-Me-isoxazol-5-yl | C$_6$H$_5$ | Me | | |
| 2502 | 3-Me-isoxazol-5-yl | 2-F—C$_6$H$_4$ | Me | | |
| 2503 | 3-Me-isoxazol-5-yl | 3-F—C$_6$H$_4$ | Me | | |
| 2504 | 3-Me-isoxazol-5-yl | 4-F—C$_6$H$_4$ | Me | | |

-continued

| No | R¹ | R² | R³ | n | Physical data |
|---|---|---|---|---|---|
| 2505 | 3-Me-isoxazol-5-yl | 2-Cl—C₆H₄ | Me | | |
| 2506 | 3-Me-isoxazol-5-yl | 3-Cl—C₆H₄ | Me | | |
| 2507 | 3-Me-isoxazol-5-yl | 4-Cl—C₆H₄ | Me | | ¹H-NMR(CDCl₃)δ ppm: 2.03(3H, S), 2.19(3H, S), 4.03(3H, S), 5.12(2H, S), 5.94(2H, S), 7.19–7.56(8H, m) |
| 2508 | 3-Me-isoxazol-5-yl | 2-Br—C₆H₄ | Me | | |
| 2509 | 3-Me-isoxazol-5-yl | 3-Br—C₆H₄ | Me | | |
| 2510 | 3-Me-isoxazol-5-yl | 4-Br—C₆H₄ | Me | | |
| 2511 | 3-Me-isoxazol-5-yl | 3-I—C₆H₄ | Me | | |
| 2512 | 3-Me-isoxazol-5-yl | 2-Me—C₆H₄ | Me | | |
| 2513 | 3-Me-isoxazol-5-yl | 3-Me—C₆H₄ | Me | | |
| 2514 | 3-Me-isoxazol-5-yl | 4-Me—C₆H₄ | Me | | |
| 2515 | 3-Me-isoxazol-5-yl | 3-Et—C₆H₄ | Me | | |
| 2516 | 3-Me-isoxazol-5-yl | 4-Et—C₆H₄ | Me | | |
| 2517 | 3-Me-isoxazol-5-yl | 3-MeO—C₆H₄ | Me | | |
| 2518 | 3-Me-isoxazol-5-yl | 4-MeO—C₆H₄ | Me | | |
| 2519 | 3-Me-isoxazol-5-yl | 3-CF₃—C₆H₄ | Me | | |
| 2520 | 3-Me-isoxazol-5-yl | 4-CF₃—C₆H₄ | Me | | |
| 2521 | 3-Me-isoxazol-5-yl | 2,4-F₂—C₆H₃ | Me | | |
| 2522 | 3-Me-isoxazol-5-yl | 2,5-F₂—C₆H₃ | Me | | |
| 2523 | 3-Me-isoxazol-5-yl | 3,4-F₂—C₆H₃ | Me | | |
| 2524 | 3-Me-isoxazol-5-yl | 3,5-F₂—C₆H₃ | Me | | |
| 2525 | 3-Me-isoxazol-5-yl | 2,3-Cl₂—C₆H₃ | Me | | |
| 2526 | 3-Me-isoxazol-5-yl | 2,4-Cl₂—C₆H₃ | Me | | |
| 2527 | 3-Me-isoxazol-5-yl | 2,5-Cl₂—C₆H₃ | Me | | |
| 2528 | 3-Me-isoxazol-5-yl | 3,4-Cl₂—C₆H₃ | Me | | mp 84.0–85.0° C. |
| 2529 | 3-Me-isoxazol-5-yl | 3,5-Cl₂—C₆H₃ | Me | | |
| 2530 | 3-Me-isoxazol-5-yl | 3,4-Me₂—C₆H₃ | Me | | |
| 2531 | 3-Me-isoxazol-5-yl | 2,4-Me₂—C₆H₃ | Me | | |
| 2532 | 3-Me-isoxazol-5-yl | 3-Ph—C₆H₄ | Me | | |
| 2533 | 3-Me-isoxazol-5-yl | 4-Ph—C₆H₄ | Me | | |
| 2534 | 3-Me-isoxazol-5-yl | Morpholino | Me | | |
| 2535 | 3-Me-isoxazol-5-yl | 2,6-Me₂-morpholino | Me | | |
| 2536 | 3-Me-isoxazol-5-yl | C₆H₅ | Et | | |
| 2537 | 3-Me-isoxazol-5-yl | 4-F—C₆H₄ | Et | | |
| 2538 | 3-Me-isoxazol-5-yl | 4-Cl—C₆H₄ | Et | | |
| 2539 | 3-Me-isoxazol-5-yl | 4-Me—C₆H₄ | Et | | |
| 2540 | 3-Me-isoxazol-5-yl | 3,4-Cl₂—C₆H₃ | Et | | |
| 2541 | 1,3,4-Oxadiazol-2-yl | C₆H₅ | Me | | |

| No | R¹ | R² | R³ | n | Physical data |
|---|---|---|---|---|---|
| 2542 | 1,3,4-Oxadiazol-2-yl | 2-F—C$_6$H$_4$ | Me | | |
| 2543 | 1,3,4-Oxadiazol-2-yl | 3-F—C$_6$H$_4$ | Me | | |
| 2544 | 1,3,4-Oxadiazol-2-yl | 4-F—C$_6$H$_4$ | Me | | |
| 2545 | 1,3,4-Oxadiazol-2-yl | 2-Cl—C$_6$H$_4$ | Me | | |
| 2546 | 1,3,4-Oxadiazol-2-yl | 3-Cl—C$_6$H$_4$ | Me | | |
| 2547 | 1,3,4-Oxadiazol-2-yl | 4-Cl—C$_6$H$_4$ | Me | | |
| 2548 | 1,3,4-Oxadiazol-2-yl | 2-Br—C$_6$H$_4$ | Me | | |
| 2549 | 1,3,4-Oxadiazol-2-yl | 3-Br—C$_6$H$_4$ | Me | | |
| 2550 | 1,3,4-Oxadiazol-2-yl | 4-Br—C$_6$H$_4$ | Me | | |
| 2551 | 1,3,4-Oxadiazol-2-yl | 3-I—C$_6$H$_4$ | Me | | |
| 2552 | 1,3,4-Oxadiazol-2-yl | 2-Me—C$_6$H$_4$ | Me | | |
| 2553 | 1,3,4-Oxadiazol-2-yl | 3-Me—C$_6$H$_4$ | Me | | |
| 2554 | 1,3,4-Oxadiazol-2-yl | 4-Me—C$_6$H$_4$ | Me | | |
| 2555 | 1,3,4-Oxadiazol-2-yl | 3-Et—C$_6$H$_4$ | Me | | |
| 2556 | 1,3,4-Oxadiazol-2-yl | 4-Et—C$_6$H$_4$ | Me | | |
| 2557 | 1,3,4-Oxadiazol-2-yl | 3-MeO—C$_6$H$_4$ | Me | | |
| 2558 | 1,3,4-Oxadiazol-2-yl | 4-MeO—C$_6$H$_4$ | Me | | |
| 2559 | 1,3,4-Oxadiazol-2-yl | 3-CF$_3$—C$_6$H$_4$ | Me | | |
| 2560 | 1,3,4-Oxadiazol-2-yl | 4-CF$_3$—C$_6$H$_4$ | Me | | |
| 2561 | 1,3,4-Oxadiazol-2-yl | 2,4-F$_2$—C$_6$H$_3$ | Me | | |
| 2562 | 1,3,4-Oxadiazol-2-yl | 2,5-F$_2$—C$_6$H$_3$ | Me | | |
| 2563 | 1,3,4-Oxadiazol-2-yl | 3,4-F$_2$—C$_6$H$_3$ | Me | | |
| 2564 | 1,3,4-Oxadiazol-2-yl | 3,5-F$_2$—C$_6$H$_3$ | Me | | |
| 2565 | 1,3,4-Oxadiazol-2-yl | 2,3-Cl$_2$—C$_6$H$_3$ | Me | | |
| 2566 | 1,3,4-Oxadiazol-2-yl | 2,4-Cl$_2$—C$_6$H$_3$ | Me | | |
| 2567 | 1,3,4-Oxadiazol-2-yl | 2,5-Cl$_2$—C$_6$H$_3$ | Me | | |
| 2568 | 1,3,4-Oxadiazol-2-yl | 3,4-Cl$_2$—C$_6$H$_3$ | Me | | |
| 2569 | 1,3,4-Oxadiazol-2-yl | 3,5-Cl$_2$—C$_6$H$_3$ | Me | | |
| 2570 | 1,3,4-Oxadiazol-2-yl | 3,4-Me$_2$—C$_6$H$_3$ | Me | | |
| 2571 | 1,3,4-Oxadiazol-2-yl | 2,4-Me$_2$—C$_6$H$_3$ | Me | | |
| 2572 | 1,3,4-Oxadiazol-2-yl | 3-Ph—C$_6$H$_4$ | Me | | |
| 2573 | 1,3,4-Oxadiazol-2-yl | 4-Ph—C$_6$H$_4$ | Me | | |
| 2574 | 1,3,4-Oxadiazol-2-yl | Morpholino | Me | | |
| 2575 | 1,3,4-Oxadiazol-2-yl | 2,6-Me$_2$-morpholino | Me | | |
| 2576 | 1,3,4-Oxadiazol-2-yl | C$_6$H$_5$ | Et | | |
| 2577 | 1,3,4-Oxadiazol-2-yl | 4-F—C$_6$H$_4$ | Et | | |
| 2578 | 1,3,4-Oxadiazol-2-yl | 4-Cl—C$_6$H$_4$ | Et | | |
| 2579 | 1,3,4-Oxadiazol-2-yl | 4-Me—C$_6$H$_4$ | Et | | |

-continued

| No | R¹ | R² | R³ | n | Physical data |
|---|---|---|---|---|---|
| 2580 | 1,3,4-Oxadiazol-2-yl | 3,4-Cl$_2$—C$_6$H$_3$ | Et | | |
| 2581 | 5-Me-1,3,4-oxadiazol-2-yl | C$_6$H$_5$ | Me | | |
| 2582 | 5-Me-1,3,4-oxadiazol-2-yl | 2-F—C$_6$H$_4$ | Me | | |
| 2583 | 5-Me-1,3,4-oxadiazol-2-yl | 3-F—C$_6$H$_4$ | Me | | |
| 2584 | 5-Me-1,3,4-oxadiazol-2-yl | 4-F—C$_6$H$_4$ | Me | | |
| 2585 | 5-Me-1,3,4-oxadiazol-2-yl | 2-Cl—C$_6$H$_4$ | Me | | |
| 2586 | 5-Me-1,3,4-oxadiazol-2-yl | 3-Cl—C$_6$H$_4$ | Me | | |
| 2587 | 5-Me-1,3,4-oxadiazol-2-yl | 4-Cl—C$_6$H$_4$ | Me | | |
| 2588 | 5-Me-1,3,4-oxadiazol-2-yl | 2-Br—C$_6$H$_4$ | Me | | |
| 2589 | 5-Me-1,3,4-oxadiazol-2-yl | 3-Br—C$_6$H$_4$ | Me | | |
| 2590 | 5-Me-1,3,4-oxadiazol-2-yl | 4-Br—C$_6$H$_4$ | Me | | |
| 2591 | 5-Me-1,3,4-oxadiazol-2-yl | 3-I—C$_6$H$_4$ | Me | | |
| 2592 | 5-Me-1,3,4-oxadiazol-2-yl | 2-Me—C$_6$H$_4$ | Me | | |
| 2593 | 5-Me-1,3,4-oxadiazol-2-yl | 3-Me—C$_6$H$_4$ | Me | | |
| 2594 | 5-Me-1,3,4-oxadiazol-2-yl | 4-Me—C$_6$H$_4$ | Me | | |
| 2595 | 5-Me-1,3,4-oxadiazol-2-yl | 3-Et—C$_6$H$_4$ | Me | | |
| 2596 | 5-Me-1,3,4-oxadiazol-2-yl | 4-Et—C$_6$H$_4$ | Me | | |
| 2597 | 5-Me-1,3,4-oxadiazol-2-yl | 3-MeO—C$_6$H$_4$ | Me | | |
| 2598 | 5-Me-1,3,4-oxadiazol-2-yl | 4-MeO—C$_6$H$_4$ | Me | | |
| 2599 | 5-Me-1,3,4-oxadiazol-2-yl | 3-CF$_3$—C$_6$H$_4$ | Me | | |
| 2600 | 5-Me-1,3,4-oxadiazol-2-yl | 4-CF$_3$—C$_6$H$_4$ | Me | | |
| 2601 | 5-Me-1,3,4-oxadiazol-2-yl | 2,4-F$_2$—C$_6$H$_3$ | Me | | |
| 2602 | 5-Me-1,3,4-oxadiazol-2-yl | 2,5-F$_2$—C$_6$H$_3$ | Me | | |
| 2603 | 5-Me-1,3,4-oxadiazol-2-yl | 3,4-F$_2$—C$_6$H$_3$ | Me | | |
| 2604 | 5-Me-1,3,4-oxadiazol-2-yl | 3,5-F$_2$—C$_6$H$_3$ | Me | | |
| 2605 | 5-Me-1,3,4-oxadiazol-2-yl | 2,3-Cl$_2$—C$_6$H$_3$ | Me | | |
| 2606 | 5-Me-1,3,4-oxadiazol-2-yl | 2,4-Cl$_2$—C$_6$H$_3$ | Me | | |
| 2607 | 5-Me-1,3,4-oxadiazol-2-yl | 2,5-Cl$_2$—C$_6$H$_3$ | Me | | |
| 2608 | 5-Me-1,3,4-oxadiazol-2-yl | 3,4-Cl$_2$—C$_6$H$_3$ | Me | | |
| 2609 | 5-Me-1,3,4-oxadiazol-2-yl | 3,5-Cl$_2$—C$_6$H$_3$ | Me | | |
| 2610 | 5-Me-1,3,4-oxadiazol-2-yl | 3,4-Me$_2$—C$_6$H$_3$ | Me | | |
| 2611 | 5-Me-1,3,4-oxadiazol-2-yl | 2,4-Me$_2$—C$_6$H$_3$ | Me | | |
| 2612 | 5-Me-1,3,4-oxadiazol-2-yl | 3-Ph—C$_6$H$_4$ | Me | | |
| 2613 | 5-Me-1,3,4-oxadiazol-2-yl | 4-Ph—C$_6$H$_4$ | Me | | |
| 2614 | 5-Me-1,3,4-oxadiazol-2-yl | Morpholino | Me | | |
| 2615 | 5-Me-1,3,4-oxadiazol-2-yl | 2,6-Me$_2$-morpholino | Me | | |
| 2616 | 5-Me-1,3,4-oxadiazol-2-yl | C$_6$H$_5$ | Et | | |
| 2617 | 5-Me-1,3,4-oxadiazol-2-yl | 4-F—C$_6$H$_4$ | Et | | |

-continued

| No | R¹ | R² | R³ | n | Physical data |
|---|---|---|---|---|---|
| 2618 | 5-Me-1,3,4-oxadiazol-2-yl | 4-Cl—C₆H₄ | Et | | |
| 2619 | 5-Me-1,3,4-oxadiazol-2-yl | 4-Me—C₆H₄ | Et | | |
| 2620 | 5-Me-1,3,4-oxadiazol-2-yl | 3,4-Cl₂—C₆H₃ | Et | | |
| 2621 | Oxazol-5-yl | C₆H₅ | Me | | mp 92.0–93.5° C. |
| 2622 | Oxazol-5-yl | 2-F—C₆H₄ | Me | | |
| 2623 | Oxazol-5-yl | 3-F—C₆H₄ | Me | | |
| 2624 | Oxazol-5-yl | 4-F—C₆H₄ | Me | | |
| 2625 | Oxazol-5-yl | 2-Cl—C₆H₄ | Me | | |
| 2626 | Oxazol-5-yl | 3-Cl—C₆H₄ | Me | | |
| 2627 | Oxazol-5-yl | 4-Cl—C₆H₄ | Me | | ¹H-NMR(CDCl₃)δ ppm: 2.02(3H, S), 4.01(3H, S), 5.14(2H, S), 6.82(1H, S), 7.21–7.58(8H, m), 7.90(1H, S) |
| 2628 | Oxazol-5-yl | 2-Br—C₆H₄ | Me | | |
| 2629 | Oxazol-5-yl | 3-Br—C₆H₄ | Me | | |
| 2630 | Oxazol-5-yl | 4-Br—C₆H₄ | Me | | |
| 2631 | Oxazol-5-yl | 3-I—C₆H₄ | Me | | |
| 2632 | Oxazol-5-yl | 2-Me—C₆H₄ | Me | | |
| 2633 | Oxazol-5-yl | 3-Me—C₆H₄ | Me | | |
| 2634 | Oxazol-5-yl | 4-Me—C₆H₄ | Me | | |
| 2635 | Oxazol-5-yl | 3-Et—C₆H₄ | Me | | |
| 2636 | Oxazol-5-yl | 4-Et—C₆H₄ | Me | | |
| 2637 | Oxazol-5-yl | 3-MeO—C₆H₄ | Me | | |
| 2638 | Oxazol-5-yl | 4-MeO—C₆H₄ | Me | | |
| 2639 | Oxazol-5-yl | 3-CF₃—C₆H₄ | Me | | ¹H-NMR(CDCl₃)δ ppm: 2.06(3H, S), 4.01(3H, S), 5.17(2H, S), 6.83(1H, S), 7.22–7.26(1H, m), 7.38–7.59(5H, m), 7.72(1H, d, j=7.9), 7.81(1H, S), 7.91(1H, S) |
| 2640 | Oxazol-5-yl | 4-CF₃—C₆H₄ | Me | | |
| 2641 | Oxazol-5-yl | 2,4-F₂—C₆H₃ | Me | | |
| 2642 | Oxazol-5-yl | 2,5-F₂—C₆H₃ | Me | | |
| 2643 | Oxazol-5-yl | 3,4-F₂—C₆H₃ | Me | | |
| 2644 | Oxazol-5-yl | 3,5-F₂—C₆H₃ | Me | | |
| 2645 | Oxazol-5-yl | 2,3-Cl₂—C₆H₃ | Me | | |
| 2646 | Oxazol-5-yl | 2,4-Cl₂—C₆H₃ | Me | | ¹H-NMR(CDCl₃)δ ppm: 2.02(3H, S), 4.00(3H, S), 5.13(2H, S), 6.85(1H, S), 7.13–7.58(7H, m)7.91(1H, S) |
| 2647 | Oxazol-5-yl | 2,5-Cl₂—C₆H₃ | Me | | |
| 2648 | Oxazol-5-yl | 3,4-Cl₂—C₆H₃ | Me | | mp 94.0–95.0° C. |
| 2649 | Oxazol-5-yl | 3,5-Cl₂—C₆H₃ | Me | | |
| 2650 | Oxazol-5-yl | 3,4-Me₂—C₆H₃ | Me | | |
| 2651 | Oxazol-5-yl | 2,4-Me₂—C₆H₃ | Me | | |
| 2652 | Oxazol-5-yl | 3-Ph—C₆H₄ | Me | | |
| 2653 | Oxazol-5-yl | 4-Ph—C₆H₄ | Me | | |
| 2654 | Oxazol-5-yl | Morpholino | Me | | |
| 2655 | Oxazol-5-yl | 2,6-Me₂-morpholino | Me | | |
| 2656 | Oxazol-5-yl | C₆H₅ | Et | | |
| 2657 | Oxazol-5-yl | 4-F—C₆H₄ | Et | | |
| 2658 | Oxazol-5-yl | 4-Cl—C₆H₄ | Et | | |
| 2659 | Oxazol-5-yl | 4-Me—C₆H₄ | Et | | |
| 2660 | Oxazol-5-yl | 3,4-Cl₂—C₆H₃ | Et | | |
| 2661 | 5-Me-1,2,4-oxadiazol-3-yl | C₆H₅ | Me | | ¹H-NMR(CDCl₃)δ ppm: 2.11(3H, s), 2.95(3H, s), 4.08(3H, s), 5.16(2H, s), 7.26–7.58(9H, m) |
| 2662 | 5-Me-1,2,4-oxadiazol-3-yl | 2-F—C₆H₄ | Me | | |
| 2663 | 5-Me-1,2,4-oxadiazol-3-yl | 3-F—C₆H₄ | Me | | |
| 2664 | 5-Me-1,2,4-oxadiazol-3-yl | 4-F—C₆H₄ | Me | | |
| 2665 | 5-Me-1,2,4-oxadiazol-3-yl | 2-Cl—C₆H₄ | Me | | |
| 2666 | 5-Me-1,2,4-oxadiazol-3-yl | 3-Cl—C₆H₄ | Me | | |
| 2667 | 5-Me-1,2,4-oxadiazol-3-yl | 4-Cl—C₆H₄ | Me | | |
| 2668 | 5-Me-1,2,4-oxadiazol-3-yl | 2-Br—C₆H₄ | Me | | |

-continued

| No | R¹ | R² | R³ | n | Physical data |
|---|---|---|---|---|---|
| 2669 | 5-Me-1,2,4-oxadiazol-3-yl | 3-Br—C₆H₄ | Me | | |
| 2670 | 5-Me-1,2,4-oxadiazol-3-yl | 4-Br—C₆H₄ | Me | | |
| 2671 | 5-Me-1,2,4-oxadiazol-3-yl | 3-I—C₆H₄ | Me | | |
| 2672 | 5-Me-1,2,4-oxadiazol-3-yl | 2-Me—C₆H₄ | Me | | |
| 2673 | 5-Me-1,2,4-oxadiazol-3-yl | 3-Me—C₆H₄ | Me | | |
| 2674 | 5-Me-1,2,4-oxadiazol-3-yl | 4-Me—C₆H₄ | Me | | |
| 2675 | 5-Me-1,2,4-oxadiazol-3-yl | 3-Et—C₆H₄ | Me | | |
| 2676 | 5-Me-1,2,4-oxadiazol-3-yl | 4-Et—C₆H₄ | Me | | |
| 2677 | 5-Me-1,2,4-oxadiazol-3-yl | 3-MeO—C₆H₄ | Me | | |
| 2678 | 5-Me-1,2,4-oxadiazol-3-yl | 4-MeO—C₆H₄ | Me | | |
| 2679 | 5-Me-1,2,4-oxadiazol-3-yl | 3-CF₃—C₆H₄ | Me | | |
| 2680 | 5-Me-1,2,4-oxadiazol-3-yl | 4-CF₃—C₆H₄ | Me | | |
| 2681 | 5-Me-1,2,4-oxadiazol-3-yl | 2,4-F₂—C₆H₃ | Me | | |
| 2682 | 5-Me-1,2,4-oxadiazol-3-yl | 2,5-F₂—C₆H₃ | Me | | |
| 2683 | 5-Me-1,2,4-oxadiazol-3-yl | 3,4-F₂—C₆H₃ | Me | | |
| 2684 | 5-Me-1,2,4-oxadiazol-3-yl | 3,5-F₂—C₆H₃ | Me | | |
| 2685 | 5-Me-1,2,4-oxadiazol-3-yl | 2,3-Cl₂—C₆H₃ | Me | | |
| 2686 | 5-Me-1,2,4-oxadiazol-3-yl | 2,4-Cl₂—C₆H₃ | Me | | |
| 2687 | 5-Me-1,2,4-oxadiazol-3-yl | 2,5-Cl₂—C₆H₃ | Me | | |
| 2688 | 5-Me-1,2,4-oxadiazol-3-yl | 3,4-Cl₂—C₆H₃ | Me | | |
| 2689 | 5-Me-1,2,4-oxadiazol-3-yl | 3,5-Cl₂—C₆H₃ | Me | | |
| 2690 | 5-Me-1,2,4-oxadiazol-3-yl | 3,4-Me₂—C₆H₃ | Me | | |
| 2691 | 5-Me-1,2,4-oxadiazol-3-yl | 2,4-Me₂—C₆H₃ | Me | | |
| 2692 | 5-Me-1,2,4-oxadiazol-3-yl | 3-Ph—C₆H₄ | Me | | |
| 2693 | 5-Me-1,2,4-oxadiazol-3-yl | 4-Ph—C₆H₄ | Me | | |
| 2694 | 5-Me-1,2,4-oxadiazol-3-yl | Morpholino | Me | | |
| 2695 | 5-Me-1,2,4-oxadiazol-3-yl | 2,6-Me₂-morpholino | Me | | |
| 2696 | 5-Me-1,2,4-oxadiazol-3-yl | C₆H₅ | Et | | |
| 2697 | 5-Me-1,2,4-oxadiazol-3-yl | 4-F—C₆H₄ | Et | | |
| 2698 | 5-Me-1,2,4-oxadiazol-3-yl | 4-Cl—C₆H₄ | Et | | |
| 2699 | 5-Me-1,2,4-oxadiazol-3-yl | 4-Me—C₆H₄ | Et | | |
| 2700 | 5-Me-1,2,4-oxadiazol-3-yl | 3,4-Cl₂—C₆H₃ | Et | | |
| 2701 | 1-Me-1H-tetrazol-5-yl | C₆H₅ | Me | | mp 119–120° C. |
| 2702 | 1-Me-1H-tetrazol-5-yl | 2-F—C₆H₄ | Me | | |
| 2703 | 1-Me-1H-tetrazol-5-yl | 3-F—C₆H₄ | Me | | |
| 2704 | 1-Me-1H-tetrazol-5-yl | 4-F—C₆H₄ | Me | | |
| 2705 | 1-Me-1H-tetrazol-5-yl | 2-Cl—C₆H₄ | Me | | |
| 2706 | 1-Me-1H-tetrazol-5-yl | 3-Cl—C₆H₄ | Me | | |

-continued

| No | R¹ | R² | R³ | n | Physical data |
|---|---|---|---|---|---|
| 2707 | 1-Me-1H-tetrazol-5-yl | 4-Cl—$C_6H_4$ | Me | | |
| 2708 | 1-Me-1H-tetrazol-5-yl | 2-Br—$C_6H_4$ | Me | | |
| 2709 | 1-Me-1H-tetrazol-5-yl | 3-Br—$C_6H_4$ | Me | | |
| 2710 | 1-Me-1H-tetrazol-5-yl | 4-Br—$C_6H_4$ | Me | | |
| 2711 | 1-Me-1H-tetrazol-5-yl | 3-I—$C_6H_4$ | Me | | |
| 2712 | 1-Me-1H-tetrazol-5-yl | 2-Me—$C_6H_4$ | Me | | |
| 2713 | 1-Me-1H-tetrazol-5-yl | 3-Me—$C_6H_4$ | Me | | |
| 2714 | 1-Me-1H-tetrazol-5-yl | 4-Me—$C_6H_4$ | Me | | |
| 2715 | 1-Me-1H-tetrazol-5-yl | 3-Et—$C_6H_4$ | Me | | |
| 2716 | 1-Me-1H-tetrazol-5-yl | 4-Et—$C_6H_4$ | Me | | |
| 2717 | 1-Me-1H-tetrazol-5-yl | 3-MeO—$C_6H_4$ | Me | | |
| 2718 | 1-Me-1H-tetrazol-5-yl | 4-MeO—$C_6H_4$ | Me | | |
| 2719 | 1-Me-1H-tetrazol-5-yl | 3-$CF_3$—$C_6H_4$ | Me | | |
| 2720 | 1-Me-1H-tetrazol-5-yl | 4-$CF_3$—$C_6H_4$ | Me | | |
| 2721 | 1-Me-1H-tetrazol-5-yl | 2,4-$F_2$—$C_6H_3$ | Me | | |
| 2722 | 1-Me-1H-tetrazol-5-yl | 2,5-$F_2$—$C_6H_3$ | Me | | |
| 2723 | 1-Me-1H-tetrazol-5-yl | 3,4-$F_2$—$C_6H_3$ | Me | | |
| 2724 | 1-Me-1H-tetrazol-5-yl | 3,5-$F_2$—$C_6H_3$ | Me | | |
| 2725 | 1-Me-1H-tetrazol-5-yl | 2,3-$Cl_2$—$C_6H_3$ | Me | | |
| 2726 | 1-Me-1H-tetrazol-5-yl | 2,4-$Cl_2$—$C_6H_3$ | Me | | |
| 2727 | 1-Me-1H-tetrazol-5-yl | 2,5-$Cl_2$—$C_6H_3$ | Me | | |
| 2728 | 1-Me-1H-tetrazol-5-yl | 3,4-$Cl_2$—$C_6H_3$ | Me | | |
| 2729 | 1-Me-1H-tetrazol-5-yl | 3,5-$Cl_2$—$C_6H_3$ | Me | | |
| 2730 | 1-Me-1H-tetrazol-5-yl | 3,4-$Me_2$—$C_6H_3$ | Me | | |
| 2731 | 1-Me-1H-tetrazol-5-yl | 2,4-$Me_2$—$C_6H_3$ | Me | | |
| 2732 | 1-Me-1H-tetrazol-5-yl | 3-Ph—$C_6H_4$ | Me | | |
| 2733 | 1-Me-1H-tetrazol-5-yl | 4-Ph—$C_6H_4$ | Me | | |
| 2734 | 1-Me-1H-tetrazol-5-yl | Morpholino | Me | | |
| 2735 | 1-Me-1H-tetrazol-5-yl | 2,6-$Me_2$-morpholino | Me | | |
| 2736 | 1-Me-1H-tetrazol-5-yl | $C_6H_5$ | Et | | |
| 2737 | 1-Me-1H-tetrazol-5-yl | 4-F—$C_6H_4$ | Et | | |
| 2738 | 1-Me-1H-tetrazol-5-yl | 4-Cl—$C_6H_4$ | Et | | |
| 2739 | 1-Me-1H-tetrazol-5-yl | 4-Me—$C_6H_4$ | Et | | |
| 2740 | 1-Me-1H-tetrazol-5-yl | 3,4-$Cl_2$—$C_6H_3$ | Et | | |
| 2741 | 2-Me-2H-tetrazol-5-yl | $C_6H_5$ | Me | | mp 96–98° C. |
| 2742 | 2-Me-2H-tetrazol-5-yl | 2-F—$C_6H_4$ | Me | | |
| 2743 | 2-Me-2H-tetrazol-5-yl | 3-F—$C_6H_4$ | Me | | |

-continued

| No | R¹ | R² | R³ | n | Physical data |
|---|---|---|---|---|---|
| 2744 | 2-Me-2H-tetrazol-5-yl | 4-F—C₆H₄ | Me | | |
| 2745 | 2-Me-2H-tetrazol-5-yl | 2-Cl—C₆H₄ | Me | | |
| 2746 | 2-Me-2H-tetrazol-5-yl | 3-Cl—C₆H₄ | Me | | |
| 2747 | 2-Me-2H-tetrazol-5-yl | 4-Cl—C₆H₄ | Me | | |
| 2748 | 2-Me-2H-tetrazol-5-yl | 2-Br—C₆H₄ | Me | | |
| 2749 | 2-Me-2H-tetrazol-5-yl | 3-Br—C₆H₄ | Me | | |
| 2750 | 2-Me-2H-tetrazol-5-yl | 4-Br—C₆H₄ | Me | | |
| 2751 | 2-Me-2H-tetrazol-5-yl | 3-I—C₆H₄ | Me | | |
| 2752 | 2-Me-2H-tetrazol-5-yl | 2-Me—C₆H₄ | Me | | |
| 2753 | 2-Me-2H-tetrazol-5-yl | 3-Me—C₆H₄ | Me | | |
| 2754 | 2-Me-2H-tetrazol-5-yl | 4-Me—C₆H₄ | Me | | |
| 2755 | 2-Me-2H-tetrazol-5-yl | 3-Et—C₆H₄ | Me | | |
| 2756 | 2-Me-2H-tetrazol-5-yl | 4-Et—C₆H₄ | Me | | |
| 2757 | 2-Me-2H-tetrazol-5-yl | 3-MeO—C₆H₄ | Me | | |
| 2758 | 2-Me-2H-tetrazol-5-yl | 4-MeO—C₆H₄ | Me | | |
| 2759 | 2-Me-2H-tetrazol-5-yl | 3-CF₃—C₆H₄ | Me | | |
| 2760 | 2-Me-2H-tetrazol-5-yl | 4-CF₃—C₆H₄ | Me | | |
| 2761 | 2-Me-2H-tetrazol-5-yl | 2,4-F₂—C₆H₃ | Me | | |
| 2762 | 2-Me-2H-tetrazol-5-yl | 2,5-F₂—C₆H₃ | Me | | |
| 2763 | 2-Me-2H-tetrazol-5-yl | 3,4-F₂—C₆H₃ | Me | | |
| 2764 | 2-Me-2H-tetrazol-5-yl | 3,5-F₂—C₆H₃ | Me | | |
| 2765 | 2-Me-2H-tetrazol-5-yl | 2,3-Cl₂—C₆H₃ | Me | | |
| 2766 | 2-Me-2H-tetrazol-5-yl | 2,4-Cl₂—C₆H₃ | Me | | |
| 2767 | 2-Me-2H-tetrazol-5-yl | 2,5-Cl₂—C₆H₃ | Me | | |
| 2768 | 2-Me-2H-tetrazol-5-yl | 3,4-Cl₂—C₆H₃ | Me | | |

-continued

| No | R¹ | R² | R³ | n | Physical data |
|---|---|---|---|---|---|
| 2769 | 2-Me-2H-tetrazol-5-yl | 3,5-Cl₂—C₆H₃ | Me | | |
| 2770 | 2-Me-2H-tetrazol-5-yl | 3,4-Me₂—C₆H₃ | Me | | |
| 2771 | 2-Me-2H-tetrazol-5-yl | 2,4-Me₂—C₆H₃ | Me | | |
| 2772 | 2-Me-2H-tetrazol-5-yl | 3-Ph—C₆H₄ | Me | | |
| 2773 | 2-Me-2H-tetrazol-5-yl | 4-Ph—C₆H₄ | Me | | |
| 2774 | 2-Me-2H-tetrazol-5-yl | Morpholino | Me | | |
| 2775 | 2-Me-2H-tetrazol-5-yl | 2,6-Me₂-morpholino | Me | | |
| 2776 | 2-Me-2H-tetrazol-5-yl | C₆H₅ | Et | | |
| 2777 | 2-Me-2H-tetrazol-5-yl | 4-F—C₆H₄ | Et | | |
| 2778 | 2-Me-2H-tetrazol-5-yl | 4-Cl—C₆H₄ | Et | | |
| 2779 | 2-Me-2H-tetrazol-5-yl | 4-Me—C₆H₄ | Et | | |
| 2780 | 2-Me-2H-tetrazol-5-yl | 3,4-Cl₂—C₆H₃ | Et | | |
| 2781 | Thiazolidin-2-yl | C₆H₅ | Me | | |
| 2782 | Thiazolidin-2-yl | 2-F—C₆H₄ | Me | | |
| 2783 | Thiazolidin-2-yl | 3-F—C₆H₄ | Me | | |
| 2784 | Thiazolidin-2-yl | 4-F—C₆H₄ | Me | | |
| 2785 | Thiazolidin-2-yl | 2-Cl—C₆H₄ | Me | | |
| 2786 | Thiazolidin-2-yl | 3-Cl—C₆H₄ | Me | | |
| 2787 | Thiazolidin-2-yl | 4-Cl—C₆H₄ | Me | | |
| 2788 | Thiazolidin-2-yl | 2-Br—C₆H₄ | Me | | |
| 2789 | Thiazolidin-2-yl | 3-Br—C₆H₄ | Me | | |
| 2790 | Thiazolidin-2-yl | 4-Br—C₆H₄ | Me | | |
| 2791 | Thiazolidin-2-yl | 3-I—C₆H₄ | Me | | |
| 2792 | Thiazolidin-2-yl | 2-Me—C₆H₄ | Me | | |
| 2793 | Thiazolidin-2-yl | 3-Me—C₆H₄ | Me | | |
| 2794 | Thiazolidin-2-yl | 4-Me—C₆H₄ | Me | | |
| 2795 | Thiazolidin-2-yl | 3-Et—C₆H₄ | Me | | |
| 2796 | Thiazolidin-2-yl | 4-Et—C₆H₄ | Me | | |
| 2797 | Thiazolidin-2-yl | 3-MeO—C₆H₄ | Me | | |
| 2798 | Thiazolidin-2-yl | 4-MeO—C₆H₄ | Me | | |
| 2799 | Thiazolidin-2-yl | 3-CF₃—C₆H₄ | Me | | ¹H-NMR(CDCl₃)δ ppm: 2.39(3H, S), 2.75–3.10(3H, m)3.50(2H, m), 3.86(3H, S), 5.20–5.30(2H, m), 5.30–5.50(1H, m), 7.37–7.61(6H, m), 7.82(1H, j=7.9), 7.91(1H, S) |
| 2800 | Thiazolidin-2-yl | 4-CF₃—C₆H₄ | Me | | |
| 2801 | Thiazolidin-2-yl | 2,4-F₂—C₆H₃ | Me | | |
| 2802 | Thiazolidin-2-yl | 2,5-F₂—C₆H₃ | Me | | |
| 2803 | Thiazolidin-2-yl | 3,4-F₂—C₆H₃ | Me | | |
| 2804 | Thiazolidin-2-yl | 3,5-F₂—C₆H₃ | Me | | |
| 2805 | Thiazolidin-2-yl | 2,3-Cl₂—C₆H₃ | Me | | |
| 2806 | Thiazolidin-2-yl | 2,4-Cl₂—C₆H₃ | Me | | |
| 2807 | Thiazolidin-2-yl | 2,5-Cl₂—C₆H₃ | Me | | |
| 2808 | Thiazolidin-2-yl | 3,4-Cl₂—C₆H₃ | Me | | |
| 2809 | Thiazolidin-2-yl | 3,5-Cl₂—C₆H₃ | Me | | |
| 2810 | Thiazolidin-2-yl | 3,4-Me₂—C₆H₃ | Me | | |
| 2811 | Thiazolidin-2-yl | 2,4-Me₂—C₆H₃ | Me | | |
| 2812 | Thiazolidin-2-yl | 3-Ph—C₆H₄ | Me | | |
| 2813 | Thiazolidin-2-yl | 4-Ph—C₆H₄ | Me | | |

-continued

| No | R¹ | R² | R³ | n | Physical data |
|---|---|---|---|---|---|
| 2814 | Thiazolidin-2-yl | Morpholino | Me | | ¹H-NMR(CDCl₃)δ ppm: 1.98(3H, S), 2.70–2.80(1H, m), 2.89–3.06(2H, m), 3.10(4H, t j=4.9), 3.4–3.5(2H, m), 3.69(4H, t j=4.9), 3.83(3H, S), 4.91(2H, S), 5.40(1H, S)7.33–7.55(4H, m) |
| 2815 | Thiazolidin-2-yl | 2,6-Me₂-morpholino | Me | | |
| 2816 | Thiazolidin-2-yl | C₆H₅ | Et | | |
| 2817 | Thiazolidin-2-yl | 4-F—C₆H₄ | Et | | |
| 2818 | Thiazolidin-2-yl | 4-Cl—C₆H₄ | Et | | |
| 2819 | Thiazolidin-2-yl | 4-Me—C₆H₄ | Et | | |
| 2820 | Thiazolidin-2-yl | 3,4-Cl₂—C₆H₃ | Et | | |
| 2821 | 3-Me-thiazolidin-2-yl | C₆H₅ | Me | | |
| 2822 | 3-Me-thiazolidin-2-yl | 2-F—C₆H₄ | Me | | |
| 2823 | 3-Me-thiazolidin-2-yl | 3-F—C₆H₄ | Me | | |
| 2824 | 3-Me-thiazolidin-2-yl | 4-F—C₆H₄ | Me | | |
| 2825 | 3-Me-thiazolidin-2-yl | 2-Cl—C₆H₄ | Me | | |
| 2826 | 3-Me-thiazolidin-2-yl | 3-Cl—C₆H₄ | Me | | |
| 2827 | 3-Me-thiazolidin-2-yl | 4-Cl—C₆H₄ | Me | | |
| 2828 | 3-Me-thiazolidin-2-yl | 2-Br—C₆H₄ | Me | | |
| 2829 | 3-Me-thiazolidin-2-yl | 3-Br—C₆H₄ | Me | | |
| 2830 | 3-Me-thiazolidin-2-yl | 4-Br—C₆H₄ | Me | | |
| 2831 | 3-Me-thiazolidin-2-yl | 3-I—C₆H₄ | Me | | |
| 2832 | 3-Me-thiazolidin-2-yl | 2-Me—C₆H₄ | Me | | |
| 2833 | 3-Me-thiazolidin-2-yl | 3-Me—C₆H₄ | Me | | |
| 2834 | 3-Me-thiazolidin-2-yl | 4-Me—C₆H₄ | Me | | |
| 2835 | 3-Me-thiazolidin-2-yl | 3-Et—C₆H₄ | Me | | |
| 2836 | 3-Me-thiazolidin-2-yl | 4-Et—C₆H₄ | Me | | |
| 2837 | 3-Me-thiazolidin-2-yl | 3-MeO—C₆H₄ | Me | | |
| 2838 | 3-Me-thiazolidin-2-yl | 4-MeO—C₆H₄ | Me | | |
| 2839 | 3-Me-thiazolidin-2-yl | 3-CF₃—C₆H₄ | Me | | ¹H-NMR(CDCl₃)δ ppm: 2.31(3H, d j=3.7), 2.47(3H, d j=14.7), 2.83–3.25(4H, m), 3.84(3H, S), 4.94((1H, d j=54.9), 5.14–5.35(2H, m), 7.19–7.60(6H, m), 7.83(1H, d j=7.9), 7.93(1H, S) |
| 2840 | 3-Me-thiazolidin-2-yl | 4-CF₃—C₆H₄ | Me | | |
| 2841 | 3-Me-thiazolidin-2-yl | 2,4-F₂—C₆H₃ | Me | | |
| 2842 | 3-Me-thiazolidin-2-yl | 2,5-F₂—C₆H₃ | Me | | |
| 2843 | 3-Me-thiazolidin-2-yl | 3,4-F₂—C₆H₃ | Me | | |
| 2844 | 3-Me-thiazolidin-2-yl | 3,5-F₂—C₆H₃ | Me | | |
| 2845 | 3-Me-thiazolidin-2-yl | 2,3-Cl₂—C₆H₃ | Me | | |
| 2846 | 3-Me-thiazolidin-2-yl | 2,4-Cl₂—C₆H₃ | Me | | |
| 2847 | 3-Me-thiazolidin-2-yl | 2,5-Cl₂—C₆H₃ | Me | | |
| 2848 | 3-Me-thiazolidin-2-yl | 3,4-Cl₂—C₆H₃ | Me | | |
| 2849 | 3-Me-thiazolidin-2-yl | 3,5-Cl₂—C₆H₃ | Me | | |

-continued

| No | R¹ | R² | R³ | n | Physical data |
|---|---|---|---|---|---|
| 2850 | 3-Me-thiazolidin-2-yl | 3,4-Me$_2$—C$_6$H$_3$ | Me | | |
| 2851 | 3-Me-thiazolidin-2-yl | 2,4-Me$_2$—C$_6$H$_3$ | Me | | |
| 2852 | 3-Me-thiazolidin-2-yl | 3-Ph—C$_6$H$_4$ | Me | | |
| 2853 | 3-Me-thiazolidin-2-yl | 4-Ph—C$_6$H$_4$ | Me | | |
| 2854 | 3-Me-thiazolidin-2-yl | Morpholino | Me | | |
| 2855 | 3-Me-thiazolidin-2-yl | 2,6-Me$_2$-morpholino | Me | | |
| 2856 | 3-Me-thiazolidin-2-yl | C$_6$H$_5$ | Et | | |
| 2857 | 3-Me-thiazolidin-2-yl | 4-F—C$_6$H$_4$ | Et | | |
| 2858 | 3-Me-thiazolidin-2-yl | 4-Cl—C$_6$H$_4$ | Et | | |
| 2859 | 3-Me-thiazolidin-2-yl | 4-Me—C$_6$H$_4$ | Et | | |
| 2860 | 3-Me-thiazolidin-2-yl | 3,4-Cl$_2$—C$_6$H$_3$ | Et | | |
| 2861 | 2-Isoxazolin-3-yl | C$_6$H$_5$ | Me | | |
| 2862 | 2-Isoxazolin-3-yl | 2-F—C$_6$H$_4$ | Me | | |
| 2863 | 2-Isoxazolin-3-yl | 3-F—C$_6$H$_4$ | Me | | |
| 2864 | 2-Isoxazolin-3-yl | 4-F—C$_6$H$_4$ | Me | | |
| 2865 | 2-Isoxazolin-3-yl | 2-Cl—C$_6$H$_4$ | Me | | |
| 2866 | 2-Isoxazolin-3-yl | 3-Cl—C$_6$H$_4$ | Me | | |
| 2867 | 2-Isoxazolin-3-yl | 4-Cl—C$_6$H$_4$ | Me | | |
| 2868 | 2-Isoxazolin-3-yl | 2-Br—C$_6$H$_4$ | Me | | |
| 2869 | 2-Isoxazolin-3-yl | 3-Br—C$_6$H$_4$ | Me | | |
| 2870 | 2-Isoxazolin-3-yl | 4-Br—C$_6$H$_4$ | Me | | |
| 2871 | 2-Isoxazolin-3-yl | 3-I—C$_6$H$_4$ | Me | | |
| 2872 | 2-Isoxazolin-3-yl | 2-Me—C$_6$H$_4$ | Me | | |
| 2873 | 2-Isoxazolin-3-yl | 3-Me—C$_6$H$_4$ | Me | | |
| 2874 | 2-Isoxazolin-3-yl | 4-Me—C$_6$H$_4$ | Me | | |
| 2875 | 2-Isoxazolin-3-yl | 3-Et—C$_6$H$_4$ | Me | | |
| 2876 | 2-Isoxazolin-3-yl | 4-Et—C$_6$H$_4$ | Me | | |
| 2877 | 2-Isoxazolin-3-yl | 3-MeO—C$_6$H$_4$ | Me | | |
| 2878 | 2-Isoxazolin-3-yl | 4-MeO—C$_6$H$_4$ | Me | | |
| 2879 | 2-Isoxazolin-3-yl | 3-CF$_3$—C$_6$H$_4$ | Me | | |
| 2880 | 2-Isoxazolin-3-yl | 4-CF$_3$—C$_6$H$_4$ | Me | | |
| 2881 | 2-Isoxazolin-3-yl | 2,4-F$_2$—C$_6$H$_3$ | Me | | |
| 2882 | 2-Isoxazolin-3-yl | 2,5-F$_2$—C$_6$H$_3$ | Me | | |
| 2883 | 2-Isoxazolin-3-yl | 3,4-F$_2$—C$_6$H$_3$ | Me | | |
| 2884 | 2-Isoxazolin-3-yl | 3,5-F$_2$—C$_6$H$_3$ | Me | | |
| 2885 | 2-Isoxazolin-3-yl | 2,3-Cl$_2$—C$_6$H$_3$ | Me | | |
| 2886 | 2-Isoxazolin-3-yl | 2,4-Cl$_2$—C$_6$H$_3$ | Me | | |
| 2887 | 2-Isoxazolin-3-yl | 2,5-Cl$_2$—C$_6$H$_3$ | Me | | |
| 2888 | 2-Isoxazolin-3-yl | 3,4-Cl$_2$—C$_6$H$_3$ | Me | | |
| 2889 | 2-Isoxazolin-3-yl | 3,5-Cl$_2$—C$_6$H$_3$ | Me | | |
| 2890 | 2-Isoxazolin-3-yl | 3,4-Me$_2$—C$_6$H$_3$ | Me | | |
| 2891 | 2-Isoxazolin-3-yl | 2,4-Me$_2$—C$_6$H$_3$ | Me | | |
| 2892 | 2-Isoxazolin-3-yl | 3-Ph—C$_6$H$_4$ | Me | | |
| 2893 | 2-Isoxazolin-3-yl | 4-Ph—C$_6$H$_4$ | Me | | |
| 2894 | 2-Isoxazolin-3-yl | Morpholino | Me | | |
| 2895 | 2-Isoxazolin-3-yl | 2,6-Me$_2$-morpholino | Me | | |
| 2896 | 2-Isoxazolin-3-yl | C$_6$H$_5$ | Et | | |
| 2897 | 2-Isoxazolin-3-yl | 4-F—C$_6$H$_4$ | Et | | |
| 2898 | 2-Isoxazolin-3-yl | 4-Cl—C$_6$H$_4$ | Et | | |
| 2899 | 2-Isoxazolin-3-yl | 4-Me—C$_6$H$_4$ | Et | | |
| 2990 | 2-Isoxazolin-3-yl | 3,4-Cl$_2$—C$_6$H$_3$ | Et | | |
| 2901 | 5-Me-2-isoxazolin-3-yl | C$_6$H$_5$ | Me | | |
| 2902 | 5-Me-2-isoxazolin-3-yl | 2-F—C$_6$H$_4$ | Me | | |
| 2903 | 5-Me-2-isoxazolin-3-yl | 3-F—C$_6$H$_4$ | Me | | |
| 2904 | 5-Me-2-isoxazolin-3-yl | 4-F—C$_6$H$_4$ | Me | | |
| 2905 | 5-Me-2-isoxazolin-3-yl | 2-Cl—C$_6$H$_4$ | Me | | |
| 2906 | 5-Me-2-isoxazolin-3-yl | 3-Cl—C$_6$H$_4$ | Me | | |
| 2907 | 5-Me-2-isoxazolin-3-yl | 4-Cl—C$_6$H$_4$ | Me | | |

-continued

| No | R¹ | R² | R³ | n | Physical data |
|---|---|---|---|---|---|
| 2908 | 5-Me-2-isoxazolin-3-yl | 2-Br—C₆H₄ | Me | | |
| 2909 | 5-Me-2-isoxazolin-3-yl | 3-Br—C₆H₄ | Me | | |
| 2910 | 5-Me-2-isoxazolin-3-yl | 4-Br—C₆H₄ | Me | | |
| 2911 | 5-Me-2-isoxazolin-3-yl | 3-I—C₆H₄ | Me | | |
| 2912 | 5-Me-2-isoxazolin-3-yl | 2-Me—C₆H₄ | Me | | |
| 2913 | 5-Me-2-isoxazolin-3-yl | 3-Me—C₆H₄ | Me | | |
| 2914 | 5-Me-2-isoxazolin-3-yl | 4-Me—C₆H₄ | Me | | |
| 2915 | 5-Me-2-isoxazolin-3-yl | 3-Et—C₆H₄ | Me | | |
| 2916 | 5-Me-2-isoxazolin-3-yl | 4-Et—C₆H₄ | Me | | |
| 2917 | 5-Me-2-isoxazolin-3-yl | 3-MeO—C₆H₄ | Me | | |
| 2918 | 5-Me-2-isoxazolin-3-yl | 4-MeO—C₆H₄ | Me | | |
| 2919 | 5-Me-2-isoxazolin-3-yl | 3-CF₃—C₆H₄ | Me | | |
| 2920 | 5-Me-2-isoxazolin-3-yl | 4-CF₃—C₆H₄ | Me | | |
| 2921 | 5-Me-2-isoxazolin-3-yl | 2,4-F₂—C₆H₃ | Me | | |
| 2922 | 5-Me-2-isoxazolin-3-yl | 2,5-F₂—C₆H₃ | Me | | |
| 2923 | 5-Me-2-isoxazolin-3-yl | 3,4-F₂—C₆H₃ | Me | | |
| 2924 | 5-Me-2-isoxazolin-3-yl | 3,5-F₂—C₆H₃ | Me | | |
| 2925 | 5-Me-2-isoxazolin-3-yl | 2,3-Cl₂—C₆H₃ | Me | | |
| 2926 | 5-Me-2-isoxazolin-3-yl | 2,4-Cl₂—C₆H₃ | Me | | |
| 2927 | 5-Me-2-isoxazolin-3-yl | 2,5-Cl₂—C₆H₃ | Me | | |
| 2928 | 5-Me-2-isoxazolin-3-yl | 3,4-Cl₂—C₆H₃ | Me | | |
| 2929 | 5-Me-2-isoxazolin-3-yl | 3,5-Cl₂—C₆H₃ | Me | | |
| 2930 | 5-Me-2-isoxazolin-3-yl | 3,4-Me₂—C₆H₃ | Me | | |
| 2931 | 5-Me-2-isoxazolin-3-yl | 2,4-Me₂—C₆H₃ | Me | | |
| 2932 | 5-Me-2-isoxazolin-3-yl | 3-Ph—C₆H₄ | Me | | |
| 2933 | 5-Me-2-isoxazolin-3-yl | 4-Ph—C₆H₄ | Me | | |
| 2934 | 5-Me-2-isoxazolin-3-yl | Morpholino | Me | | |
| 2935 | 5-Me-2-isoxazolin-3-yl | 2,6-Me₂-morpholino | Me | | |
| 2936 | 5-Me-2-isoxazolin-3-yl | C₆H₅ | Et | | |
| 2937 | 5-Me-2-isoxazolin-3-yl | 4-F—C₆H₄ | Et | | |
| 2938 | 5-Me-2-isoxazolin-3-yl | 4-Cl—C₆H₄ | Et | | |
| 2939 | 5-Me-2-isoxazolin-3-yl | 4-Me—C₆H₄ | Et | | |
| 2940 | 5-Me-2-isoxazolin-3-yl | 3,4-Cl₂—C₆H₃ | Et | | |
| 2941 | Imidazol-1-yl | C₆H₅ | H | | ¹H-NMR(CDCl₃)δ ppm: 4.04(3H, S), 5.18(2H, S), 7.03(1H, S), 7.15–7.17(1H, m), 7.29–7.65(9H, m), 7.90(1H, S), 8.05(1H, S) |
| 2942 | Imidazol-1-yl | 4-F—C₆H₄ | H | | |
| 2943 | Imidazol-1-yl | 4-Cl—C₆H₄ | H | | mp 92.5–93.0° C. |
| 2944 | Imidazol-1-yl | 4-Me—C₆H₄ | H | | |
| 2945 | Imidazol-1-yl | 3,4-Cl₂—C₆H₃ | H | | |
| 2946 | 1-Me-imidazol-2-yl | C₆H₅ | H | | |

-continued

| No | R¹ | R² | R³ | n | Physical data |
|---|---|---|---|---|---|
| 2947 | 1-Me-imidazol-2-yl | 4-F—C₆H₄ | H | | |
| 2948 | 1-Me-imidazol-2-yl | 4-Cl—C₆H₄ | H | | |
| 2949 | 1-Me-imidazol-2-yl | 4-Me—C₆H₄ | H | | |
| 2950 | 1-Me-imidazol-2-yl | 3,4-Cl₂—C₆H₃ | H | | |
| 2951 | 1,2,4-Triazol-1-yl | C₆H₅ | H | | mp 76.5–77.5° C. |
| 2952 | 1,2,4-Triazol-1-yl | 4-F—C₆H₄ | H | | |
| 2953 | 1,2,4-Triazol-1-yl | 4-Cl—C₆H₄ | H | | |
| 2954 | 1,2,4-Triazol-1-yl | 4-Me—C₆H₄ | H | | |
| 2955 | 1,2,4-Triazol-1-yl | 3,4-Cl₂—C₆H₃ | H | | |
| 2956 | 5-Me-1,2,4-oxadiazol-3-yl | C₆H₅ | H | | |
| 2957 | 5-Me-1,2,4-oxadiazol-3-yl | 4-F—C₆H₄ | H | | |
| 2958 | 5-Me-1,2,4-oxadiazol-3-yl | 4-Cl—C₆H₄ | H | | |
| 2959 | 5-Me-1,2,4-oxadiazol-3-yl | 4-Me—C₆H₄ | H | | |
| 2960 | 5-Me-1,2,4-oxadiazol-3-yl | 3,4-Cl₂—C₆H₃ | H | | |
| 2961 | Isoxazol-3-yl | C₆H₅ | H | | |
| 2962 | Isoxazol-3-yl | 4-F—C₆H₄ | H | | |
| 2963 | Isoxazol-3-yl | 4-Cl—C₆H₄ | H | | |
| 2964 | Isoxazol-3-yl | 4-Me—C₆H₄ | H | | |
| 2965 | Isoxazol-3-yl | 3,4-Cl₂—C₆H₃ | H | | |
| 2966 | 5-Me-isoxazol-3-yl | C₆H₅ | H | | |
| 2967 | 5-Me-isoxazol-3-yl | 4-F—C₆H₄ | H | | |
| 2968 | 5-Me-isoxazol-3-yl | 4-Cl—C₆H₄ | H | | |
| 2969 | 5-Me-isoxazol-3-yl | 4-Me—C₆H₄ | H | | |
| 2970 | 5-Me-isoxazol-3-yl | 3,4-Cl₂—C₆H₃ | H | | |
| 2971 | Isoxazol-5-yl | C₆H₅ | H | | |
| 2972 | Isoxazol-5-yl | 4-F—C₆H₄ | H | | |
| 2973 | Isoxazol-5-yl | 4-Cl—C₆H₄ | H | | |
| 2974 | Isoxazol-5-yl | 4-Me—C₆H₄ | H | | |
| 2975 | Isoxazol-5-yl | 3,4-Cl₂—C₆H₃ | H | | |
| 2976 | 3-Me-isoxazol-5-yl | C₆H₅ | H | | |
| 2977 | 3-Me-isoxazol-5-yl | 4-F—C₆H₄ | H | | |
| 2978 | 3-Me-isoxazol-5-yl | 4-Cl—C₆H₄ | H | | |
| 2979 | 3-Me-isoxazol-5-yl | 4-Me—C₆H₄ | H | | |
| 2980 | 3-Me-isoxazol-5-yl | 3,4-Cl₂—C₆H₃ | H | | |
| 2981 | Oxazol-5-yl | C₆H₅ | H | | mp 77–78.5° C. |
| 2982 | Oxazol-5-yl | 4-F—C₆H₄ | H | | |
| 2983 | Oxazol-5-yl | 4-Cl—C₆H₄ | H | | |
| 2984 | Oxazol-5-yl | 4-Me—C₆H₄ | H | | |
| 2985 | Oxazol-5-yl | 3,4-Cl₂—C₆H₃ | H | | |
| 2986 | 2-Isoxazolin-3-yl | C₆H₅ | H | | |
| 2987 | 2-Isoxazolin-3-yl | 4-F—C₆H₄ | H | | |
| 2988 | 2-Isoxazolin-3-yl | 4-Cl—C₆H₄ | H | | |
| 2989 | 2-Isoxazolin-3-yl | 4-Me—C₆H₄ | H | | |
| 2990 | 2-Isoxazolin-3-yl | 3,4-Cl₂—C₆H₃ | H | | |
| 2991 | Thiazolidin-2-yl | C₆H₅ | H | | |
| 2992 | Thiazolidin-2-yl | 4-F—C₆H₄ | H | | |
| 2993 | Thiazolidin-2-yl | 4-Cl—C₆H₄ | H | | |
| 2994 | Thiazolidin-2-yl | 4-Me—C₆H₄ | H | | |
| 2995 | Thiazolidin-2-yl | 3,4-Cl₂—C₆H₃ | H | | |
| 2996 | 3-Me-thiazolidin-2-yl | C₆H₅ | H | | |
| 2997 | 3-Me-thiazolidin-2-yl | 4-F—C₆H₄ | H | | |
| 2998 | 3-Me-thiazolidin-2-yl | 4-Cl—C₆H₄ | H | | |
| 2999 | 3-Me-thiazolidin-2-yl | 4-Me—C₆H₄ | H | | |

-continued

| No | R¹ | R² | R³ | n | Physical data |
|---|---|---|---|---|---|
| 3000 | 3-Me-thiazolidin-2-yl | 3,4-Cl₂—C₆H₃ | H | | |
| 3001 | Oxazol-4-yl | C₆H₅ | Me | | mp 94.5–96.0° C. |
| 3002 | Oxazol-4-yl | 4-F—C₆H₄ | Me | | |
| 3003 | Oxazol-4-yl | 4-Cl—C₆H₄ | Me | | ¹H-NMR(CDCl₃)δ ppm: 2.04(3H, S), 4.14(3H, S), 5.22(2H, S), 7.27–7.56(8H, m), 7.77(1H, S), 7.97(1H, S) |
| 3004 | Oxazol-4-yl | 4-Me—C₆H₄ | Me | | |
| 3005 | Oxazol-4-yl | 3,4-Cl₂—C₆H₃ | Me | | ¹H-NMR(CDCl₃)δ ppm: 2.01(3H, S), 4.15(3H, S), 5.24(2H, S), 5.50–7.62(6H, m), 7.66(1H, t j=1.2), 7.76(1H, S), 7.97(1H, S) |
| 3006 | Oxazol-4-yl | C₆H₅ | H | | mp 97–98° C. |
| 3007 | Oxazol-4-yl | 4-Cl—C₆H₄ | H | | |
| 3008 | Oxazol-4-yl | C₆H₅ | Et | | |
| 3009 | Oxazol-4-yl | 4-Cl—C₆H₄ | Et | | |
| 3010 | Oxazol-4-yl | 3,4-Cl₂—C₆H₃ | Et | | |
| 3011 | 1-Me-1H-tetrazol-5-yl | C₆H₅ | H | | mp 119–120° C. |
| 3012 | 1-Me-1H-tetrazol-5-yl | 4-F—C₆H₄ | H | | |
| 3013 | 1-Me-1H-tetrazol-5-yl | 4-Cl—C₆H₄ | H | | |
| 3014 | 1-Me-1H-tetrazol-5-yl | 4-Me—C₆H₄ | H | | |
| 3015 | 1-Me-1H-tetrazol-5-yl | 3,4-Cl₂—C₆H₃ | H | | |
| 3016 | Oxazol-4-yl | 3-CF₃—C₆H₄ | Me | | ¹H-NMR(CDCl₃)δ ppm: 2.07(3H, S), 4.15(3H, S), 5.26(2H, S), 7.35–7.77(8H, m), 7.82(1H, S), 7.97(1H, S) |
| 3017 | 1-Me-1H-tetrazol-5-yl | 4-Cl—C₆H₄ | H | | |
| 3018 | 1-Me-1H-tetrazol-5-yl | C₆H₅ | Et | | |
| 3019 | 1-Me-1H-tetrazol-5-yl | 4-Cl—C₆H₄ | Et | | |
| 3020 | Oxazol-4-yl | 2,4-Cl₂—C₆H₃ | Me | | ¹H-NMR(CDCl₃)δ ppm: 2.04(3H, S), 4.14(3H, S), 5.22(2H, S), 7.13–7.56(7H, m) 7.78(1H, S), 7.98(1H, S) |
| 3021 | 1,2,4-Oxadiazol-5-yl | C₆H₅ | Me | | |
| 3022 | 1,2,4-Oxadiazol-5-yl | 4-F—C₆H₄ | Me | | |
| 3023 | 1,2,4-Oxadiazol-5-yl | 4-Cl—C₆H₄ | Me | | |
| 3024 | 1,2,4-Oxadiazol-5-yl | 4-Me—C₆H₄ | Me | | |
| 3025 | 1,2,4-Oxadiazol-5-yl | 3,4-Cl₂—C₆H₃ | Me | | |
| 3026 | 1,2,4-Oxadiazol-5-yl | C₆H₅ | H | | mp 120–121° C. |
| 3027 | 1,2,4-Oxadiazol-5-yl | 4-Cl—C₆H₄ | H | | |
| 3028 | 1,2,4-Oxadiazol-5-yl | C₆H₅ | Et | | |
| 3029 | 1,2,4-Oxadiazol-5-yl | 4-Cl—C₆H₄ | Et | | |
| 3030 | 1,2,4-Oxadiazol-5-yl | 3,4-Cl₂—C₆H₃ | Et | | |
| 3031 | 1-Me-1,2,4-triazol-5-yl | C₆H₅ | Me | | |
| 3032 | 1-Me-1,2,4-triazol-5-yl | 4-F—C₆H₄ | Me | | |
| 3033 | 1-Me-1,2,4-triazol-5-yl | 4-Cl—C₆H₄ | Me | | |
| 3034 | 1-Me-1,2,4-triazol-5-yl | 4-Me—C₆H₄ | Me | | |
| 3035 | 1-Me-1,2,4-triazol-5-yl | 3,4-Cl₂—C₆H₃ | Me | | |
| 3036 | 1-Me-1,2,4-triazol-5-yl | C₆H₅ | H | | ¹H-NMR(CDCl₃)δ ppm: 4.03(3H, S), 4.12(3H, S), 5.07(2H, S), 7.27–7.55(9H, m), 7.79(1H, S), 7.80(1H, S) |

-continued

| No | R¹ | R² | R³ | n | Physical data |
|---|---|---|---|---|---|
| 3037 | 1-Me-1,2,4-triazol-5-yl | 4-Cl—C₆H₄ | H | | |
| 3038 | 1-Me-1,2,4-triazol-5-yl | C₆H₅ | Et | | |
| 3039 | 1-Me-1,2,4-triazol-5-yl | 4-Cl—C₆H₄ | Et | | |
| 3040 | 1-Me-1,2,4-triazol-5-yl | 3,4-Cl₂—C₆H₃ | Et | | |
| 3041 | Imidazol-1-yl | C₆H₅ | Me | | ¹H-NMR(CDCl₃)δ ppm: 2.09(3H, s), 4.03(3H, s), 5.28(2H, s), 7.01(1H, s), 7.14(1H, d, j=2.4), 7.30–7.62(9H, m), m), 8.03(1H, s) |
| 3042 | Imidazol-1-yl | 2-F—C₆H₄ | Me | | |
| 3043 | Imidazol-1-yl | 3-F—C₆H₄ | Me | | |
| 3044 | Imidazol-1-yl | 4-F—C₆H₄ | Me | | |
| 3045 | Imidazol-1-yl | 2-Cl—C₆H₄ | Me | | |
| 3046 | Imidazol-1-yl | 3-Cl—C₆H₄ | Me | | |
| 3047 | Imidazol-1-yl | 4-Cl—C₆H₄ | Me | | ¹H-NMR(CDCl₃)δ ppm: 2.07(3H, s), 4.06(3H, s), 5.18(2H, s), 7.01–7.52(10H, m), 8.01(1H, s) |
| 3048 | Imidazol-1-yl | 2-Br—C₆H₄ | Me | | |
| 3049 | Imidazol-1-yl | 3-Br—C₆H₄ | Me | | |
| 3050 | Imidazol-1-yl | 4-Br—C₆H₄ | Me | | |
| 3051 | Imidazol-1-yl | 3-I—C₆H₄ | Me | | |
| 3052 | Imidazol-1-yl | 2-Me—C₆H₄ | Me | | |
| 3053 | Imidazol-1-yl | 3-Me—C₆H₄ | Me | | |
| 3054 | Imidazol-1-yl | 4-Me—C₆H₄ | Me | | |
| 3055 | Imidazol-1-yl | 3-Et—C₆H₄ | Me | | |
| 3056 | Imidazol-1-yl | 4-Et—C₆H₄ | Me | | |
| 3057 | Imidazol-1-yl | 3-MeO—C₆H₄ | Me | | |
| 3058 | Imidazol-1-yl | 4-MeO—C₆H₄ | Me | | |
| 3059 | Imidazol-1-yl | 3-CF₃—C₆H₄ | Me | | ¹H-NMR(CDCl₃)δ ppm: 2.09(3H, s), 4.04(3H, s), 5.22(2H, s), 7.01(1H, d, J=1.2), 7.15(1H, d, J=1.2), 7.35–7.85(8H, m), 8.02(1H, s) |
| 3060 | Imidazol-1-yl | 4-CF₃—C₆H₄ | Me | | |
| 3061 | Imidazol-1-yl | 2,4-F₂—C₆H₃ | Me | | |
| 3062 | Imidazol-1-yl | 2,5-F₂—C₆H₃ | Me | | |
| 3063 | Imidazol-1-yl | 3,4-F₂—C₆H₃ | Me | | |
| 3064 | Imidazol-1-yl | 3,5-F₂—C₆H₃ | Me | | |
| 3065 | Imidazol-1-yl | 2,3-Cl₂—C₆H₃ | Me | | |
| 3066 | Imidazol-1-yl | 2,4-Cl₂—C₆H₃ | Me | | ¹H-NMR(CDCl₃)δ ppm: 2.06(3H, s), 4.03(3H, s), 5.16(2H, s), 7.02(1H, s), 7.13–7.52(8H, m), 8.01(1H, s) |
| 3067 | Imidazol-1-yl | 2,5-Cl₂—C₆H₃ | Me | | |
| 3068 | Imidazol-1-yl | 3,4-Cl₂—C₆H₃ | Me | | ¹H-NMR(CDCl₃)δ ppm: 2.03(3H, s), 4.04(3H, s), 5.19(2H, s), 7.01(1H, s), 7.13–7.52(7H, m), 7.66(1H, s), 8.01(1H, s) |
| 3069 | Imidazol-1-yl | 3,5-Cl₂—C₆H₃ | Me | | |
| 3070 | Imidazol-1-yl | 3,4-Me₂—C₆H₃ | Me | | |
| 3071 | Imidazol-1-yl | 2,4-Me₂—C₆H₃ | Me | | |
| 3072 | Imidazol-1-yl | 3-Ph—C₆H₄ | Me | | |
| 3073 | Imidazol-1-yl | 4-Ph—C₆H₄ | Me | | |
| 3074 | Imidazol-1-yl | Morpholino | Me | | |
| 3075 | Imidazol-1-yl | 2,6-Me₂-morpholino | Me | | |
| 3076 | Imidazol-1-yl | C₆H₅ | Et | | |
| 3077 | Imidazol-1-yl | 4-F—C₆H₄ | Et | | |
| 3078 | Imidazol-1-yl | 4-Cl—C₆H₄ | Et | | |
| 3079 | Imidazol-1-yl | 4-Me—C₆H₄ | Et | | |
| 3080 | Imidazol-1-yl | 3,4-Cl₂—C₆H₃ | Et | | |
| 3081 | 1-Me-imidazol-2-yl | C₆H₅ | Me | | |
| 3082 | 1-Me-imidazol-2-yl | 2-F—C₆H₄ | Me | | |
| 3083 | 1-Me-imidazol-2-yl | 3-F—C₆H₄ | Me | | |
| 3084 | 1-Me-imidazol-2-yl | 4-F—C₆H₄ | Me | | |
| 3085 | 1-Me-imidazol-2-yl | 2-Cl—C₆H₄ | Me | | |

-continued

| No | R¹ | R² | R³ | n | Physical data |
|---|---|---|---|---|---|
| 3086 | 1-Me-imidazol-2-yl | 3-Cl—C₆H₄ | Me | | |
| 3087 | 1-Me-imidazol-2-yl | 4-Cl—C₆H₄ | Me | | |
| 3088 | 1-Me-imidazol-2-yl | 2-Br—C₆H₄ | Me | | |
| 3089 | 1-Me-imidazol-2-yl | 3-Br—C₆H₄ | Me | | |
| 3090 | 1-Me-imidazol-2-yl | 4-Br—C₆H₄ | Me | | |
| 3091 | 1-Me-imidazol-2-yl | 3-I—C₆H₄ | Me | | |
| 3092 | 1-Me-imidazol-2-yl | 2-Me—C₆H₄ | Me | | |
| 3093 | 1-Me-imidazol-2-yl | 3-Me—C₆H₄ | Me | | |
| 3094 | 1-Me-imidazol-2-yl | 4-Me—C₆H₄ | Me | | |
| 3095 | 1-Me-imidazol-2-yl | 3-Et—C₆H₄ | Me | | |
| 3096 | 1-Me-imidazol-2-yl | 4-Et—C₆H₄ | Me | | |
| 3097 | 1-Me-imidazol-2-yl | 3-MeO—C₆H₄ | Me | | |
| 3098 | 1-Me-imidazol-2-yl | 4-MeO—C₆H₄ | Me | | |
| 3099 | 1-Me-imidazol-2-yl | 3-CF₃—C₆H₄ | Me | | |
| 3100 | 1-Me-imidazol-2-yl | 4-CF₃—C₆H₄ | Me | | |
| 3101 | Imidazol-1-yl | Me | Me | | $^1$H-NMR(CDCl₃)δ ppm: 1.70(3H, s), 1.78(3H, s), 4.03(3H, s), 5.01(2H, s), 7.02(1H, s), 7.16(1H, d, J=1.2), 7.31–7.49(4H, m), 7.99(1H, s) |
| 3102 | Imidazol-1-yl | Cyclohexyl | Me | | |
| 3103 | Imidazol-1-yl | t-Bu | Me | | |
| 3104 | Imidazol-1-yl | 5-Me-isoxazol-3-yl | Me | | |
| 3105 | Imidazol-1-yl | Pyridin-3-yl | Me | | |
| 3106 | 1-Me-imidazol-2-yl | Me | Me | | |
| 3107 | 1-Me-imidazol-2-yl | Cyclohexyl | Me | | |
| 3108 | 1-Me-imidazol-2-yl | t-Bu | Me | | |
| 3109 | 1-Me-imidazol-2-yl | 5-Me-isoxazol-3-yl | Me | | |
| 3110 | 1-Me-imidazol-2-yl | Pyridin-3-yl | Me | | |
| 3111 | Isoxazol-3-yl | Me | Me | | |
| 3112 | Isoxazol-3-yl | Cyclohexyl | Me | | |
| 3113 | Isoxazol-3-yl | t-Bu | Me | | |
| 3114 | Isoxazol-3-yl | 5-Me-isoxazol-3-yl | Me | | |
| 3115 | Isoxazol-3-yl | Pyridin-3-yl | Me | | |
| 3116 | 5-Me-isoxazol-3-yl | Me | Me | | |
| 3117 | 5-Me-isoxazol-3-yl | Cyclohexyl | Me | | |
| 3118 | 5-Me-isoxazol-3-yl | t-Bu | Me | | |
| 3119 | 5-Me-isoxazol-3-yl | 5-Me-isoxazol-3-yl | Me | | |
| 3120 | 5-Me-isoxazol-3-yl | Pyridin-3-yl | Me | | |
| 3121 | 3-Me-isoxazol-5-yl | Me | Me | | |
| 3122 | 3-Me-isoxazol-5-yl | Cyclohexyl | Me | | |
| 3123 | 3-Me-isoxazol-5-yl | t-Bu | Me | | |
| 3124 | 3-Me-isoxazol-5-yl | 5-Me-isoxazol-3-yl | Me | | |
| 3125 | 3-Me-isoxazol-5-yl | Pyridin-3-yl | Me | | |

-continued

| No | R¹ | R² | R³ | n | Physical data |
|---|---|---|---|---|---|
| 3126 | 1,3,4-Oxadiazol-2-yl | Me | Me | | |
| 3127 | 1,3,4-Oxadiazol-2-yl | Cyclohexyl | Me | | |
| 3128 | 1,3,4-Oxadiazol-2-yl | t-Bu | Me | | |
| 3129 | 1,3,4-Oxadiazol-2-yl | 5-Me-isoxazol-3-yl | Me | | |
| 3130 | 1,3,4-Oxadiazol-2-yl | Pyridin-3-yl | Me | | |
| 3131 | Thiazolidin-2-yl | Me | Me | | |
| 3132 | Thiazolidin-2-yl | Cyclohexyl | Me | | |
| 3133 | Thiazolidin-2-yl | t-Bu | Me | | |
| 3134 | Thiazolidin-2-yl | 5-Me-isoxazol-3-yl | Me | | |
| 3135 | Thiazolidin-2-yl | Pyridin-3-yl | Me | | |
| 3136 | Pyrazol-1-yl | $C_6H_5$ | H | | $^1$H-NMR(CDCl$_3$)δ ppm: 4.03(3H, s), 4.93(2H, s), 6.43(1H, t, J=2.4), 7.31–7.60(10H, m), 7.99(1H, s), 8.51(1H, d, J=2.4) |
| 3137 | Pyrazol-1-yl | $C_6H_5$ | Me | | |
| 3138 | Pyrazol-1-yl | 4-F—$C_6H_4$ | Me | | |
| 3139 | Pyrazol-1-yl | 4-Cl—$C_6H_4$ | Me | | |
| 3140 | Pyrazol-1-yl | 4-Me—$C_6H_4$ | Me | | |

The following Test Examples illustrate the effects of the fungicide of the present invention.

I. Controlling Effects on Various Plant Diseases by Foliage Application (Pot Experiment)

Experimental Method

A test compound was dissolved in a small amount of N,N-dimethylformamide, and the solution was diluted to a given concentration with distilled water containing a spreader. Thus, a liquid sample to be tested was prepared. The liquid sample was sprayed to test plants, and 24 hours thereafter, pathogens were inoculated by the method described below.

The percent control was calculated according to the following equation:

$$\text{Percent control}(\%) = 100 \times \frac{\substack{\text{severity, number of} \\ \text{lesions, etc. in} \\ \text{untreated plot}} - \substack{\text{severity, number of} \\ \text{lesions, etc. in} \\ \text{treated plot}}}{\substack{\text{severity, number of lesions, etc.} \\ \text{in untreated plot}}}$$

Test Example 1

Controlling Effect on *Pyricularia oryzae*

Two-week rice seedlings (cv.: AICHIASAHI) were transplanted in plastic cups (each 9 cm in diameter) and cultivated further 2 weeks. The test compound in the form of a solution or a suspension was sprayed to the foliage of the rice seedlings, to which a conidia suspension of *Pyricularia oryzae* cultured in an oatmeal medium was inoculated by spraying. After the inoculation, the test plant was kept in a moist chamber (28° C., 100% R.H.) for 24 hours, followed by cultivation in a greenhouse for 5 days. Six days after the inoculation, the number of lesions on the leaves of the inoculated plant was measured to calculate the percent control.

The results are as follows.

| Compound No. | Controlling effect on *Pyricularia oryzae* by foliage application at 500 ppm (percent control) |
|---|---|
| 1 | 90 |
| 5 | 97 |
| 6 | 90 |
| 7 | 97 |
| 13 | 90 |
| 15 | 90 |
| 16 | 90 |
| 39 | 70 |
| 40 | 90 |
| 61 | 97 |
| 81 | 97 |
| 105A | 97 |
| 106A | 97 |
| 107A | 90 |
| 112A | 97 |
| 113A | 97 |
| 114A | 90 |
| 118B | 70 |
| 122A | 97 |
| 131A | 90 |
| 132A | 70 |
| 136A | 90 |
| 136B | 70 |
| 141A | 70 |
| 141B | 70 |
| 146A | 97 |
| 201 | 90 |
| 205 | 90 |
| 206 | 90 |
| 207 | 90 |
| 215 | 70 |
| 221 | 70 |
| 225 | 70 |
| 226 | 70 |
| 241 | 70 |
| 261 | 70 |
| 266 | 90 |
| 267 | 90 |
| 281 | 70 |

-continued

| Compound No. | Controlling effect on Pyricularia oryzae by foliage application at 500 ppm (percent control) |
|---|---|
| 287 | 90 |
| 295 | 90 |
| 300 | 70 |
| 305 | 70 |
| 306 | 70 |
| 312 | 70 |
| 313 | 90 |
| 314 | 90 |
| 322 | 70 |
| 336 | 90 |
| 436 | 70 |
| 512A | 90 |
| 512B | 97 |
| 536B | 70 |
| 541B | 70 |
| 605A | 90 |
| 607A | 90 |
| 612A | 90 |
| 613A | 70 |
| 614B | 70 |
| 636A | 97 |
| 636B | 70 |
| 641A | 70 |
| 690A | 97 |
| 705 | 70 |
| 706 | 70 |
| 712 | 90 |
| 713 | 97 |
| 716 | 70 |
| 722 | 90 |
| 731 | 70 |
| 732 | 70 |
| 741 | 70 |
| 801 | 70 |
| 812 | 70 |
| 912 | 70 |
| 936A | 97 |
| 1112 | 97 |
| 1236 | 97 |
| 1310 | 70 |
| 1328 | 90 |
| 1460 | 90 |
| 1461 | 70 |
| 1554A | 70 |
| 1581 | 70 |
| 1584 | 70 |
| 1674 | 70 |
| 2799 | 100 |
| 2839 | 90 |
| 3041 | 90 |
| Reference Fthalide | 97 |

Test Example 2

Controlling Effect on *Sphaerotheca fuliginea*

Seeds of cucumber (cv.: TSUKUBASHIROIBO) were sown in plastic cups (each 9 cm in diameter), followed by cultivation for 2 to 3 weeks. The liquid test sample in the form of a solution or suspension was sprayed on the surface of their first leaves. The pathogen was inoculated to the leaves by spraying a conidia suspension of *Sphaerotheca fuliginea* which had been cultured on the cucumber leaves. After the inoculation, the plants were kept in a greenhouse at 20° C. for 10 days. Then, the infected area on the leaf was observed, and the percent control was calculated.

The results are as follows.

| Compound No. | Controlling effect on Sphaerotheca fuliginea by foliage application at 500 ppm (percent control) |
|---|---|
| 1 | 100 |
| 5 | 100 |
| 7 | 100 |
| 13 | 100 |
| 15 | 100 |
| 16 | 100 |
| 39 | 100 |
| 40 | 100 |
| 57 | 90 |
| 101A | 70 |
| 104A | 97 |
| 105A | 100 |
| 106A | 100 |
| 106B | 97 |
| 107A | 100 |
| 112A | 100 |
| 112B | 90 |
| 113A | 100 |
| 113B | 90 |
| 114A | 100 |
| 119A | 97 |
| 122A | 100 |
| 122B | 100 |
| 130A | 100 |
| 131A | 100 |
| 131B | 100 |
| 132A | 100 |
| 136A | 100 |
| 136B | 100 |
| 141A | 100 |
| 141B | 100 |
| 144A | 100 |
| 144B | 70 |
| 146A | 97 |
| 161 | 100 |
| 201 | 100 |
| 205 | 100 |
| 206 | 100 |
| 207 | 100 |
| 215 | 100 |
| 221 | 97 |
| 226 | 70 |
| 227 | 97 |
| 261 | 97 |
| 266 | 97 |
| 267 | 100 |
| 270 | 97 |
| 275 | 100 |
| 278 | 97 |
| 294 | 97 |
| 300 | 70 |
| 305 | 100 |
| 306 | 97 |
| 312 | 100 |
| 313 | 100 |
| 314 | 100 |
| 322 | 100 |
| 336 | 100 |
| 412 | 100 |
| 436 | 100 |
| 512A | 100 |
| 512B | 100 |
| 536A | 90 |
| 536B | 100 |
| 541A | 100 |
| 541B | 100 |
| 605A | 100 |
| 605B | 100 |
| 606A | 100 |
| 606B | 90 |
| 607A | 97 |
| 607B | 97 |

-continued

| Compound No. | Controlling effect on Sphaerotheca fuliginea by foliage application at 500 ppm (percent control) |
|---|---|
| 612A | 100 |
| 612B | 100 |
| 613A | 100 |
| 613B | 97 |
| 614B | 97 |
| 636A | 100 |
| 636B | 100 |
| 641A | 100 |
| 641B | 100 |
| 690A | 100 |
| 690B | 100 |
| 701 | 97 |
| 705 | 100 |
| 706 | 100 |
| 707 | 100 |
| 712 | 100 |
| 713 | 100 |
| 716 | 100 |
| 722 | 100 |
| 731 | 100 |
| 732 | 100 |
| 736 | 100 |
| 741 | 100 |
| 801 | 100 |
| 805 | 97 |
| 807 | 100 |
| 812 | 100 |
| 836A | 100 |
| 836B | 100 |
| 844 | 97 |
| 905 | 90 |
| 912 | 100 |
| 936A | 100 |
| 936B | 97 |
| 1112 | 100 |
| 1114 | 70 |
| 1121 | 100 |
| 1122B | 100 |
| 1123 | 90 |
| 1136 | 100 |
| 1161 | 70 |
| 1236 | 100 |
| 1305 | 70 |
| 1310 | 90 |
| 1311 | 70 |
| 1312 | 70 |
| 1328 | 100 |
| 1341A | 70 |
| 1341B | 70 |
| 1428 | 100 |
| 1478 | 70 |
| 1514 | 97 |
| 1515 | 70 |
| 1581 | 70 |
| 1584 | 100 |
| 1590 | 70 |
| 1634A | 100 |
| 1634B | 70 |
| 1674 | 70 |
| 1721 | 100 |
| 1734 | 90 |
| 1735 | 100 |
| 1826 | 70 |
| 2001 | 70 |
| 2012 | 100 |
| 2014 | 100 |
| 2036 | 100 |
| 2044 | 97 |
| 2120 | 70 |
| 2507 | 100 |
| 2528 | 100 |
| 2799 | 100 |

-continued

| Compound No. | Controlling effect on Sphaerotheca fuliginea by foliage application at 500 ppm (percent control) |
|---|---|
| 2839 | 100 |
| 3041 | 97 |
| Reference Fenarimol | 97 |

Test Example 3

Controlling Effect on *Botrytis cinerea*

The seeds of cucumber (cv.: TSUKUBASHIROIBO) were sown in plastic cups (each 9 cm in diameter), followed by cultivation for 2 to 3 weeks. The test compound in the form of a solution or suspension was sprayed to the surface of their first leaves, and mycelial disks (4 mm $\phi$) of *Botrytis cinerea* cultured on the potato sucrose agar medium were put on the leaf surfaces to inoculate the cucumber seedlings with the pathogen. The plants were kept in a moist chamber at 20° C. for 3 days. The diameter of the lesions on the leaves was measured and the percent control was calculated.

The results were as follows.

| Compound No. | Controlling effect on Botrytis cinerea by foliage application at 500 ppm (percent control) |
|---|---|
| 1 | 100 |
| 5 | 70 |
| 6 | 100 |
| 7 | 100 |
| 13 | 70 |
| 15 | 100 |
| 40 | 70 |
| 61 | 100 |
| 81 | 90 |
| 106A | 70 |
| 122A | 70 |
| 130A | 70 |
| 132A | 70 |
| 141A | 90 |
| 144A | 70 |
| 201 | 70 |
| 205 | 70 |
| 206 | 97 |
| 207 | 100 |
| 215 | 97 |
| 314 | 70 |
| 605A | 70 |
| 607A | 70 |
| 713 | 70 |
| 732 | 70 |
| 741 | 90 |
| Reference Fenarimol | 97 |

Test Example 4

Controlling Effect on *Erysiphe graminis* f. sp. *tritici*

The seeds of wheat (cv.: NORIN No. 61) were sown in plastic cups (each 9 cm in diameter), followed by cultivation for 2 to 3 weeks. The test compound in the form of a solution or suspension was sprayed to the seedlings, and conidia of *Erysiphe graminis* f. sp. *tritici* cultured on wheat leaves were dropped on the test plants to inoculate the plants with the pathogen. After the inoculation, the plants were kept in a greenhouse at 20° C. for 20 days. The infected area on the leaf was observed, and the percent control was calculated.

The results are as follows:

| Compound No. | Controlling effect on Erysiphe graminis f. sp. tritici by foliage application at 500 ppm (percent control) |
|---|---|
| 1 | 90 |
| 5 | 90 |
| 6 | 100 |
| 7 | 100 |
| 13 | 90 |
| 15 | 97 |
| 16 | 90 |
| 40 | 97 |
| 57 | 70 |
| 61 | 97 |
| 81 | 97 |
| 104A | 90 |
| 104B | 70 |
| 105A | 70 |
| 106A | 70 |
| 107A | 70 |
| 112A | 100 |
| 113A | 90 |
| 114A | 90 |
| 122A | 97 |
| 131A | 90 |
| 132A | 70 |
| 136A | 90 |
| 136B | 70 |
| 141A | 90 |
| 161 | 70 |
| 201 | 90 |
| 206 | 90 |
| 207 | 100 |
| 215 | 90 |
| 221 | 70 |
| 226 | 70 |
| 227 | 70 |
| 235 | 90 |
| 261 | 97 |
| 265 | 70 |
| 266 | 97 |
| 267 | 97 |
| 270 | 90 |
| 275 | 90 |
| 278 | 90 |
| 281 | 90 |
| 295 | 90 |
| 305 | 90 |
| 306 | 70 |
| 312 | 100 |
| 313 | 70 |
| 314 | 70 |
| 322 | 70 |
| 336 | 97 |
| 412 | 70 |
| 436 | 90 |
| 512A | 97 |
| 512B | 97 |
| 536A | 97 |
| 536B | 100 |
| 541A | 90 |
| 541B | 90 |
| 605A | 90 |
| 605B | 90 |
| 606A | 70 |
| 607A | 90 |
| 607B | 70 |
| 612A | 100 |
| 612B | 100 |
| 613A | 90 |
| 613B | 70 |
| 614B | 70 |
| 636A | 100 |
| 636B | 100 |
| 641A | 90 |
| 641B | 90 |
| 690A | 100 |
| 690B | 100 |
| 701 | 70 |
| 706 | 90 |
| 707 | 90 |
| 712 | 100 |
| 713 | 90 |
| 716 | 70 |
| 722 | 90 |
| 731 | 70 |
| 732 | 70 |
| 736 | 100 |
| 741 | 90 |
| 801 | 90 |
| 812 | 100 |
| 836A | 97 |
| 836B | 97 |
| 912 | 90 |
| 936A | 97 |
| 936B | 90 |
| 1101 | 90 |
| 1112 | 90 |
| 1114 | 70 |
| 1121 | 90 |
| 1122A | 70 |
| 1122B | 90 |
| 1123 | 90 |
| 1136 | 90 |
| 1161 | 90 |
| 1236 | 90 |
| 1310 | 90 |
| 1311 | 70 |
| 1328 | 90 |
| 1341A | 90 |
| 1341B | 90 |
| 1428 | 70 |
| 1455 | 70 |
| 1460 | 90 |
| 1478 | 90 |
| 1514 | 70 |
| 1515 | 90 |
| 1554A | 70 |
| 1554B | 70 |
| 1584 | 100 |
| 1634A | 97 |
| 1654 | 70 |
| 1665 | 70 |
| 1667 | 70 |
| 1674 | 70 |
| 1721 | 90 |
| 1734 | 70 |
| 1735 | 97 |
| 1829 | 90 |
| 2012 | 70 |
| 2036 | 90 |
| 2799 | 97 |
| 2839 | 97 |
| Reference Fenarimol | 97 |

Test Example 5

Controlling Effect on *Puccinia coronata*

The seeds of oat (cv.: PC-38) were sown in plastic cups (each 9 cm in diameter), followed by cultivation for 2 to 3 weeks. The test compound in the form of a solution or suspension was sprayed to the seedlings. Spores of *Puccinia coronata* cultured on oat leaves were collected, diluted about 10-fold with talc, and sprayed to the test plants to inoculate the plants with the pathogen. After the inoculation, the plants were kept in a moist chamber at 20° C. for 1 day and then in a greenhouse at 20° C. for 8 days. The infected area on the leaf was observed, and the percent control was calculated.

The results are as follows.

| Compound No. | Controlling effect on *Puccinia coronata* by foliage application at 500 ppm (percent control) |
|---|---|
| 1 | 97 |
| 5 | 90 |
| 6 | 100 |
| 7 | 97 |
| 13 | 97 |
| 15 | 100 |
| 16 | 100 |
| 40 | 70 |
| 57 | 90 |
| 61 | 97 |
| 81 | 97 |
| 112A | 100 |
| 136A | 100 |
| 136B | 97 |
| 161 | 97 |
| 201 | 90 |
| 205 | 70 |
| 206 | 97 |
| 207 | 97 |
| 215 | 90 |
| 267 | 90 |
| 275 | 90 |
| 278 | 90 |
| 298 | 70 |
| 312 | 97 |
| 336 | 100 |
| 436 | 90 |
| 536A | 90 |
| 536B | 97 |
| 612A | 97 |
| 636A | 100 |
| 636B | 90 |
| 701 | 97 |
| 712 | 100 |
| 722 | 97 |
| 736 | 100 |
| 801 | 97 |
| 914 | 97 |
| 936A | 90 |
| 1001 | 70 |
| 1112 | 70 |
| 1113 | 70 |
| 1136 | 90 |
| 1236 | 97 |
| 1328 | 70 |
| 1478 | 70 |
| 1584 | 70 |
| 1721 | 70 |
| 2001 | 70 |
| Reference Fenarimol | 97 |

Test Example 6

Controlling Effect on *Pseudoperonospora cubensis*

The seeds of cucumber (var.: TSUKUBASHIROIBO) were sown in plastic cups (each 9 cm in diameter), followed by cultivation for 2 to 3 weeks. The test compound in the form of a solution or suspension was sprayed to the surface of their first leaves, and a zoosporangia suspension of *Pseudoperonospora cubensis* cultured on cucumber leaves was dropped on the above leaf surfaces to inoculate the test plants with the pathogen. After the inoculation, the plants were kept in a moist chamber at 20° C. for 10 days. Then, the area of the lesions around the inoculum were observed and the percent control was calculated.

The results are as follows.

| Compound No. | Controlling effect on *Pseudoperonospora cubensis* by foliage application at 500 ppm (percent control) |
|---|---|
| 105A | 100 |
| 106A | 100 |
| 106B | 100 |
| 112A | 97 |
| 113A | 100 |
| 119A | 85 |
| 122A | 100 |
| 130A | 100 |
| 131A | 100 |
| 132A | 100 |
| 141A | 100 |
| 144A | 100 |
| 146A | 100 |
| 305 | 100 |
| 306 | 100 |
| 313 | 100 |
| 314 | 100 |
| 412 | 100 |
| 512A | 100 |
| 512B | 100 |
| 536B | 100 |
| 541A | 100 |
| 541B | 100 |
| 605A | 100 |
| 606A | 95 |
| 606B | 100 |
| 607A | 97 |
| 607B | 97 |
| 612A | 100 |
| 612B | 100 |
| 613A | 70 |
| 613B | 100 |
| 614B | 100 |
| 641A | 100 |
| 690A | 100 |
| 690B | 100 |
| 701 | 100 |
| 705 | 100 |
| 706 | 100 |
| 713 | 100 |
| 716 | 100 |
| 722 | 100 |
| 731 | 100 |
| 732 | 100 |
| 741 | 100 |
| 801 | 100 |
| 844 | 100 |
| 905 | 99 |
| 1721 | 100 |
| 2014 | 100 |
| 2044 | 100 |
| 2507 | 100 |
| 2528 | 100 |
| 2799 | 95 |
| 2839 | 95 |
| Reference Benalaxyl | 97 |

As described above, the present invention provides a novel oxime derivative, particularly a heterocyclic compound substituted with α-(O-substituted oxyimino)-2-substituted benzyl, having potent fungicidal activity, a process for producing it, intermediates therefor, and a fungicide containing it as an active ingredient.

We claim:

1. A compound of the formula (I):

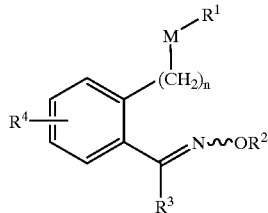

wherein $R^1$ is phenyl optionally substituted with a group selected from the group consisting of lower alkyl, lower alkenyl, lower alkynyl, cycloalkyl, cycloalkenyl, lower alkanoyl, lower alkylsilyl, halogenated lower alkyl, di(lower)alkylamino, phenyl, phenyl(lower)alkyl, phenyl(lower)alkenyl, furyl(lower)alkyl, furyl(lower)alkenyl, halogen, nitro, cyano, lower alkylthio, —$OR^{11}$, wherein $R^{11}$ is hydrogen, lower alkyl, lower alkenyl, lower alkynyl, lower alkanoyl, phenyl, lower alkoxyphenyl, nitrophenyl, phenyl(lower)alkyl, cyanophenyl(lower)alkyl, benzoyl, tetrahydropyranyl, pyridyl, trifluoromethylpyridyl, pyrimidinyl, benzothiazolyl, quinolyl, benzoyl(lower)alkyl, benzosulfonyl or lower alkylbenzenesulfonyl, or —$CH_2$—$Z$—$R^{12}$, wherein Z is —O—, —S—, or —$NR^{13}$— wherein $R^{13}$ is hydrogen or lower alkyl, $R^{12}$ is phenyl, halophenyl, lower alkoxyphenyl, pyridyl, or pyrimidinyl;

$R^2$ is alkyl, alkenyl, alkynyl or cycloalkyl;

$R^3$ is an isoxazolyl group optionally substituted with a group selected from the group consisting of lower alkyl, lower alkenyl, lower alkynyl, cycloalkyl, cycloalkenyl, lower alkanoyl, lower alkylsilyl, halogenated lower alkyl, di(lower)alkylamino, phenyl, phenyl (lower)alkyl, phenyl(lower)alkenyl, furyl(lower)alkyl, furyl(lower)alkenyl, halogen, nitro, cyano, lower alkylthio, —$OR^{11}$, wherein $R^{11}$ is hydrogen, lower alkyl, lower alkenyl, lower alkynyl, lower alkanoyl, phenyl, lower alkoxyphenyl, nitrophenyl, phenyl (lower)alkyl, cyanophenyl(lower)alkyl, benzoyl, tetrahydropyranyl, pyridyl, trifluoromethylpyridyl, pyrimidinyl, benzothiazolyl, quinolyl, benzoyl(lower)alkyl, benzosulfonyl or lower alkylbenzenesulfonyl, or —$CH_2$—$Z$—$R^{12}$, wherein Z is —O—, —S—, or —$NH^{13}$— wherein $R^{13}$ is hydrogen or lower alkyl, $R^{12}$ is phenyl, halophenyl, lower alkoxyphenyl, pyridyl, or pyrimidinyl or an isoxazolinyl group optionally substituted with a group selected from the group consisting of lower alkyl, lower alkenyl, lower alkynyl, cycloalkyl, cycloalkenyl, lower alkanoyl, lower alkylsilyl, halogenated lower alkyl, di(lower) alkylamino, phenyl, phenyl(lower)alkyl, phenyl(lower)alkenyl, furyl(lower)alkyl, furyl(lower)alkenyl, halogen, nitro, cyano, lower alkylthio, —$OR^{11}$, wherein $R^{11}$ is hydrogen, lower alkyl, lower alkenyl, lower alkynyl, lower alkanoyl, phenyl, lower alkoxyphenyl, nitrophenyl, phenyl(lower)alkyl, cyanophenyl (lower)alkyl, benzoyl, tetrahydropyranyl, pyridyl, trifluoromethylpyridyl, pyrimidinyl, benzothiazolyl, quinolyl, benzoyl(lower)alkyl, benzosulfonyl or lower alkylbenzenesulfonyl, or —$CH_2$—$Z$—$R^{12}$, wherein Z is —O—, —S—, or —$NR^{13}$— wherein $R^{13}$ is hydrogen or lower alkyl, $R^{12}$ is phenyl, halophenyl, lower alkoxyphenyl, pyridyl, or pyrimidinyl;

$R^4$ is hydrogen, alkyl, alkoxy, halogen, nitro, cyano or halogenated alkyl; M is an oxygen atom, $S(O)_i$, wherein i is 0, 1 or 2, $NR^{16}$, wherein $R^{16}$ is hydrogen, alkyl, or acyl, or a single bond;

n is 0 or 1, or a salt thereof.

2. A compound according to claim 1, wherein $R^1$ is phenyl or phenyl substituted with halogen and/or lower alkyl; or a salt thereof.

3. A compound according to claim 1, wherein $R^1$ is phenyl, 2-chlorophenyl, 3-chlorophenyl, 4-chlorophenyl, 2-methylphenyl, 3-methylphenyl, 4-methylphenyl, 2-ethylphenyl, 2,5-dimethylphenyl, 2,6-dimethylphenyl, 4-chloro-2-methylphenyl, or a salt thereof.

4. A compound according to claim 1, wherein $R^2$ is alkyl or alkenyl, or a salt thereof.

5. A compound according to claim 1, wherein $R^2$ is methyl, ethyl or allyl, or a salt thereof.

6. A compound according to claim 1, wherein $R^3$ is isoxazolyl; isoxazolyl substituted with lower alkyl; isoxazolinyl; or isoxazolinyl substituted with lower alkyl.

7. A compound according to claim 1, wherein $R^3$ is isoxazol-3-yl, 3-methylisoxazol-5-yl, 5-methylisoxazol-3-yl, 2-isoxazolin-3-yl, 3-methyl-2-isoxazolin-5-yl, or isoxazol-5-yl.

8. A compound according to claim 1, wherein $R^4$ is hydrogen, or a salt thereof.

9. A compound according to claim 1, wherein M is an oxygen atom, or a salt thereof.

10. A compound according to claim 9, wherein $R^1$ is 2,5-dimethylphenyl, $R^2$ is methyl, $R^3$ is isoxazol-3-yl, $R^4$ is hydrogen, and n is 1 (Compound No. 336);

$R^1$ is 2,5-dimethylphenyl, $R^2$ is methyl, $R^3$ is 5-methylisoxazol-3-yl, $R^4$ is hydrogen, and n is 1 (Compound No. 436);

$R^1$ is 2,5-dimethylphenyl, $R^2$ is methyl, $R^3$ is 3-methylisoxazol-5-yl, $R^4$ is hydrogen, and n is 1 (Compound No. 636).

11. A fungicidal composition comprising a compound according to claim 1 as an active ingredient.

12. A process for producing a compound of the formula (I):

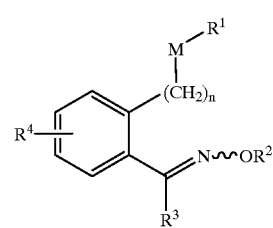

wherein each symbol is as defined in claim 1, which comprises reacting the compound of the formula (V)

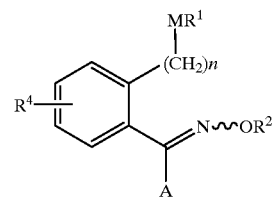

wherein A is halogen and the other symbols are as defined in claim 1, with a compound of the formula (X):

$$R^3\text{—H} \qquad\qquad (X)$$

wherein $R^3$ is an optionally substituted heterocyclic group as defined in claim 1.

13. A method for controlling or preventing phytopathogenic fungi which comprises applying as an active ingredient a compound according to claim 1 to a locus where phytopathogenic fungi propagate or will propagate.

* * * * *